US008008263B2

(12) United States Patent
Britt et al.

(10) Patent No.: US 8,008,263 B2
(45) Date of Patent: Aug. 30, 2011

(54) ORGANIC COMPOUNDS AND THEIR USES

(75) Inventors: Shawn D. Britt, Andover, MA (US);
Lech Andrzej Ciszewski, Morristown, NJ (US); Jiping Fu, Arlington, MA (US); Subramanian Karur, Arlington, MA (US); Yugang Liu, Bridgewater, NJ (US); Peichao Lu, Malden, MA (US); David Thomas Parker, Lexington, MA (US); Mahavir Prashad, Montville, NJ (US); Prakash Raman, Acton, MA (US); Pascal Rigollier, Mulhouse (FR); Mohindra Seepersaud, Acton, MA (US); Aregahegn Yifru, Somerville, MA (US); Rui Zheng, Waltham, MA (US)

(73) Assignee: Novartis AG, Basel (CH)

( * ) Notice: Subject to any disclaimer, the term of this patent is extended or adjusted under 35 U.S.C. 154(b) by 353 days.

(21) Appl. No.: 12/249,186

(22) Filed: Oct. 10, 2008

(65) Prior Publication Data

US 2009/0137495 A1 May 28, 2009

Related U.S. Application Data

(60) Provisional application No. 60/978,974, filed on Oct. 10, 2007.

(51) Int. Cl.
*A61K 38/07* (2006.01)
*A61K 38/55* (2006.01)

(52) U.S. Cl. ...... 514/21.9; 514/3.7; 514/20.1; 514/20.3; 530/330

(58) Field of Classification Search .................. None
See application file for complete search history.

(56) References Cited

U.S. PATENT DOCUMENTS

| | | | |
|---|---|---|---|
| 6,894,072 B2 | 5/2005 | Arasappan et al. | |
| 2003/0216325 A1 | 11/2003 | Saksena et al. | |
| 2005/0197301 A1 | 9/2005 | Njoroge et al. | |
| 2005/0209164 A1 | 9/2005 | Bogen et al. | |
| 2005/0249702 A1 | 11/2005 | Njoroge et al. | |
| 2006/0046956 A1 | 3/2006 | Sannigrahi et al. | |
| 2006/0281689 A1 | 12/2006 | Malcolm | |
| 2007/0049536 A1 | 3/2007 | Venkatraman et al. | |
| 2007/0093430 A1 | 4/2007 | Chen et al. | |
| 2007/0286842 A1* | 12/2007 | Brandl et al. ............ | 424/85.7 |

FOREIGN PATENT DOCUMENTS

| | | |
|---|---|---|
| WO | 0208244 | 1/2002 |
| WO | 0218369 | 3/2002 |
| WO | 03062265 | 7/2003 |
| WO | 2004113295 | 12/2004 |
| WO | 2005021584 | 3/2005 |
| WO | 2005028502 | 3/2005 |
| WO | 2005035525 | 4/2005 |
| WO | 2005042020 | 5/2005 |
| WO | 2005/058821 A1 | 6/2005 |
| WO | 2005058821 | 6/2005 |
| WO | 2005077969 | 8/2005 |
| WO | 2005085242 | 9/2005 |
| WO | 2005085275 | 9/2005 |
| WO | 2005087731 | 9/2005 |
| WO | 2005123076 | 12/2005 |
| WO | 2006039488 | 4/2006 |
| WO | 2006050250 | 5/2006 |
| WO | 2006130553 | 12/2006 |
| WO | 2006130666 | 12/2006 |
| WO | 2006130686 | 12/2006 |
| WO | 2006130687 | 12/2006 |
| WO | 2007005838 | 1/2007 |
| WO | 2007016589 | 2/2007 |
| WO | 2007025307 | 3/2007 |
| WO | 2007/120595 A2 | 10/2007 |
| WO | 2007120595 | 10/2007 |
| WO | 2007121124 | 10/2007 |
| WO | 2007121125 | 10/2007 |
| WO | 2007/133865 | 11/2007 |

OTHER PUBLICATIONS

Chen, Kevin X. et al.: "Novel Potent Hepatitis C Virus NS3 Serine Protease Inhibitors Derived from Proline-Based Macrocycles", J. Med. Chem., 2006, 995-1005; vol. 49 (3). Published on Web Jan. 7, 2006.
Chen, Kevin X. et al.; "Potent 7-hydroxy-1,2,3,4-tetrahydroisoquinoline-3-carboxylic acid-based macrocyclic inhibitors of hepatitis C virus NS3 protease", Journal of Medicinal Chemistry, Jun. 3, 2005 (Pub. 2006); pp. 567-574; vol. 49 (2).
Chen, Kevin X. et al.; "Proline-based macrocyclic inhibitors of the hepatitis C virus: Stereoselective synthesis and biological activity"; Angewandte Chemie, International Edition; 2005, pp. 7024-7028; vol. 44 (43).
Bogen, S. et al.; "Hepatitis C virus NS3-4A serine protease inhibitors: Use of a P2-P1 cyclopropyl alanine combination for improved potency": Bioorganic & Medicinal Chemistry Letters; 2005: pp. 4515-4519; vol. 15 (20).
Chen, Kevin X. et al. "Synthesis and biological activity of macrocyclic inhibitors of hepatitis C virus (HCV) NS3 protease" Bioorganic & Medicianal Chemistry Letters; May 13, 2005 (Pub. Aug. 19, 2005), pp. 4475-4478, vol. 15 (20).
Arasappan, A. et al. "Hepatitis C virus NS3-4A serine protease inhibitors: SAR of P'2 moiety with improved potency", Bioorganic & Medicinal Chemistry Letters, 2005, pp. 4180-4184, vol. 15(19).
Venkatraman, Srikanth et al. "Design and synthesis of depeptidized macrocyclic inhibitors of hepatitis C NS3-4A Protease Using structure-based drug design" Journal Medicinal Chemistry, 2005, pp. 5088-5091, vol. 48(16).
Arasappan, A. et al. "Novel 2-oxoimidazolidine-4-carboxylic acid derivatives as hepatitis C virus NS3-4A serine protease inhibitors: synthesis, activity, and X-ray crystal structure of an enzyme inhibitor complex", Bioorganic & Medicinal Chemistry Letters, 2004, pp. 5751-5755, vol. 14(23).
Tsantrizos, Youla et al. "Olefin ring-closing metathesis as a powerful tool in drug discovery and development-potent macrocyclic inhibitors of the hepatitis C virus NS3 protease" Journal of Orgnaomettalic Chemistry, 2006, pp. 5163-5171, vol. 691 (24-25).

(Continued)

Primary Examiner — Anish Gupta
(74) Attorney, Agent, or Firm — John Alexander, Esq.

(57) ABSTRACT

The present application describes organic compounds that are useful for the treatment, prevention and/or amelioration of human diseases.

17 Claims, 26 Drawing Sheets

OTHER PUBLICATIONS

Llinas-Brunet, Montse et al.; "Structure-Activity Study on a Novel Series of Macrocyclic Inhibitors of the Hepatitis C Virus NS3 Protease Leading to the Discovery of BILN 2061", Journal of Medicinal Chemistry, 2004, pp. 1605-1608, vol. 47(7).

Lamarre, Daniel et al. "An NS3 protease inhibitor with antiviral effects in humans infected with hepatitis C virus", Nature Letters (London), 2003, pp. 186-189, vol. 426 (6963).

Tsantrizos, Youla S. et al. "Macrocyclic inhibitors of the NS3 protease as potential therapeutic agents of hepatitis C virus infection", Angewandte chemie, International Edition, 2003, pp. 1356-1360, vol. 42(12).

Robert, Ronn et al. "Exploration of acyl sulfonamides as carboxylic acid replacements in protease inhibitors of the hepatitis C virus full-length NS3", Bioorganic & Medicinal Chemistry, 2006, pp. 544-559, vol. 14(2).

Malancona, Savina et al. "SAR and pharmacokinetic studies on penethylamide inhibitors of the hepatitis C virus NS3/NS4A serine protease", Bioorganic & Medicinal chemistry Letters, 2004, pp. 4575-4579, vol. 14(17).

Frutos, Rogelio P. et al. "Practical synthesis of 2-[2-Isopropylaminothiazol-4-yl]-7-methoxy-1H-quinolin-4-one; key intermediate for the synthesis of potent HCV NS3 protease inhibitor BILN 2061", 2006, Synthesis, pp. 2563-2567, Vol.

Yee, Nathan K. et al., "Efficient Large-Scale Synthesis of BILN 2061 a potent HCV protease inhibitor by a convergent approach based on ring-closing metathesis", 2006, Journal of Organic Chemistry, pp. 7133-7145, vol. 71(19).

Beaulieu, Pierrre L. et al., "Synthesis of (1R,2S)-1-Amino-2-vinylcyclopropanecarboxylic acid vinyl-ACCA) Derivatives: Key intermediates for the preparation of inhibitors of the hepatitis C virus NS3 protease", Journal of Organic Chemistry, 2005, pp. 5869-5879, vol. 70 (15).

LaPlante, Steven R. et al., "Dynamics and structure-based design of drugs targeting the critical serine protease of the hepatitis C virus-from a peptidic substrate to BILN 2061", Current Medicinal Chemistry: Anti-Infective Agents, 2005, pp. 111-132, vol. 4(2).

Liinas-Brunet, Montse et al. "A systematic approach to the optimization of substrate-based inhibitors of the hepatitis C virus NS3 protease: discovery of potent and specific tripeptide inhibitors", Journal of Medicinal Chemistry, 2004, pp: 6584-6594, vol. 47(26).

Goudreau, Nathalie et al. "Potent inhibitors of the hepatitis C virus NS3 protease: design and synthesis of macrocyclic substrate-based Beta-strand mimics", Journal of Organic Chemistry, 2004, pp. 6185-6201, vol. 69(19).

Faucher, Anne-Marie et al., "Synthesis of BILN 2061, an HCV NS3 protease inhibitor with proven antiviral effect in humans", Organic Letters, 2004, pp. 2901-2904, vol. 6(17).

Lin, Kai et al., "Combination of Hepatitis C Virus NS3-NS4A protease inhibitor and alpha interferon synergistically inhibits viral RNA replication and facilities viral RNA clearance in replicon cells", Antimicrobial Agents and Chemotherapy, 2004, pp. 4784-4792, vol. 48(12).

Perni, Robert B. et al., "Inhibitors of hepatitis C virus NS3.4A protease. Effect of P4 capping groups on inhibitory potency and pharmacokinetics", Bioorganic and Medicinal Chemistry Letters, 2007, pp. 3406-3411, vol. 17(12).

Thomson, John A. et al., "Hepatitis C virus NS3.4A protease inhibitors: countering viral subversion in vitro and showing promise in the clinic", Current Opinion in Drug Discovery & Development, 2006, pp. 606-617, vol. 9(5).

Perni, Robert B. et al. "Inhibitors of hepatitis C virus NS3.4A protease 2. Warhead SAR and optimization" Bioorganic & medicinal Chemistry Letters, 2004, pp. 1441-1446, vol. 14(6).

Lin, C. et al., "Discovery and development of VX-950, a novel, covalent, and reversible inhibitor of hepatitis C virus NS3.bul.4A serine protease", Infectious Disorders: Drug Targets, 2006, pp. 3-16, vol. 6(1).

Venkatraman, Srikanth et al., "Discovery of (1R,55)-N-[3-Amino-1-(cyclobutylmethyl)-2,3-dioxopropyl]-3-[2(S)-[[[(1-dimethylethyl)amino]carbonyl]amino]-3,3-dimethyl-1-oxobutyl]-6,6-dimethyl-3-azabicyclo[3.1.0]hexan-2(S)-carboxamide(SCH 503034), a selective, potent, orally bioavailable hepatitis C virus NS3 Protease inhibitor: a potential therapeutic agent for the treatment of hepatitis C infection", Journal of Medicinal Chemistry, 2006, pp. 6074-6086, vol. 49(20).

Bogen, Stephane L. et al., Discovery of SCH446211 (SCH6): A new ketoamide inhibitor of the HCV NS3 Serine Protease and HCV subgenomic RNA replication: Journal of Medicinal Chemistry, 2006, pp. 2750-2757, vol. 49(9).

Prongay, Andrew J. et al, "Discovery of the HCV NS3/4A Protease Inhibitor (1R,5S)-N-[3-amino-1-(cyclobutylmethyl)-2,3-dioxopropyl]-3-[2(S)-[[[(1,1-dimethylethyl)amono]carbonyl]amino'-3,3-dimethyl-1-oxobutyl]-6,6-dimethyl-3-azabicyclo[3.1.0]hexan-2(s)-carboxamide (Sch503034). Key steps in structure-based optimization." Journal of Medicinal Chemistry, 2007, pp. 2310-2318, vol. 50(10).

Liu, Rong et al., "In vitro antiviral activity of SCH446211 (SCH6), a novel inhibitor of the hepatitis C virus NS3 serine protease", Journal of Antimicrobial Chemotherapy, 2007, pp. 51-58, vol. 59(1).

Perni, Robert B. et al., "Inhibitors of hepatitis C virus NS3-4A protease 1. Non-charged tetrapeptide variants", Bioorganic & Medicinal Chemistry Letters, 2003, pp. 4059-4063, vol. 13(22).

Venkatraman, Srikanth et al., "Novel inhibitors of hepatitis C NS3-NS4A serine protease derived from 2-aza-bicyclo [2.2.1]heptane-3-carboxylic acid", Medicinal Chemistry Letters, 2006, pp. 1628-1632, vol. 16(6).

Velazquez, Francisco et al., "Application of ring-closing metathesis for the synthesis of macrocyclic peptidomimetics as inhibitors of HCV NS3 protease", Organic Letters, 2007, pp. 3061-3064, vol. 9(16).

Arasappan, Ashok et al., "P2-P4 Macrocyclic inhibitors of hepatitis C virus NS3-4A serine protease", Bioorganic & Medicinal Chemistry Letters, 2006, pp. 3960-3966, vol. 16(15).

Arasappan, Ashok et al. "Practical and efficient method for amino acid derivatives containing beta-quaternary center: application toward synthesis of hepatitis C virus NS3 serine protease inhibitors", Tetrahedron Letters, 2007, pp. 6343-6347, vol. 48(36).

Chen, Shu-Hui et al., "P1 and P1' optimization of [3,4]-bicycloproline P2 incorporated tetrapeptidyl alpha-ketoamide based HCV protease inhibitors", Letters-in Drug Design & Discovery, 2005, pp. 118-123, vol. 2.

Farmer, Luc J. et al., "Inhibitors of hepatitis C virus NS3.bul.4A protease: P2 proline variants", Letters in Drug Design & Discovery, 2005, pp. 497-502, vol. 2(7).

De Francesco et al: "Advances in the development of new therapeutic agents targeting the NS3-4A serine protease or the NS5B RNA-dependent RNA polymerase of the hepatitis C virus" Advanced Drug Delivery Reviews, vol. 59, No. 12, Aug. 11, 2007, pp. 1242-1262. Figure 2.

Malancona et al., "SAR and pharmacokinetic studies on phenethylamide inhibitors of the hepatitis C virus NS3/NS4A serine protease," Bioorganic & Medicinal Chemistry Letters 14:4575-4579 (2004).

De Francesco et al., "Advances in the development of new therapeutic agents targeting the NS3-4A serine protease or the NS5B RNA-dependent RNA polymerase of the hepatitis C virus" Advanced Drug Delivery Reviews 59 (12):1242-1262 (Aug. 11, 2007).

Lin et al., "VX-950, a novel hepatitis C virus (HCV) NS3-4A protease inhibitor, exhibits potent antiviral activities in HCV replicon cells," Antimicrobial Agents and Chemotherapy 50(5):1811-1822 (2006).

* cited by examiner

ORGANIC COMPOUNDS AND THEIR USES

BACKGROUND

Chronic hepatitis C virus (HCV) infection is a major global health burden, with an estimated 170 million people infected worldwide and an additional 3 to 4 million infected each year (See e.g. World Health Organization Fact Sheet No. 164. October 2000). Although 25% of new infections are symptomatic, 60-80% of patients will develop chronic liver disease, of whom an estimated 20% will progress to cirrhosis with a 1-4% annual risk of developing hepatocellular carcinoma (See e.g. World Health Organization Guide on Hepatitis C. 2002; Pawlotsky, J-M. (2006) Therapy of Hepatitis C: From Empiricism to Eradication. Hepatology 43:S207-S220). Overall, HCV is responsible for 50-76% of all liver cancer cases and two thirds of all liver transplants in the developed world (See e.g. World Health Organization Guide on Viral Cancers. 2006). And ultimately, 5-7% of infected patients will die from the consequences of HCV infection (See e.g. World Health Organization Guide on Hepatitis C. 2002).

The current standard therapy for HCV infection is pegylated interferon alpha (IFN-α) in combination with ribavirin. However, only up to 50% of patients with genotype 1 virus can be successfully treated with this interferon-based therapy. Moreover, both interferon and ribavirin can induce significant adverse effects, ranging from flu-like symptoms (fever and fatigue), hematologic complications (leukopenia, thrombocytopenia), neuropsychiatric issues (depression, insomnia, irritability), weight loss, and autoimmune dysfunctions (hypothyroidism, diabetes) from treatment with interferon to significant hemolytic anemia from treatment with ribavirin. Therefore, more effective and better tolerated drugs are still greatly needed.

HCV, first identified in 1989 (See e.g. Choo, Q. L. et al. *Science* (1989) 244:359-362), is a single-stranded RNA virus with a 9.6-kilobase genome of positive polarity. It encodes a single polyprotein that is cleaved upon translation by cellular and viral proteases into at least ten individual proteins: C, E1, E2, p7, NS2, NS3, NS4A, NS4B, NS5A, and NS5B (See e.g. Lindenbach, B. D. et al. (2001). Flaviviridae: the viruses and their replication, p. 991-1041. In D. M. Knipe, P. M. Howley, and D. E. Griffin (ed.), Fields virology, 4th ed, vol. 1. Lippincott Williams & Wilkins, Philadelphia, Pa.).

NS3, an approximately 70 kDa protein, has two distinct domains: a N-terminal serine protease domain of 180 amino acids (AA) and a C-terminal helicase/NTPase domain (AA 181 to 631). The NS3 protease is considered a member of the chymotrypsin family because of similarities in protein sequence, overall three-dimensional structure and mechanism of catalysis. The HCV NS3 serine protease is responsible for proteolytic cleavage of the polyprotein at the NS3/NS4A, NS4A/NS4B, NS4B/NS5A and NS5A/NS5B junctions (See e.g. Bartenschlager, R., L. et al. (1993) J. Virol. 67:3835-3844; Grakoui, A. et al. (1993) J. Virol. 67:2832-2843; Tomei, L. et al. (1993) J. Virol. 67:4017-4026). NS4A, an approximately 6 kDa protein of 54 AA, is a co-factor for the serine protease activity of NS3 (See e.g. Failla, C. et al. (1994) J. Virol. 68:3753-3760; Tanji, Y. et al. (1995) J. Virol. 69:1575-1581). Autocleavage of the NS3/NS4A junction by the NS3/NS4A serine protease occurs intramolecularly (i.e., cis) while the other cleavage sites are processed intermolecularly (i.e., trans). It has been demonstrated that HCV NS3 protease is essential for viral replication and thus represents an attractive target for antiviral chemotherapy.

SUMMARY OF THE INVENTION

There remains a need for new treatments and therapies for HCV infection, as well as HCV-associated disorders. There is also a need for compounds useful in the treatment or prevention or amelioration of one or more symptoms of HCV, as well as a need for methods of treatment or prevention or amelioration of one or more symptoms of HCV. Furthermore, there is a need for methods for modulating the activity of HCV-serine proteases, particularly the HCV NS3/NS4a serine protease, using the compounds provided herein.

In one aspect, the invention provides compounds of Formula I:

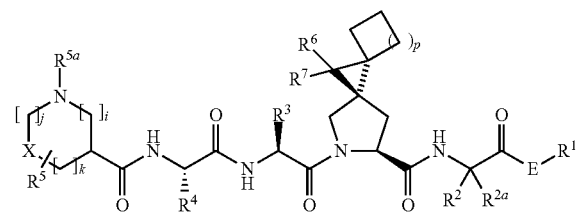

and pharmaceutically acceptable salts and stereoisomers thereof.

Compounds of Formula I possess excellent solubility in acidic or physiologic pH aqueous solutions (e.g., aqueous solutions having a pH of between about 1 and about 7.5). Certain compounds of Formula I discussed infra are soluble in acidic aqueous solutions (pH about 1) at concentrations in excess of about 100 micromolar or in excess of about 500 micromolar. Certain other compounds of Formula I discussed infra are soluble are in physiologic pH (e.g., pH of about 6.8) at concentrations in excess of about 10 micromolar, in excess of about 50 micromolar, in excess of about 100 micromolar or in excess of about 250 micromolar.

Certain compounds of Formula I provide superior pharmacokinetic profiles compared to prior compounds. In particular, certain compounds of Formula I offer oral bioavailability, as measured by the procedure of Example 15, in excess of about 20%, in excess of about 25%, in excess of about 30%, or in excess of about 40%.

In one embodiment, the invention provides a method of treating an HCV-associated disorder comprising administering to a subject in need thereof a pharmaceutically acceptable amount of a compound of the invention, such that the HCV-associated disorder is treated.

In another embodiment, the invention provides a method of treating an HIV infection comprising administering to a subject in need thereof a pharmaceutically acceptable amount of a compound of the invention.

In still another embodiment, the invention provides a method of treating, inhibiting or preventing the activity of HCV in a subject in need thereof, comprising administering to the subject a pharmaceutically acceptable amount of a compound of the invention. In one embodiment, the compounds of the invention inhibit the activity of the NS2 protease, the NS3 protease, the NS3 helicase, the NS5a protein, and/or the NS5b polymerase. In another embodiment, the interaction between the NS3 protease and NS4A cofactor is disrupted. In yet another embodiment, the compounds of the invention prevent or alter the severing of one or more of the NS4A-NS4B, NS4B-NS5A and NS5A-NS5B junctions of the HCV. In another embodiment, the invention provides a method of inhibiting the activity of a serine protease, comprising the step of contacting said serine protease with a compound of the invention. In another embodiment, the invention provides a method of treating, inhibiting or preventing the activity of HCV in a subject in need thereof, comprising administering to the subject a pharmaceutically acceptable amount of a compound of the invention, wherein the compound interacts with any target in the HCV life cycle. In one embodiment, the target of the HCV life cycle is selected from the group consisting of NS2 protease, NS3 protease, NS3 helicase, NS5a protein and NS5b polymerase.

In another embodiment, the invention provides a method of decreasing the HCV RNA load in a subject in need thereof comprising administering to the subject a pharmaceutically acceptable amount of a compound of the invention.

In another embodiment, the compounds of the invention exhibit HCV protease activity. In one embodiment, the compounds are an HCV NS3-4A protease inhibitor.

In another embodiment, the invention provides a method of treating an HCV-associated disorder in a subject, comprising administering to a subject in need thereof a pharmaceutically acceptable amount of a compound of the invention, and a pharmaceutically acceptable carrier, such that the HCV-associated disorder is treated.

In still another embodiment, the invention provides a method of treating an HCV-associated disorder comprising administering to a subject in need thereof a pharmaceutically effective amount of a compound of the invention, in combination with a pharmaceutically effective amount of an additional HCV-modulating compound, such as interferon or derivatized interferon, or a cytochrome P450 monooxygenase inhibitor, such that the HCV-associated disorder is treated. In one embodiment, the additional HCV-modulating compound is selected from the group consisting of ITMN191, MK-7009, TMC 435350, Sch 503034 and VX-950.

In another embodiment, the invention provides a method of inhibiting hepatitis C virus replication in a cell, comprising contacting said cell with a compound of the invention.

In yet another embodiment, the invention provides a packaged HCV-associated disorder treatment, comprising an HCV-modulating compound of the invention, packaged with instructions for using an effective amount of the HCV-modulating compound to treat an HCV-associated disorder.

In certain embodiments, the HCV-associated disorder is selected from the group consisting of HCV infection, liver cirrhosis, chronic liver disease, hepatocellular carcinoma, cryoglobulinaemia, non-Hodgkin's lymphoma, and a suppressed innate intracellular immune response.

In another embodiment, the invention provides a method of treating HCV infection, liver cirrhosis, chronic liver disease, hepatocellular carcinoma, cryoglobulinaemia, non-Hodgkin's lymphoma, and/or a suppressed innate intracellular immune response in subject in need thereof comprising administering to the subject a pharmaceutically acceptable amount of a compound of the invention.

In one embodiment, the HCV to be treated is selected of any HCV genotype. In another embodiment, the HCV is selected from HCV genotype 1, 2 and/or 3.

In yet another embodiment, the invention provides methods of preparing a compound of Formula II:

II x is zero, one or two;

$Z^1$ and $Z^3$ are each independently selected $CR^8R^9$;

$Z^2$ is absent or is selected from the group consisting of O, S, $CR^8R^9$, or $NR^{10}$;

$R^6$, $R^7$, $R^{13}$ and $R^{14}$ are independently selected from the group consisting of hydrogen, $C_{1-6}$alkyl, or aryl; or $R^6$ and $R^7$ taken in combination form a three to six membered saturated three to seven membered carbocycle, which is optionally substituted by zero to three substituents;

$R^8$, $R^9$, $R^{11}$ and $R^{12}$ are independently selected from the group consisting of hydrogen, halogen, $C_{1-6}$alkyl, $C_{1-6}$alkoxy, halo$C_{1-6}$alkyl, halo$C_{1-6}$alkoxy, hydroxy$C_{1-6}$alkyl, $C_{1-6}$alkoxy$C_{1-6}$alkyl, or aryl;

$R^{10}$ is selected from hydrogen, $C_{1-6}$alkyl, halo$C_{1-6}$alkyl, hydroxy$C_{1-6}$alkyl, $C_{1-6}$alkoxy$C_{1-6}$alkyl, aryl and aralkyl;

$R^{15}$ is hydrogen, $C_{1-10}$alkyl, $C_{3-10}$cycloalkyl, aryl, or heteroaryl;

$R^{16}$ is $C_{1-10}$alkyl, $C_{3-10}$cycloalkyl, aryl, or heteroaryl; and $R_{17}$ is cyano, nitro, $C_{1-6}$alkylsulfonate, halo$C_{1-6}$alkylsulfonate, arylsulfonate, or halogen.

In certain other embodiments, the invention provides methods of preparing amino-alcohol compounds of Formula V by deprotection of compounds of Formula II prepared supra, wherein a compound of Formula V has the structure:

V

Other aspects of the invention are discussed infra.

DETAILED DESCRIPTION OF THE INVENTION

Figure 1:
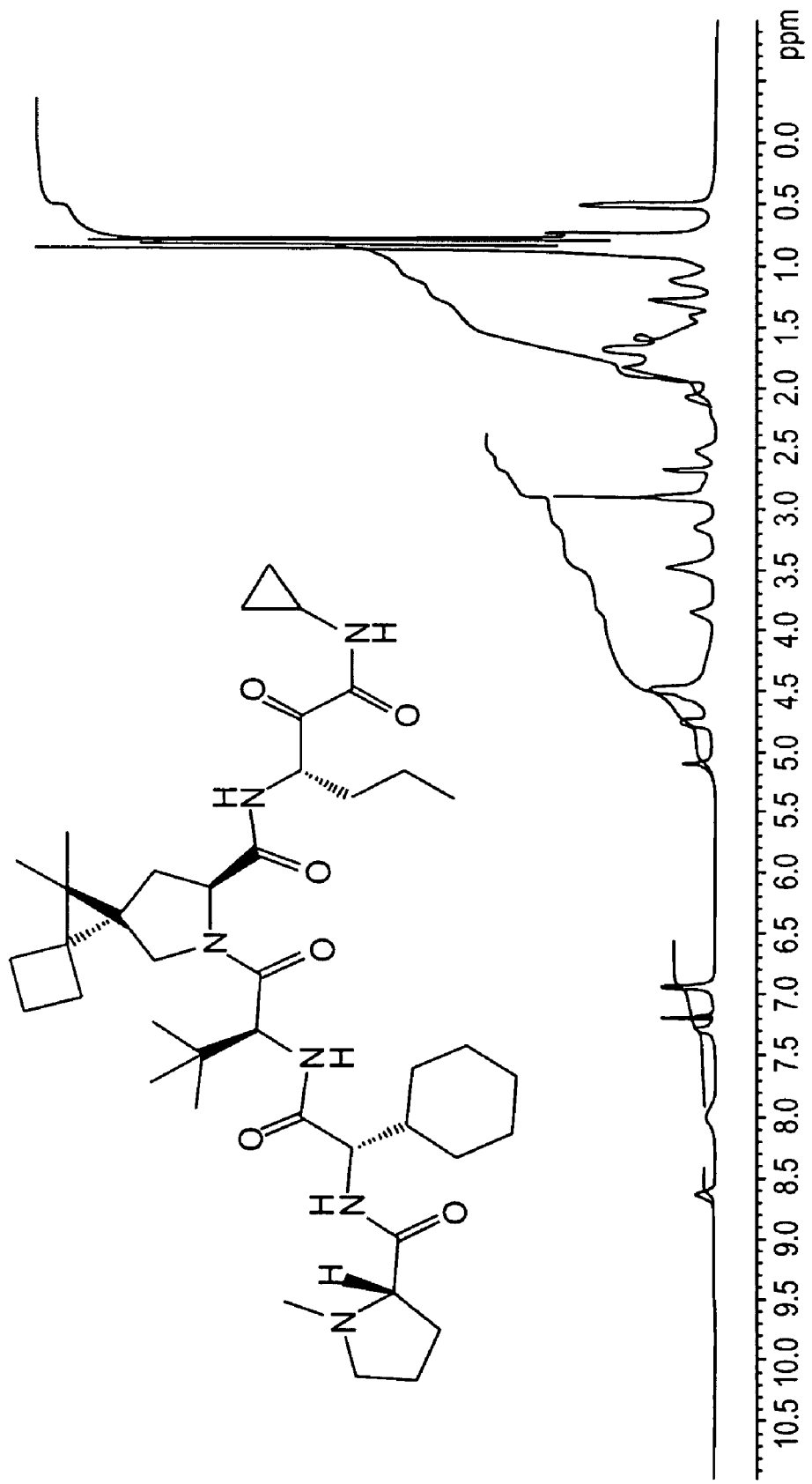
FIG. 1 is a proton NMR spectra of compound A-33 in $CDCl_3$.
Figure 2:
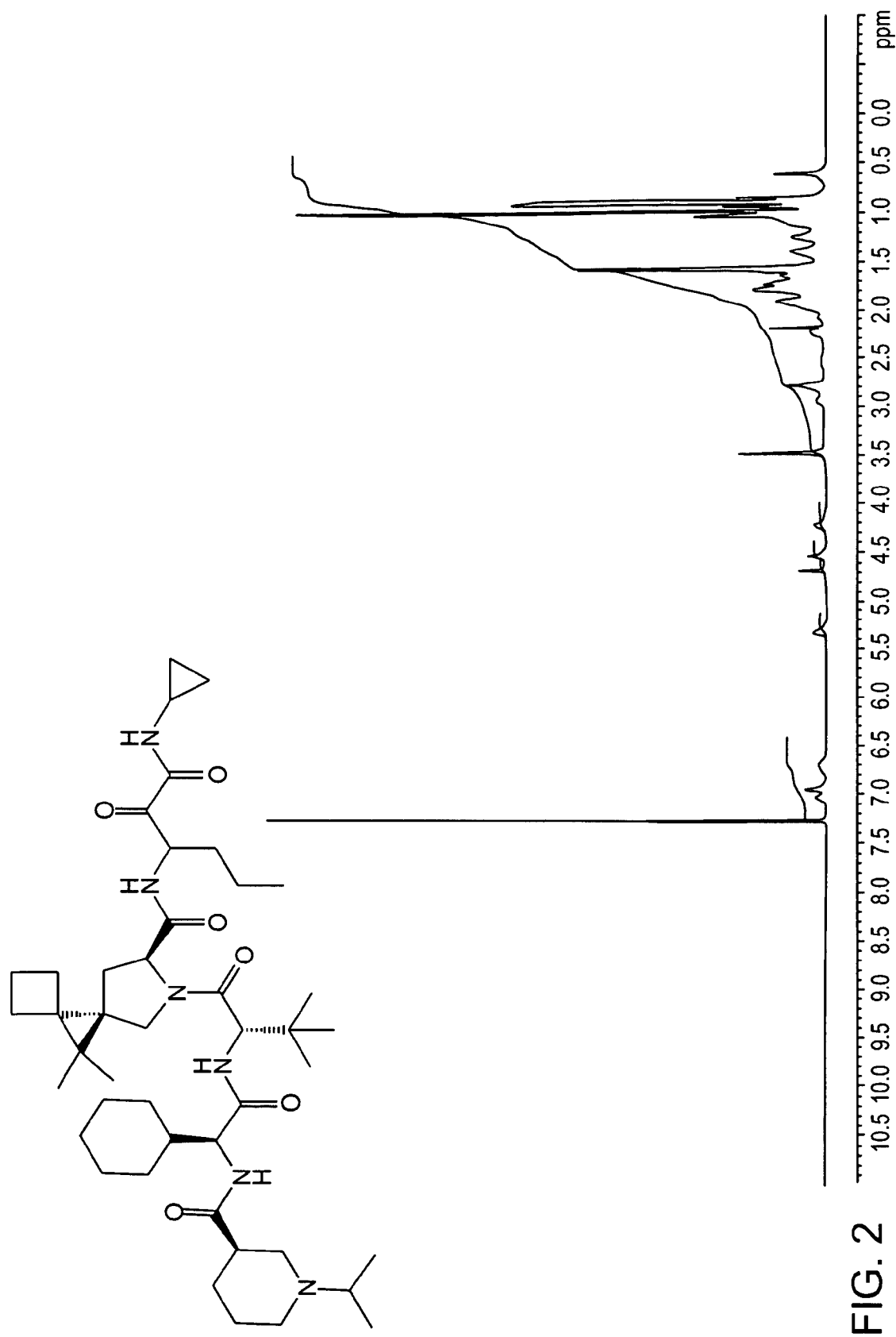
FIG. 2 is a proton NMR spectra of compound A-4 in $CDCl_3$.
Figure 3:
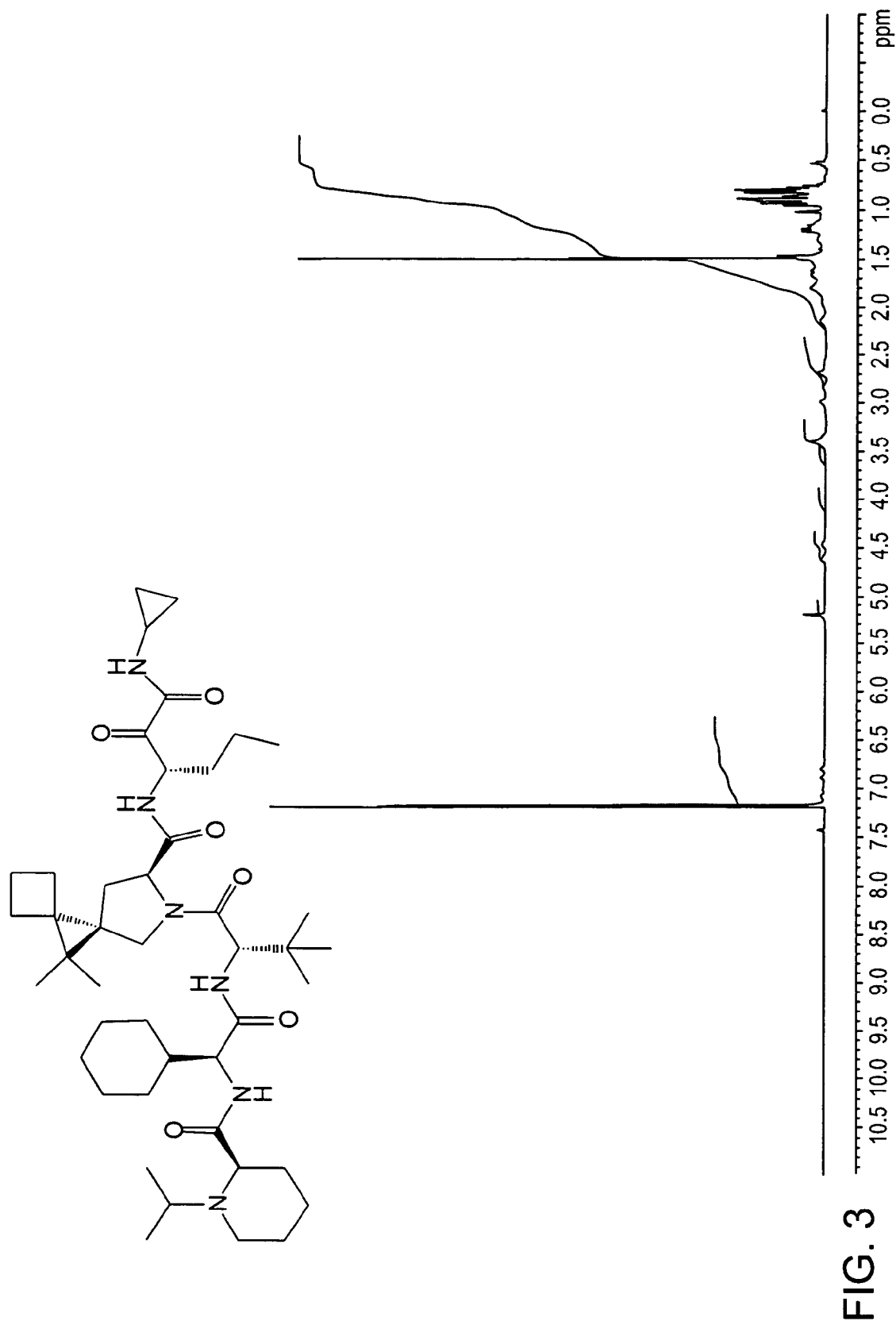
FIG. 3 is a proton NMR spectra of compound A-5 in $CDCl_3$.
Figure 4:
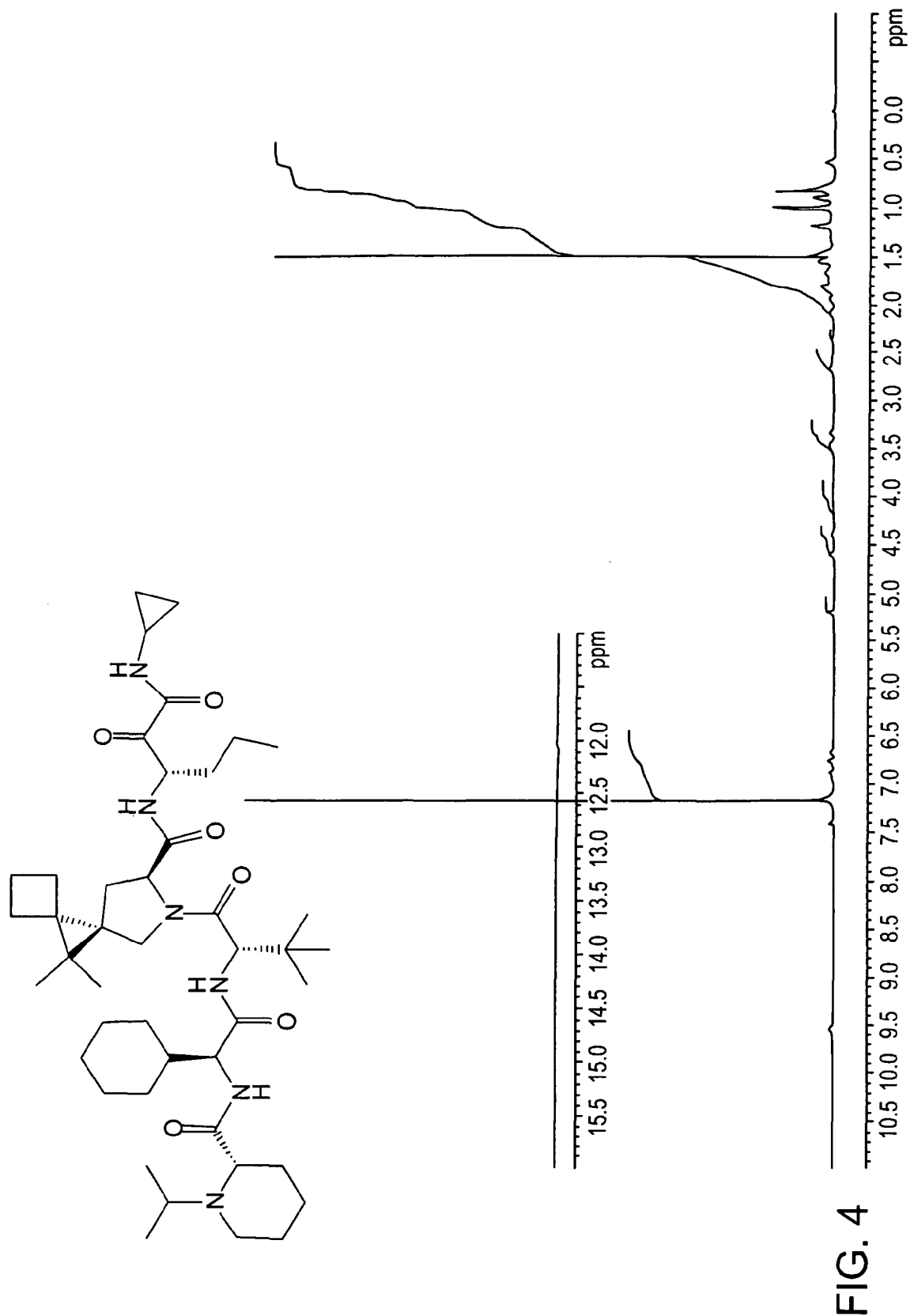
FIG. 4 is a proton NMR spectra of compound A-6 in $CDCl_3$.
Figure 5:
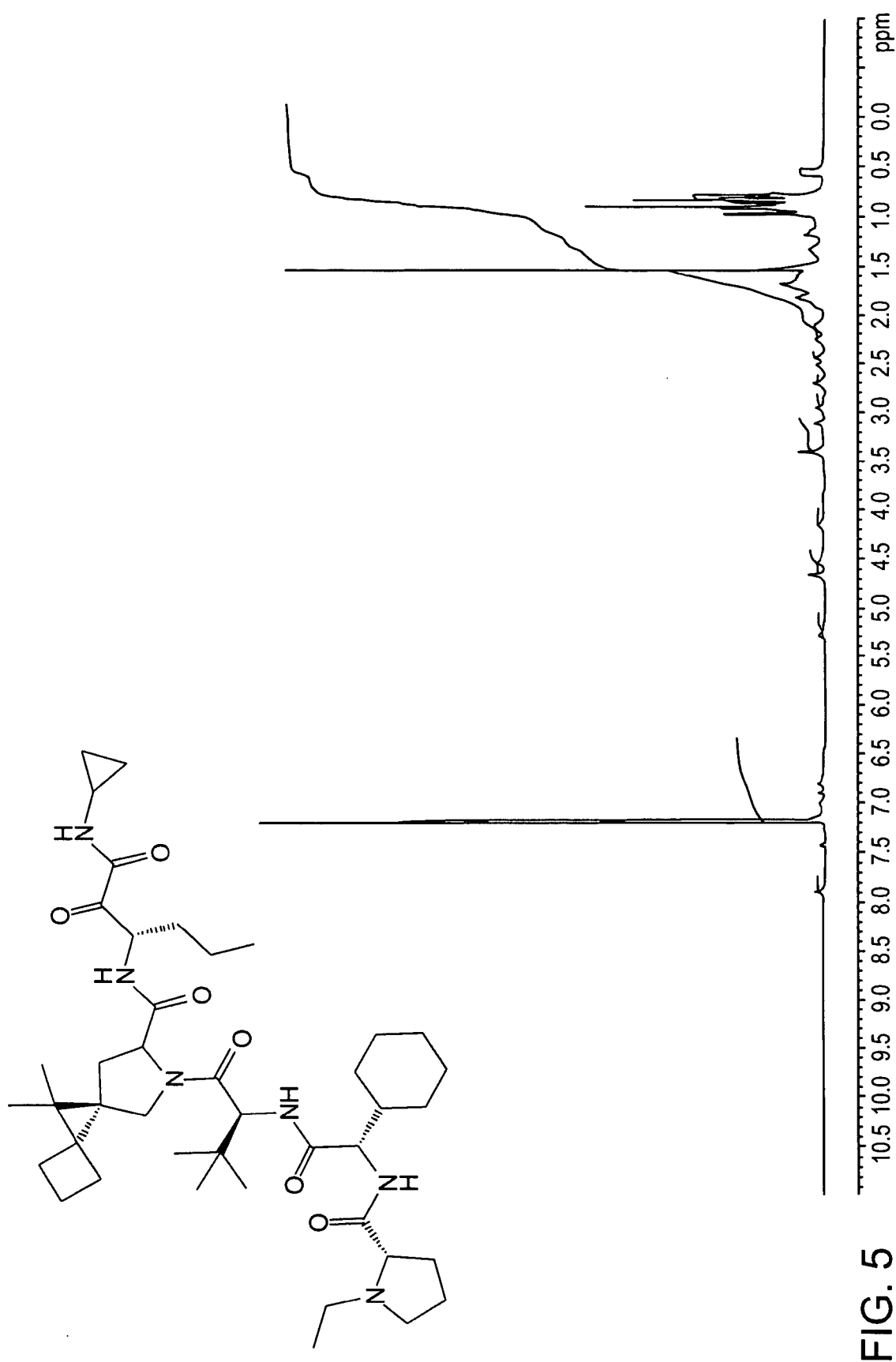
FIG. 5 is a proton NMR spectra of compound A-10 in CDCl$_3$.
Figure 6:
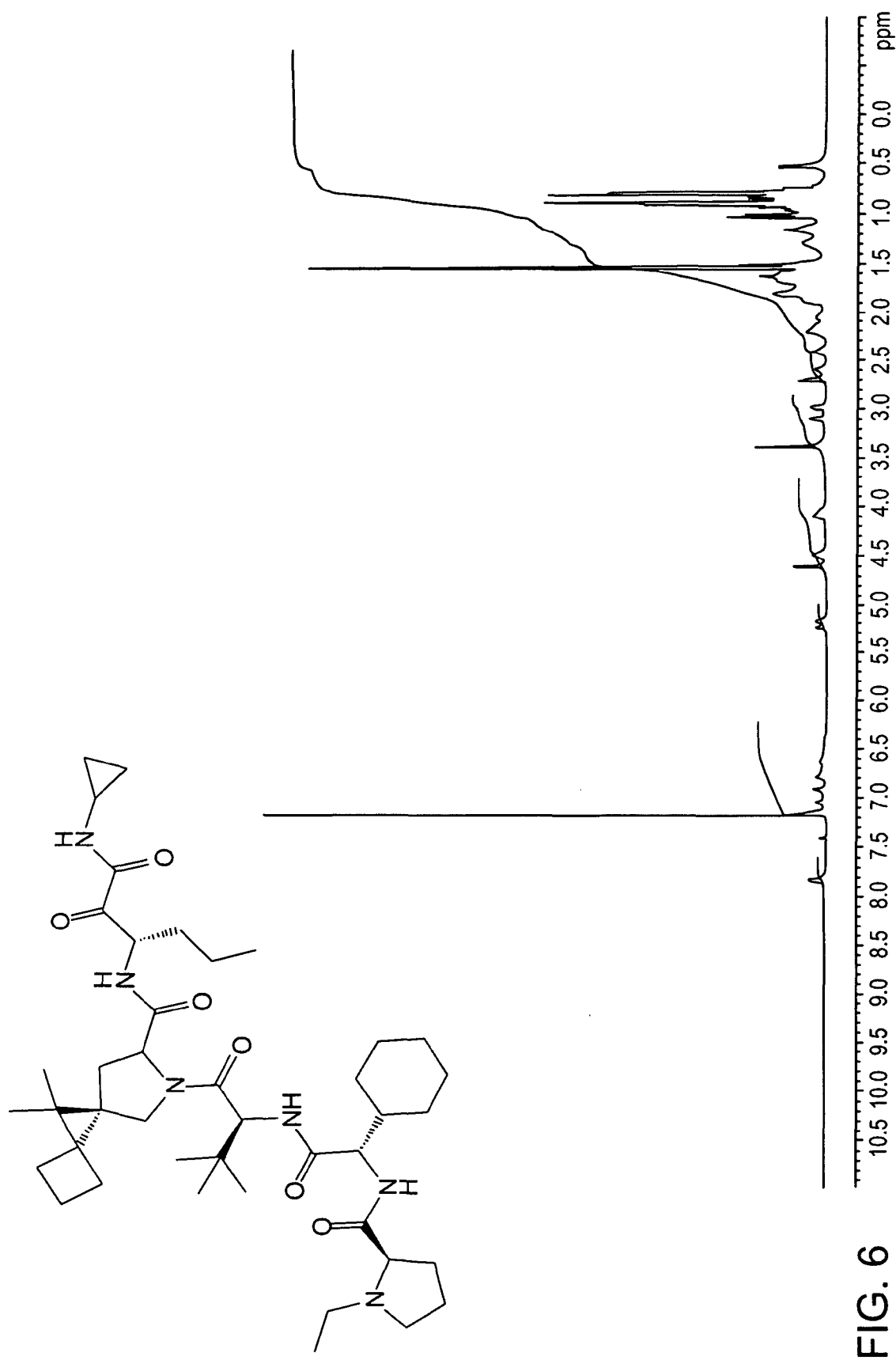
FIG. 6 is a proton NMR spectra of compound A-11 in CDCl$_3$.
Figure 7:
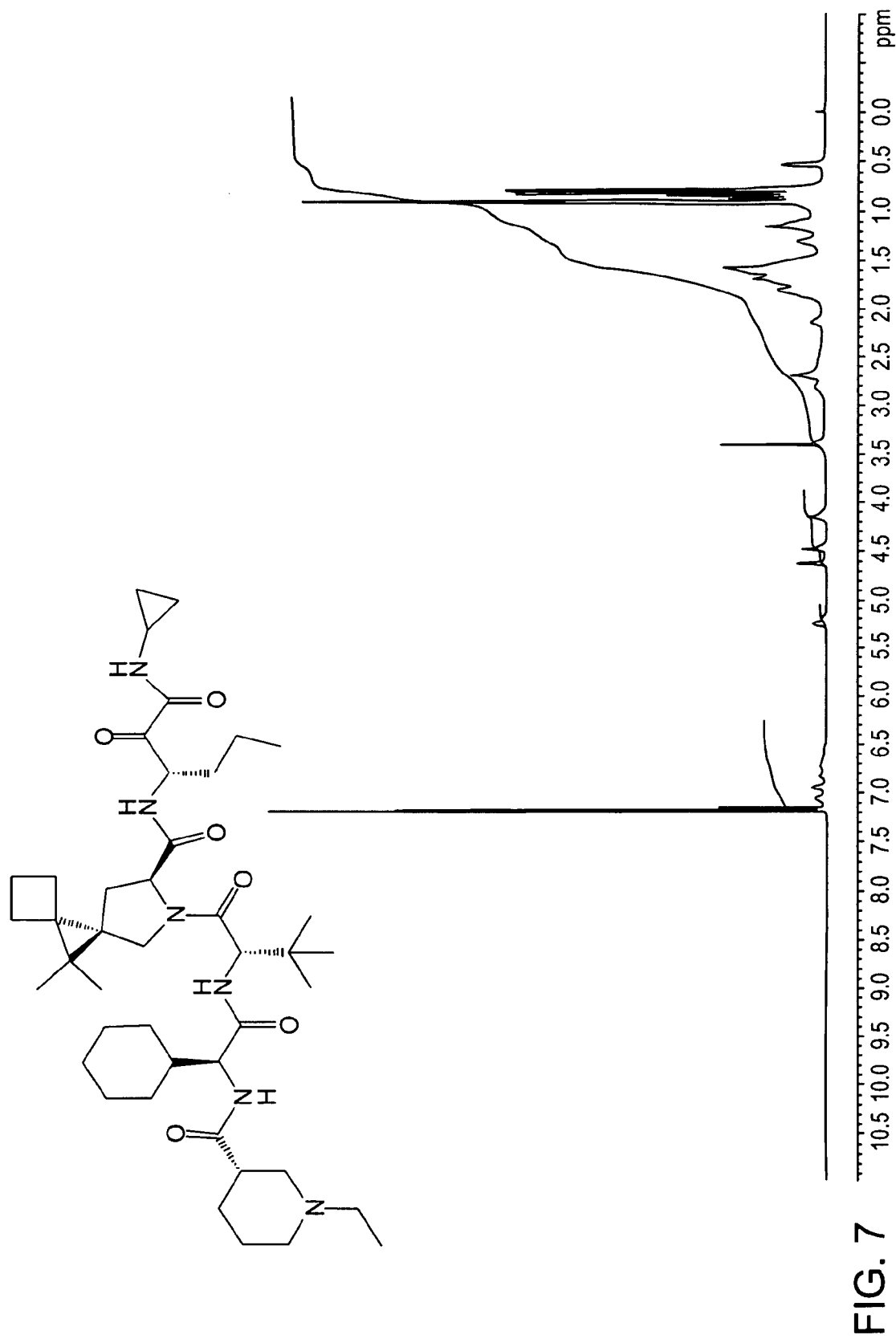
FIG. 7 is a proton NMR spectra of compound A-14 in CDCl$_3$.
Figure 8:
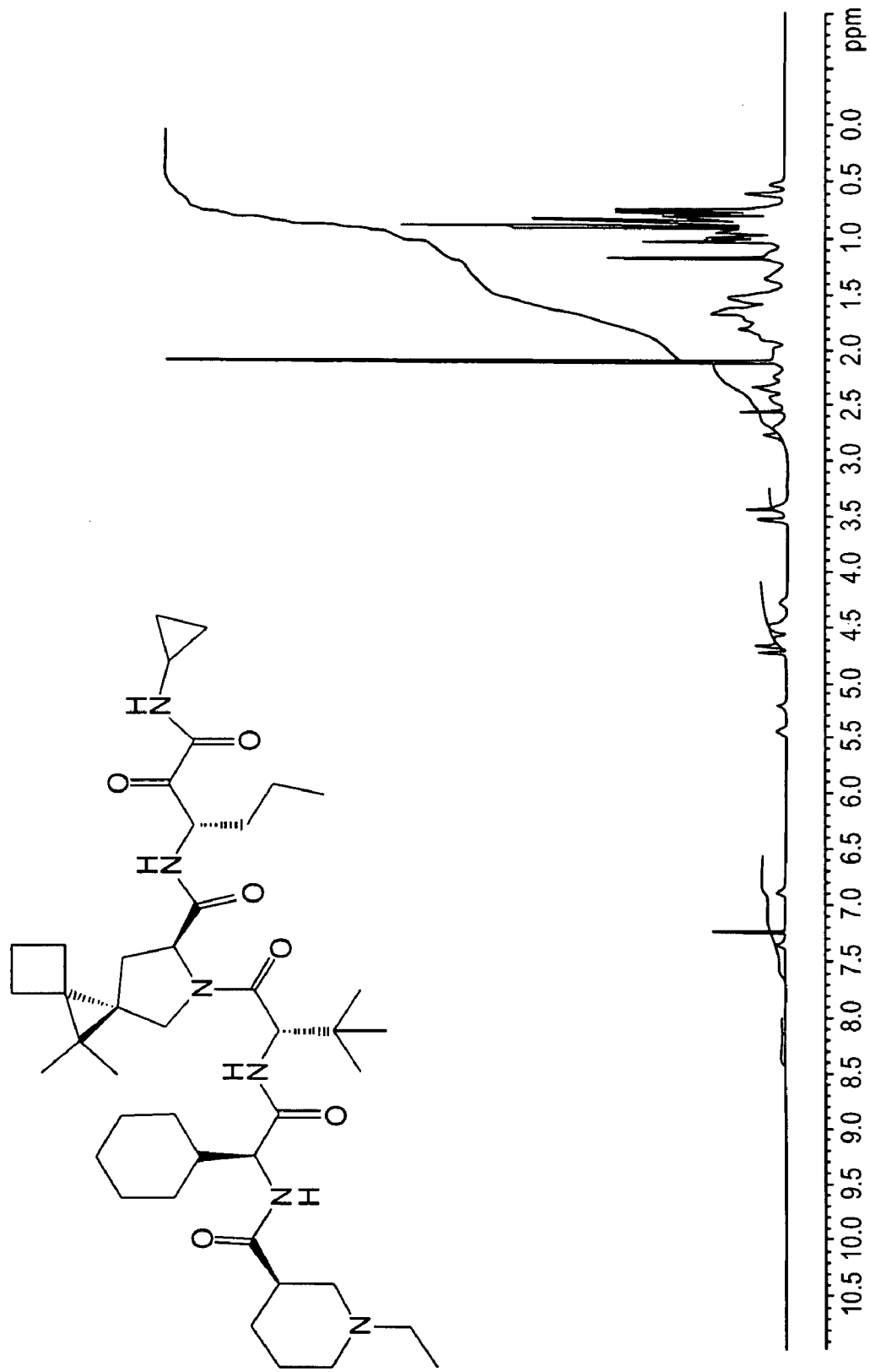
FIG. 8 is a proton NMR spectra of compound A-15 in CDCl$_3$.
Figure 9:
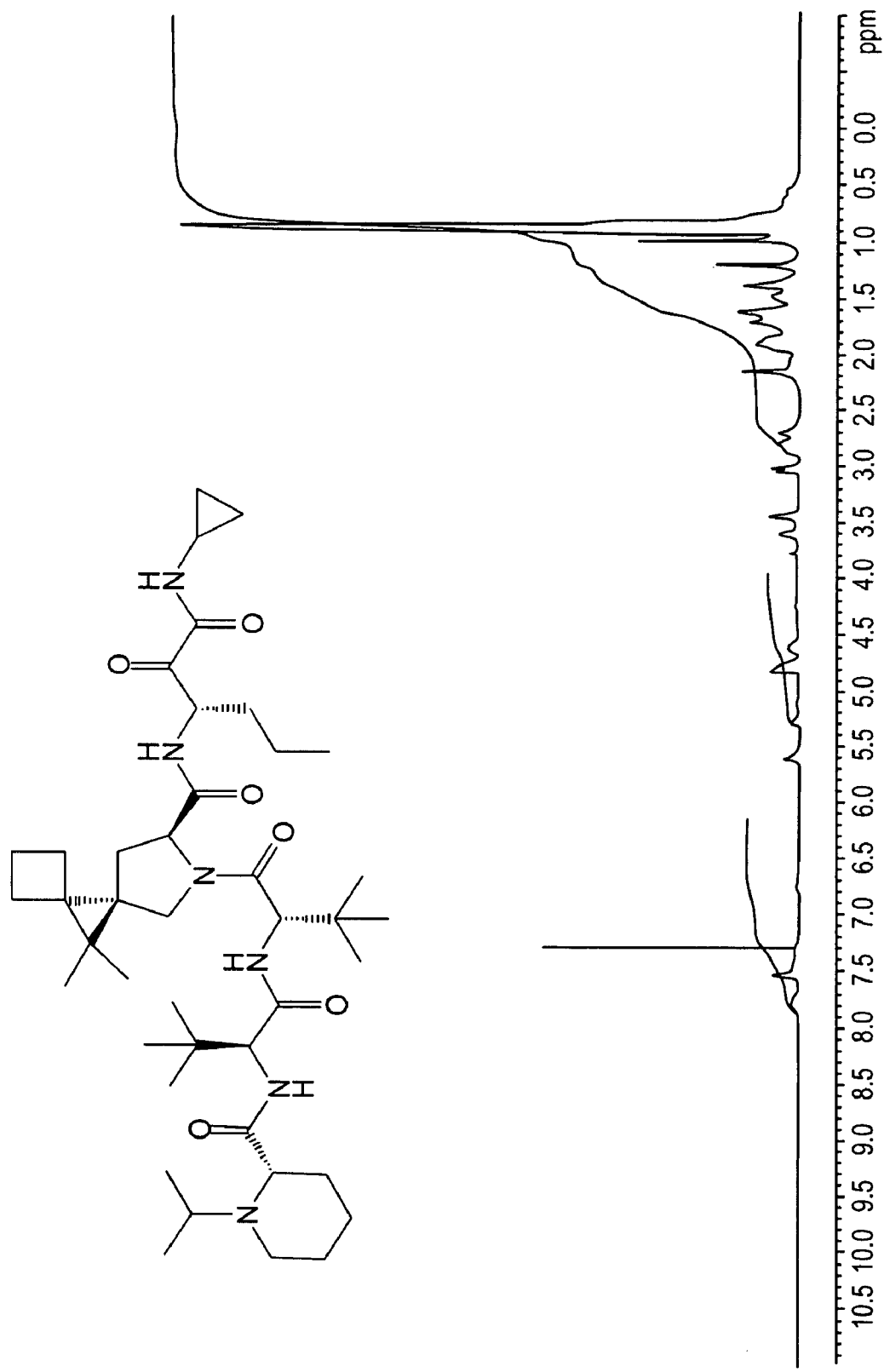
FIG. 9 is a proton NMR spectra of compound A-44 in CDCl$_3$.
Figure 10:
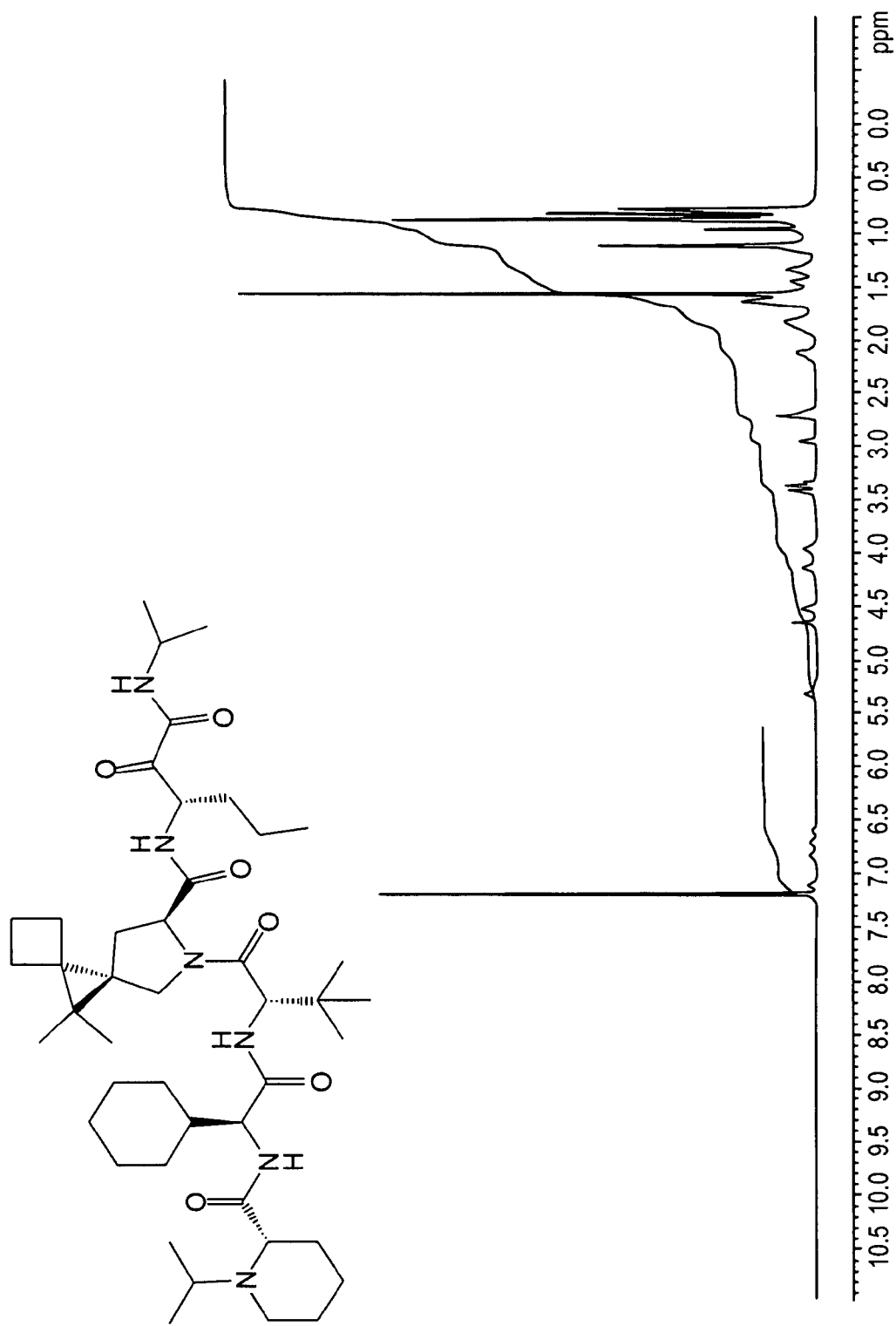
FIG. 10 is a proton NMR spectra of compound A-54 in CDCl$_3$.
Figure 11:
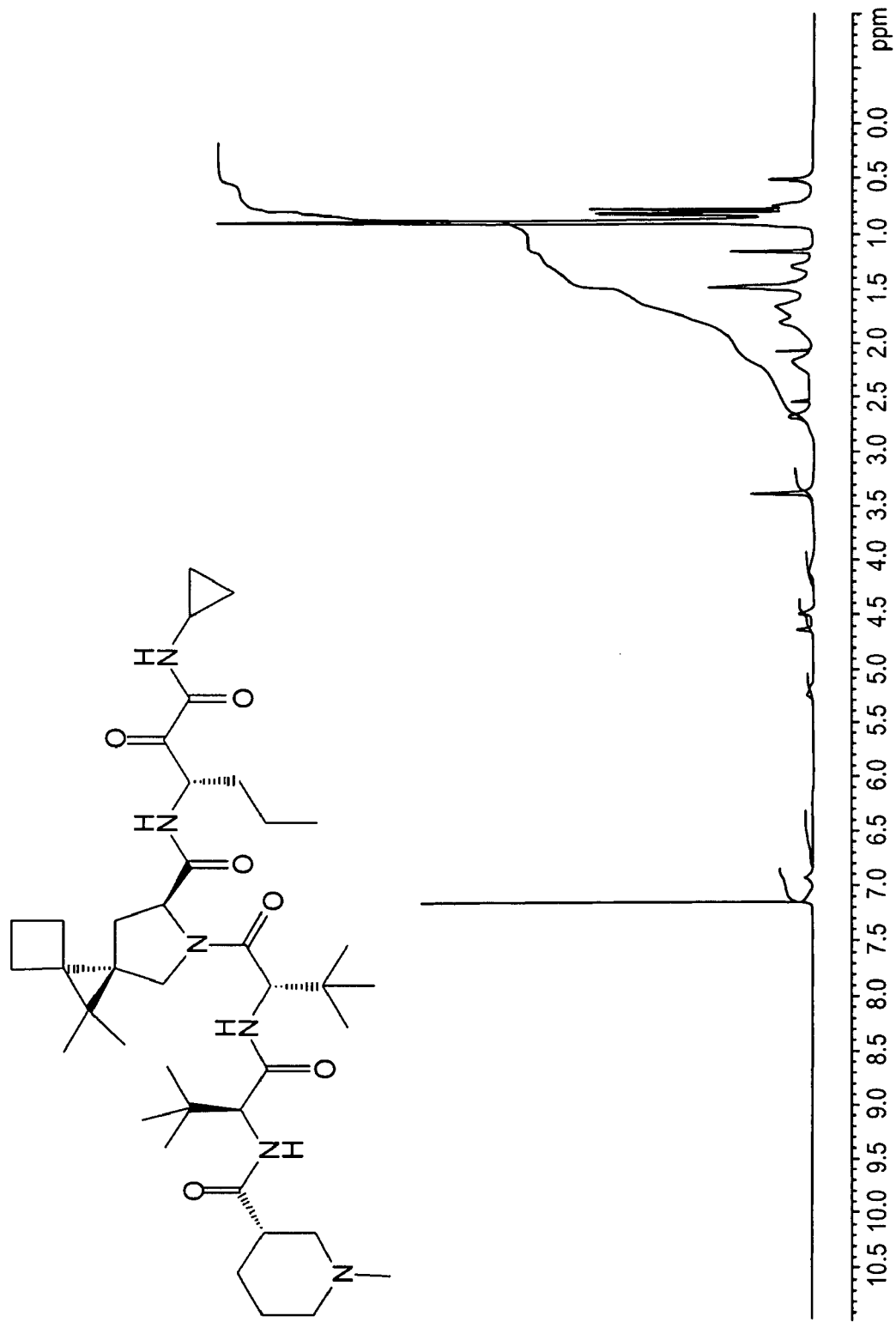
FIG. 11 is a proton NMR spectra of compound A-57 in CDCl$_3$.
Figure 12:
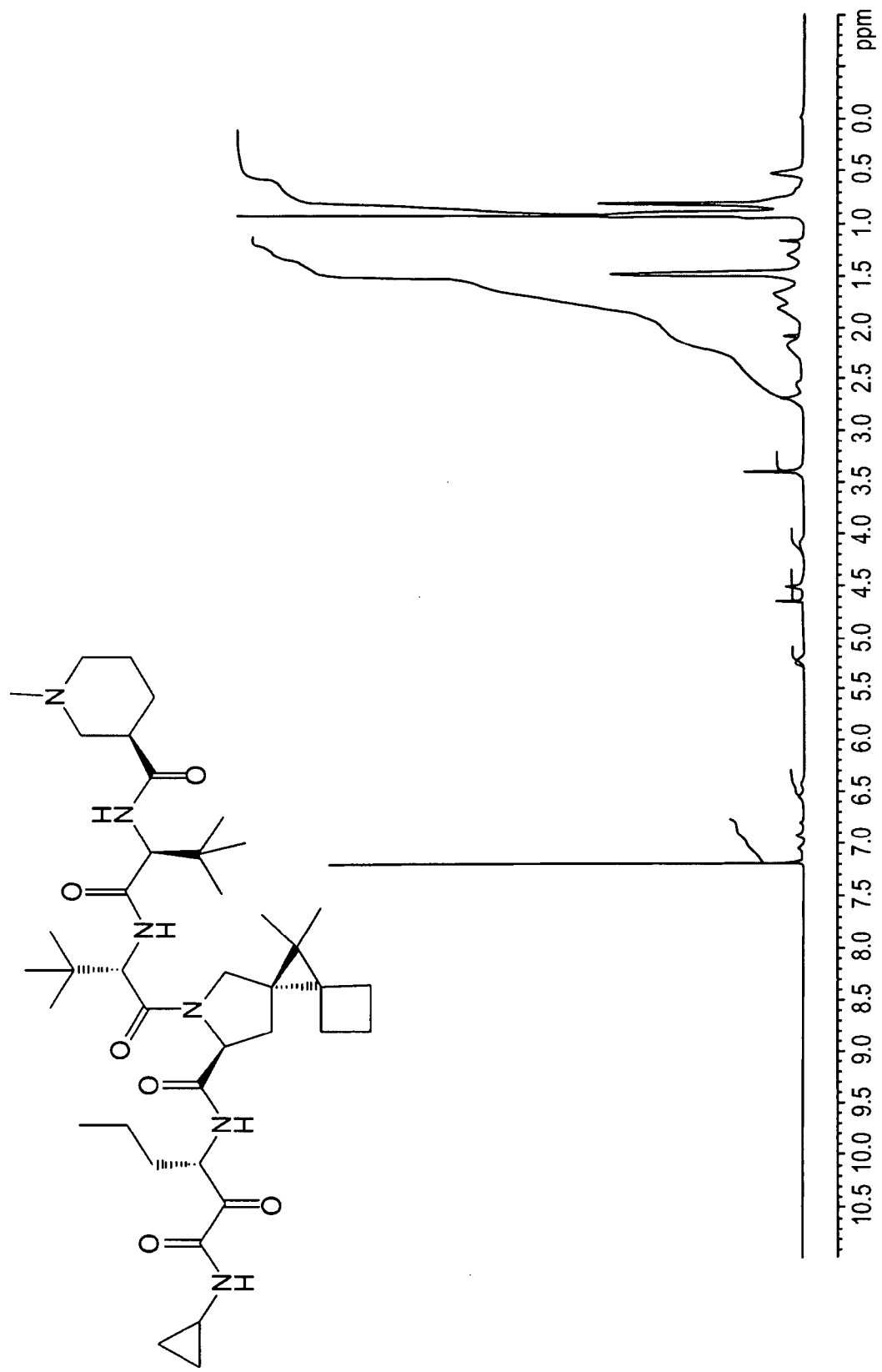
FIG. 12 is a proton NMR spectra of compound A-58 in CDCl$_3$.
Figure 13:
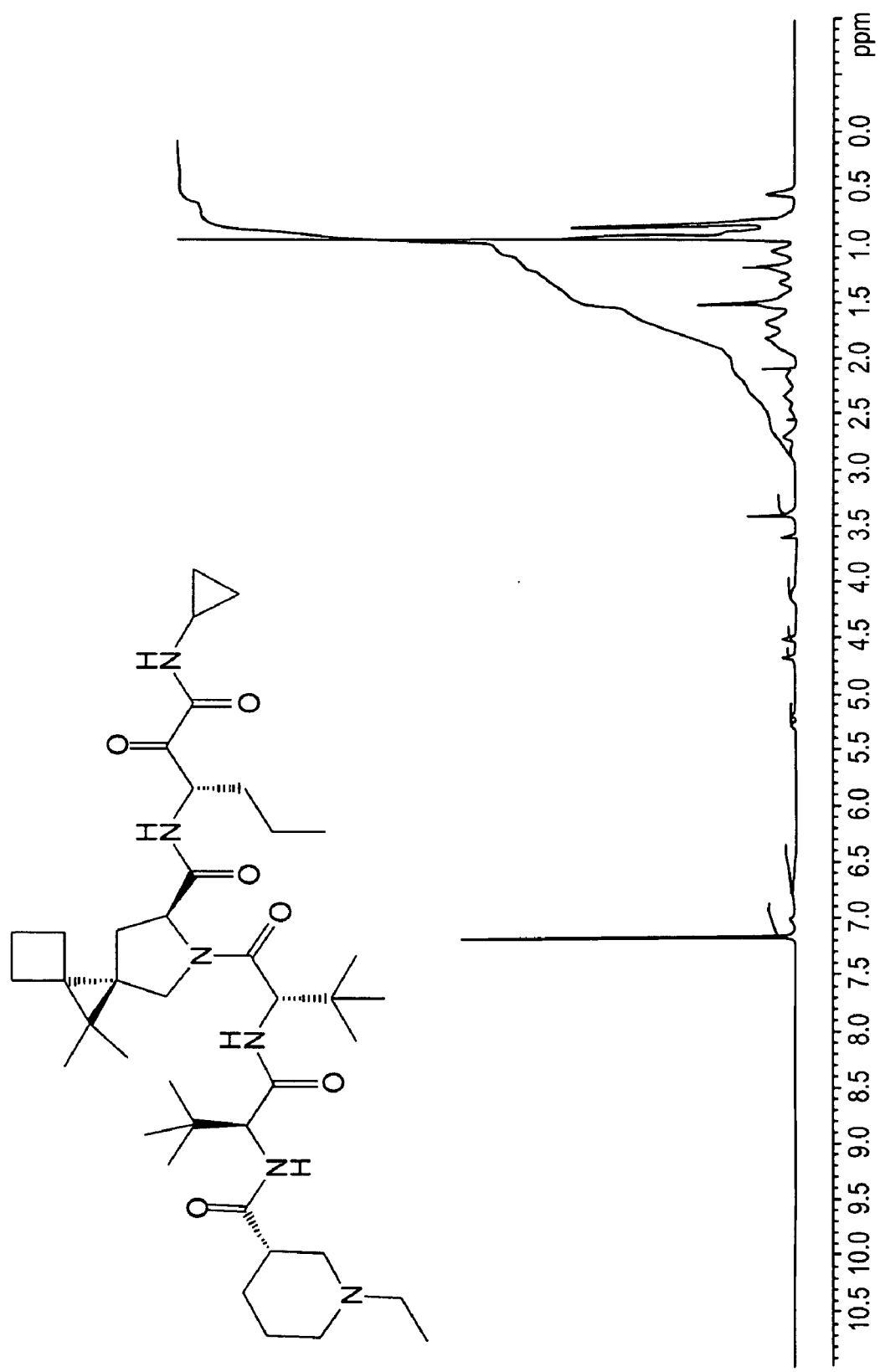
FIG. 13 is a proton NMR spectra of compound A-59 in CDCl$_3$.
Figure 14:
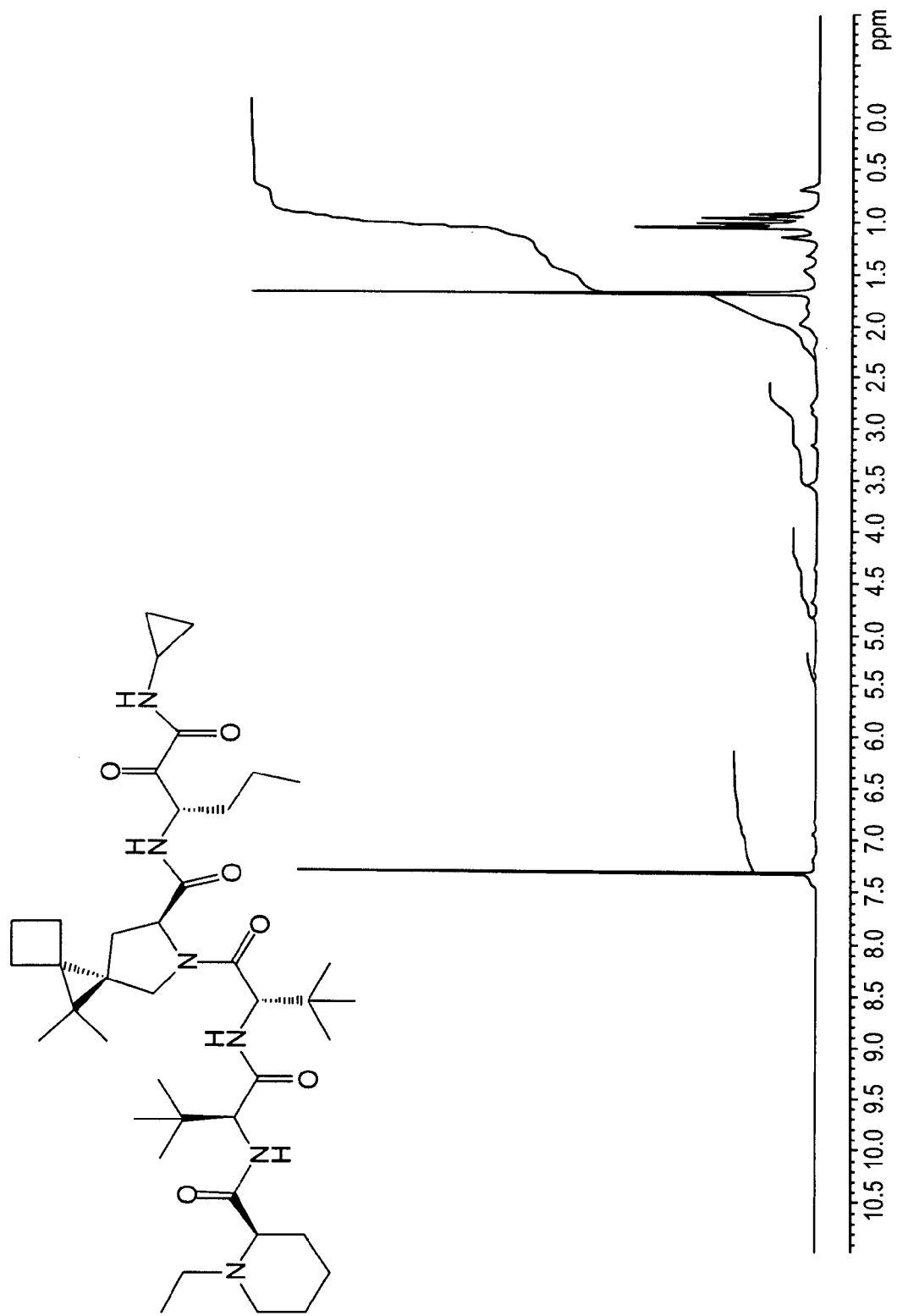
FIG. 14 is a proton NMR spectra of compound A-72 in CDCl$_3$.
Figure 15:
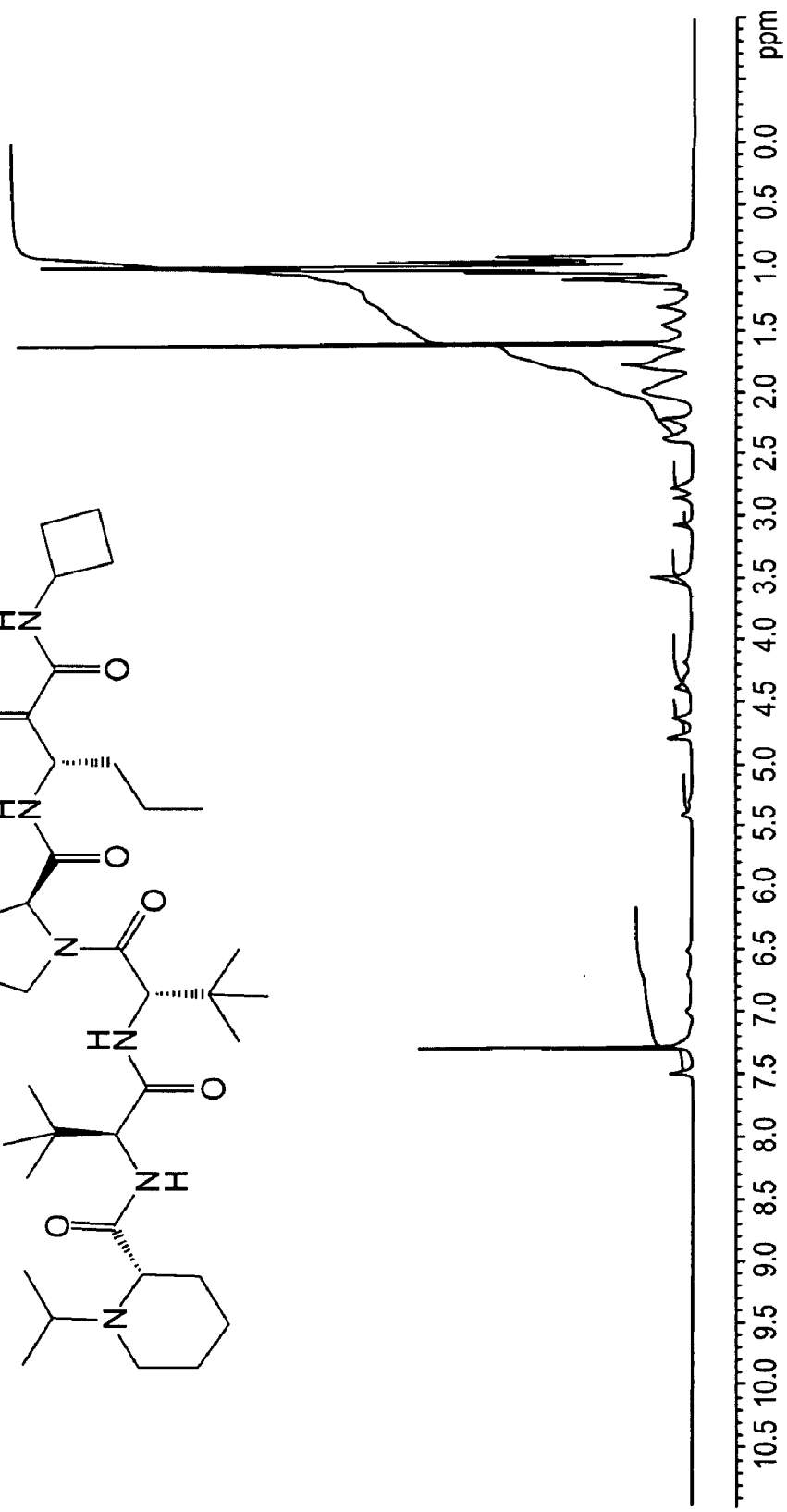
FIG. 15 is a proton NMR spectra of compound A-82 in CDCl$_3$.
Figure 16:
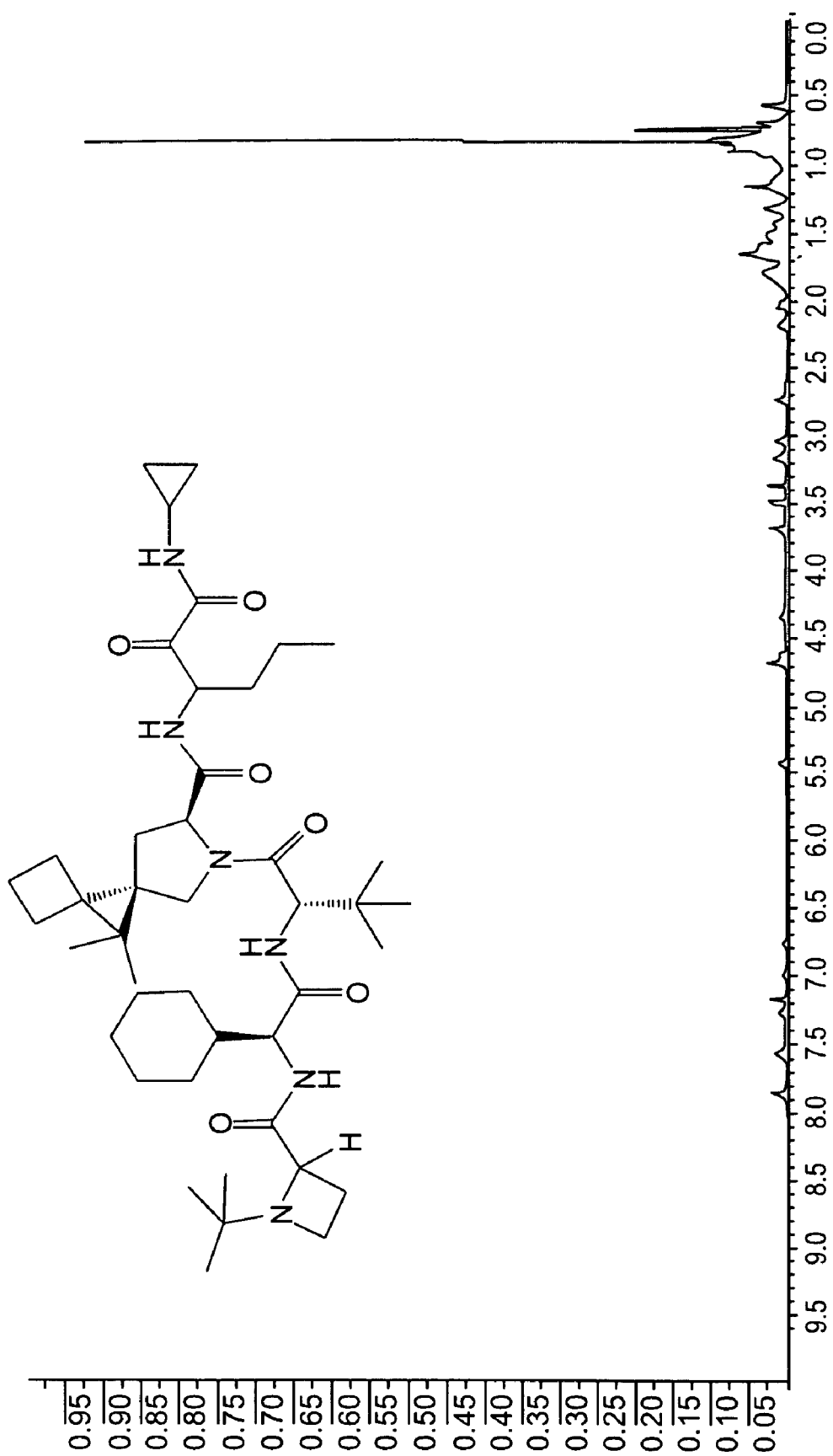
FIG. 16 is a proton NMR spectra of compound A-64 in CDCl$_3$.
Figure 17:
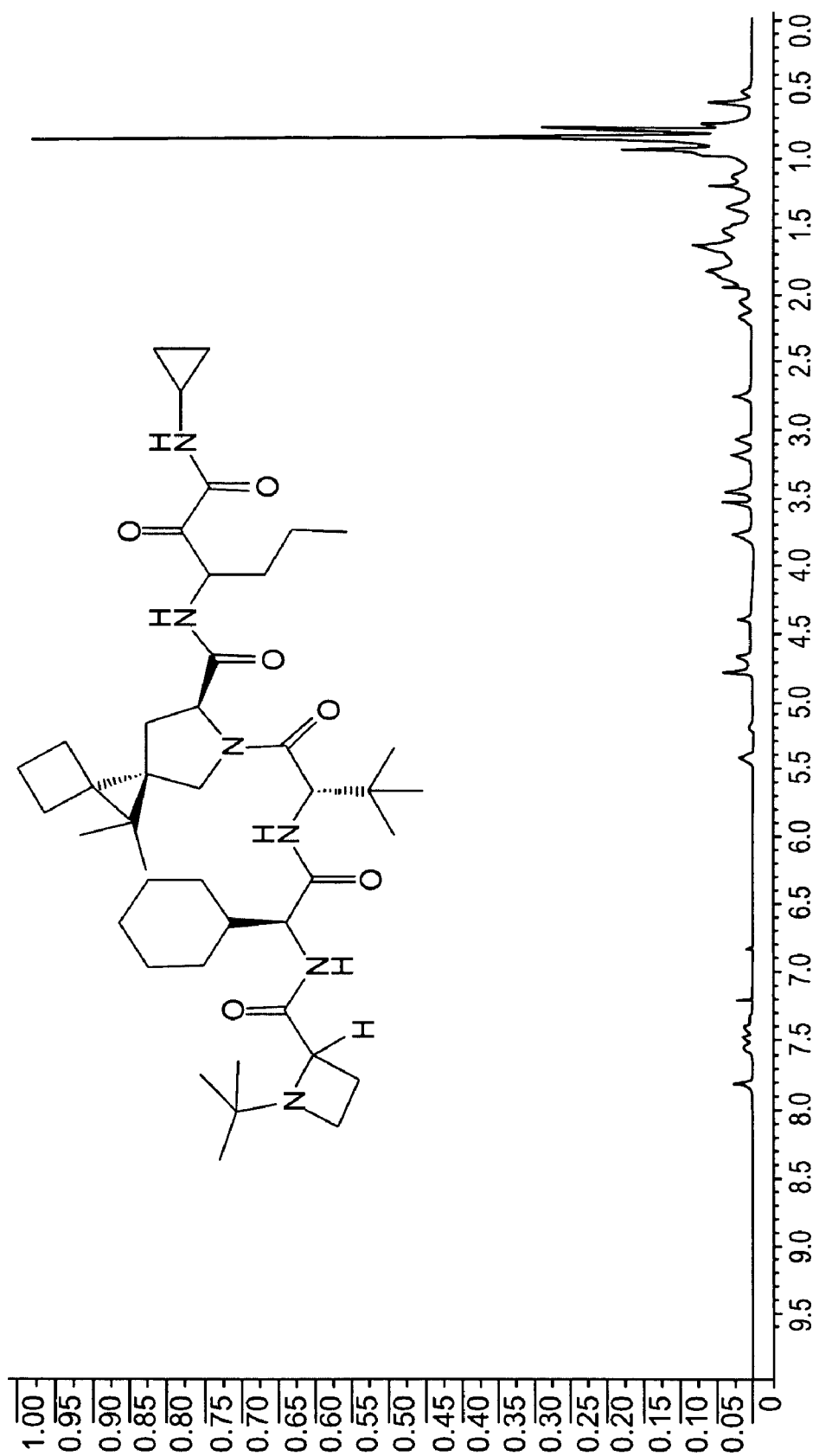
FIG. 17 is a proton NMR spectra of compound A-65 in CDCl$_3$.
Figure 18:
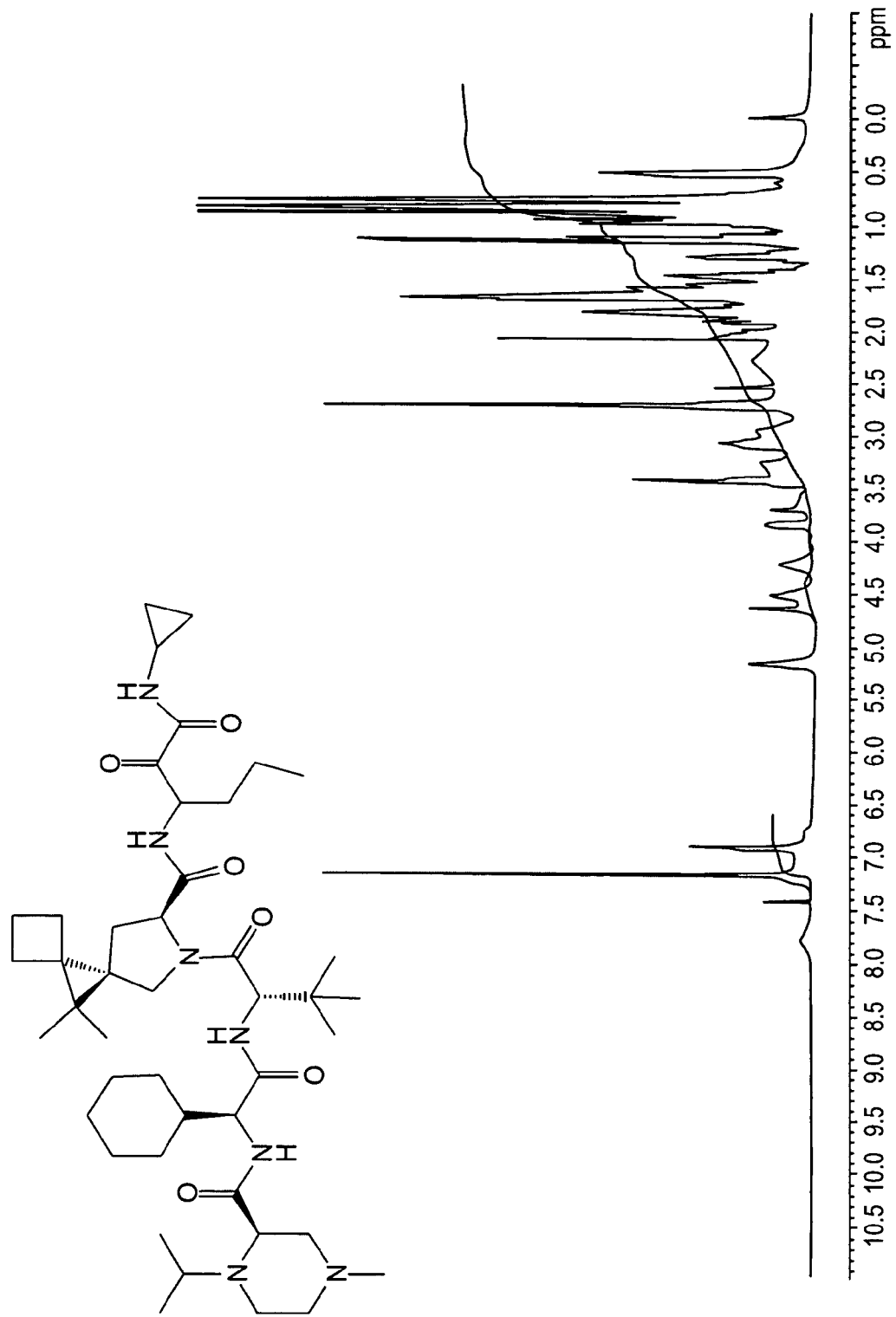
FIG. 18 is a proton NMR spectra of compound A-42 in CDCl$_3$.
Figure 19:
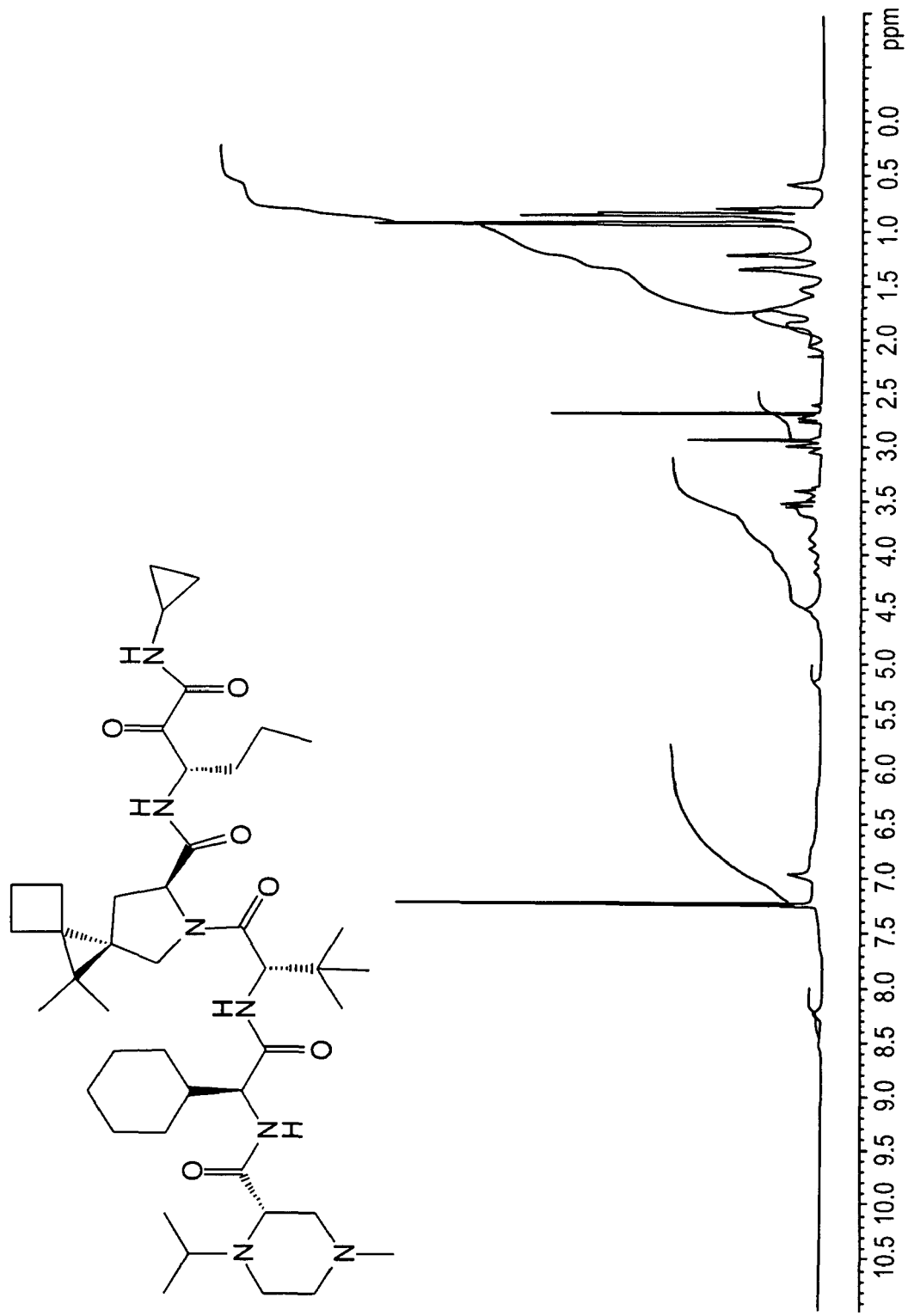
FIG. 19 is a proton NMR spectra of compound A-43 in CDCl$_3$.
Figure 20:
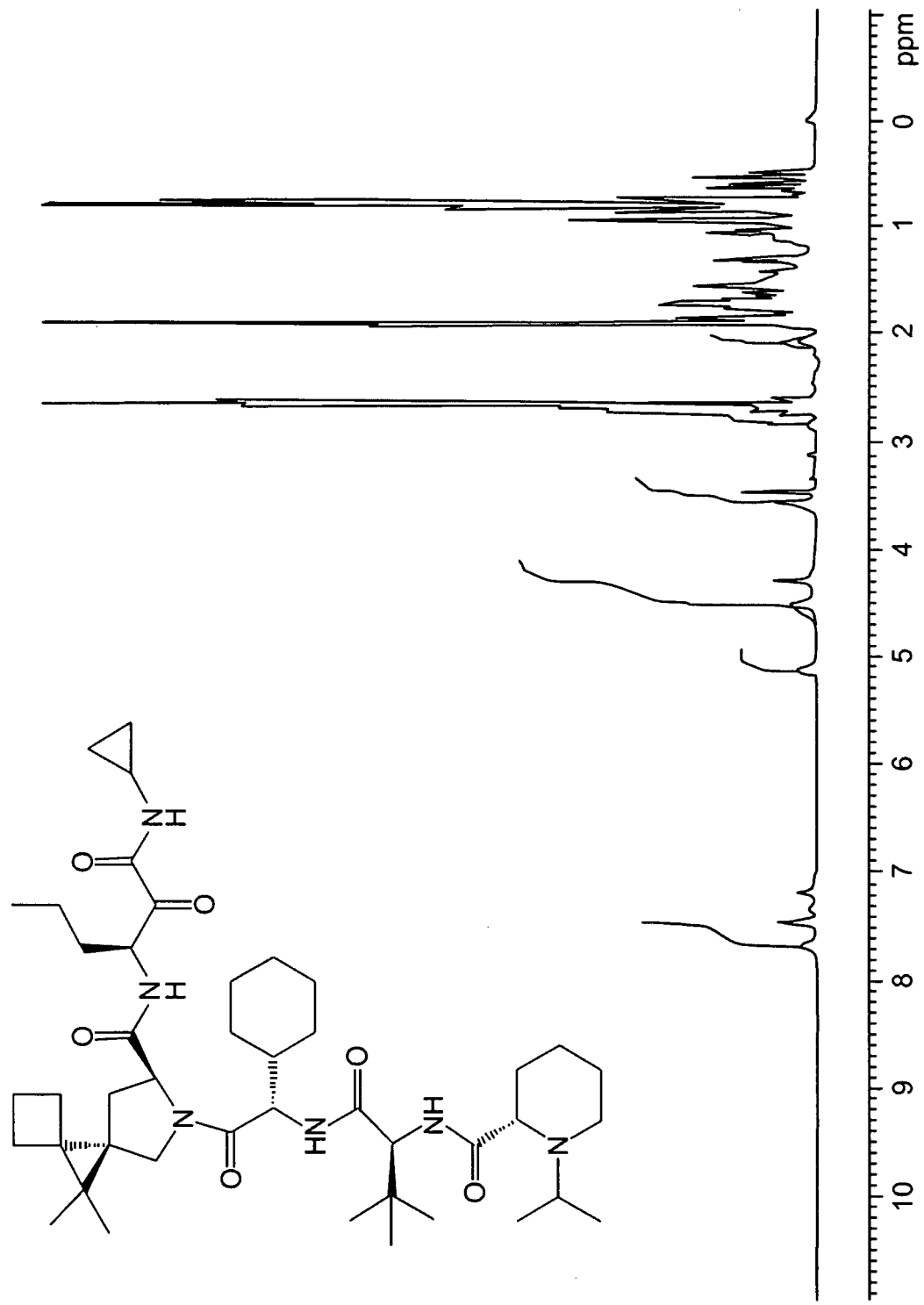
FIG. 20 is a proton NMR spectra of compound A-45 in acetone-d6.
Figure 21:
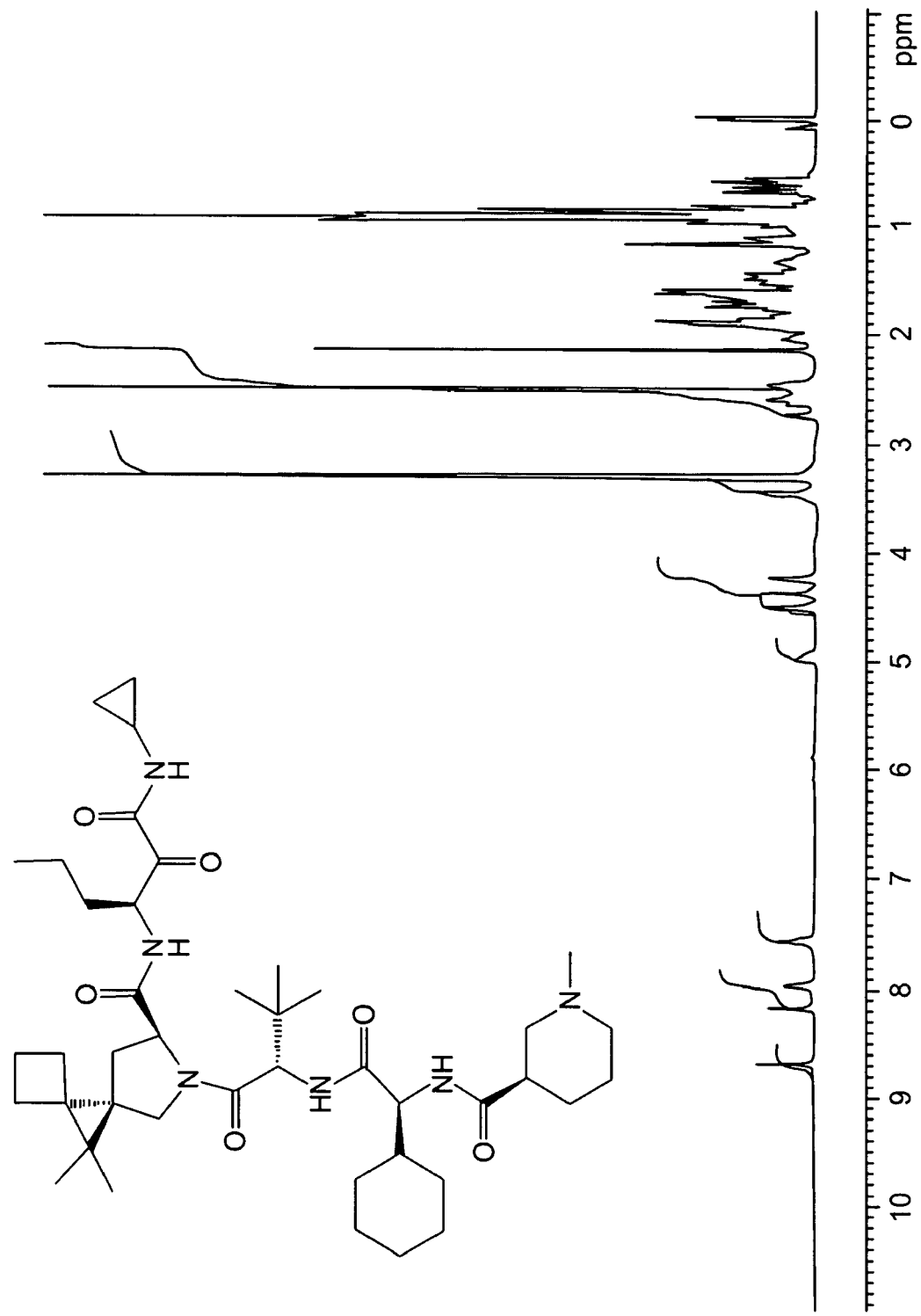
FIG. 21 is a proton NMR spectra of compound A-50 in DMSO-d6.
Figure 22:
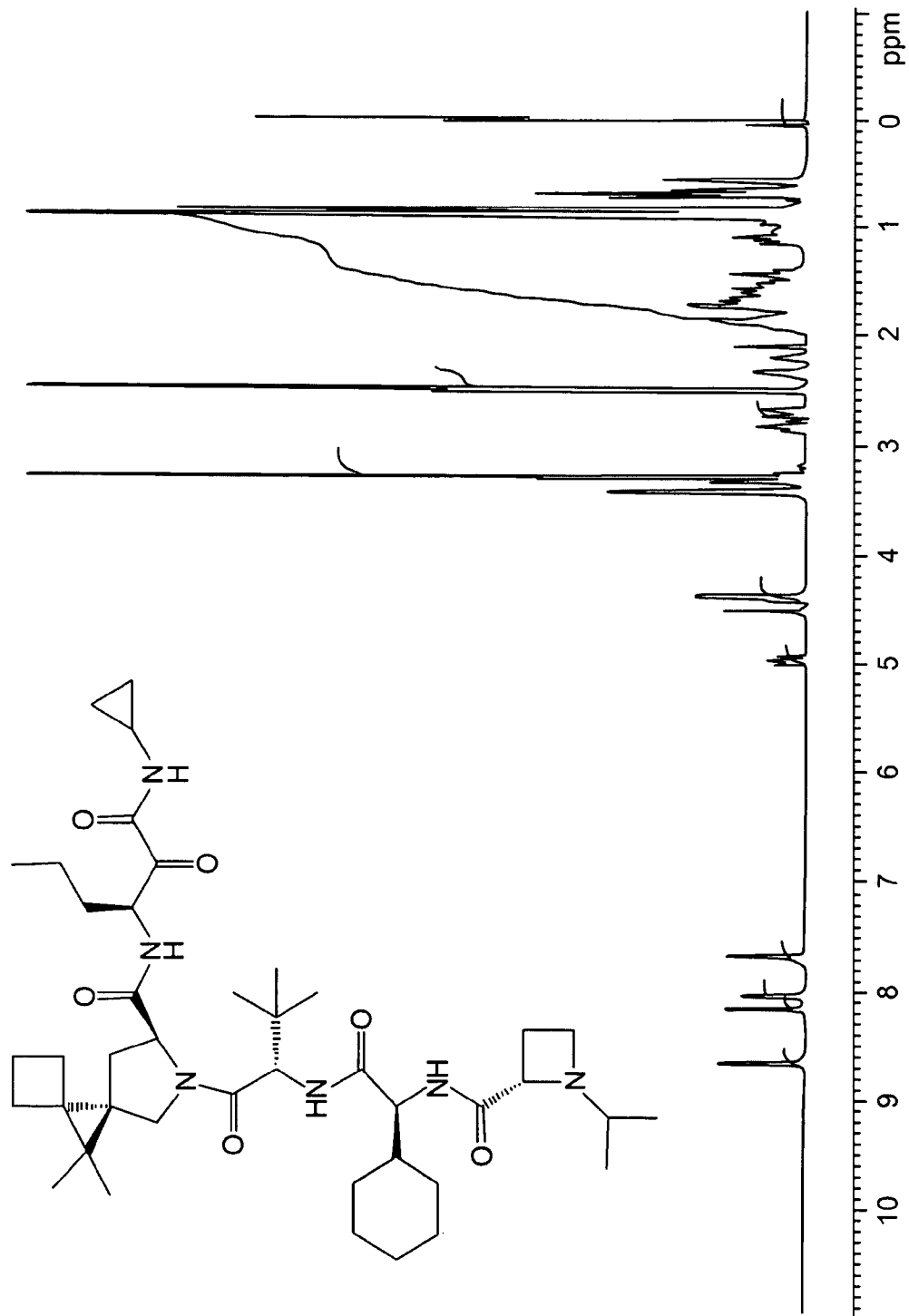
FIG. 22 is a proton NMR spectra of compound A-62 in DMSO-d6.
Figure 23:
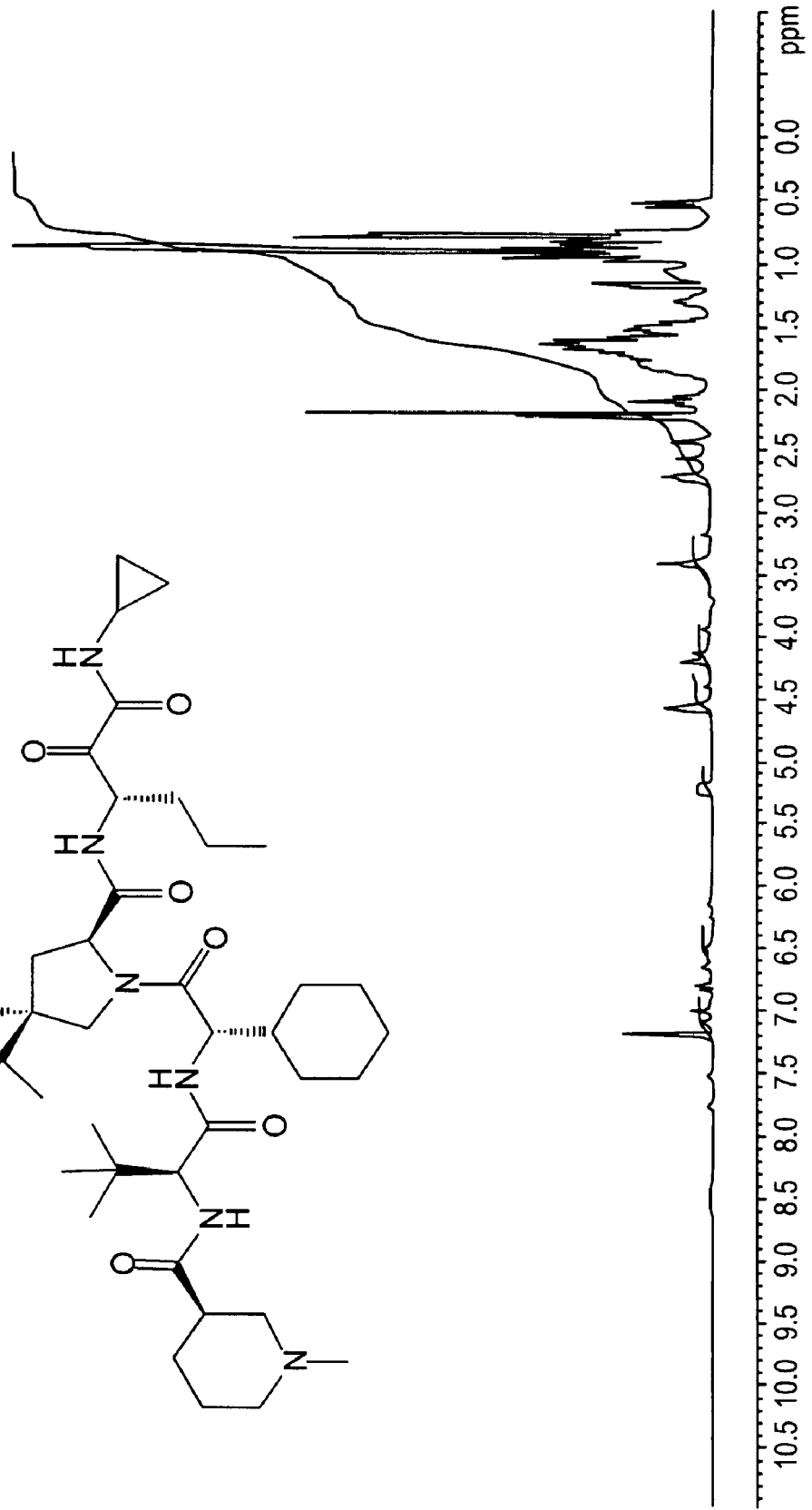
FIG. 23 is a proton NMR spectra of compound A-66 in CDCl$_3$.
Figure 24:
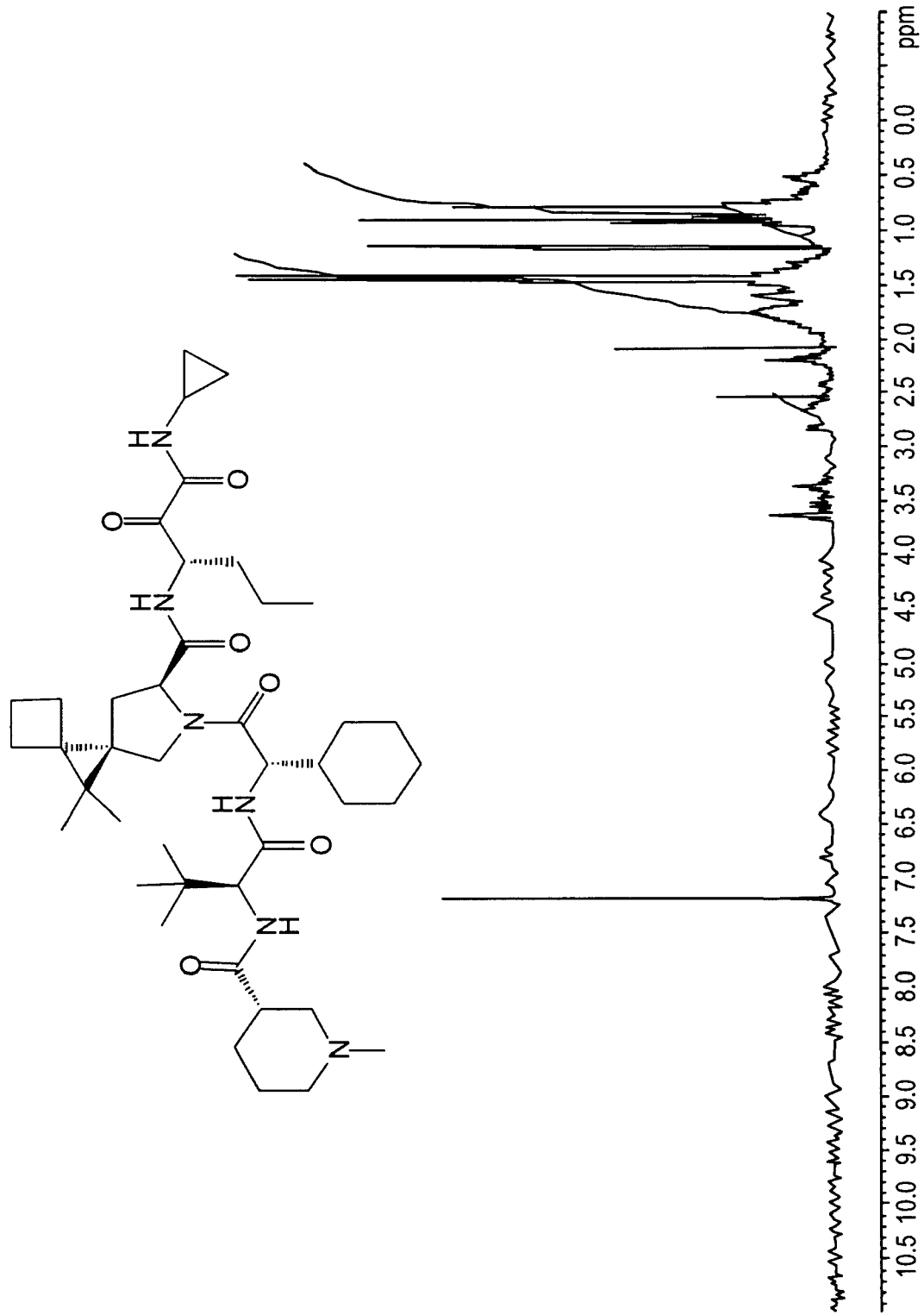
FIG. 24 is a proton NMR spectra of compound A-67 in CDCl$_3$.
Figure 25:
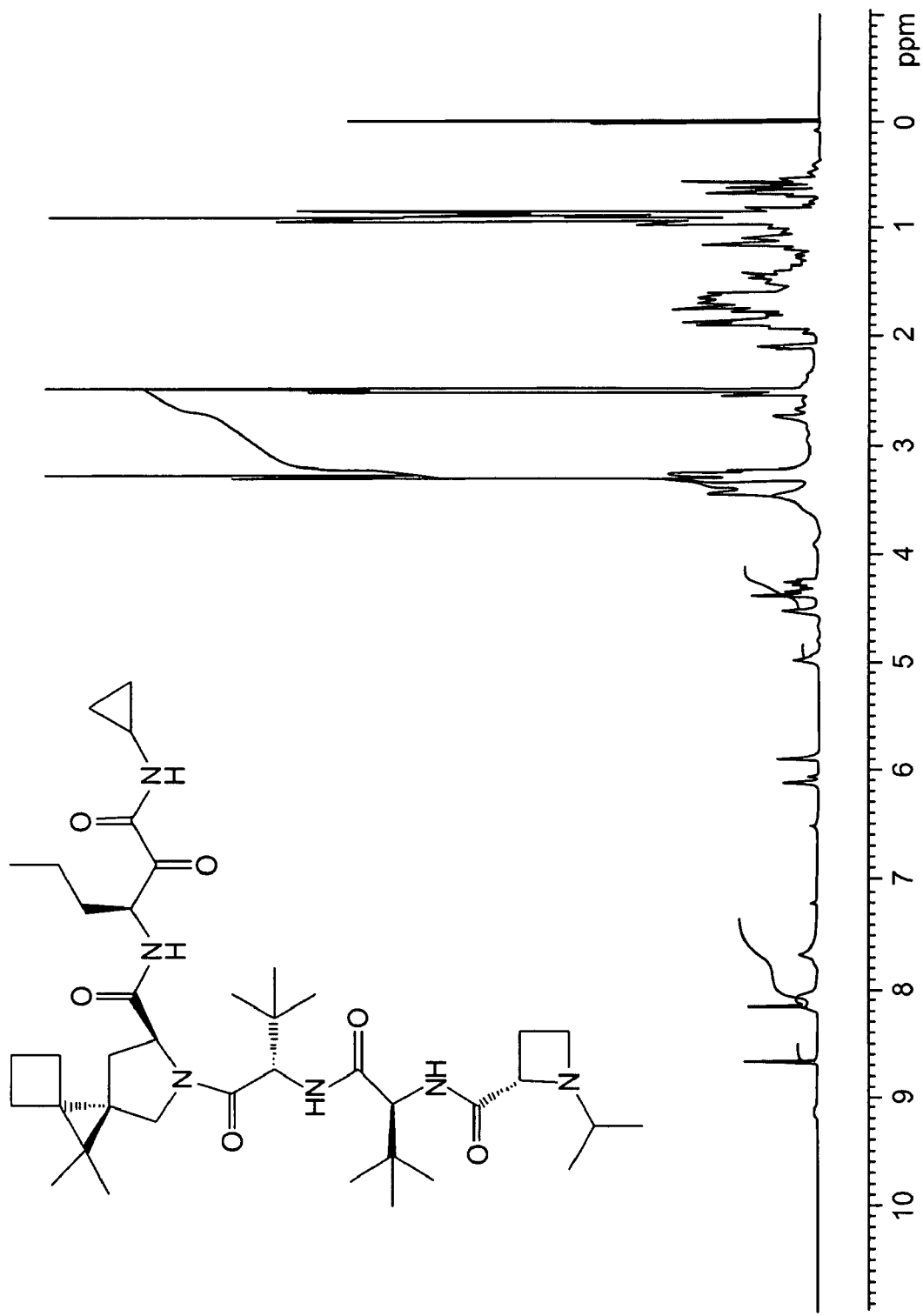
FIG. 25 is a proton NMR spectra of compound A-73 in DMSO-d6.
Figure 26:
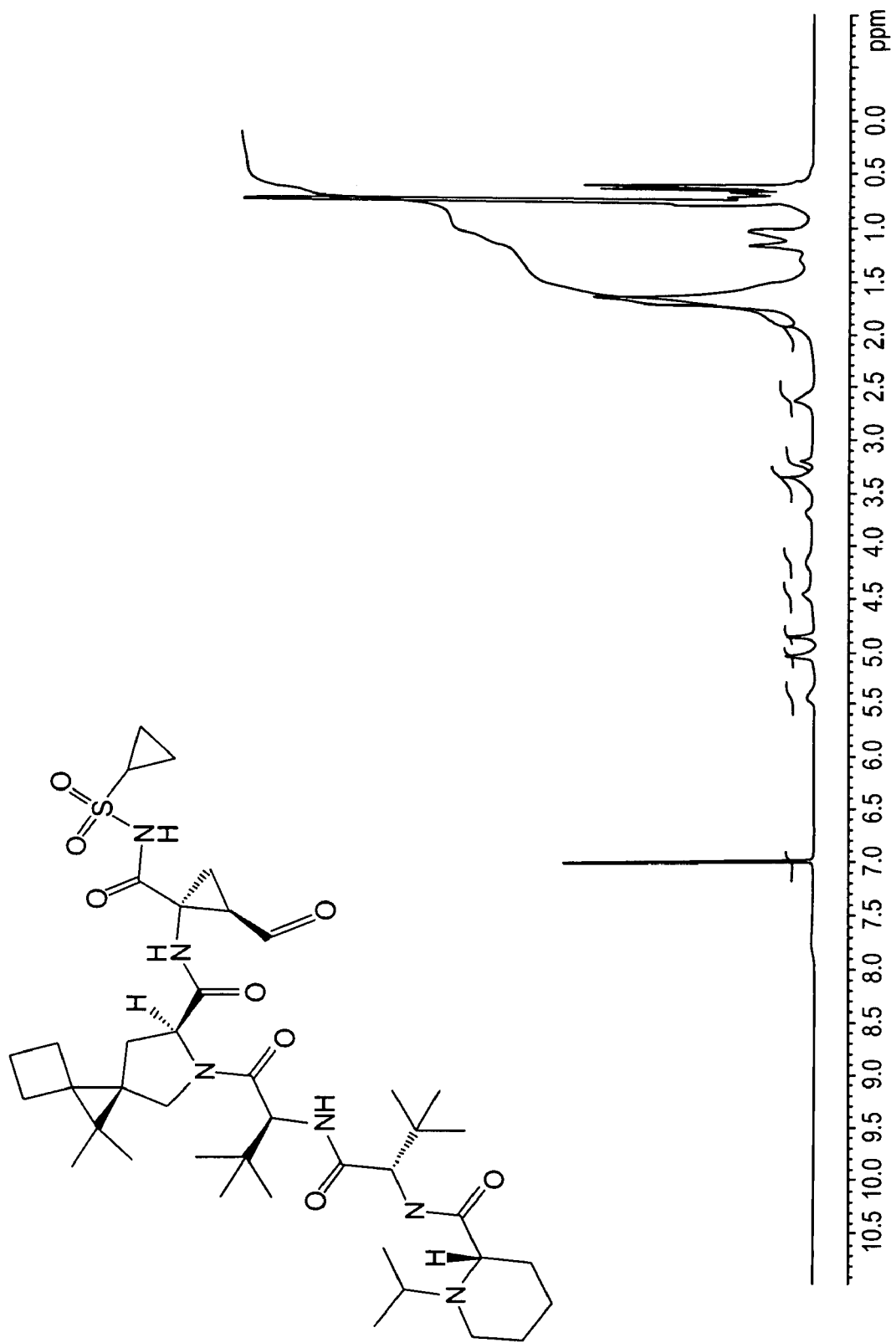
FIG. 26 is a proton NMR spectra of compound A-7 in CDCl$_3$.

This invention is directed to compounds, e.g., peptide compounds, and intermediates thereto, as well as pharmaceutical compositions containing the compounds for use in treatment of HCV infection. This invention is also directed to the compounds of the invention or compositions thereof as protease inhibitors, particularly as serine protease inhibitors, and more particularly as HCV NS3 protease inhibitors. The compounds are particularly useful in interfering with the life cycle of the hepatitis C virus and in treating or preventing an HCV infection or physiological conditions associated therewith. The present invention is also directed to methods of combination therapy for inhibiting HCV replication in cells, or for treating or preventing an HCV infection in patients using the compounds of the invention or pharmaceutical compositions, or kits thereof.

The compounds of the present invention possess increased potency, increased solubility and/or improved pharmokinetic properties compared to the corresponding properties of known NS3 protease inhibitors previously described in the art. Certain compounds of the invention combine exquisite potency (e.g., IC$_{50}$<10 nM in the assay of Example 12 or 13), high aqueous solubility (e.g., solubilities in excess of 0.5 mM in water at pH=1 and in excess of 50 micromolar in water at pH=6.8) or increased bioavailability (e.g., as measured by the assay of Example 15).

Certain compounds of the instant invention include those compounds of Formula I:

I and pharmaceutically acceptable salts and stereoisomers thereof;

wherein

X is absent or selected from NR$^{5a}$ or oxygen;

i and k are independently selected integers selected from the group consisting of 0, 1, 2, 3 and 4;

j is an integer selected from the group consisting of 1, 2, 3 and 4, wherein the sum of i+j+k is less than or equal to 5 and greater than or equal to 2 when X is absent and the sum of i+j+k is less than or equal to 4 and greater than or equal to 1 when X is oxygen;

p is 0, 1, 2 or 3;

E is OH, NH$_2$, N(H)C$_{1-4}$alkyl, N(H)C$_{3-6}$cycloalkyl, —C(O)NH— or —N(H)S(O)$_2$—;

R$^1$ is absent, hydrogen, C$_{1-4}$alkyl or C$_{3-6}$cycloalkyl;

R$^2$ is C$_{1-4}$alkyl, haloC$_{1-4}$alkyl, or C$_{3-6}$cycloalkylC$_{0-2}$alkyl;

R$^{2a}$ is hydrogen, C$_{1-4}$alkyl, haloC$_{1-4}$alkyl, or C$_{3-6}$cycloalkylC$_{0-2}$alkyl; or R$^2$ and R$^{2a}$, taken in combination form a three to seven membered saturated ring comprising zero or one nitrogen, oxygen or sulfur ring atoms, which ring is substituted with zero, one or two substituents independently selected from C$_{1-4}$alkyl and C$_{2-4}$alkenyl;

R$^3$ and R$^4$ are independently selected from the group consisting of C$_{1-6}$alkyl, C$_{4-7}$cycloalkyl and C$_{4-7}$cycloalkyl substituted with a C$_{1-4}$alkyl residue;

R$^5$ represents zero to three residues each independently selected at each occurrence from the group consisting of halogen, hydroxy, amino, C$_{1-4}$alkyl, C$_{3-6}$cycloalkyl, C$_{1-4}$alkoxy, mono- and di-C$_{1-4}$alkylamino, hydroxyC$_{1-4}$alkyl, and C$_{1-4}$alkoxyC$_{1-4}$alkyl;

R$^{5a}$ is independently selected at each occurrence from the group consisting of hydrogen, C$_{1-4}$alkyl, haloC$_{1-4}$alkyl, C$_{3-6}$cycloalkyl, hydroxyC$_{1-4}$alkyl, and C$_{1-4}$alkoxyC$_{1-4}$alkyl; and R$^6$ and R$^7$ are independently selected from hydrogen and C$_{1-4}$alkyl.

Certain other compounds of the invention include compounds of the Formula Ia:

Ia and pharmaceutically acceptable salts and stereoisomers thereof;
wherein
i is an integer selected from the group consisting of 0, 1, 2, 3 and 4;
j is an integer selected from the group consisting of 1, 2, 3 and 4, wherein the sum of i+j is less than or equal to 5 and greater than or equal to 2;
p is 0, 1, 2 or 3;
E is OH, $NH_2$, $N(H)C_{1-4}$alkyl, $N(H)C_{3-6}$cycloalkyl, —C(O)NH— or —N(H)S(O)$_2$—;
$R^1$ is absent, hydrogen, $C_{1-4}$alkyl or $C_{3-6}$cycloalkyl;
$R^2$ is $C_{1-4}$alkyl, halo$C_{1-4}$alkyl, or $C_{3-6}$cycloalkyl$C_{0-2}$alkyl;
$R^{2a}$ is hydrogen, $C_{1-4}$alkyl, halo$C_{1-4}$alkyl, or $C_{3-6}$cycloalkyl$C_{0-2}$alkyl; or
$R^2$ and $R^{2a}$, taken in combination form a three to seven membered saturated ring comprising zero or one nitrogen, oxygen or sulfur ring atoms, which ring is substituted with zero, one or two substituents independently selected from $C_{1-4}$alkyl and $C_{2-4}$alkenyl;
$R^3$ and $R^4$ are independently selected from the group consisting of $C_{1-6}$alkyl, $C_{4-7}$cycloalkyl and $C_{4-7}$cycloalkyl substituted with a $C_{1-4}$alkyl residue;
$R^5$ represents zero to three residues each independently selected at each occurrence from the group consisting of halogen, hydroxy, amino, $C_{1-4}$alkyl, $C_{3-6}$cycloalkyl, $C_{1-4}$alkoxy, mono- and di-$C_{1-4}$alkylamino, hydroxy$C_{1-4}$alkyl, and $C_{1-4}$alkoxy$C_{1-4}$alkyl;
$R^{5a}$ is independently selected at each occurrence from the group consisting of hydrogen, $C_{1-4}$alkyl, halo$C_{1-4}$alkyl, $C_{3-6}$cycloalkyl, hydroxy$C_{1-4}$alkyl, and $C_{1-4}$alkoxy$C_{1-4}$alkyl; and
$R^6$ and $R^7$ are independently selected from hydrogen and $C_{1-4}$alkyl.

Certain preferred compounds of Formula I, wherein
X is carbon;
i is 0 or 1;
j+k is 2, 3, or 4;
p is 1;
E is C(O)NH or N(H)SO$_2$;
$R^1$ is cyclopropyl or $C_{2-4}$alkyl;
$R^2$ is propyl or cyclobutylmethyl;
$R^{2a}$ is hydrogen; or
$R^2$ and $R^{2a}$ form a cyclopropyl ring substituted by zero or one ethyl or vinyl residues;
$R^3$ and $R^4$ are independently selected from tert-butyl, cyclohexyl, and 1-methylcyclohexyl;
$R^5$ represents zero or one $C_{1-4}$alkyl residues;
$R^{5a}$ is $C_{1-4}$alkyl;
$R^6$ and $R^7$ are independently selected from hydrogen and methyl.

Certain preferred compounds of Formula I, wherein
X is carbon;
i is 0 or 1;
j+k is 2, 3, or 4;
p is 1;
E is C(O)NH;
$R^1$ is cyclopropyl, ethyl, iso-propyl, or tert-butyl;
$R^2$ is propyl;
$R^{2a}$ is hydrogen;
$R^3$ and $R^4$ are independently selected from tert-butyl and cyclohexyl;
$R^5$ is absent;
$R^{5a}$ is ethyl, iso-propyl, or tert-butyl; and
$R^6$ and $R^7$ are methyl.

In certain other compounds of Formula I, $R^{2a}$ is selected from hydrogen, deuterium, tritium or a combination thereof. In certain compounds of Formula I, $R^{2a}$ is enriched in deuterium, e.g., at least about 50% of the hydrogen atoms at $R^{2a}$ are deuterium ($^2$H), or at least about 95% of the hydrogen atoms are deuterium.

In certain other aspects, the invention provides compounds of Table A and Table B infra.

In yet other aspects of the invention, methods of making compounds of Formula II

II the method comprising the steps of
(a) providing a compound of Formula III:

III (b) providing a compound of Formula IV:

IV (c) contacting the compound of Formula III with the compound of Formula IV and a base in a solvent under conditions conducive to formation of a compound of Formula II:

(b) providing a compound of Formula IV:

*[Structure IV: R⁶, R⁷, R¹⁷ on central carbon]*

(c) contacting the compound of Formula III with the compound of Formula IV and a base in a solvent under conditions conducive to formation of a compound of Formula II:

*[Structure II]* wherein
x is zero, one or two;
$Z^1$ and $Z^3$ are each independently selected $CR^8R^9$;
$Z^2$ is absent or is selected from the group consisting of O, S, $CR^8R^9$, or $NR^{10}$;
$R^6$, $R^7$, $R^{13}$ and $R^{14}$ are independently selected from the group consisting of hydrogen, $C_{1-6}$alkyl, or aryl; or
$R^6$ and $R^7$ taken in combination form a three to six membered saturated three to seven membered carbocycle, which is optionally substituted by zero to three substituents;
$R^8$, $R^9$, $R^{11}$ and $R^{12}$ are independently selected from the group consisting of hydrogen, halogen, $C_{1-6}$alkyl, $C_{1-6}$alkoxy, halo$C_{1-6}$alkyl, halo$C_{1-6}$alkoxy, hydroxy$C_{1-6}$alkyl, $C_{1-6}$alkoxy$C_{1-6}$alkyl, or aryl;
$R^{10}$ is selected from hydrogen, $C_{1-6}$alkyl, halo$C_{1-6}$alkyl, hydroxy$C_{1-6}$alkyl, $C_{1-6}$alkoxy$C_{1-6}$alkyl, aryl and aralkyl;
$R^{15}$ is hydrogen, $C_{1-10}$alkyl, $C_{3-10}$cycloalkyl, aryl, or heteroaryl;
$R^{16}$ is $C_{1-10}$alkyl, $C_{3-10}$cycloalkyl, aryl, or heteroaryl; and
$R_{17}$ is cyano, nitro, $C_{1-6}$alkylsulfonate, halo$C_{1-6}$alkylsulfonate, arylsulfonate, or halogen.

In still other aspect of the invention, methods are provided for the synthesis of compounds of Formula V:

*[Structure V]* the method comprising the steps of
(a) providing a compound of Formula III:

*[Structure III]*

(d) contacting the compound of Formula II with an inorganic or organometallic compound or salt comprising at least one metal hydrogen bond in a solvent under conditions conducive to formation of a compound of Formula VI:

*[Structure VI]*

(e) contacting the compound of Formula VI with dihydrogen and a hydrogenation catalyst in a solvent under conditions conducive to formation of a compound of Formula V:

*[Structure V]* wherein
x is zero, one or two;
$Z^1$ and $Z^3$ are each independently selected $CR^8R^9$;
$Z^2$ is absent or is selected from the group consisting of O, S, $CR^8R^9$, or $NR^{10}$;
$R^6$, $R^7$, $R^{13}$ and $R^{14}$ are independently selected from the group consisting of hydrogen, $C_{1-6}$alkyl, or aryl; or $R^6$ and $R^7$ taken in combination form a three to six membered saturated three to seven membered carbocycle, which is optionally substituted by zero to three substituents;

$R^8$, $R^9$, $R^{11}$ and $R^{12}$ are independently selected from the group consisting of hydrogen, halogen, $C_{1-6}$alkyl, $C_{1-6}$alkoxy, halo$C_{1-6}$alkyl, halo$C_{1-6}$alkoxy, hydroxy$C_{1-6}$alkyl, $C_{1-6}$alkoxy$C_{1-6}$alkyl, or aryl; or $R^{11}$ and $R^{12}$ taken in combination form a three to six membered saturated three to seven membered carbocycle, which is optionally substituted by zero to three substituents;

$R^{10}$ is selected from hydrogen, $C_{1-6}$alkyl, halo$C_{1-6}$alkyl, hydroxy$C_{1-6}$alkyl, $C_{1-6}$alkoxy$C_{1-6}$alkyl, aryl and aralkyl;

$R^{15}$ is hydrogen, $C_{1-10}$alkyl, $C_{3-10}$cycloalkyl, aryl, or heteroaryl;

$R^{16}$ is $C_{1-10}$alkyl, $C_{3-10}$cycloalkyl, aryl, or heteroaryl; and $R^{17}$ is cyano, nitro, $C_{1-6}$alkylsulfonate, halo$C_{1-6}$alkylsulfonate, arylsulfonate, or halogen.

In certain preferred methods of synthesis of compounds of Formula II or Formula V, $R^{17}$ is an electron withdrawing group such as nitro or cyano. In certain embodiments, $R^{17}$ is nitro.

In certain preferred methods of synthesis of compounds of Formula II or Formula V, $R^6$ and $R^7$ are independently selected from hydrogen and $C_{1-4}$alkyl; $R^{17}$ is nitro.

$R^{11}$, $R^{12}$, $R^{13}$, $R^{14}$ and $R^{18}$ are hydrogen; and $R^{16}$ is phenyl or a five or six membered heteroaryl, each of which is substituted with zero to three substituents selected from halogen, $C_{1-4}$alkyl, trifluoromethyl, $C_{1-4}$alkoxy, and trifluoromethoxy.

In certain other methods of synthesis of compounds of Formula II or Formula V, $Z^1$ and $Z^3$ are each $CR^8R^9$; $Z^2$ is $CR^8R^9$ or O; and each occurrence of $R^8$ and $R^9$ is hydrogen.

Although any solvent capable of solvating the reactants and products are contemplated for use with the synthetic methods of the instant invention, certain preferred solvents for step (c) in the preparation of compounds of Formula II supra, include dialkyl sulfoxides (e.g., dimethyl sulfoxide), cyclic ethers, dialkylformamides (e.g., dimethylformamide), dialkyl acetamides (e.g., dimethyl acetamide), acetonitrile, alcohols (e.g., $C_{1-6}$alcohols) or pyrrolidines (e.g., N-alkylpyrrolidine) and combinations thereof.

Although any solvent capable of solvating the reactants and products are contemplated for use with the synthetic methods of the instant invention, certain preferred solvents for the preparation of compounds of Formula V supra include:

For step (c) dialkyl sulfoxides (e.g., dimethyl sulfoxide), cyclic ethers, dialkylformamides (e.g., dimethylformamide), dialkyl acetamides (e.g., dimethyl acetamide), acetonitrile, alcohols (e.g., $C_{1-6}$alcohols) or pyrrolidines (e.g., N-alkylpyrrolidine) and combinations thereof. 23. The method of claim 18, wherein For step (d): ethers, cyclic ethers, aromatic hydrocarbons, and mixtures thereof; and For step (e): esters, ethers, cyclic ethers, $C_{1-6}$alcohols (e.g., methanol, ethanol, iso-propanol), $C_{1-6}$alkanoic acids (e.g., acetic acid), and mixtures thereof.

In certain preferred methods of preparing a compound of Formula V, the inorganic or organometallic compound or salt is a aluminum or boron compound or salt comprising at least one aluminum-hydrogen bond or at least one boron-hydrogen bond. More preferably, the aluminum compound or salt is selected from aluminum hydride, lithium aluminum hydride, sodium aluminum hydride, di($C_{1-4}$alkyl)aluminum hydrides, di($C_{1-4}$alkoxy)aluminum hydrides, or di($C_{1-4}$alkoxy$C_{1-4}$alkoxy)aluminum hydrides and the boron compounds are selected from metal borohydrides, metal cyanoborohydrides, borane, and diborane.

In certain preferred methods of preparing a compound of Formula V, the hydrogenation catalyst is selected from rhodium, iridium, nickel, palladium, platinum, and mixtures thereof deposited onto a substrate, wherein the substrate is selected from carbon, alumina, and silica. In certain embodiments, palladium on carbon, platinum on carbon, rhodium on carbon, and Adam's catalyst are preferred hydrogenation catalysts.

Preferred embodiments of the compounds of the invention (including pharmaceutically acceptable salts thereof, as well as enantiomers, stereoisomers, rotamers, tautomers, diastereomers, or racemates thereof) are shown below in Table A and Table B, and are also considered to be "compounds of the invention."

TABLE A

| Structure | Compound No. |
|---|---|
| 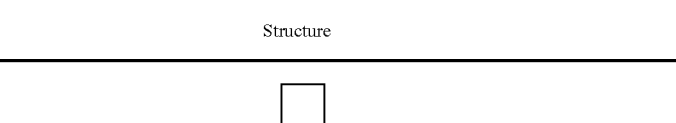 | A-1 |

TABLE A-continued
| Structure | Compound No. |
|---|---|
| 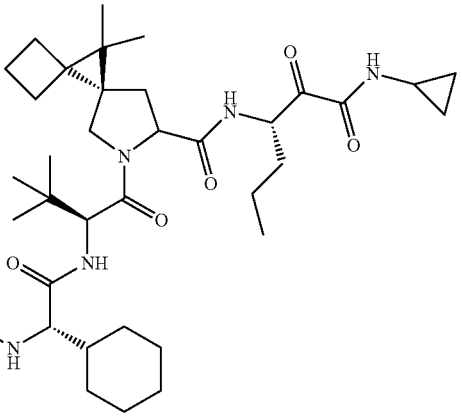 | A-2 |
| 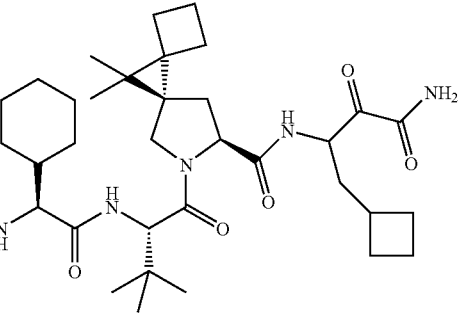 | A-3 |
| 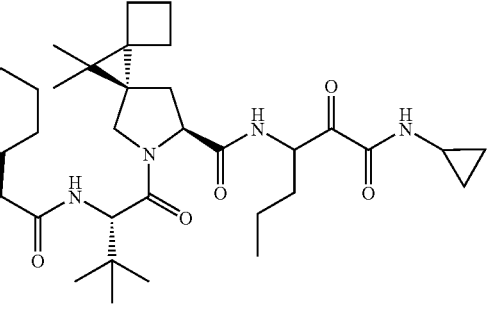 | A-4 |
| 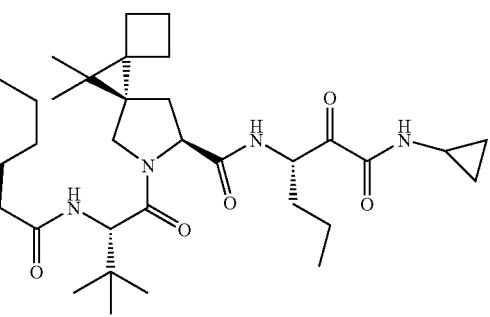 | A-5 |

TABLE A-continued

| Structure | Compound No. |
|---|---|
| 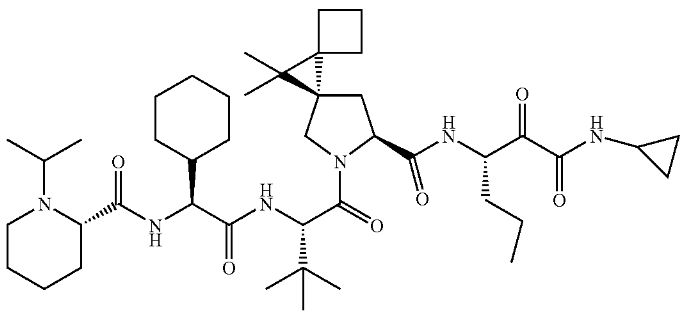 | A-6 |
| 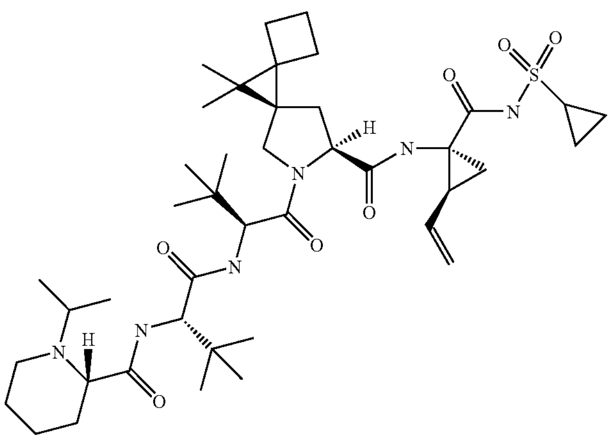 | A-7 |
| 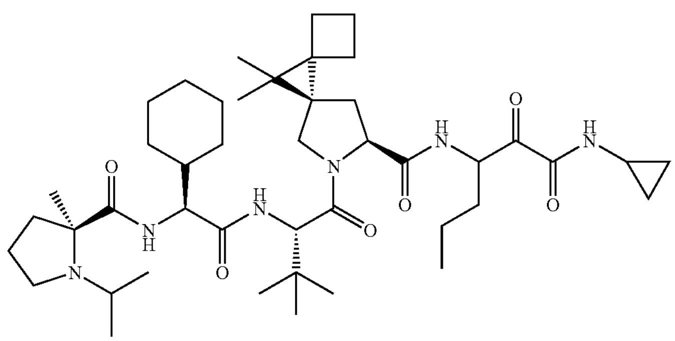 | A-8 |
| 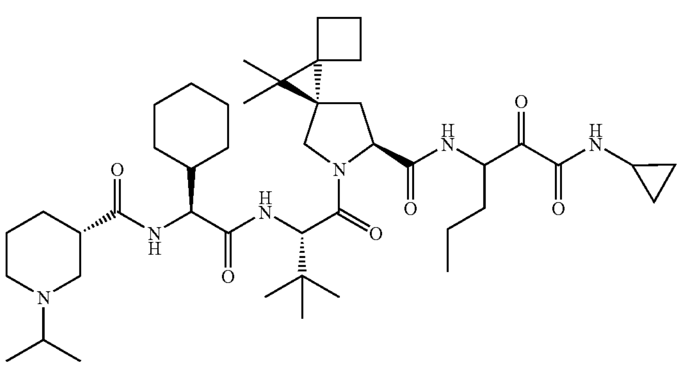 | A-9 |

TABLE A-continued
| Structure | Compound No. |
|---|---|
| 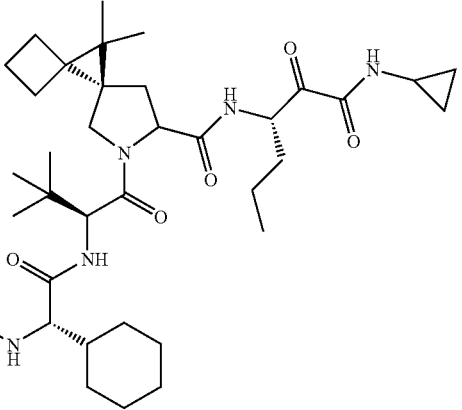 | A-10 |
| 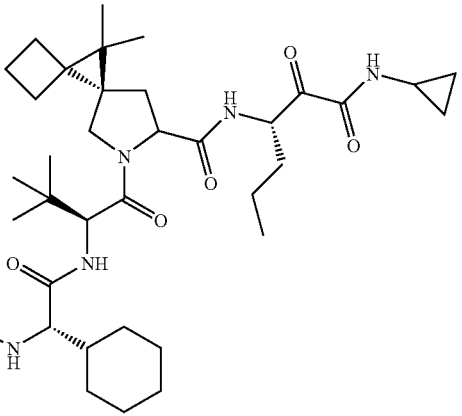 | A-11 |
| 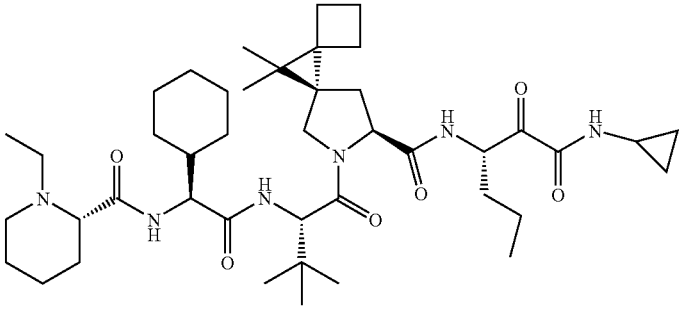 | A-12 |
| 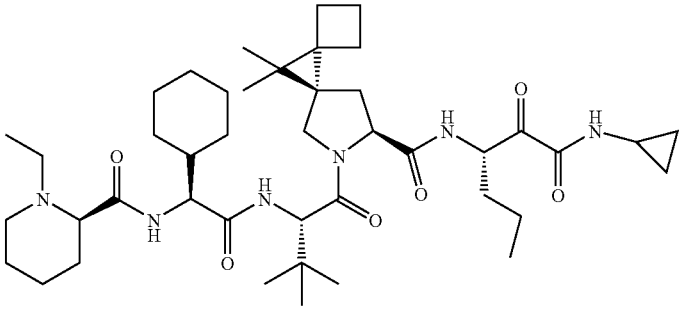 | A-13 |

TABLE A-continued

| Structure | Compound No. |
|---|---|
| 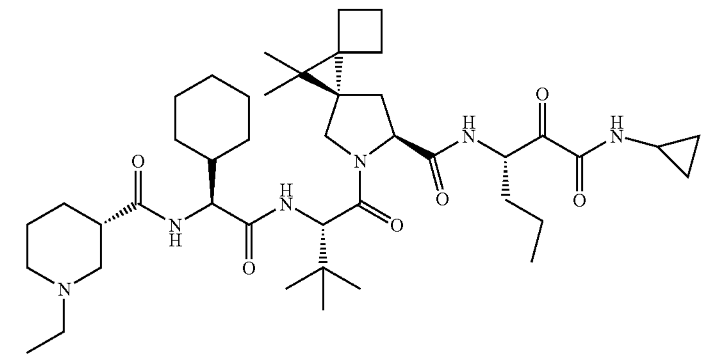 | A-14 |
| 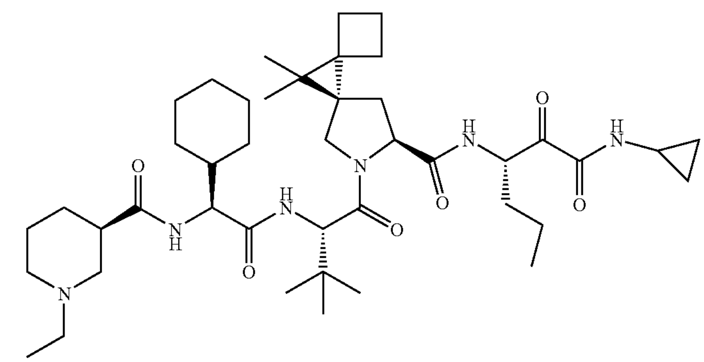 | A-15 |
| 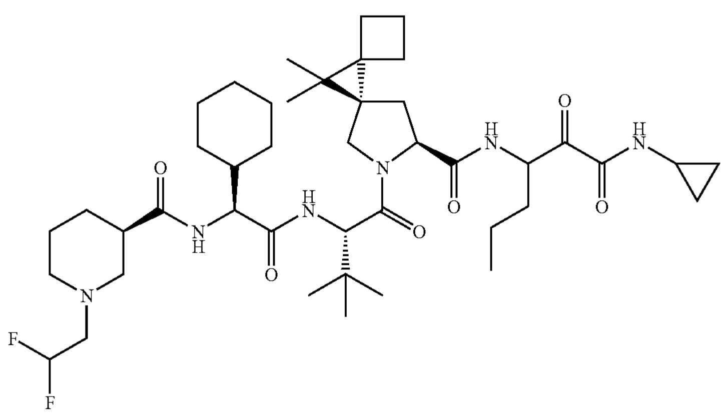 | A-16 |
| 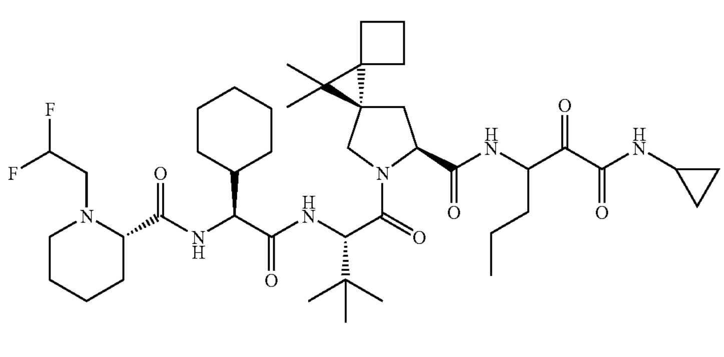 | A-17 |

TABLE A-continued

| Structure | Compound No. |
|---|---|
| 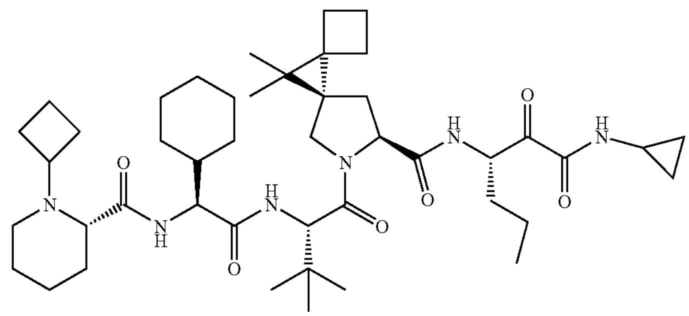 | A-18 |
| 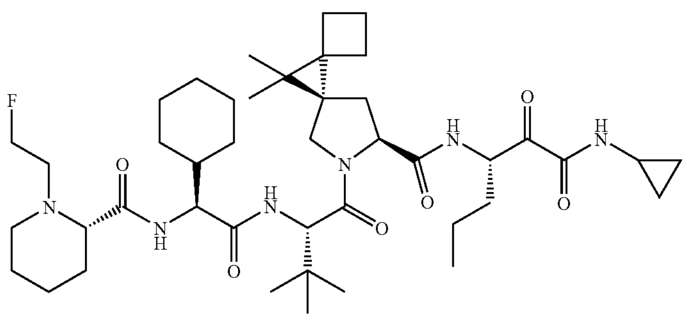 | A-19 |
| 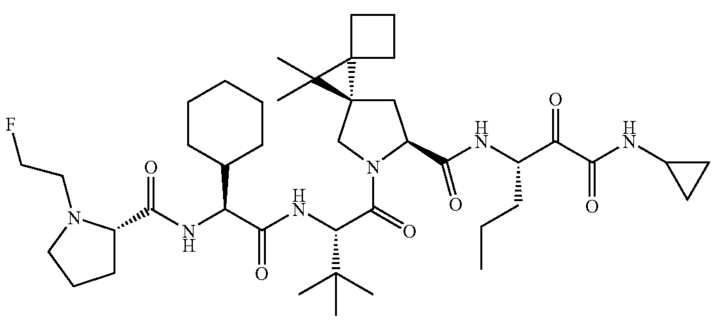 | A-20 |
| 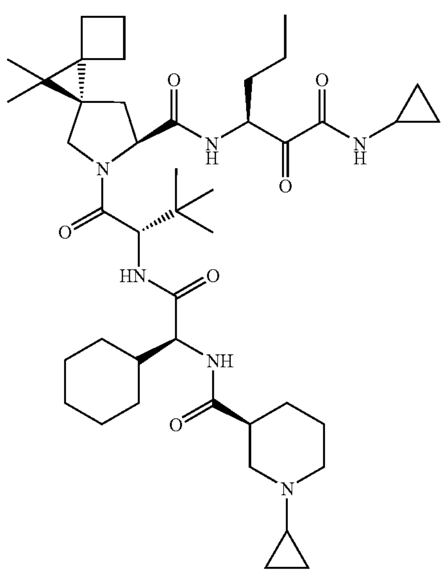 | A-21 |

TABLE A-continued
| Structure | Compound No. |
|---|---|
| 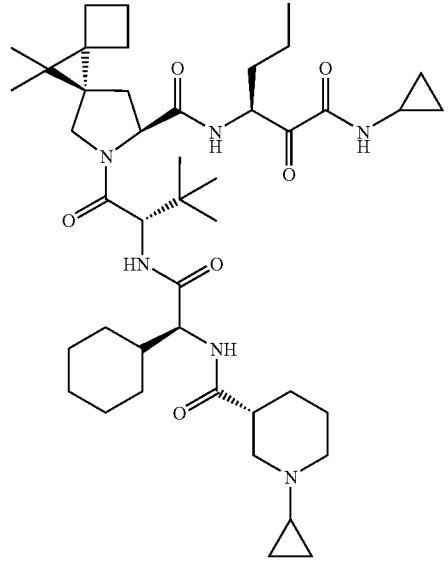 | A-22 |
| 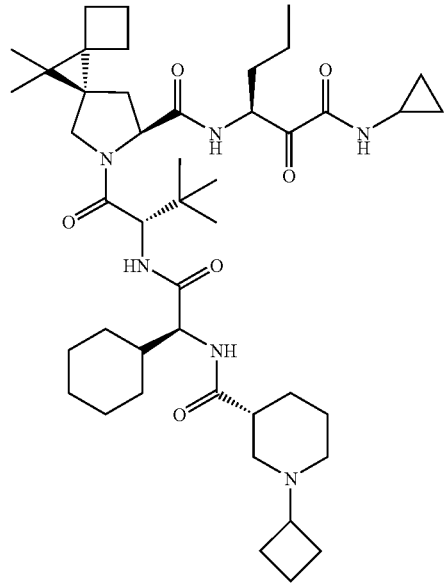 | A-23 |
| 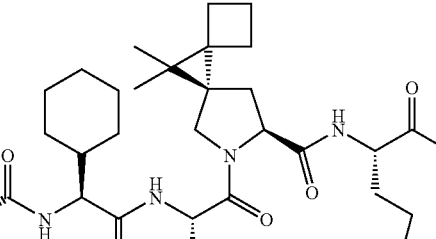 | A-24 |

TABLE A-continued

| Structure | Compound No. |
|---|---|
| 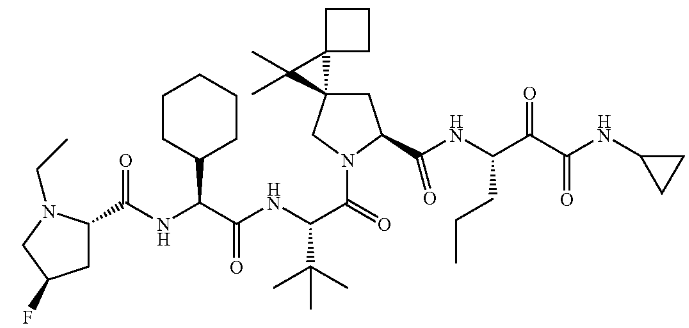 | A-25 |
| 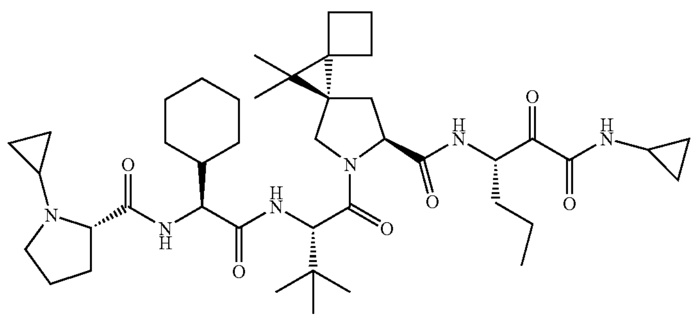 | A-26 |
| 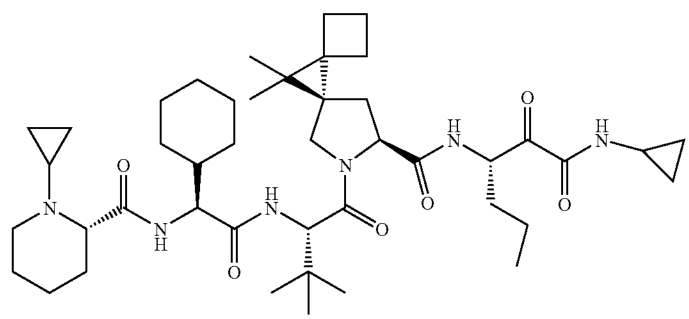 | A-27 |
| 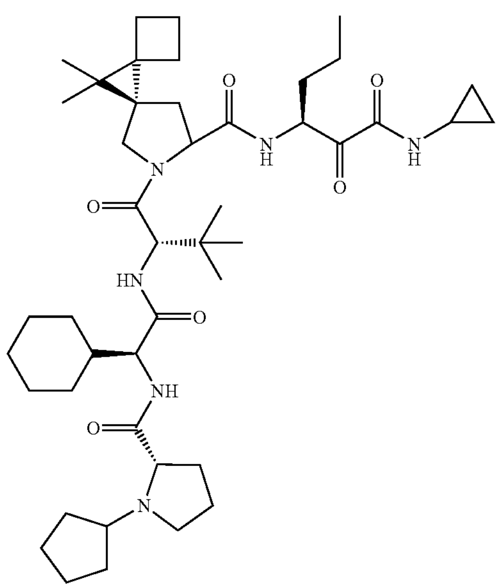 | A-28 |

TABLE A-continued
| Structure | Compound No. |
|---|---|
| 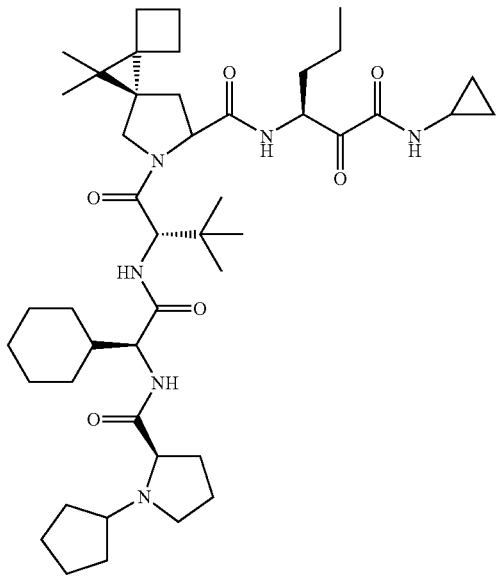 | A-29 |
| 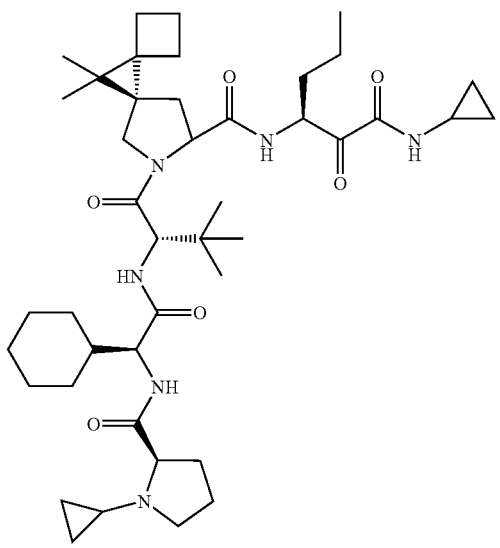 | A-30 |

TABLE A-continued
| Structure | Compound No. |
|---|---|
| 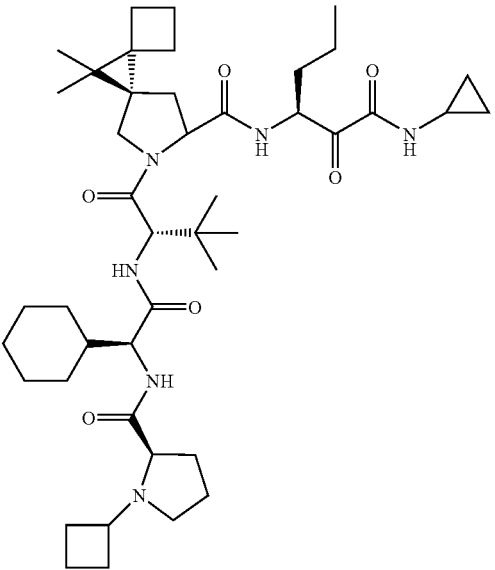 | A-31 |
| 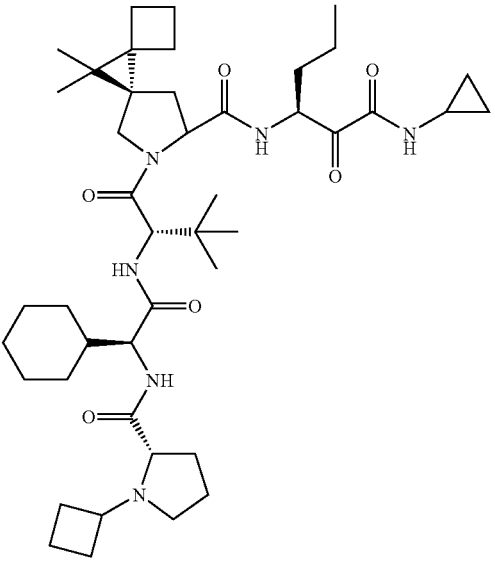 | A-32 |
| 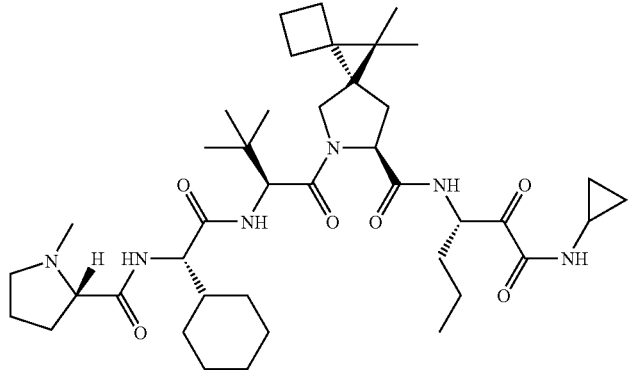 | A-33 |

TABLE A-continued

| Structure | Compound No. |
|---|---|
| 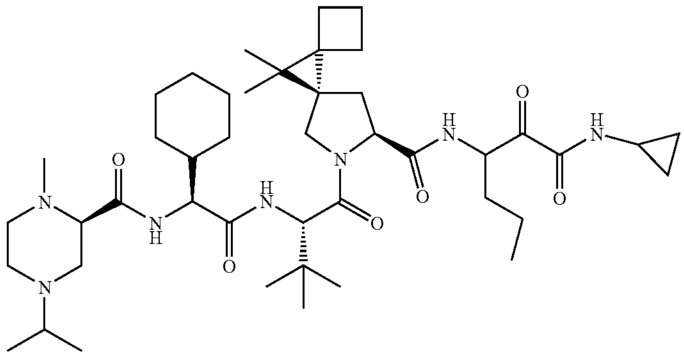 | A-34 |
| 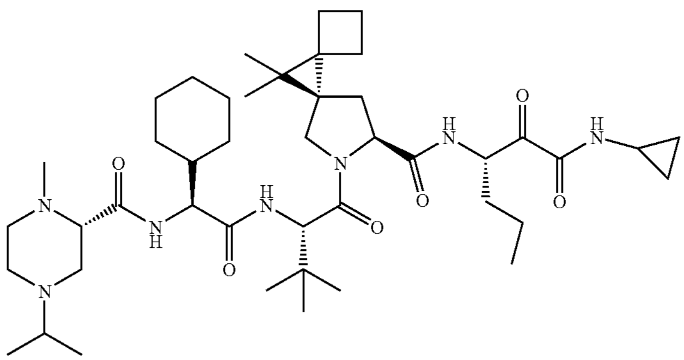 | A-35 |
| 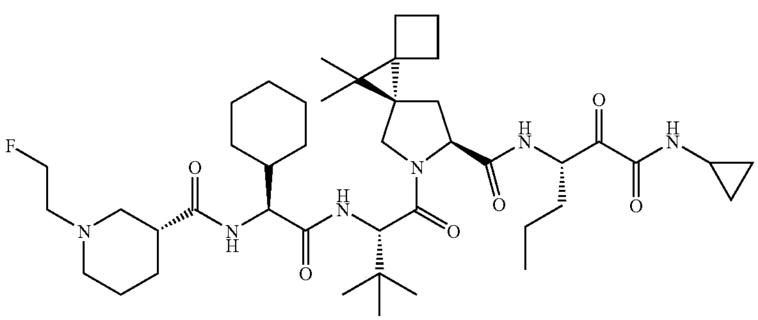 | A-36 |
| 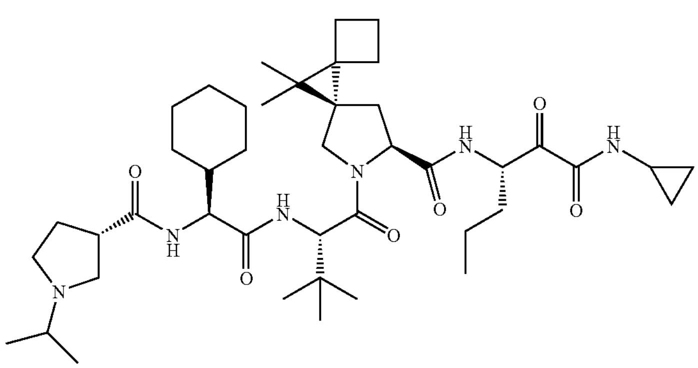 | A-37 |

TABLE A-continued

| Structure | Compound No. |
|---|---|
| 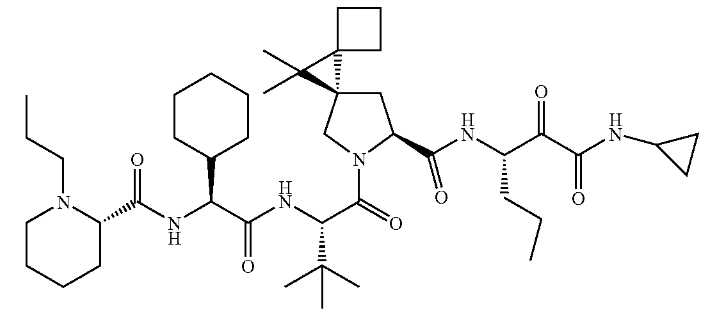 | A-38 |
| 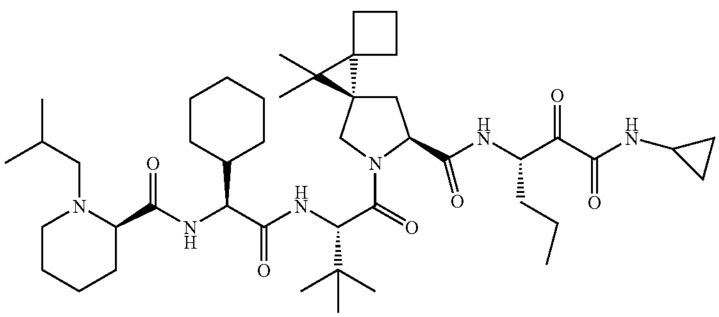 | A-39 |
| 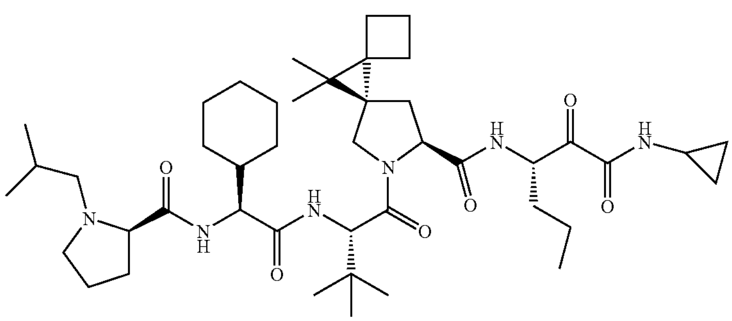 | A-40 |
| 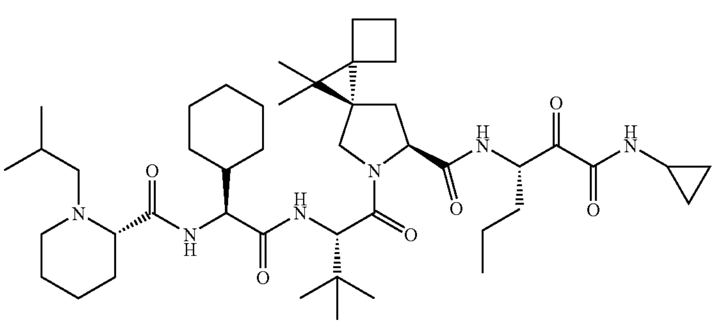 | A-41 |

TABLE A-continued

| Structure | Compound No. |
|---|---|
| 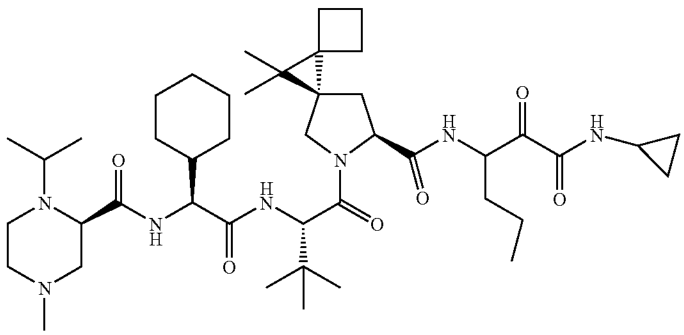 | A-42 |
| 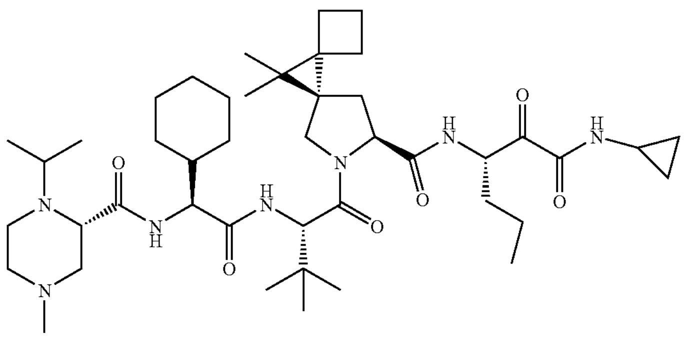 | A-43 |
| 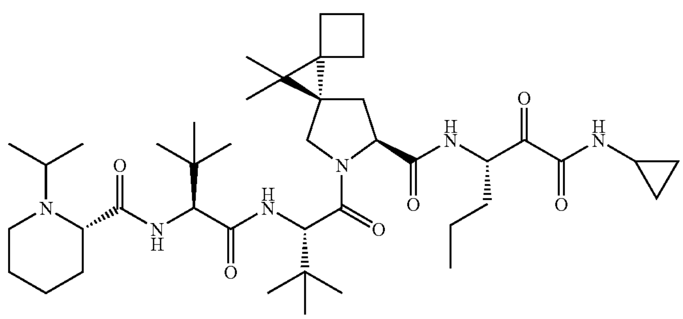 | A-44 |
| 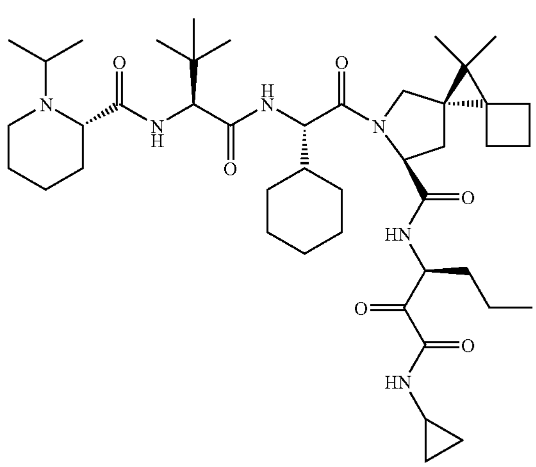 | A-45 |

TABLE A-continued

| Structure | Compound No. |
|---|---|
| 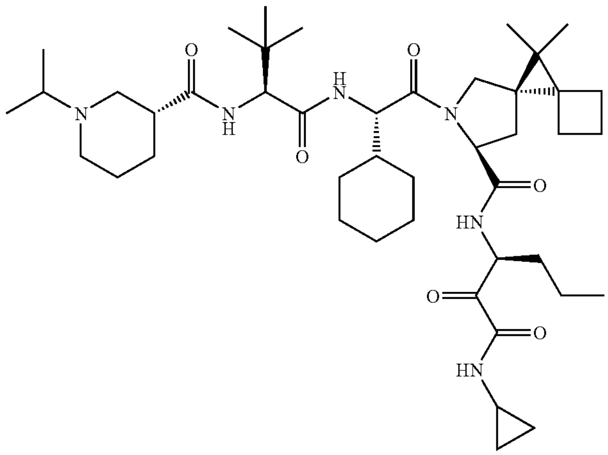 | A-46 |
| 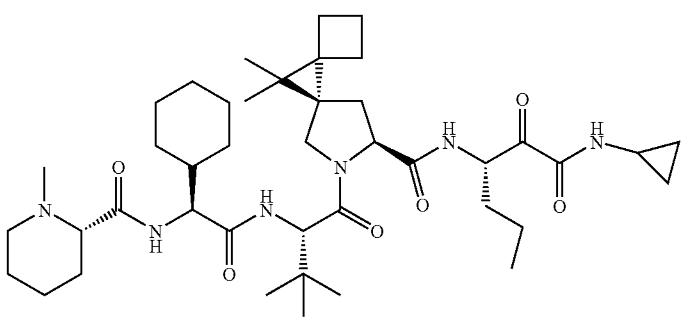 | A-47 |
| 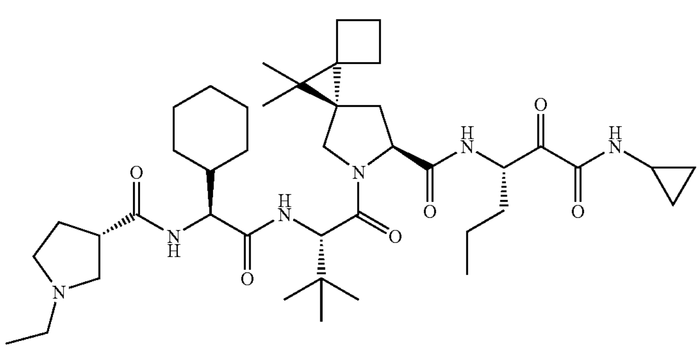 | A-48 |

TABLE A-continued
| Structure | Compound No. |
|---|---|
| 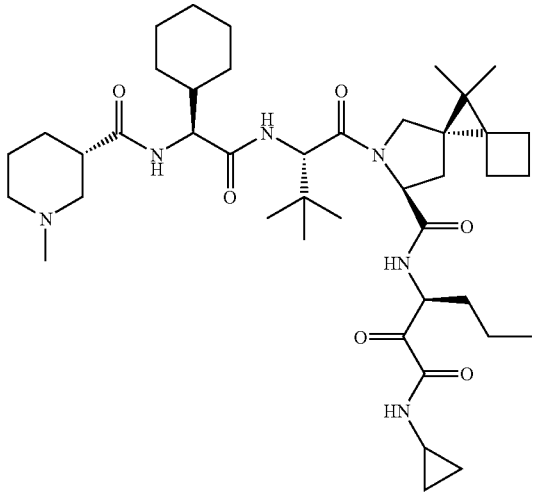 | A-49 |
| 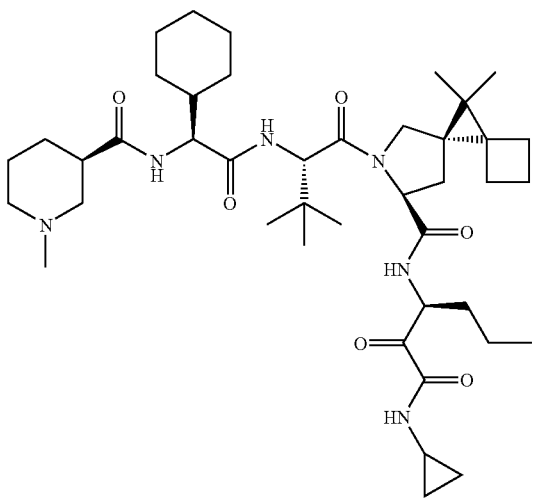 | A-50 |
| 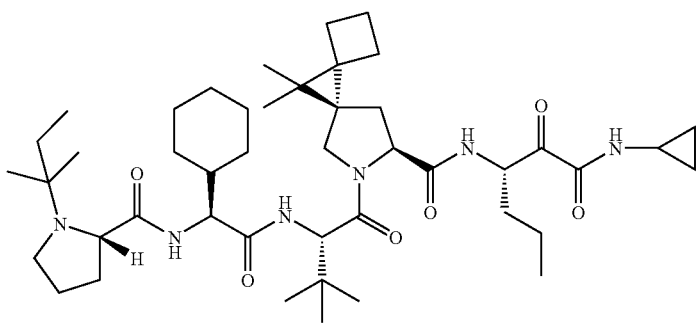 | A-51 |

TABLE A-continued

| Structure | Compound No. |
|---|---|
| 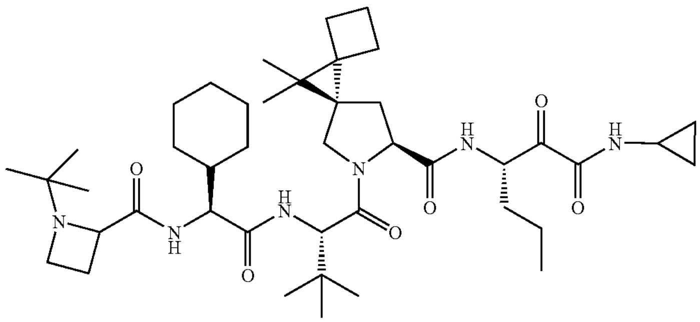 | A-52 |
| 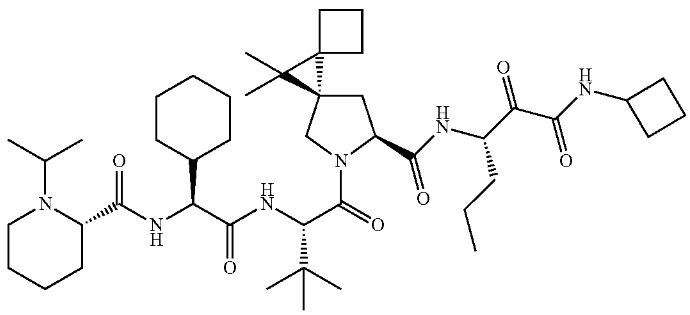 | A-53 |
| 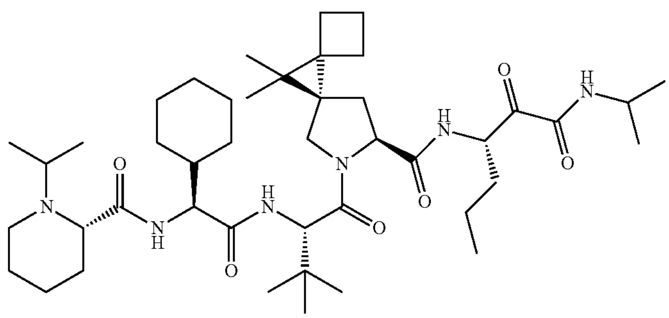 | A-54 |
| 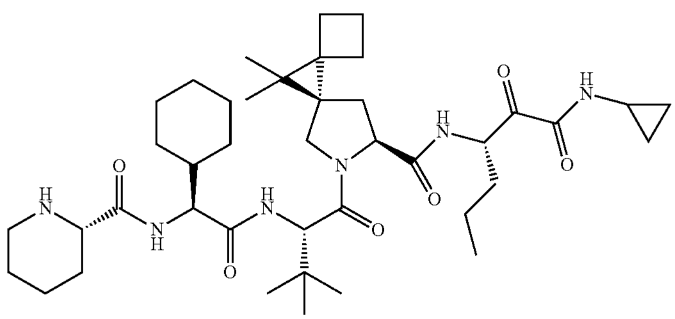 | A-55 |
| 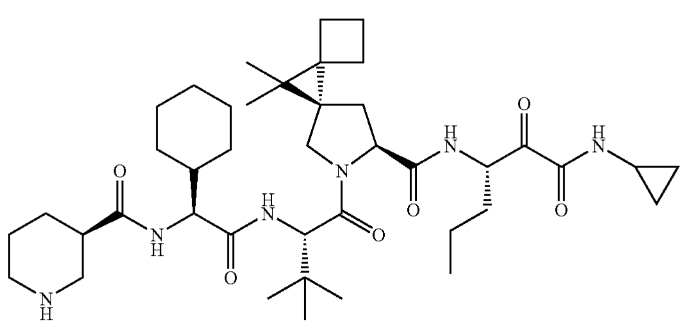 | A-56 |

TABLE A-continued

| Structure | Compound No. |
|---|---|
| 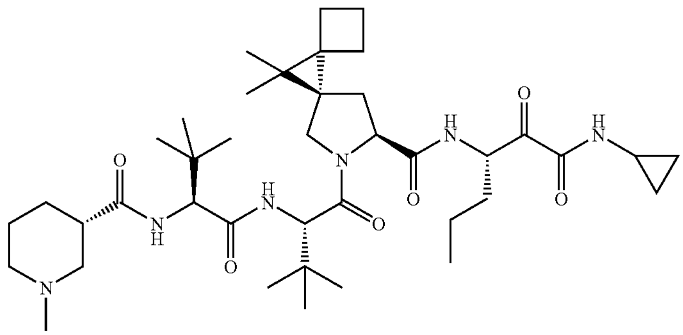 | A-57 |
| 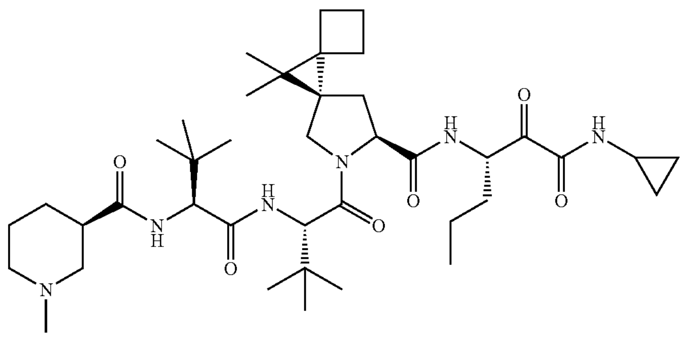 | A-58 |
| 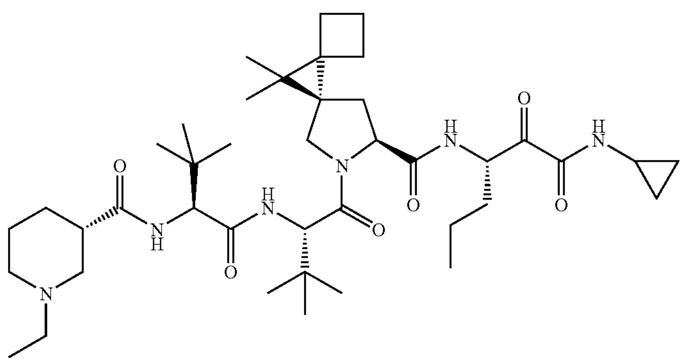 | A-59 |
| 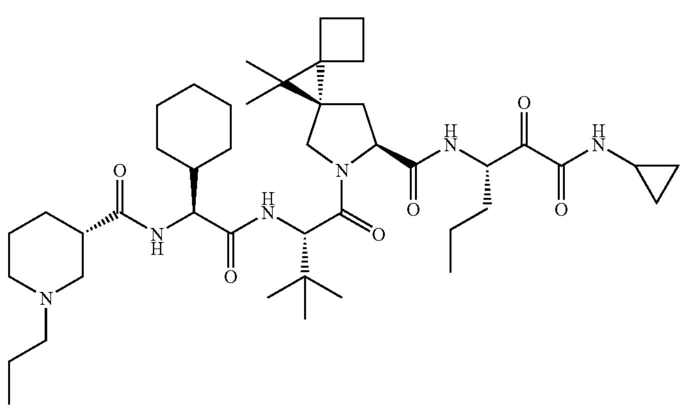 | A-60 |

TABLE A-continued

| Structure | Compound No. |
|---|---|
| 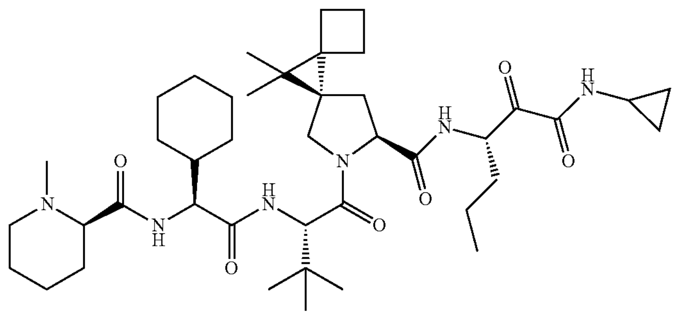 | A-61 |
| 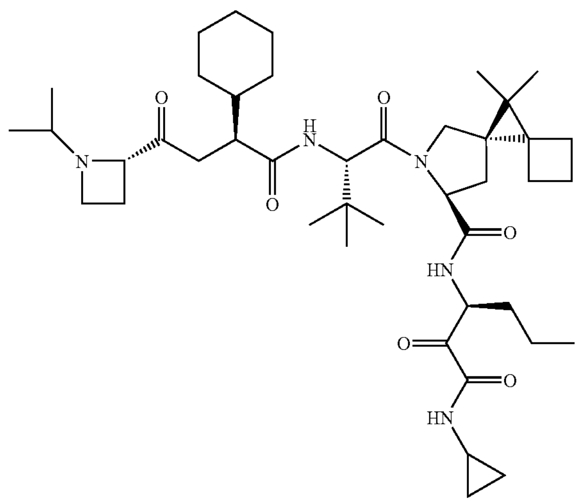 | A-62 |
| 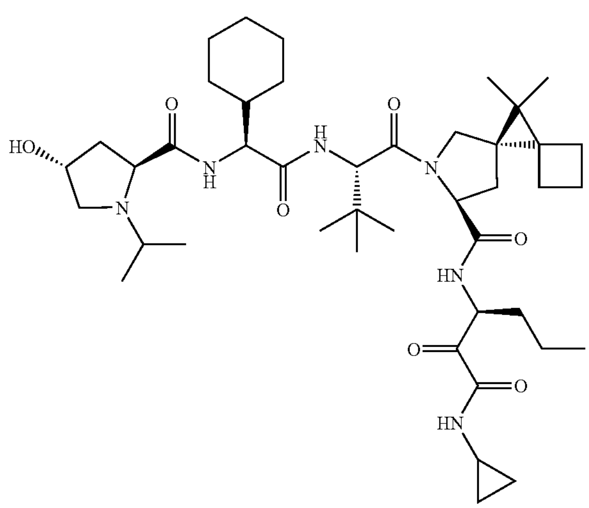 | A-63 |

TABLE A-continued
| Structure | Compound No. |
|---|---|
| 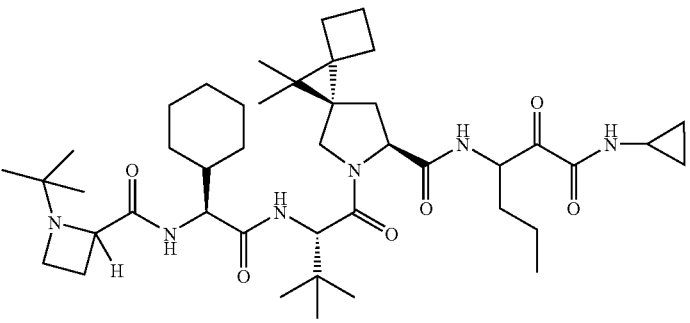 | A-64 |
| 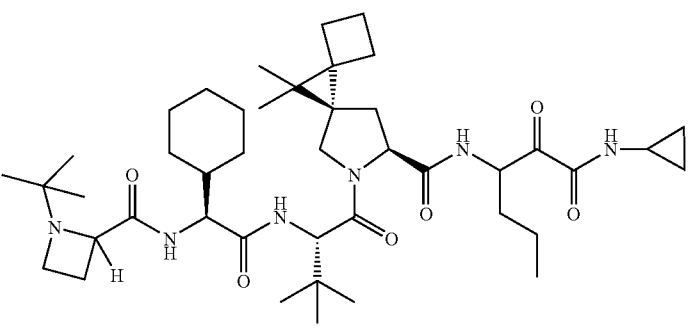 | A-65 |
| 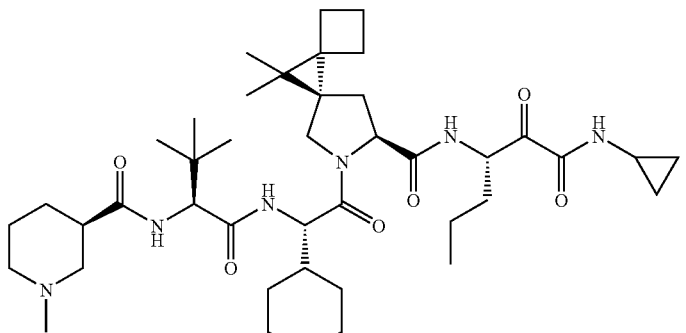 | A-66 |
| 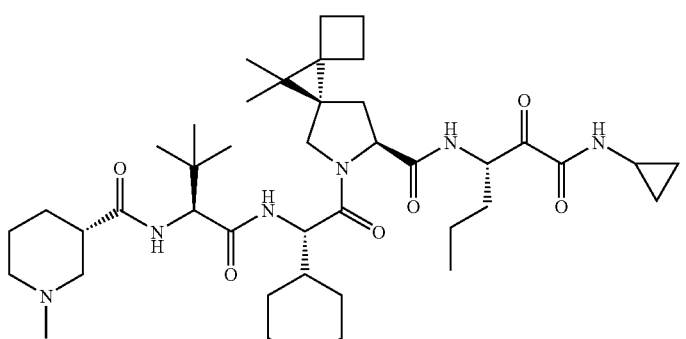 | A-67 |

TABLE A-continued
| Structure | Compound No. |
|---|---|
| 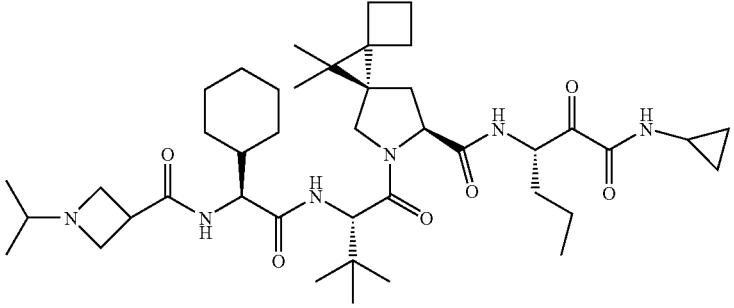 | A-68 |
| 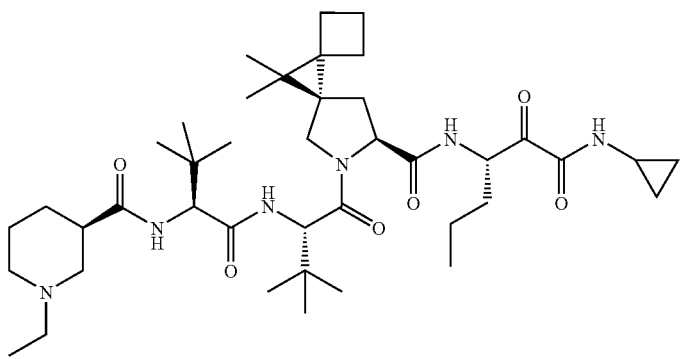 | A-69 |
| 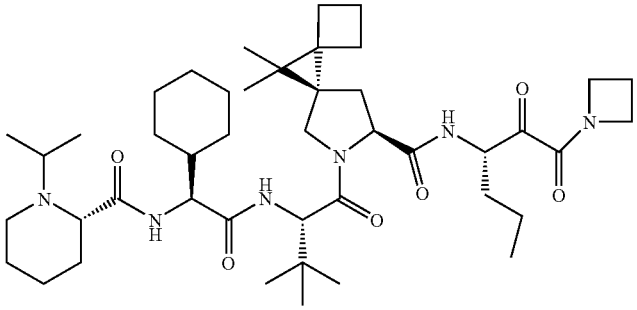 | A-70 |
| 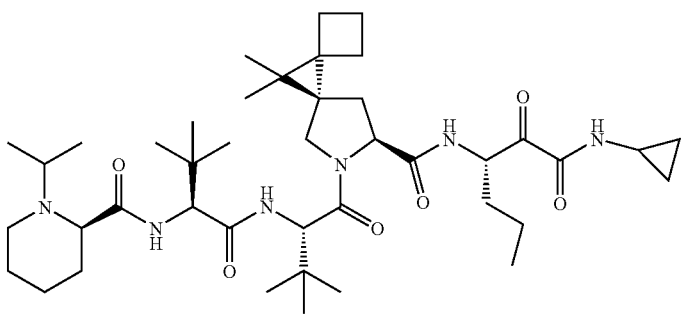 | A-71 |

TABLE A-continued
| Structure | Compound No. |
|---|---|
| 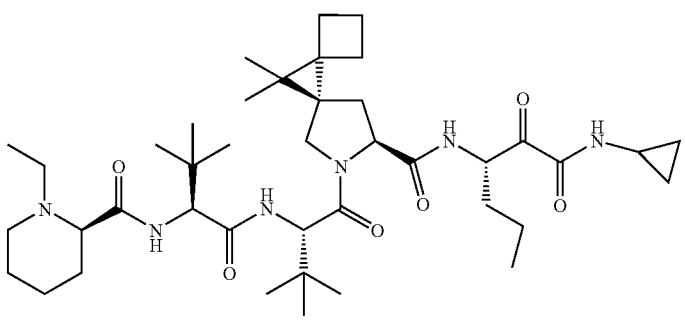 | A-72 |
| 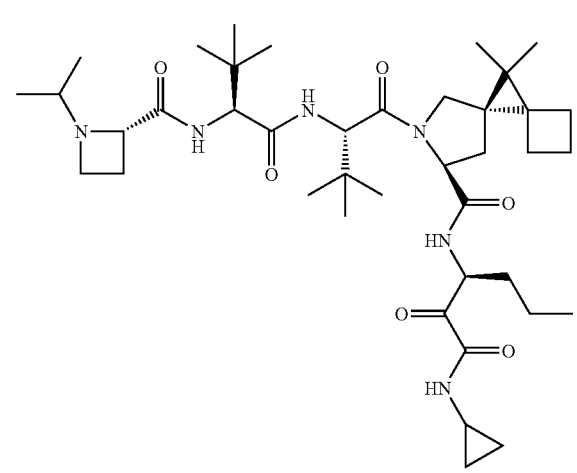 | A-73 |
| 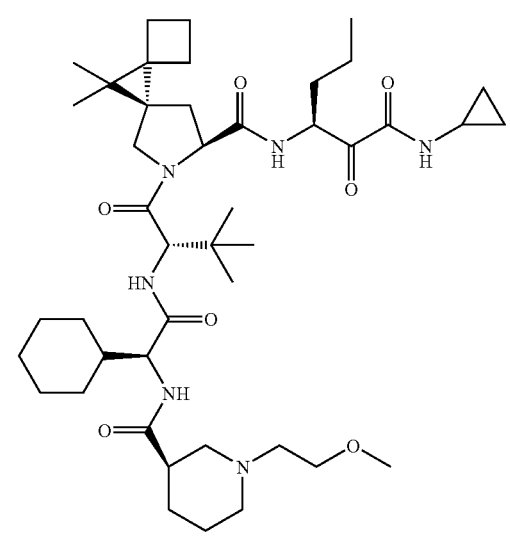 | A-74 |

TABLE A-continued
| Structure | Compound No. |
|---|---|
| 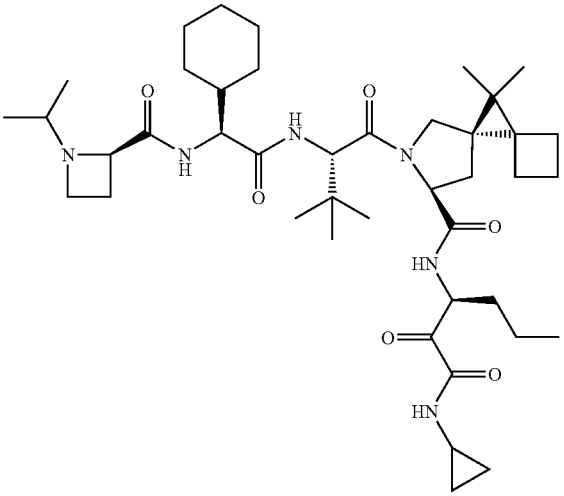 | A-75 |
| 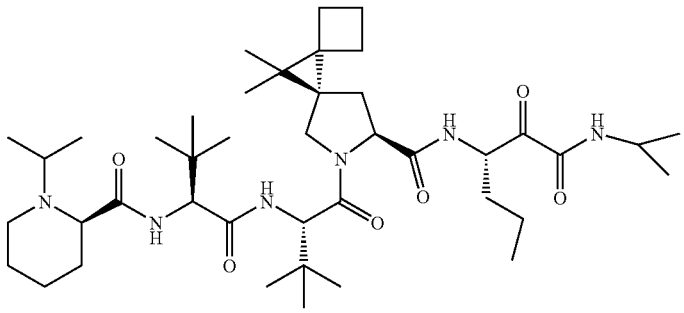 | A-76 |
| 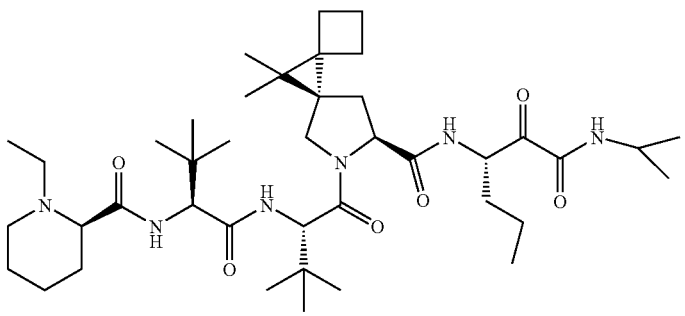 | A-77 |
| 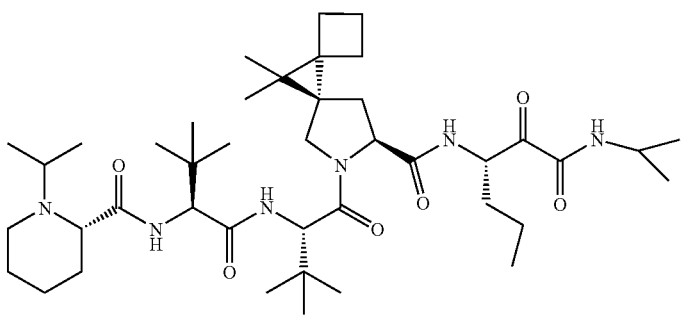 | A-78 |

TABLE A-continued

| Structure | Compound No. |
|---|---|
| 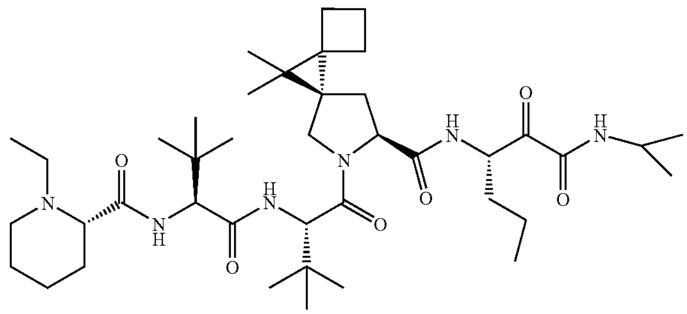 | A-79 |
| 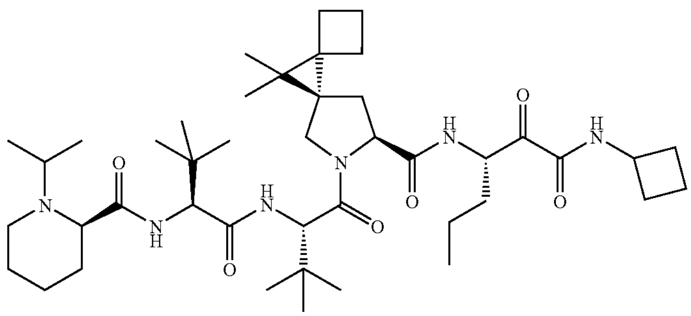 | A-80 |
| 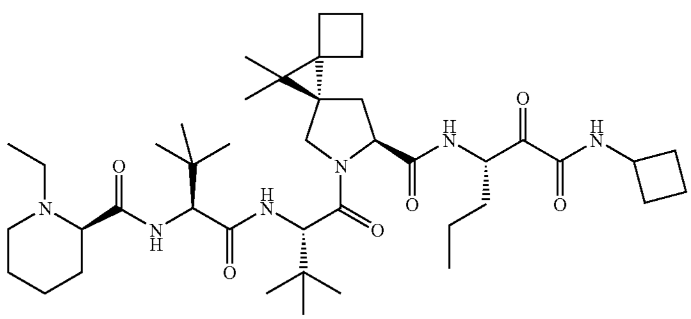 | A-81 |
| 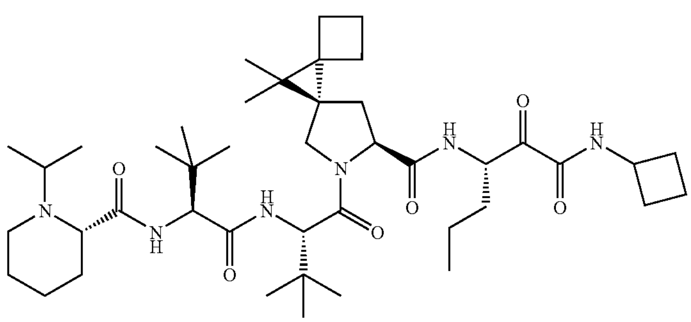 | A-82 |
| 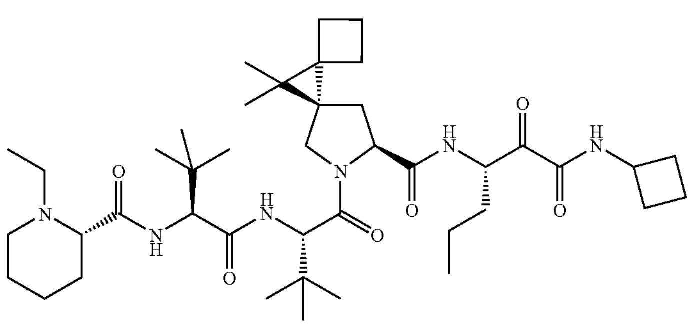 | A-83 |

TABLE A-continued

| Structure | Compound No. |
|---|---|
| 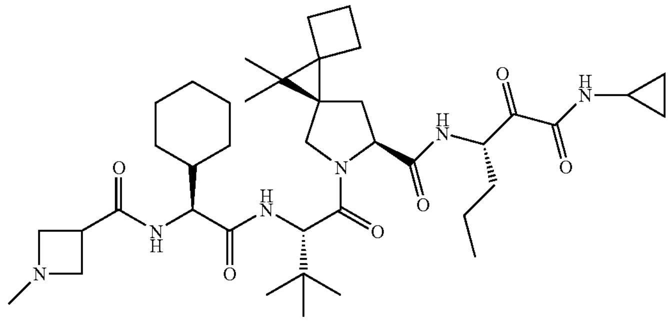 | A-84 |
| 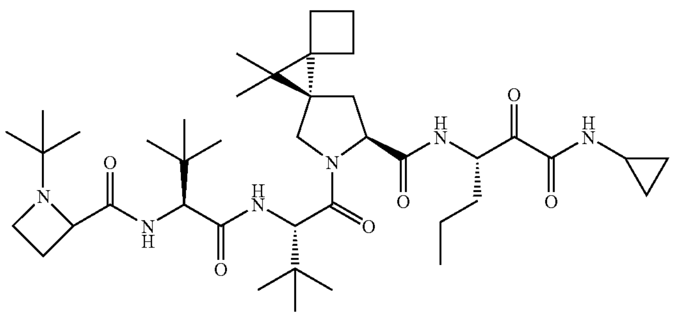 | A-85 |
| 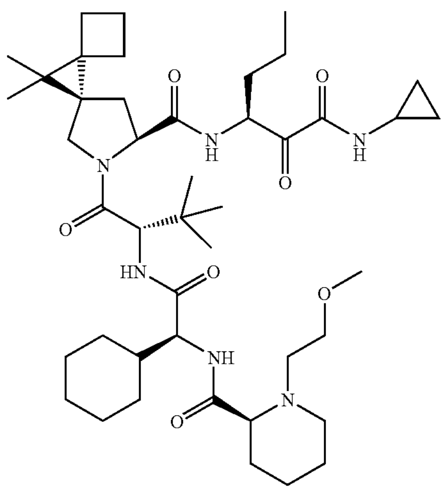 | A-86 |
| 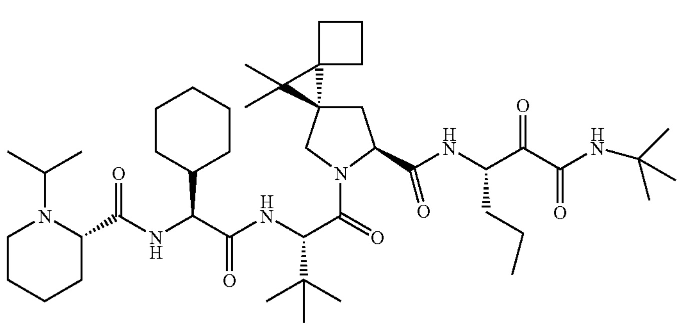 | A-87 |

TABLE B

| Structure | Compound No. |
|---|---|
| 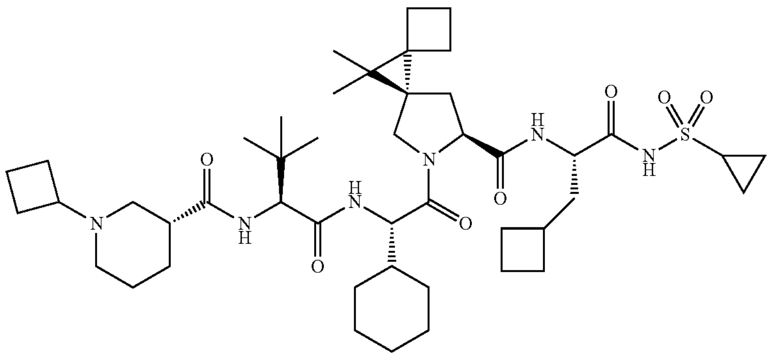 | B-1 |
| 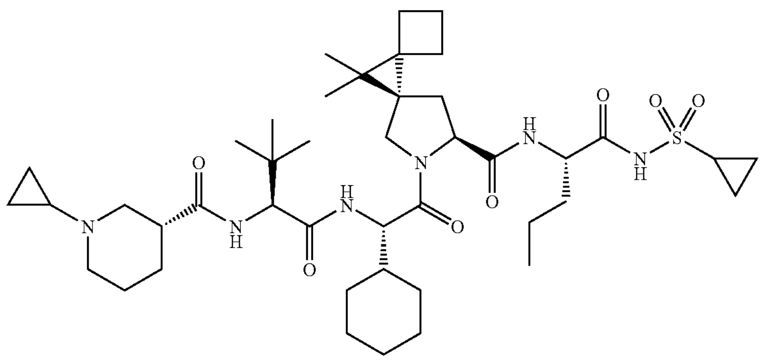 | B-2 |
| 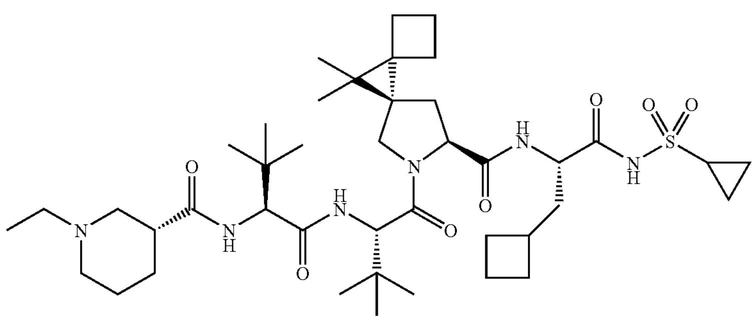 | B-3 |
| 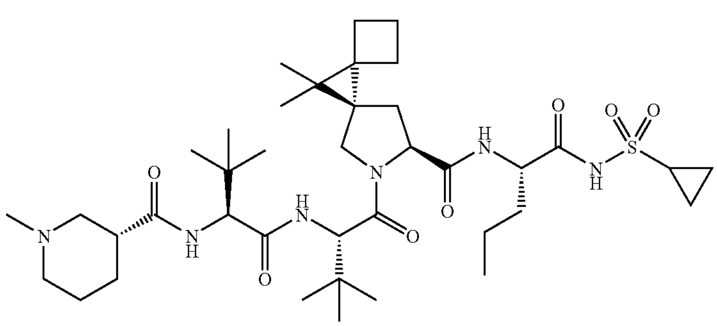 | B-4 |

TABLE B-continued

| Structure | Compound No. |
|---|---|
| 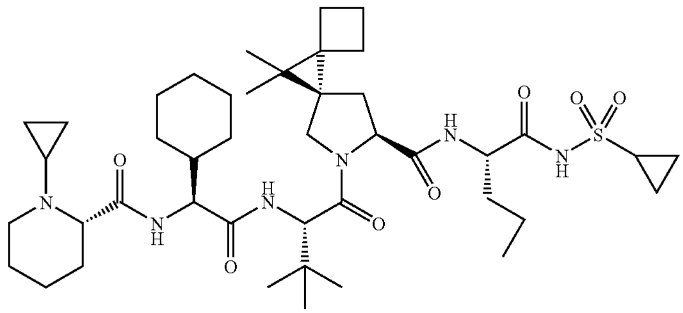 | B-5 |
| 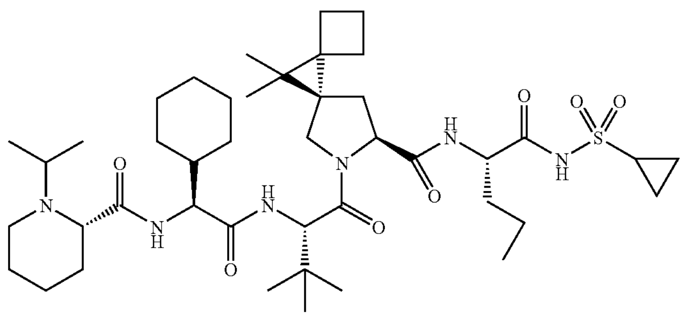 | B-6 |
| 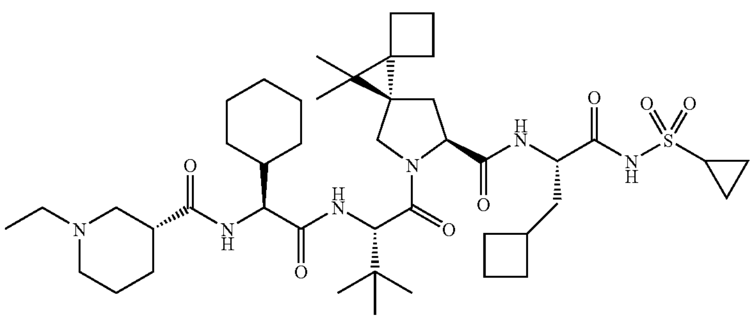 | B-7 |
| 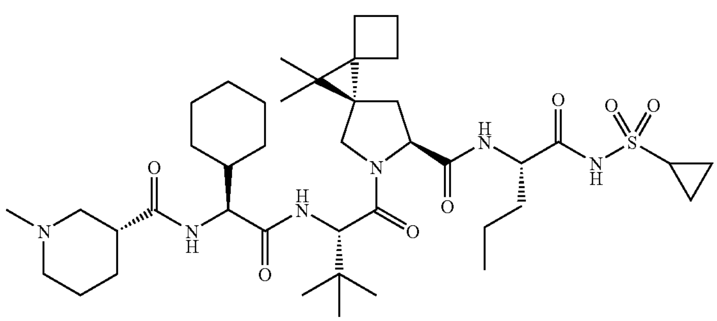 | B-8 |
| 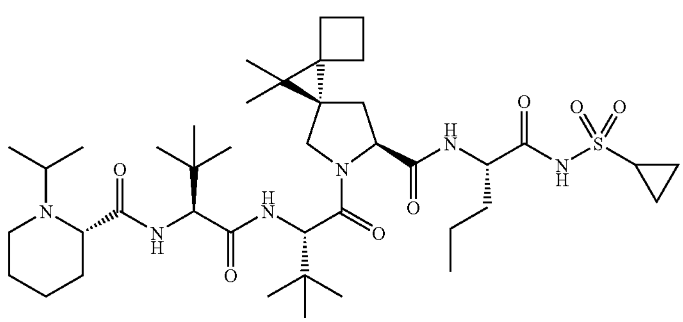 | B-9 |

TABLE B-continued

| Structure | Compound No. |
|---|---|
| 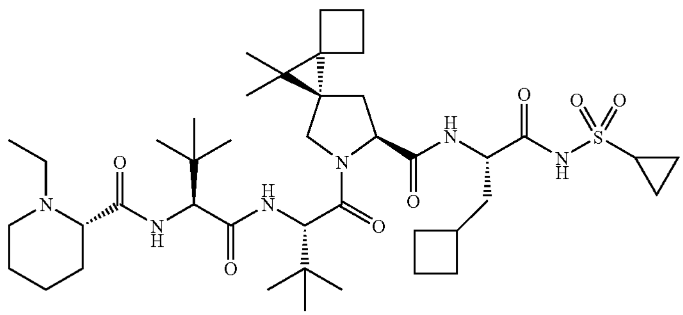 | B-10 |
| 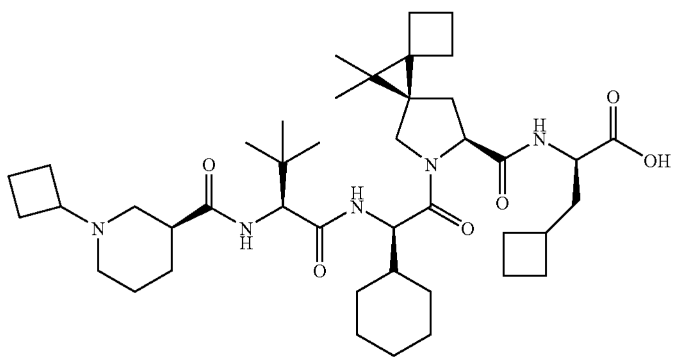 | B-11 |
| 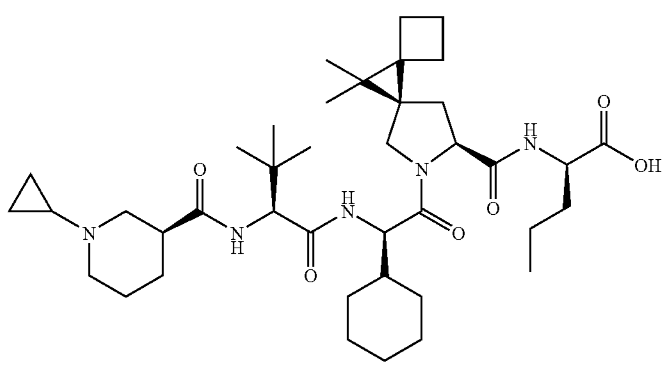 | B-12 |
| 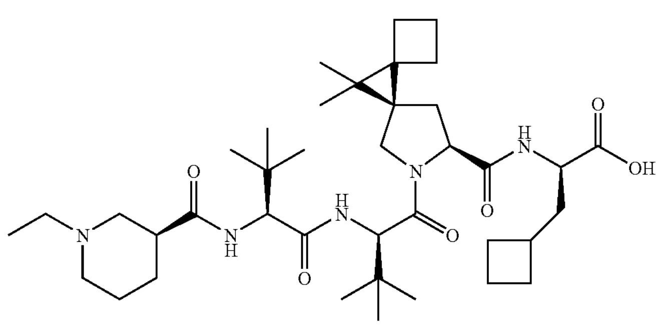 | B-13 |

TABLE B-continued

| Structure | Compound No. |
|---|---|
| 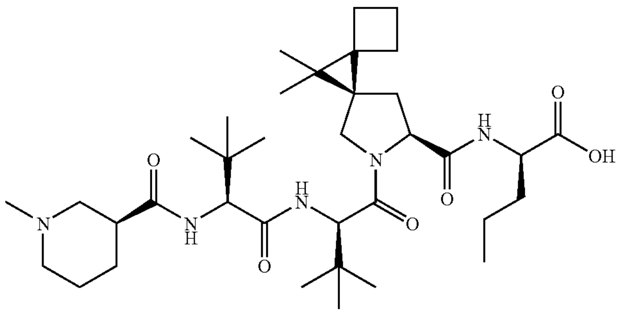 | B-14 |
| 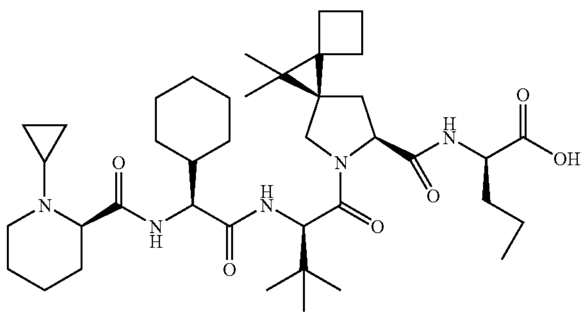 | B-15 |
| 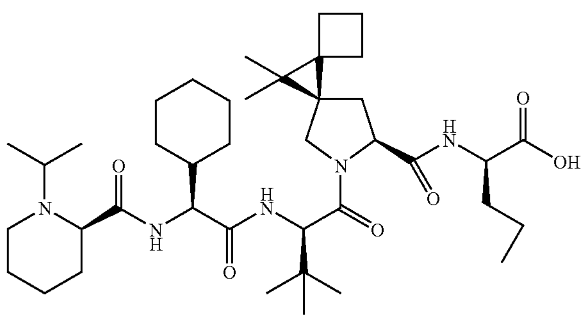 | B-16 |
| 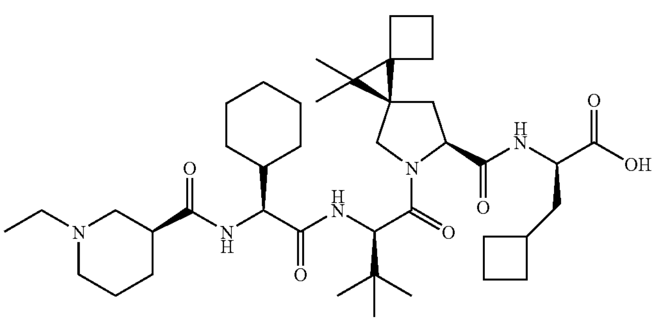 | B-17 |
| 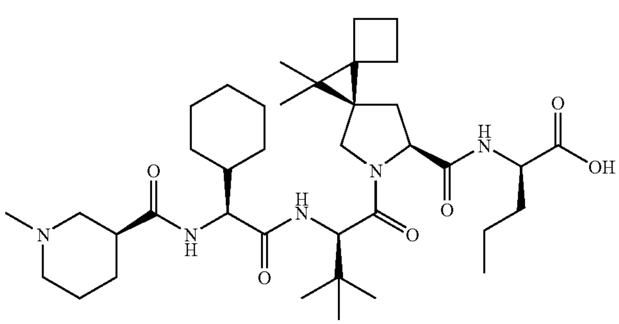 | B-18 |

TABLE B-continued

| Structure | Compound No. |
|---|---|
| 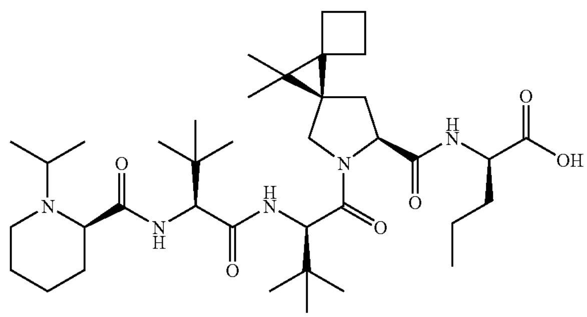 | B-19 |
| 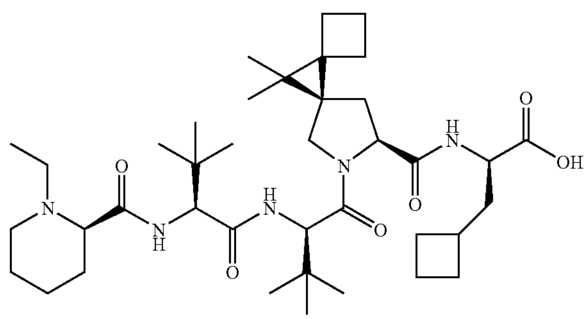 | B-20 |
| 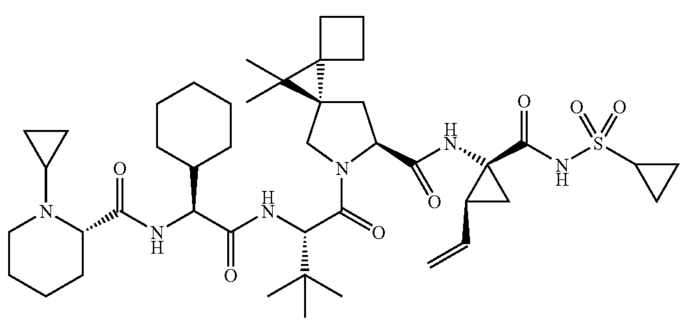 | B-21 |
| 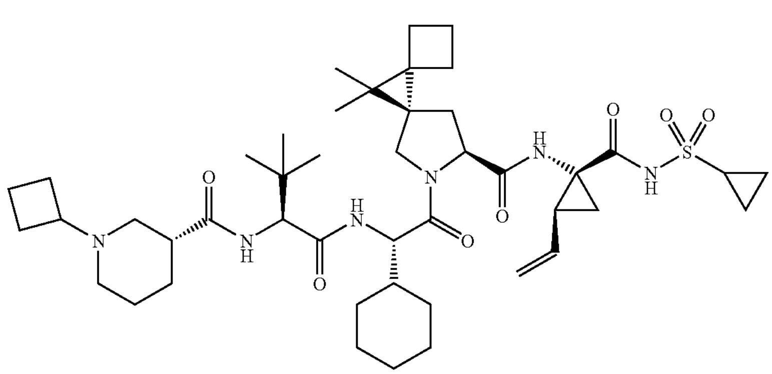 | B-22 |

TABLE B-continued

| Structure | Compound No. |
|---|---|
| 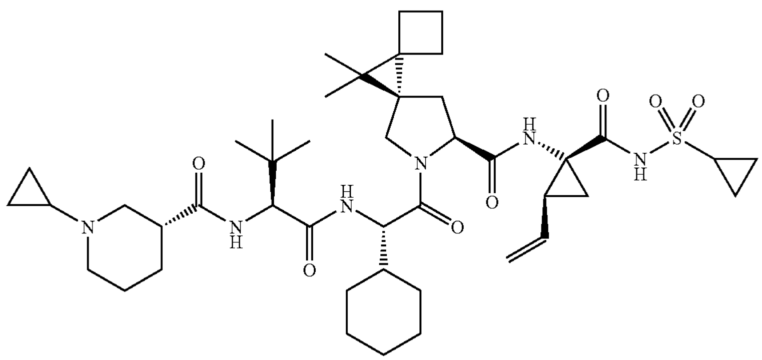 | B-23 |
| 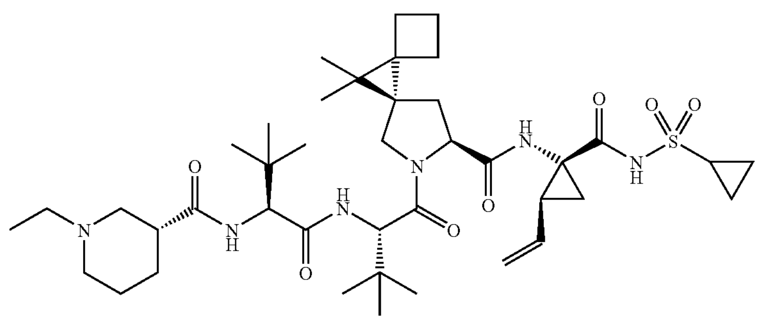 | B-24 |
| 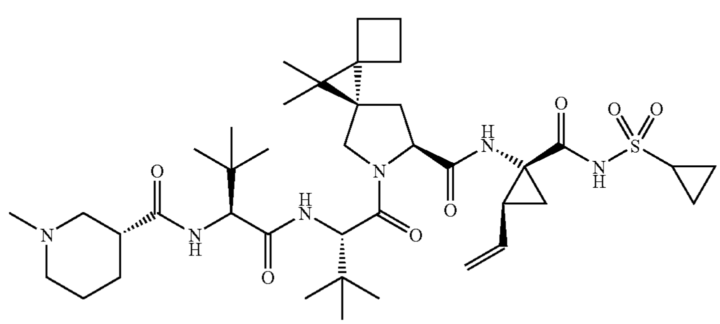 | B-25 |
| 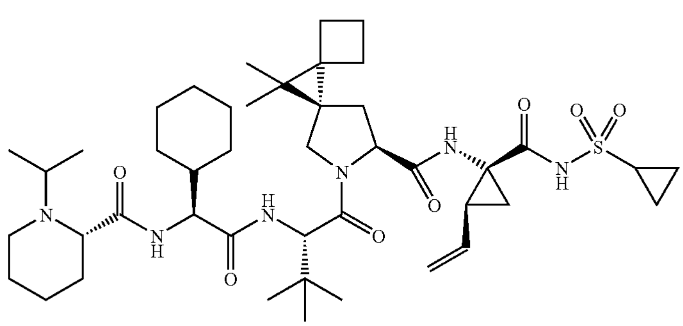 | B-26 |

TABLE B-continued

| Structure | Compound No. |
|---|---|
| 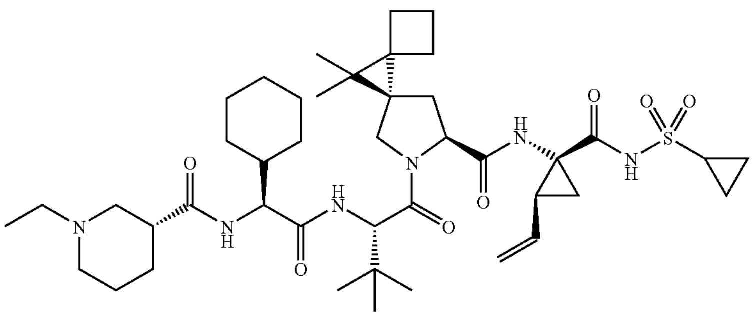 | B-27 |
| 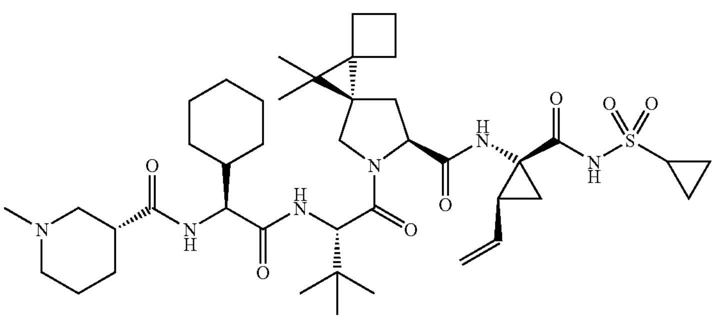 | B-28 |
| 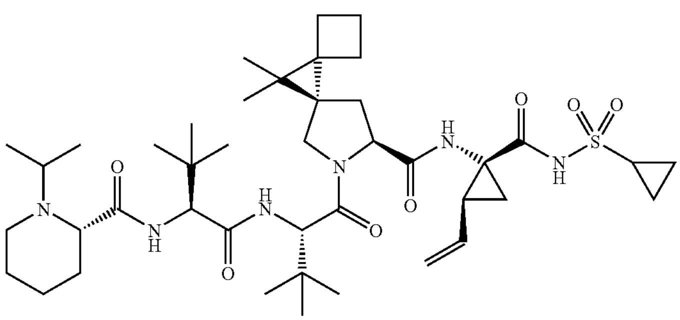 | B-29 |
| 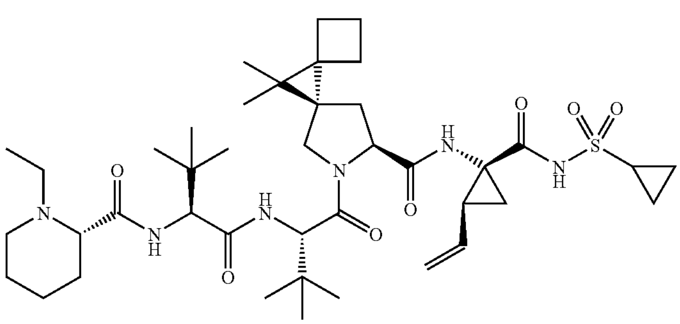 | B-30 |

TABLE B-continued

| Structure | Compound No. |
|---|---|
| 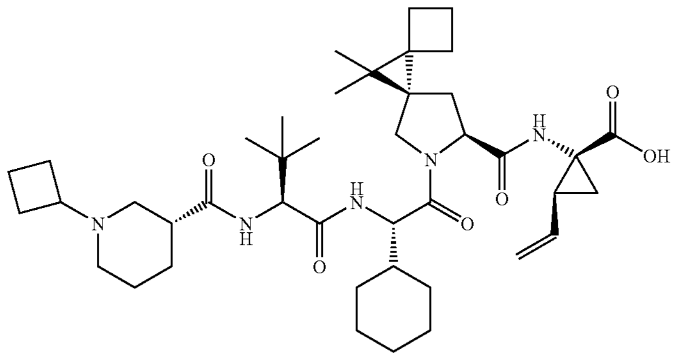 | B-31 |
| 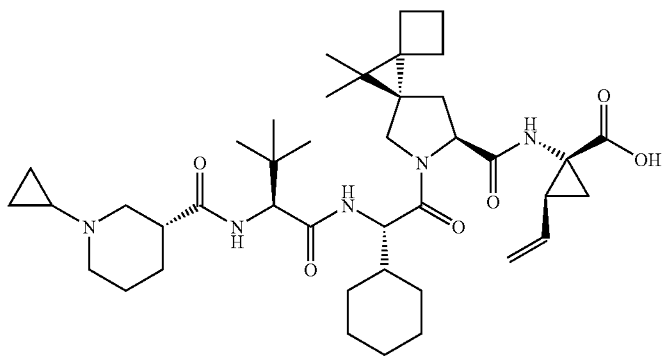 | B-32 |
| 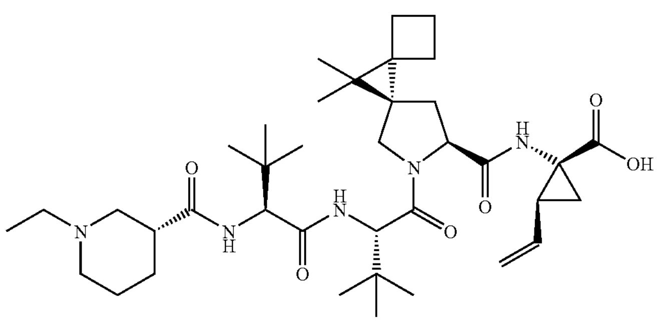 | B-33 |
| 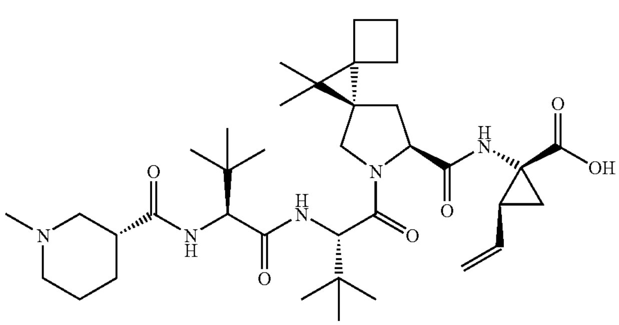 | B-34 |

TABLE B-continued

| Structure | Compound No. |
|---|---|
| 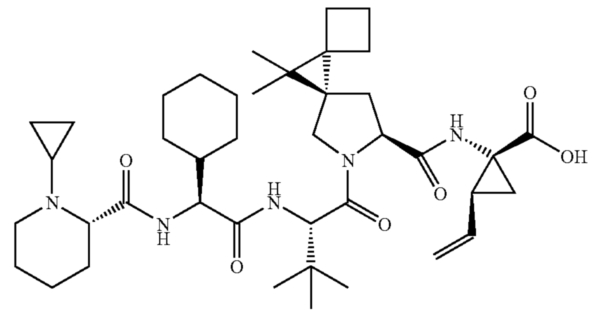 | B-35 |
| 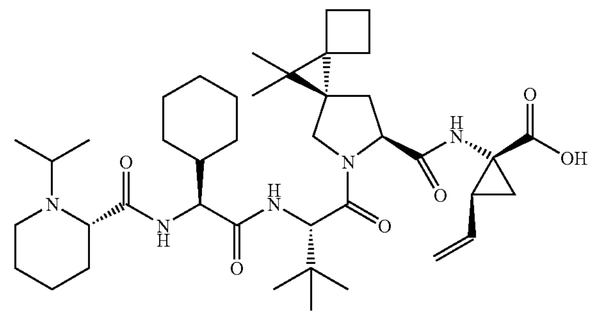 | B-36 |
| 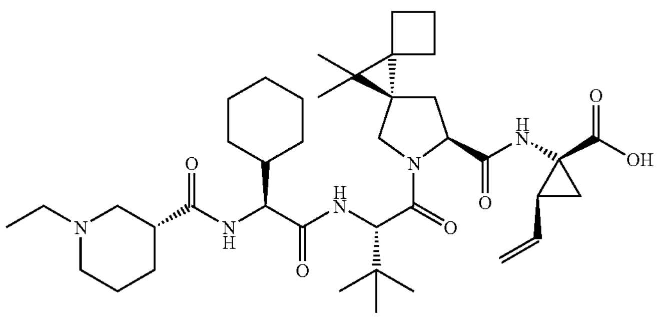 | B-37 |
| 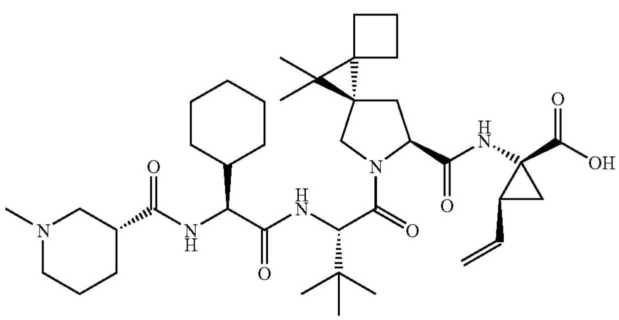 | B-38 |
| 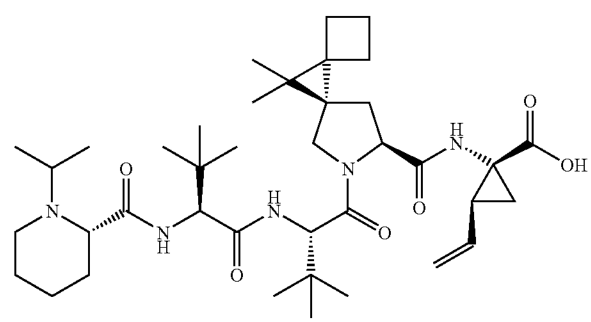 | B-39 |

TABLE B-continued

| Structure | Compound No. |
|---|---|
| 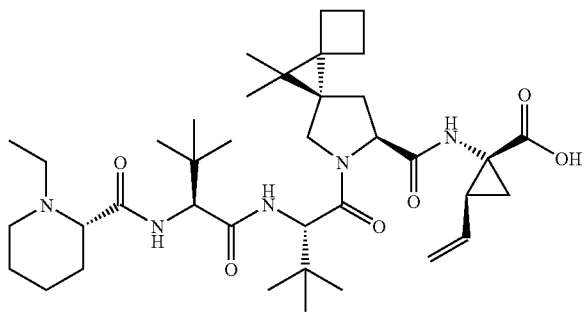 | B-40 |

Using the HCV NS3-4A protease and Luciferase-HCV replicon assays described in the exemplification section below, the compounds of the invention (including compounds of Table A depicted above) are found to show $IC_{50}$ values for HCV inhibition in the range from 0.1 to more than 100 nM, or 0.5 to 30 nM, including, for example, the range from 0.5 to 10 nM or less.

Compounds of Table A are highly soluble in aqueous media. More particularly, compounds of Table A have a solubility of at least about 100 micromolar in water at pH of about 1 and a solubility of at least 30 micromolar in water at pH of about 6.8 as measured by the solubility assay recited in the Examples infra.

Compounds of Table A further possess excellent in vivo pharmacokinetics. Generally compounds of Table A provide improved pharmacokinetics, e.g., improved oral bioavailability as measured by the procedure in Example 15 infra. More particularly, certain compounds of Table A provide at least about 20% oral bioavailability as measured by the process of Example 15 (see, Table C infra). Certain compounds of the invention, e.g., certain compounds of Formula I, provide an oral bioavailability of at least about 25%, about 30%, about 35% or about 40%.

In certain embodiments, a compound of the present invention is further characterized as a modulator of HCV, including a mammalian HCV, and especially including a human HCV. In a preferred embodiment, the compound of the invention is an HCV inhibitor.

The terms "HCV-associated state" or "HCV-associated disorder" include disorders and states (e.g., a disease state) that are associated with the activity of HCV, e.g., infection of HCV in a subject. HCV-associated states include HCV-infection, liver cirrhosis, chronic liver disease, hepatocellular carcinoma, cryoglobulinaemia, non-Hodgkin's lymphoma, and a suppressed innate intracellular immune response.

HCV-associated states are often associated with the NS3 serine protease of HCV, which is responsible for several steps in the processing of the HCV polyprotein into smaller functional proteins. NS3 protease forms a heterodimeric complex with the NS4A protein, an essential cofactor that enhances enzymatic activity, and is believed to help anchor HCV to the endoplasmic reticulum. NS3 first autocatalyzes hydrolysis of the NS3-NS4A juncture, and then cleaves the HCV polyprotein intermolecularly at the NS4A-NS4B, NS4B-NS5A and NS5A-NS5B intersections. This process is associated with replication of HCV in a subject. Inhibiting or modulating the activity of one or more of the NS3, NS4A, NS4B, NS5A and NS5B proteins will inhibit or modulate replication of HCV in a subject, thereby preventing or treating the HCV-associated state. In a particular embodiment, the HCV-associated state is associated with the activity of the NS3 protease. In another particular embodiment, the HCV-associated state is associated with the activity of NS3-NS4A heterodimeric complex.

In one embodiment, the compounds of the invention are NS3/NS4A protease inhibitors. In another embodiment, the compounds of the invention are NS2/NS3 protease inhibitors.

Without being bound by theory, it is believed that the disruption of the above protein-protein interactions by the compounds of the invention will interfere with viral polyprotein processing by the NS3 protease and thus viral replication.

HCV-associated disorders also include HCV-dependent diseases. HCV-dependent diseases include, e.g., any disease or disorder that depend on or related to activity or misregulation of at least one strain of HCV.

The present invention includes treatment of HCV-associated disorders as described above, but the invention is not intended to be limited to the manner by which the compound performs its intended function of treatment of a disease. The present invention includes treatment of diseases described herein in any manner that allows treatment to occur, e.g., HCV infection.

In a related embodiment, the compounds of the invention can be useful for treating diseases related to HIV, as well as HIV infection and AIDS (Acquired Immune Deficiency Syndrome).

In certain embodiments, the invention provides a pharmaceutical composition of any of the compounds of the present invention. In a related embodiment, the invention provides a pharmaceutical composition of any of the compounds of the present invention and a pharmaceutically acceptable carrier or excipient of any of these compounds. In certain embodiments, the invention includes the compounds as novel chemical entities.

In one embodiment, the invention includes a packaged HCV-associated disorder treatment. The packaged treatment includes a compound of the invention packaged with instructions for using an effective amount of the compound of the invention for an intended use.

The compounds of the present invention are suitable as active agents in pharmaceutical compositions that are efficacious particularly for treating HCV-associated disorders. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially an anti-HCV effect, e.g., inhibition of proliferation of the HCV virus, or of any other HCV-associated disease.

In one embodiment, the diseases to be treated by compounds of the invention include, for example, HCV infection, liver cirrhosis, chronic liver disease, hepatocellular carcinoma, cryoglobulinaemia, non-Hodgkin's lymphoma, and a suppressed innate intracellular immune response.

In other embodiments, the present invention provides a method for inhibiting the activity of HCV. The method includes contacting a cell with any of the compounds of the present invention. In a related embodiment, the method further provides that the compound is present in an amount effective to selectively inhibit the activity of one or more of the NS3, NS4A, NS4B, NS5A and NS5B proteins. In another related embodiment, the method provides that the compound is present in an amount effective to diminish the HCV RNA load in a subject.

In other embodiments, the present invention provides a use of any of the compounds of the invention for manufacture of a medicament to treat HCV infection in a subject.

In other embodiments, the invention provides a method of manufacture of a medicament, including formulating any of the compounds of the present invention for treatment of a subject.

DEFINITIONS

The term "treat," "treated," "treating" or "treatment" includes the diminishment or alleviation of at least one symptom associated or caused by the state, disorder or disease being treated. In certain embodiments, the treatment comprises the induction of an HCV-inhibited state, followed by the activation of the HCV-modulating compound, which would in turn diminish or alleviate at least one symptom associated or caused by the HCV-associated state, disorder or disease being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with an HCV-associated disorder. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from an HCV-associated disorder, and for diseases or conditions described herein, e.g., HCV infection. In another embodiment, the subject is a cell.

The language "HCV-modulating compound," "modulator of HCV" or "HCV inhibitor" refers to compounds that modulate, e.g., inhibit, or otherwise alter, the activity of HCV. Similarly, an "NS3/NS4A protease inhibitor," or an "NS2/NS3 protease inhibitor" refers to a compound that modulates, e.g., inhibits, or otherwise alters, the interaction of these proteases with one another. Examples of HCV-modulating compounds include compounds of Formula I or Formula III, as well as Table A and Table B (including pharmaceutically acceptable salts thereof, as well as enantiomers, stereoisomers, rotamers, tautomers, diastereomers, or racemates thereof).

Additionally, the method includes administering to a subject an effective amount of an HCV-modulating compound of the invention, e.g., HCV-modulating compounds of Formula I or Formula III, as well as Table A and Table B (including pharmaceutically acceptable salts thereof, as well as enantiomers, stereoisomers, rotamers, tautomers, diastereomers, or racemates thereof).

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl, isobutyl and sec-butyl. Moreover, the term $C_{3-6}$-cycloalkyl includes, but is not limited to, cyclopropyl, cyclopentyl, and cyclohexyl. As discussed below, these alkyl groups, as well as cycloalkyl groups, may be further substituted. "$C_0$-$C_n$alkyl" refers to a single covalent bond (CO) or an alkyl group having from 1 to n carbon atoms; for example "$C_0$-$C_4$alkyl" refers to a single covalent bond or a $C_1$-$C_4$alkyl group; "$C_0$-$C_8$alkyl" refers to a single covalent bond or a $C_1$-$C_8$alkyl group. In some instances, a substituent of an alkyl group is specifically indicated. For example, "$C_1$-$C_4$hydroxyalkyl" refers to a $C_1$-$C_4$alkyl group that has at least one hydroxy substituent.

"Alkylene" refers to a divalent alkyl group, as defined above. $C_0$-$C_4$alkylene is a single covalent bond or an alkylene group having from 1 to 4 carbon atoms; and $C_0$-$C_6$alkylene is a single covalent bond or an alkylene group having from 1 to 6 carbon atoms.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl. Cycloalkyl groups do not comprise an aromatic ring or a heterocyclic ring. Certain cycloalkyl groups are $C_3$-$C_8$cycloalkyl, in which the group contains a single ring with from 3 to 8 ring members. A "($C_3$-$C_8$cycloalkyl)$C_0$-$C_4$alkyl" is a $C_3$-$C_8$cycloalkyl group linked via a single covalent bond or a $C_1$-$C_4$alkylene group.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperazine, cyclopentane, cyclohexane, pyridine, 5H-tetrazole, triazole, piperidine, or an aromatic or heteroaromatic moiety.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In certain embodiments, a carbonyl moiety (C=O) may be further derivatized with an oxime moiety, e.g., an aldehyde moiety may be derivatized as its oxime (—C=N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes aromatic groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

Certain aryl groups recited herein are $C_6$-$C_{10}$aryl$C_0$-$C_8$alkyl groups (i.e., groups in which a 6- to 10-membered carbocyclic group comprising at least one aromatic ring is linked via a single covalent bond or a $C_1$-$C_8$alkylene group). Such groups include, for example, phenyl and indanyl, as well as groups in which either of the foregoing is linked via $C_1$-$C_8$alkylene, preferably via $C_1$-$C_4$alkylene. Phenyl groups linked via a single covalent bond or $C_1$-$C_6$alkylene group are designated phenyl$C_0$-$C_6$alkyl (e.g., benzyl, 1-phenyl-ethyl, 1-phenyl-propyl and 2-phenyl-ethyl).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

A "heterocycle$C_0$-$C_8$alkyl" is a heterocyclic group linked via a single covalent bond or $C_1$-$C_8$alkylene group. A (4- to 7-membered heterocycle)$C_0$-$C_8$alkyl is a heterocyclic group (e.g., monocyclic or bicyclic) having from 4 to 7 ring members linked via a single covalent bond or an alkylene group having from 1 to 8 carbon atoms. A "(6-membered heteroaryl)$C_0$-$C_6$alkyl" refers to a heteroaryl group linked via a direct bond or $C_1$-$C_6$alkyl group.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —$CH_3$ and —$CH_2CH_2CH_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

It is to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two bonds.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substitutents).

It will be noted that the structures of some of the compounds of this invention include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

Use in HCV-associated Disorders

The compounds of the present invention have valuable pharmacological properties and are useful in the treatment of diseases. In certain embodiments, compounds of the invention are useful in the treatment of HCV-associated disorders, e.g., as drugs to treat HCV infection.

The term "use" includes any one or more of the following embodiments of the invention, respectively: the use in the treatment of HCV-associated disorders; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from HCV-associated disorders, including those corresponding to HCV-infection, as well as those diseases that depend on the activity of one or more of the NS3, NS4A, NS4B, NS5A and NS5B proteins, or a NS3-NS4A, NS4A-NS4B, NS4B-NS5A or NS5A-NS5B complex. The term "use" further includes embodiments of compositions herein which bind to an HCV protein sufficiently to serve as tracers or labels, so that when coupled to a fluor or tag, or made radioactive, can be used as a research reagent or as a diagnostic or an imaging agent.

In certain embodiments, a compound of the present invention is used for treating HCV-associated diseases, and use of the compound of the present invention as an inhibitor of any one or more HCVs. It is envisioned that a use can be a treatment of inhibiting one or more strains of HCV.

Assays

The inhibition of HCV activity may be measured as using a number of assays available in the art. An example of such an assay can be found in Anal Biochem. 1996 240(1): 60-7; which is incorporated by reference in its entirety. Assays for measurement of HCV activity are also described in the experimental section below.

Pharmaceutical Compositions

The language "effective amount" of the compound is that amount necessary or sufficient to treat or prevent an HCV-associated disorder, e.g. prevent the various morphological and somatic symptoms of an HCV-associated disorder, and/or a disease or condition described herein. In an example, an effective amount of the HCV-modulating compound is the amount sufficient to treat HCV infection in a subject. In another example, an effective amount of the HCV-modulating compound is the amount sufficient to treat HCV infection, liver cirrhosis, chronic liver disease, hepatocellular carcinoma, cryoglobulinaemia, non-Hodgkin's lymphoma, and a suppressed innate intracellular immune response in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of an HCV-associated state. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats an HCV-associated disorder.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Synthetic Procedure

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups them-selves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the $H^+$ form, depending on the nature of the reaction and/or of the reactants at reduced, normal or elevated temperature, for example in a temperature range of from about $-100°$ C. to about $190°$ C., including, for example, from approximately $-80°$ C. to approximately $150°$ C., for example at from $-80$ to $-60°$ C., at room temperature, at from $-20$ to $40°$ C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Pro-drugs

The present invention also relates to pro-drugs of a compound of the present invention that are converted in vivo to the compounds of the present invention as described herein. Any reference to a compound of the present invention is therefore to be understood as referring also to the corresponding pro-drugs of the compound of the present invention, as appropriate and expedient.

Combinations

A compound of the present invention may also be used in combination with other agents, e.g., an additional HCV-modulating compound that is or is not of the formula I, for treatment of and HCV-associated disorder in a subject.

By the term "combination", is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

For example, WO 2005/042020, incorporated herein by reference in its entirety, describes the combination of various HCV inhibitors with a cytochrome P450 ("CYP") inhibitor. Any CYP inhibitor that improves the pharmacokinetics of the relevant NS3/4A protease may be used in combination with the compounds of this invention. These CYP inhibitors include, but are not limited to, ritonavir (WO 94/14436, incorporated herein by reference in its entirety), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole.

Methods for measuring the ability of a compound to inhibit CYP activity are known (see, e.g., U.S. Pat. No. 6,037,157 and Yun, et al. Drug Metabolism & Disposition, vol. 21, pp. 403-407 (1993); incorporated herein by reference). For example, a compound to be evaluated may be incubated with 0.1, 0.5, and 1.0 mg protein/ml, or other appropriate concentration of human hepatic microsomes (e.g., commercially available, pooled characterized hepatic microsomes) for 0, 5, 10, 20, and 30 minutes, or other appropriate times, in the presence of an NADPH-generating system. Control incubations may be performed in the absence of hepatic microsomes for 0 and 30 minutes (triplicate). The samples may be analyzed for the presence of the compound. Incubation conditions that produce a linear rate of compound metabolism will be used a guide for further studies. Experiments known in the art can be used to determine the kinetics of the compound metabolism ($K_m$ and $V_{max}$). The rate of disappearance of compound may be determined and the data analyzed according to Michaelis-Menten kinetics by using Lineweaver-Burk, Eadie-Hofstee, or nonlinear regression analysis.

Inhibition of metabolism experiments may then be performed. For example, a compound (one concentration, <$K_m$) may be incubated with pooled human hepatic microsomes in the absence or presence of a CYP inhibitor (such as ritonavir) under the conditions determined above. As would be recognized, control incubations should contain the same concentration of organic solvent as the incubations with the CYP inhibitor. The concentrations of the compound in the samples may be quantitated, and the rate of disappearance of parent compound may be determined, with rates being expressed as a percentage of control activity.

Methods for evaluating the influence of co-administration of a compound of the invention and a CYP inhibitor in a subject are also known (see, e.g., US2004/0028755; incorporated herein by reference). Any such methods could be used in connection with this invention to determine the pharmacokinetic impact of a combination. Subjects that would benefit from treatment according to this invention could then be selected.

Accordingly, one embodiment of this invention provides a method for administering an inhibitor of CYP3A4 and a compound of the invention. Another embodiment of this invention provides a method for administering an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In embodiments where the protease inhibitor is VX-950 (or a stereoisomer thereof), the CYP inhibitor preferably inhibits CYP3A4.

As would be appreciated, CYP3A4 activity is broadly observed in humans. Accordingly, embodiments of this invention involving inhibition of isozyme 3A4 would be expected to be applicable to a broad range of patients.

Accordingly, this invention provides methods wherein the CYP inhibitor is administered together with the compound of the invention in the same dosage form or in separate dosage forms.

The compounds of the invention (e.g., compound of Formula I or subformulae thereof) may be administered as the sole ingredient or in combination or alteration with other antiviral agents, especially agents active against HCV. In combination therapy, effective dosages of two or more agents are administered together, whereas in alternation or sequential-step therapy, an effective dosage of each agent is administered serially or sequentially. In general, combination therapy is typically preferred over alternation therapy because it induces multiple simultaneous stresses on the virus. The dosages given will depend on absorption, inactivation and excretion rate of the drug as well as other factors. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. The efficacy of a drug against the viral infection can be prolonged, augmented, or restored by administering the compound in combination or alternation with a second, and perhaps third antiviral compound that induces a different gene mutation than that caused by the principle drug in a drug resistant virus. Alternatively, the pharmacokinetic, biodistribution or other parameters of the drug can be altered by such combination or alternation therapy.

Daily dosages required in practicing the method of the present invention will vary depending upon, for example, the compound of the invention employed, the host, the mode of administration, the severity of the condition to be treated. A preferred daily dosage range is about from 1 to 50 mg/kg per day as a single dose or in divided doses. Suitable daily dosages for patients are on the order of from e.g. 1 to 20 mg/kg p.o or i.v. Suitable unit dosage forms for oral administration comprise from ca. 0.25 to 10 mg/kg active ingredient, e.g. compound of Formula I or any subformulae thereof, together with one or more pharmaceutically acceptable diluents or carriers therefor. The amount of co-agent in the dosage form can vary greatly, e.g., 0.00001 to 1000 mg/kg active ingredient.

Daily dosages with respect to the co-agent used will vary depending upon, for example, the compound employed, the host, the mode of administration and the severity of the condition to be treated. For example, lamivudine may be administered at a daily dosage of 100 mg. The pegylated interferon may be administered parenterally one to three times per week, preferably once a week, at a total weekly dose ranging from 2 to 10 million IU, more preferable 5 to 10 million IU, most preferable 8 to 10 million IU. Because of the diverse types of co-agent that may be used, the amounts can vary greatly, e.g., 0.0001 to 5,000 mg/kg per day.

The current standard of care for treating hepatitis C is the combination of pegylated interferon alpha with ribavirin, of which the recommended doses are 1.5 µg/kg/wk peginterferon alfa-2b or 180 µg/wk peginterferon alfa-2a, plus 1,000 to 1,200 mg daily of ribavirin for 48 weeks for genotype I patients, or 800 mg daily of ribavirin for 24 weeks for genotype 2/3 patients.

The compound of the invention (e.g., compound of Formula I or subformulae thereof) and co-agents of the invention may be administered by any conventional route, in particular enterally, e.g. orally, for example in the form of solutions for drinking, tablets or capsules or parenterally, for example in the form of injectable solutions or suspensions. Certain preferred pharmaceutical compositions may be e.g. those based on microemulsions as described in UK 2,222,770 A.

The compound of the invention (e.g., compound of Formula I or subformulae thereof) are administered together with other drugs (co-agents) e.g. a drug which has anti-viral activity, especially anti-Flaviviridae activity, most especially anti-HCV activity, e.g. an interferon, e.g. interferon-α-2a or interferon-α-2b, e.g. Intron® A, Roferon®, Avonex®, Rebif® or Betaferon®, or an interferon conjugated to a water soluble polymer or to human albumin, e.g. albuferon, an anti-viral agent, e.g. ribavirin, lamivudine, the compounds disclosed in U.S. Pat. No. 6,812,219 and WO 2004/002422 A2 (the disclosures of which are incorporated herein by reference in their entireties), an inhibitor of the HCV or other Flaviviridae virus encoded factors like the NS3/4A protease, helicase or RNA polymerase or a prodrug of such an inhibitor, an anti-fibrotic agent, e.g. a N-phenyl-2-pyrimidine -amine derivative, e.g. imatinib, an immune modulating agent, e.g. mycophenolic acid, a salt or a prodrug thereof, e.g. sodium mycophenolate or mycophenolate mofetil, or a SIP receptor agonist, e.g. FTY720 or an analogue thereof optionally phosphorylated, e.g. as disclosed in EP627406A1, EP778263A1, EP1002792A1, WO02/18395, WO02/76995, WO 02/06268, JP2002316985, WO03/29184, WO03/29205, WO03/62252 and WO03/62248, the disclosures of which are incorporated herein by reference in their entireties.

Conjugates of interferon to a water-soluble polymer are meant to include especially conjugates to polyalkylene oxide homopolymers such as polyethylene glycol (PEG) or polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used. Such interferon-polymer conjugates are described in U.S. Pat. Nos. 4,766,106, 4,917,888, European Patent Application No. 0 236 987, European Patent Application No. 0 510 356 and International Application Publication No. WO 95/13090, the disclosures of which are incorporated herein by reference in their entireties. Since the polymeric modification sufficiently reduces antigenic responses, the foreign interferon need not be completely autologous. Interferon used to prepare polymer conjugates may be prepared from a mammalian extract, such as human, ruminant or bovine interferon, or recombinantly produced. Preferred are conjugates of interferon to polyethylene glycol, also known as pegylated interferons.

Especially preferred conjugates of interferon are pegylated alfa-interferons, for example pegylated interferon-α-2a, pegylated interferon-α-2b; pegylated consensus interferon or pegylated purified interferon-α product. Pegylated interferon-α-2a is described e.g. in European Patent 593,868 (incorporated herein by reference in its entirety) and commercially available e.g. under the tradename PEGASYS® (Hoffmann-La Roche). Pegylated interferon-α-2b is described, e.g. in European Patent 975,369 (incorporated herein by reference in its entirety) and commercially available e.g. under the tradename PEG-INTRON A® (Schering Plough). Pegylated consensus interferon is described in WO 96/11953 (incorporated herein by reference in its entirety). The preferred pegylated α-interferons are pegylated interferon-α-2a and pegylated interferon-α-2b. Also preferred is pegylated consensus interferon.

Other preferred co-agents are fusion proteins of an interferon, for example fusion proteins of interferon-α-2a, interferon-α-2b; consensus interferon or purified interferon-α product, each of which is fused with another protein. Certain preferred fusion proteins comprise an interferon (e.g., interferon-α-2b) and an albumin as described in U.S. Pat. No. 6,973,322 and international publications WO02/60071, WO05/003296 and WO05/077042 (Human Genome Sciences). A preferred interferon conjugated to a human albumin is Albuferon (Human Genome Sciences).

Cyclosporins which bind strongly to cyclophilin but are not immunosuppressive include those cyclosporins recited in U.S. Pat. Nos. 5,767,069 and 5,981,479 and are incorporated herein by reference. MeIle[4]-Cyclosporin is a preferred non-immunosuppressive cyclosporin. Certain other cyclosporin derivatives are described in WO2006039668 (Scynexis) and WO2006038088 (Debiopharm SA) and are incorporated herein by reference. A cyclosporin is considered to be non-immunosuppressive when it has an activity in the Mixed Lymphocyte Reaction (MLR) of no more than 5%, preferably no more than 2%, that of cyclosporin A. The Mixed Lymphocyte Reaction is described by T. Meo in "Immunological Methods", L. Lefkovits and B. Peris, Eds., Academic Press, N.Y. pp. 227-239 (1979). Spleen cells ($0.5 \times 10^6$) from Balb/c mice (female, 8-10 weeks) are co-incubated for 5 days with $0.5 \times 10^6$ irradiated (2000 rads) or mitomycin C treated spleen cells from CBA mice (female, 8-10 weeks). The irradiated allogeneic cells induce a proliferative response in the Balb c spleen cells which can be measured by labeled precursor incorporation into the DNA. Since the stimulator cells are irradiated (or mitomycin C treated) they do not respond to the Balb/c cells with proliferation but do retain their antigenicity. The $IC_{50}$ found for the test compound in the MLR is compared with that found for cyclosporin A in a parallel experiment. In addition, non-immunosuppressive cyclosporins lack the capacity of inhibiting CN and the downstream NF-AT pathway. [MeIle][4]-ciclosporin is a preferred non-immunosuppressive cyclophilin-binding cyclosporin for use according to the invention.

Ribavirin (1-β-D-ribofuranosyl-1-1,2,4-triazole-3-caroxamide) is a synthetic, non-interferon-inducing, broad spectrum antiviral nucleoside analog sold under the trade name, Virazole (The Merck Index, 11th edition, Editor: Budavar, S, Merck & Co., Inc., Rahway, N.J., p1304, 1989). U.S. Pat. No. 3,798,209 and RE29,835 (incorporated herein by reference in their entireties) disclose and claim ribavirin. Ribavirin is structurally similar to guanosine, and has in vitro activity against several DNA and RNA viruses including Flaviviridae (Gary L. Davis, Gastroenterology 118:S104-S114, 2000).

Ribavirin reduces serum amino transferase levels to normal in 40% of patients, but it does not lower serum levels of HCV-RNA (Gary L. Davis, Gastroenterology 118:S104-S114, 2000). Thus, ribavirin alone is not effective in reducing viral RNA levels. Additionally, ribavirin has significant toxicity and is known to induce anemia. Ribavirin is not approved for monotherapy against HCV; it is approved in combination with interferon alpha-2a or interferon alpha-2b for the treatment of HCV.

A further preferred combination is a combination of a compound of the invention (e.g., a compound of Formula I or any subformulae thereof) with a non-immunosuppressive cyclophilin-binding cyclosporine, with mycophenolic acid, a salt or a prodrug thereof, and/or with a S1P receptor agonist, e.g. FTY720.

Additional examples of compounds that can be used in combination or alternation treatments include:

(1) Interferons, including interferon alpha 2a or 2b and pegylated (PEG) interferon alpha 2a or 2b, for example:
   (a) Intron-A®, interferon alfa-2b (Schering Corporation, Kenilworth, N.J.);
   (b) PEG-Intron®, peginteferon alfa-2b (Schering Corporation, Kenilworth, N.J.);
   (c) Roferon®, recombinant interferon alfa-2a (Hoffmann-La Roche, Nutley, N.J.);
   (d) Pegasys®, peginterferon alfa-2a (Hoffmann-La Roche, Nutley, N.J.);
   (e) Berefor®, interferon alfa 2 available (Boehringer Ingelheim Pharmaceutical, Inc., Ridgefield, Conn.);
   (f) Sumiferon®, a purified blend of natural alpha interferons (Sumitomo, Japan)
   (g) Wellferon®, lymphoblastoid interferon alpha n1 (GlaxoSmithKline);
   (h) Infergen®, consensus alpha interferon (InterMune Pharmaceuticals, Inc., Brisbane, Calif.);
   (i) Alferon®, a mixture of natural alpha interferons (Interferon Sciences, and Purdue Frederick Co., CT);
   (j) Viraferon®;
   (k) Consensus alpha interferon from Amgen, Inc., Newbury Park, Calif., Other forms of interferon include: interferon beta, gamma, tau and omega, such as Rebif (Interferon beta 1a) by Serono, Omniferon (natural interferon) by Viragen, REBIF (interferon beta-1a) by Ares-Serono, Omega Interferon by BioMedicines; oral Interferon Alpha by Amarillo Biosciences; an interferon conjugated to a water soluble polymer or to a human albumin, e.g., Albuferon (Human Genome Sciences), an antiviral agent, a consensus interferon, ovine or bovine interferon-tau Conjugates of interferon to a water-soluble polymer are meant to include especially conjugates to polyalkylene oxide homopolymers such as polyethylene glocol (PEG) or polypropylene glycols, polyoxyethylenated polyols, copolymers thereof and block copolymers thereof. As an alternative to polyalkylene oxid-based polymers, effectively non-antigenic materials such as dextran, polyvinyl pyrrolidones, polyacrylamides, polyvinyl alcohols, carbohydrate-based polymers and the like can be used. Since the polymeric modification sufficiently reduces antigenic response, the foreign interferon need not be completely autologous. Interferon used to prepare polymer conjugates may be prepared from a mammalian extract, such as human, ruminant or bovine interferon, or recombinantly produced. Preferred are conjugates of interferon to polyethylene glycol, also known as pegylated interferons.

(2) Ribavirin, such as ribavirin (1-beta-D-ribofuranosyl-1H-1,2,4-triazole-3-carboxamide) from Valeant Pharmaceuticals, Inc., Costa Mesa, Calif.); Rebetol® from Schering Corporation, Kenilworth, N.J., and Copegus® from Hoffmann-La Roche, Nutley, N.J.; and new ribavirin analogues in development such as Levovirin and Viramidine by Valeant, (3) Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

(4) Thiazolidines and benzanilides identified in Kakiuchi N. et al. *J. FEBS Letters* 421, 217-220; Takeshita N. et al. *Analytical Biochemistry*, 1997, 247, 242-246;

(5) A phenan-threnequinone possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al, *Bioorganic and Medicinal Chemistry Letters* 9, 1949-1952);

(6) Protease Inhibitors.

Examples include substrate-based NS3 protease inhibitors (Attwood et al., *Antiviral peptide derivatives*, PCT WO 98/22496, 1998; Attwood et al., *Antiviral Chemistry and Chemotherapy* 1999, 10, 259-273; Attwood et al, *Preparation and use of amino acid derivatives as anti-viral agents*, German Patent Pub. DE 19914474; Tung et al. *Inhibitors of serine proteases, particularly hepatitis C virus NS3 protease*; PCT WO 98/17679), including alphaketoamides and hydrazinoureas, and inhibitors that terminate in an electrophile such as a boronic acid or phosphonate (Llinas-Brunet et al. *Hepatitis C inhibitor peptide analogues*, PCT WO 99/07734) are being investigated.

Non-substrate-based NS3 protease inhibitors such as 2,4,6-trihydroxy-3-nitro-benzamide derivatives (Sudo K. et al., *Biochemical and Biophysical Research Communications*, 1997, 238 643-647; Sudo K. et al. *Antiviral Chemistry and Chemotherapy*, 1998, 9, 186), including RD3-4082 and RD3-4078, the former substituted on the amide with a 14 carbon chain and the latter processing apara-phenoxyphenyl group are also being investigated.

Sch 68631, a phenanthrenequinone, is an HCV protease inhibitor (Chu M et al., *Tetrahedron Letters* 37:7229-7232, 1996). In another example by the same authors, Sch 351633, isolated from the fungus *Penicillium grieofulvum*, was identified as a protease inhibitor (Chu M. et al., *Bioorganic and Medicinal Chemistry Letters* 9:1949-1952). Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, ∀-chymotrypsin, chymase and subtilisin. Qasim M. A. et al., *Biochemistry* 36:1598-1607, 1997.

U.S. patents disclosing protease inhibitors for the treatment of HCV include, for example, U.S. Pat. No. 6,004,933 to Spruce et al (incorporated herein by reference in its entirety) which discloses a class of cysteine protease inhibitors for inhibiting HCV endopeptidase 2; U.S. Pat. No. 5,990,276 to Zhang et al. (incorporated herein by reference in its entirety) which discloses synthetic inhibitors of hepatitis C virus NS3 protease; U.S. Pat. No. 5,538,865 to Reyes et al. (incorporated herein by reference in its entirety). Peptides as NS3 serine protease inhibitors of HCV are disclosed in WO 02/008251 to Corvas International, Inc., and WO 02/08187 and WO 02/008256 to Schering Corporation (incorporated herein by reference in their entireties). HCV inhibitor tripeptides are disclosed in U.S. Pat. Nos. 6,534,523, 6,410,531 and 6,420,380 to Boehringer Ingelheim and WO 02/060926 to Bristol Myers Squibb (incorporated herein by reference in their entireties). Diaryl peptides as NS3 serine protease inhibitors of HCV are disclosed in WO 02/48172 to Schering Corporation (incorporated herein by reference). Imidazoleidinones as NS3 serine protease inhibitors of HCV are disclosed in WO 02/18198 to Schering Corporation and WO 02/48157 to Bristol Myers Squibb (incorporated herein by reference in their entireties). WO 98/17679 to Vertex Pharmaceuticals and WO 02/48116 to Bristol Myers Squibb also disclose HCV protease inhibitors (incorporated herein by reference in their entireties).

HCV NS3-4A serine protease inhibitors including BILN 2061 by Boehringer Ingelheim, VX-950 by Vertex, SCH 6/7 by Schering-Plough, and other compounds currently in preclinical development;

Substrate-based NS3 protease inhibitors, including alpha-ketoamides and hydrazinoureas, and inhibitors that terminate in an elecrophile such as a boronic acid or phosphonate; Non-substrate-based NS3 protease inhibitors such as 2,4,6-trihydroxy-3-nitro-benzamide derivatives including RD3-4082 and RD3-4078, the former substituted on the amide with a 14 carbon chain and the latter processing a para-phenoxyphenyl group; and Sch68631, a phenanthrenequinone, an HCV protease inhibitor.

Sch 351633, isolated from the fungus *Penicillium griseofulvum* was identified as a protease inhibitor. Eglin c, isolated from leech is a potent inhibitor of several serine proteases such as *S. griseus* proteases A and B, a-chymotrypsin, chymase and subtilisin.

U.S. Pat. No. 6,004,933 (incorporated herein by reference in its entirety) discloses a class of cysteine protease inhibitors from inhibiting HCV endopeptidase 2; synthetic inhibitors of HCV NS3 protease (pat), HCV inhibitor tripeptides (pat), diaryl peptides such as NS3 serine protease inhibitors of HCV (pat), Imidazolidindiones as NS3 serine protease inhibitors of HCV (pat).

Thiazolidines and benzanilides (ref). Thiazolidine derivatives which show relevant inhibition in a reverse-phase HPLC assay with an NS3/4A fusion protein and NS5A/5B substrate especially compound RD-16250 possessing a fused cinnamoyl moiety substituted with a long alkyl chain, RD4 6205 and RD4 6193

Phenan-threnequinone possessing activity against protease in a SDS-PAGE and autoradiography assay isolated from the fermentation culture broth of *Streptomyces* sp, Sch68631 and Sch351633, isolated from the fungus *Penicillium griseofulvum*, which demonstrates activity in a scintillation proximity assay.

(7) Nucleoside or non-nucleoside inhibitors of HCV NS5B RNA-dependent RNA polymerase, such as 2'-C-methyl-3'-O-L-valine ester ribofuranosyl cytidine (Idenix) as disclosed in WO 2004/002422 A2 (incorporated herein by reference in its entirety), R803 (Rigel), JTK-003 (Japan Tabacco), HCV-086 (ViroPharma/Wyeth) and other compounds currently in preclinical development;

gliotoxin (ref) and the natural product cerulenin;
2'-fluoronucleosides;
other nucleoside analogues as disclosed in WO 02/057287 A2, WO 02/057425 A2, WO 01/90121, WO 01/92282, and U.S. Pat. No. 6,812,219, the disclosures of which are incorporated herein by reference in their entirety.

Idenix Pharmaceuticals discloses the use of branched nucleosides in the treatment of flaviviruses (including HCV) and pestiviruses in International Publication Nos. WO 01/90121 and WO 01/92282 (incorporated herein by reference in their entireties). Specifically, a method for the treatment of hepatitis C infection (and flaviviruses and pestiviruses) in humans and other host animals is disclosed in the Idenix publications that includes administering an effective amount of a biologically active 1', 2', 3' or 4'-branched B-D or B-L nucleosides or a pharmaceutically acceptable salt or prodrug thereof, administered either alone or in combination with another antiviral agent, optionally in a pharmaceutically acceptable carrier. Certain preferred biologically active 1', 2', 3', or 4' branched B-D or B-L nucleosides, including Telbivudine, are described in U.S. Pat. Nos. 6,395,716 and 6,875,751, each of which are incorporated herein by reference.

Other patent applications disclosing the use of certain nucleoside analogs to treat hepatitis C virus include: PCTCA00/01316 (WO 01/32153; filed Nov. 3, 2000) and PCT/CA01/00197 (WO 01/60315; filed Feb. 19, 2001) filed by BioChem Pharma, Inc., (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd. (the disclosures of which are incorporated herein by reference in their entireties)

PCT Publication No. WO 99/43691 to Emory University (incorporated herein by reference in its entirety), entitled "2'-Fluoronucleosides" discloses the use of certain 2'-fluoronucleosides to treat HCV.

Eldrup et al. (Oral Session V, Hepatitis C Virus, Flaviviridae; 16$^{th}$ International Conference on Antiviral Research (Apr. 27, 2003, Savannah, Ga.)) described the structure activity relationship of 2'-modified nucleosides for inhibition of HCV.

Bhat et al. (Oral Session V, Hepatitis C Virus, Flaviviridae, 2003 (Oral Session V, Hepatitis C Virus, Flaviviridae; 16$^{th}$ International conference on Antiviral Research (Apr. 27, 2003, Savannah, Ga.); p A75) describes the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; 16$^{th}$ International Conference on Antiviral Research (Apr. 27, 2003, Savannah, Ga.) p A76) also described the effects of the 2'-modified nucleosides on HCV RNA replication.

(8) Nucleotide polymerase inhibitors and gliotoxin (Ferrari R. et al. *Journal of Virology*, 1999, 73, 1649-1654), and the natural product cerulenin (Lohmann V. et al. *Virology*, 1998, 249, 108-118);

(9) HCV NS3 helicase inhibitors, such as VP_50406 by ViroPhama and compounds from Vertex. Other helicase inhibitors (Diana G. D. et al., Compounds, compositions and methods for treatment of hepatitis C, U.S. Pat. No. 5,633,358 (incorporated herein by reference in its entirety); Diana G. D. et al., *Piperidine derivatives, pharmaceutical compositions thereof and their use in the treatment of hepatitis C*, PCT WO 97/36554);

(10) Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 199, 181, 251-257); such as ISIS14803 by Isis Pharm/Elan, antisense by Hybridon, antisense by AVI bioPharma,

(11) Inhibitors of IRES-dependent translation (Ikeda N et al., *Agent for the prevention and treatment of hepatitis C*, Japanese Patent Pub. JP-08268890; Kai Y et al. *Prevention and treatment of viral diseases*, Japanese Patent Pub. JP-10101591); such as ISIS14803 by Isis Pharm/Elan, IRES inhibitor by Anadys, IRES inhibitors by Immusol, targeted RNA chemistry by PTC Therapeutics

(12) Ribozymes, such as nuclease-resistant ribozymes (Maccjak, D. J. et al., *Hepatology* 1999, 30, abstract 995) and those directed in U.S. Pat. No. 6,043,077 to Barber et al., and U.S. Pat. Nos. 5,869,253 and 5,610,054 to Draper et al. (incorporated herein by reference in their entireties) for example, HEPTAZYME by RPI

(13) siRNA directed against HCV genome

(14) HCV replication inhibitor of any other mechanisms such as by VP50406ViroPharama/Wyeth, inhibitors from Achillion, Arrow

(15) An inhibitor of other targets in the HCV life cycle including viral entry, assembly and maturation

(16) An immune modulating agent such as an IMPDH inhibitor, mycophenolic acid, a salt or a prodrug thereof sodium mycophenolate or mycophenolate mofetil, or Merimebodib (VX-497); thymosin alpha-1 (Zadaxin, by SciClone); or a SIP receptor agonist, e.g. FTY720 or analogue thereof optionally phosphorylated.

(17) An anti-fibrotic agent, such as a N-phenyl-2-pyrimidine-amine derivative, imatinib (Gleevac), IP-501 by Indevus, and Interferon gamma 1b from InterMune

(18) Therapeutic vaccine by Intercell, Epimmune/Genecor, Merix, Tripep (Chron-VacC), immunotherapy (Therapore) by Avant, T cell therapy by CellExSys, monoclonal antibody XTL-002 by STL, ANA 246 and ANA 246 BY Anadys,

(19) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other anti-oxidants (U.S. Pat. No. 5,922,757 to Chojkier et al.), amantadine, bile acids (U.S. Pat. No. 5,846, 99964 to Ozeki et al.), N-(phosphonoacetyl) -L-aspartic acid,) U.S. Pat. No. 5,830,905 to Diana et al.), benzenedicarboxamides (U.S. Pat. No. 5,633,388 to Diane et al.), polyadenylic acid derivatives (U.S. Pat. No. 5,496,546 to Wang et al.), 2'3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961) and piperidines (U.S. Pat. No. 5,830,905 to Diana et al.); the disclosures of which are incorporated herein by reference in their entireties. Also, squalene, telbivudine, N-(phosphonoacetyl)-L-aspartic acid, benzenedicarboxamides, polyadenylic acid derivatives, glycosylation inhibitors, and nonspecific cytoprotective agents that block cell injury caused by the virus infection.

(20) Any other compound currently in preclinical or clinical development for the treatment of HCV, including Interleukin-10 (Schering-Plough), AMANTADINE (Symmetrel) by Endo Labs Solvay, caspase inhibitor IDN-6556 by Idun Pharma, HCV/MF59 by Chiron, CIVACIR (Hepatitis C Immune Globulin) by NABI, CEPLENE (histamine dichloride) by Maxim, IDN-6556 by Idun PHARM, T67, a beta-tubulin inhibitor, by Tularik, a therapeutic vaccine directed to E2 by Innogenetics, FK788 by Fujisawa Helathcare, 1 dB1016 (Siliphos, oral silybin-phosphatidyl choline phytosome), fusion inhibitor by Trimeris, Dication by Immtech, hemopurifier by Aethlon Medical, UT 231B by United Therapeutics.

(21) Purine nucleoside analog antagonists of TlR7 (toll-like receptors) developed by Anadys, e.g., Isotorabine (ANA245) and its prodrug (ANA975), which are described in European applications EP348446 and EP636372, International Publications WO03/045968, WO05/121162 and WO05/25583, and U.S. Pat. No. 6/973322, each of which is incorporated by reference.

(21) Non-nucleoside inhibitors developed by Genelabs and described in International Publications WO2004/108687, WO2005/12288, and WO2006/076529, each of which is incorporated by reference.

(22) Other co-agents (e.g., non-immunomodulatory or immunomodulatory compounds) that may be used in combination with a compound of this invention include, but are not limited to, those specified in WO 02/18369, which is incorporated herein by reference.

Methods of this invention may also involve administration of another component comprising an additional agent selected from an immunomodulatory agent; an antiviral agent; an inhibitor of HCV protease; an inhibitor of another target in the HCV life cycle; a CYP inhibitor; or combinations thereof.

Accordingly, in another embodiment, this invention provides a method comprising administering a compound of the invention and another anti-viral agent, preferably an anti-HCV agent. Such anti-viral agents include, but are not limited to, immunomodulatory agents, such as α, β, and δ interferons, pegylated derivatized interferon-a compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase, polymerase, and metalloprotease inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above.

In accordance with the foregoing the present invention provides in a yet further aspect:

A pharmaceutical combination comprising a) a first agent which is a compound of the invention, e.g. a compound of formula I or any subformulae thereof, and b) a co-agent, e.g. a second drug agent as defined above.

A method as defined above comprising co-administration, e.g. concomitantly or in sequence, of a therapeutically effective amount of a compound of the invention, e.g. a compound of formula I or any subformulae thereof, and a co-agent, e.g. a second drug agent as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof. As recognized by skilled practitioners, dosages of interferon are typically measured in IU (e.g., about 4 million IU to about 12 million IU).

If an additional agent is selected from another CYP inhibitor, the method would, therefore, employ two or more CYP inhibitors. Each component may be administered in one or more dosage forms. Each dosage form may be administered to the patient in any order.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

EXEMPLIFICATION OF THE INVENTION

The invention is further illustrated by the following examples, which should not be construed as further limiting. The assays used throughout the Examples are accepted. Demonstration of efficacy in these assays is predictive of efficacy in subjects.

General Synthesis Methods

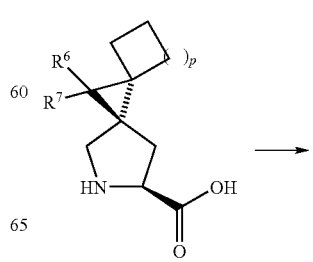

-continued

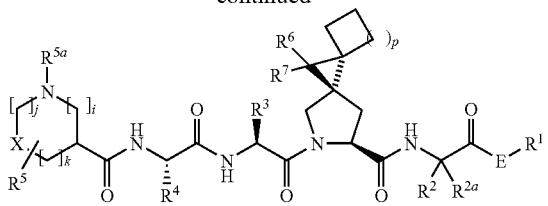

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LIST OF ABBREVIATIONS

Ac acetyl
ACN Acetonitrile
AcOEt/EtOAc Ethyl acetate
AcOH acetic acid
aq aqueous
Ar aryl
Bn benzyl
Boc tert-butyloxy carbonyl
Bu butyl (nBu=n-butyl, tBu=tert-butyl)
CDI Carbonyldiimidazole
$CH_3CN$ Acetonitrile
DBU 1,8-Diazabicyclo[5.4.0]-undec-7-ene
DCE 1,2-Dichloroethane
DCM Dichloromethane
DIPEA N-Ethyldiisopropylamine
DMAP Dimethylaminopyridine
DMF N,N'-Dimethylformamide
DMSO Dimethylsulfoxide
EI Electrospray ionization
ES+ Electrospray (positive mode)
ES− Electrospray (negative mode)
$Et_2O$ Diethylether
$Et_3N$ Triethylamine
Ether Diethylether
EtOH Ethanol
FC Flash Chromatography
h hour(s)
HATU O-(7-Azabenzotriazole-1-yl)-N,N,N'N'-tetramethyluronium hexafluorophosphate
HBTU O-(Benzotriazol-1-yl)-N,N,N',N'-tetramethyluronium hexafluorophosphate
HCl Hydrochloric acid
HOBt 1-Hydroxybenzotriazole
HPLC High Performance Liquid Chromatography
$H_2O$ Water
L liter(s)
LC-MS Liquid Chromatography Mass Spectrometry
Me methyl
MeI Iodomethane
MeOH Methanol
mg milligram
min minute(s)
mL milliliter
MS Mass Spectrometry
Pd/C palladium on charcoal
PG protecting group
Ph phenyl
Prep Preparative
Rf ratio of fronts
RP reverse phase
Rt Retention time
rt Room temperature
$SiO_2$ Silica gel
TBAF Tetrabutylammonium fluoride
TEA Triethylamine
TFA Trifluoroacetic acid
THF Tetrahydrofurane
TLC Thin Layer Chromatography
HPLC methods:
Method A:
HPLC
Instrument: Agilent system
column: waters symmetry C18, 3.5 µm, 2.1×50 mm, flow 0.6 ml/min
solvent: $CH_3CN$ (0.1% $CF_3CO_2H$); $H_2O$ (0.1% $CF_3CO_2H$)
gradient: 0-3.5 min: 20-95% $CH_3CN$, 3.5-5 min: 95% $CH_3CN$, 5.5-5.55 min 95% to 20% $CH_3CN$
Method B:
Agilent 1100 LC chromatographic system with Micromass ZMD MS detection. A binary gradient composed of A (water containing 5% acetonitrile and 0.05% trifluoroacetic acid) and B (acetonitrile containing 0.045% trifluoroacetic acid) is used as a mobile phase on a Waters X Terra™ C-18 column (30×3 mm, 2.5 µm particle size) as a stationary phase.
The following elution profile is applied: a linear gradient of 3.5 minutes at a flow rate of 0.6 ml/min from 5% of B to 95% of B, followed by an isocratic elution of 0.5 minutes at a flow rate of 0.7 ml/min of 95% of B, followed by an isocratic elution of 0.5 minutes at a flow rate of 0.8 ml/min of 95% of B, followed by a linear gradient of 0.2 minutes at a flow rate of 0.8 ml/min from 95% of B to 5% of B, followed by a isocratic elution of 0.2 minutes at a flow rate of 0.7 ml/min of 5% of B.
Method C:
HPLC
Instrument: Kontron, Kroma-System
Column: Macherey-Nagel, Lichrosphere 100-5 RP 18
Solvent: $CH_3CN$ (0.1% $CF_3CO_2H$); $H_2O$ (0.1% $CF_3CO_2H$)
Gradient: 0-5 min: 10-100% $CH_3CN$; 5-7.5 min: 100% $CH_3CN$ (Flow 1.5 mL/min)

Example 1

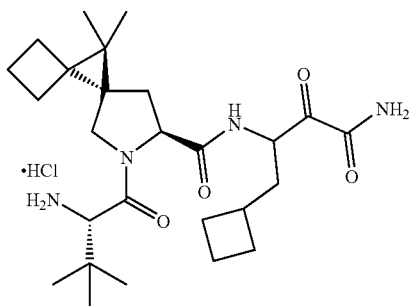

1

Step 1-A:

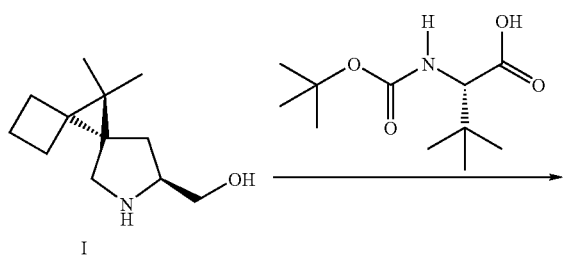

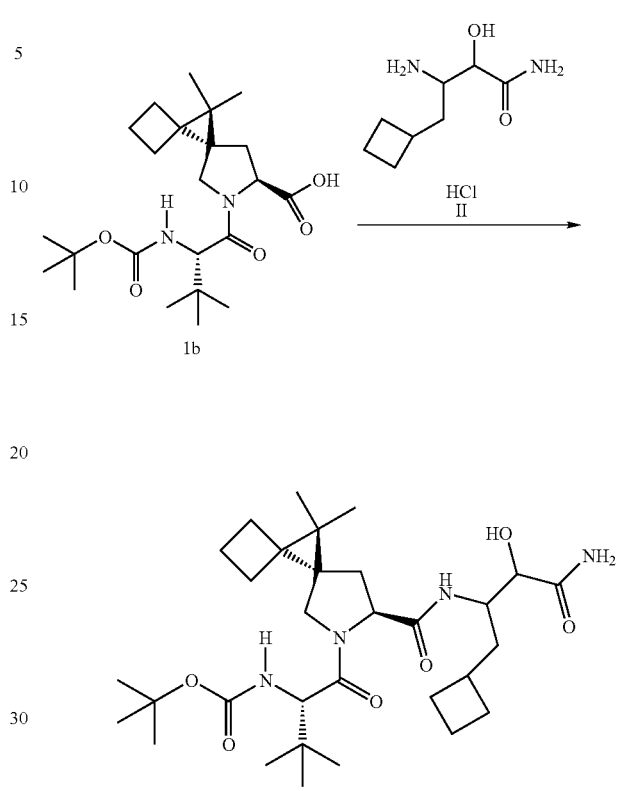

To a solution of Boc-L-t-butyl-gly-OH (711 mg, 3.08 mmol, 1.0 equiv) and amino alcohol I (600 mg, 3.08 mmol, 1.0 equiv) in CH₂Cl₂ (15.0 mL) at −20° C. is added HATU (1.4 g, 3.69 mmol, 1.2 equiv), followed by DIPEA (1.6 mL, 9.2 mmol, 3.0 equiv). The solution is stirred at −20° C. for 24 hours, 0° C. for 3 hours and room temperature for 1 hour. The reaction mixture is diluted with EtOAc and washed with 1.0 N HCl aq. solution. The phases are separated and the aqueous layer is extracted with EtOAc. The organic layers are combined and washed with saturated aqueous NaHCO₃, brine, dried over Na₂SO₄ and concentrated. The residue is purified by silica gel column chromatography (hexane/EtOAc, 1/1) to give product 1a. Found m/z ES+=409.

To a solution of alcohol 1a (890 mg) in acetone (10.0 mL) at −5° C. is added a solution of Jones' reagent (3.0 M, 5.0 mL). The mixture is warmed to 0° C. and stirred at this temperature for 2 hours. The reaction is then quenched by slow addition of i-PrOH (5.0 mL) and the mixture is then diluted with EtOAc. The phases are separated and the aqueous layer is extracted with EtOAc. The organic layers are combined, washed with brine, dried (Na₂SO₄) and concentrated to give product 1b. Found m/z ES+=423.

Step 1-B:

To a solution of acid (906 mg, 2.1 mmol) in DMF (8.0 mL) and CH₂Cl₂ (8.0 mL) at 0° C. is added HATU (958 mg, 2.5 mmol, 1.2 equiv), amino alcohol (492 mg, 2.4 mmol, 1.1 equiv) and N-methyl-morpholine (0.692 mL, 6.3 mmol, 3.0 equiv). The solution is stirred at room temperature for 3 hours. The reaction mixture is added saturated aqueous NaHCO₃ solution and EtOAc/diethyl ether 1/1. The two phases are separated and the aqueous layer is extracted with EtOAc. The organic layers are combined, washed with 1N HCl, brine, dried over Na₂SO₄ and concentrated. The crude material is purified by silica gel column chromatography (hexane/EtOH, 9/1) to give product 1c. Found m/z ES+=577.

Step 1-C:

1c ⟶

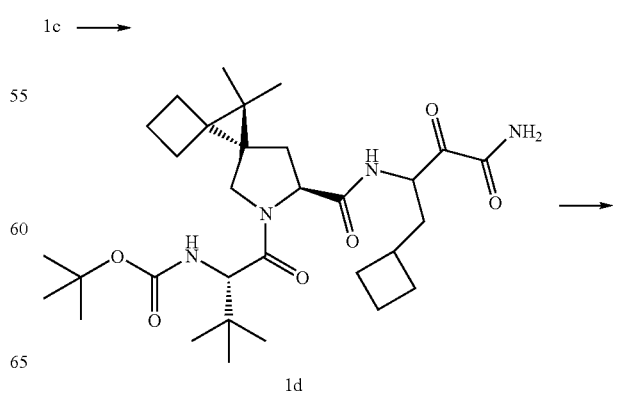

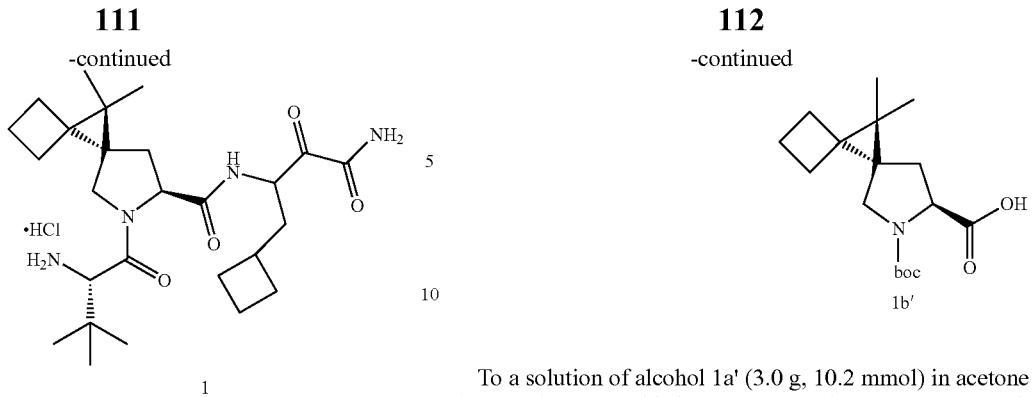

To a solution of alcohol 1c (450 mg) in CH$_2$Cl$_2$ (0.6 mL) at 0° C. is added DIPEA (0.504 mL) followed by a solution of Py.SO$_3$ complex (372 mg) in DMSO (0.6 mL). The solution is stirred at 0° C. for 10 minutes. The mixture is loaded directed to silica gel column and flushed with heptane/Acetone to give product 1d. Found m/z ES+=575.

The product is dissolved in 15 mL of 4.0 M HCl in dioxane. The solution was stirred at room temperature for 2 hours. The solution is diluted with 50 mL heptane and concentrated to give crude product 1e, which is carried on to the next step with no purification. Found m/z ES+=475.

Alternative Synthetic Route from I to 1c.

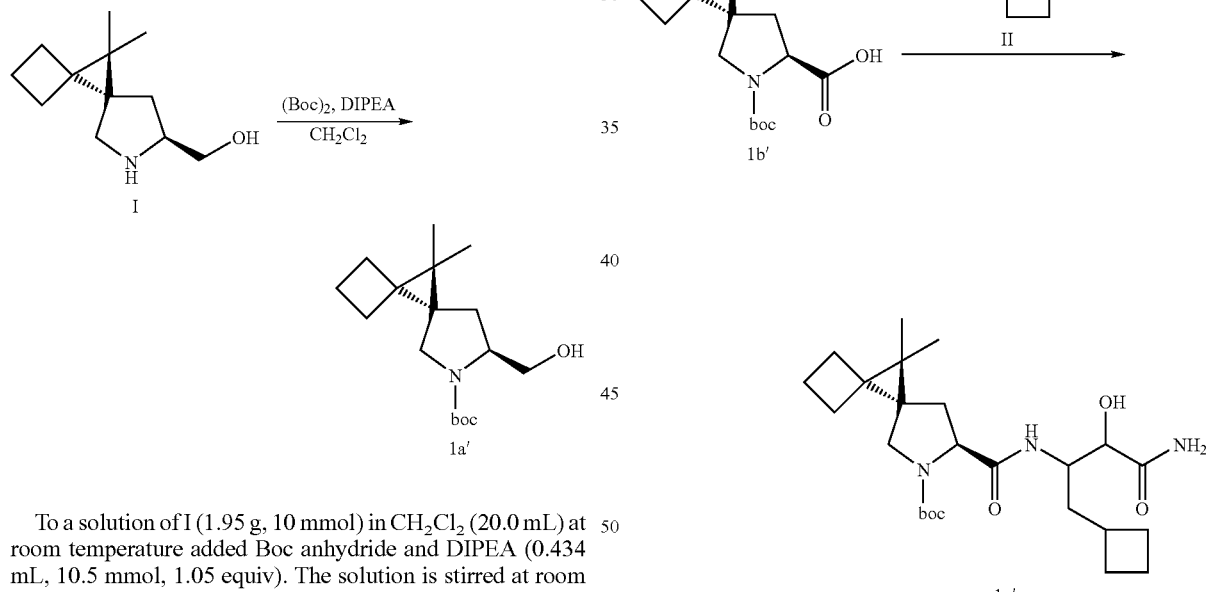

To a solution of I (1.95 g, 10 mmol) in CH$_2$Cl$_2$ (20.0 mL) at room temperature added Boc anhydride and DIPEA (0.434 mL, 10.5 mmol, 1.05 equiv). The solution is stirred at room temperature for 2 hours. The solvent is evaporated and the residue is purified by silica gel chromatography (heptane/EtOAc, 2/1) to give product 1a' 2.1 g.

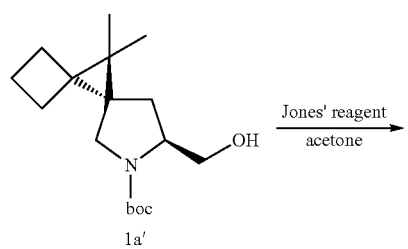

To a solution of alcohol 1a' (3.0 g, 10.2 mmol) in acetone (30.0 mL) at 0° C. added Jones' reagent (12.2 mL, 30.5 mmol, 3.0 equiv). The solution is stirred at 0° C. for 1.0 hour. The reaction is quenched by addition of i-PrOH (5.0 mL). The solution is then diluted with EtOAc and filtered. The phases are separated and the aqueous layer is extracted with EtOAc. The organic layers are combined, washed with brine, dried over Na$_2$SO$_4$ and concentrated. The crude material is 1b' is then used in the next step without further purification.

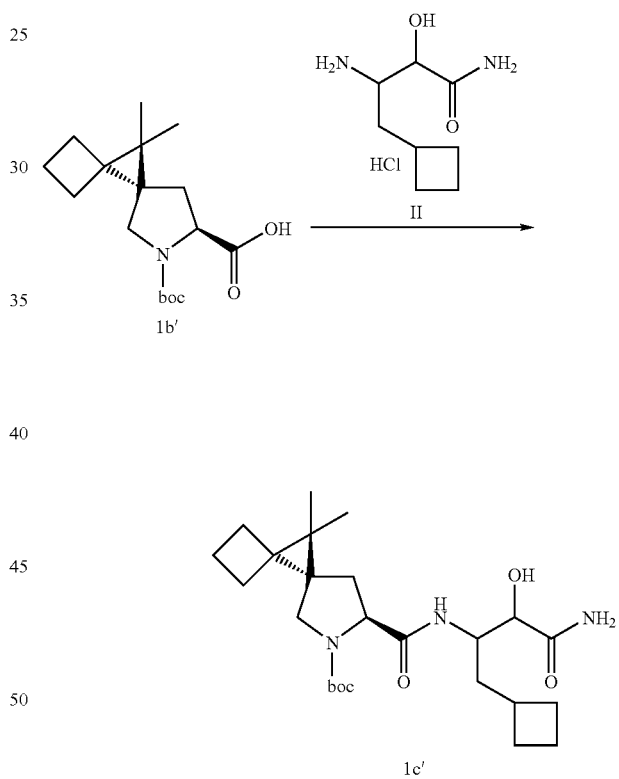

To a solution of carboxylic acid 1b' (1.0 g, 3.2 mmol) in CH$_2$Cl$_2$ (8.0 mL) and DMF (8.0 mL) at 0° C. added II (673 mg, 3.2 mmol, 1.0 equiv) followed by HATU (1.45 g, 3.8 mmol, 1.2 equiv) and N-methyl morpholine (1.05 mL, 9.6 mmol, 3.0 equiv). The solution is stirred at room temperature for 4 hours. To the solution is added EtOAc and sat. aq. NaHCO$_3$. The phases are separated and the aqueous layer is extracted with EtOAc. The organic layers are combined, washed with 1.0 N HCl aq. solution, brine, dried over Na$_2$SO$_4$ and concentrated. The residue is purified by silica gel chromatography (heptane/acetone, 1/1) to give product 1c' 975 mg. Found MS ES+=464.

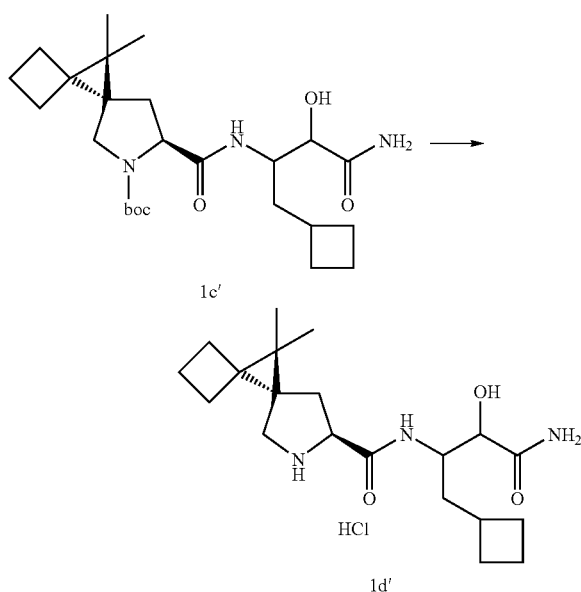

1c'

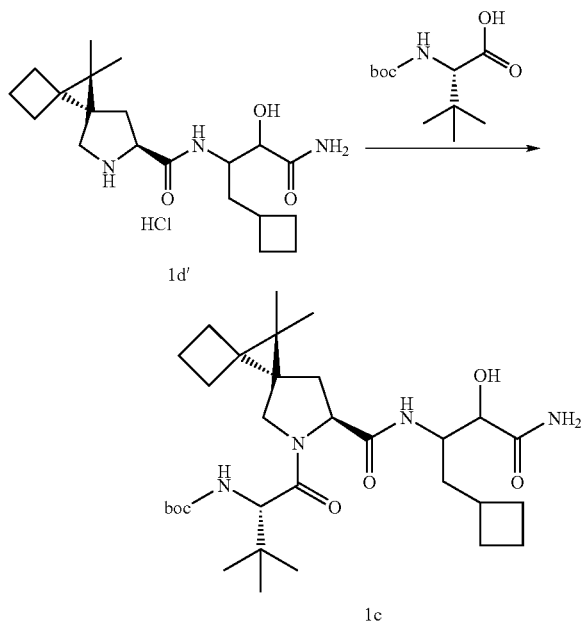

1d'

To a flask containing 1c' added 10 mL of 4.0 N HCl in dioxane. The solution is stirred at room temperature for 1.0 hour. The solvent is then evaporated to give crude product 1d', which is continued to the next step without purification. Found MS ES+=364, ES−=362.

1d'

1c

To mixtures of Boc-L-t-butyl-gly-OH (297 mg, 1.29 mmol, 1.0 equiv), 1d' (515 mg, 1.29 mmol, 1.0 equiv) in CH$_2$Cl$_2$ (7.0 mL) at −20° C. added HATU (585 mg, 1.54 mmol, 1.2 equiv) and DIPEA (0.696 mL, 4.0 mmol, 3.0 equiv). The solution is stirred at −20° C. for 12 hours then 0° C. for 1.0 hour. To the solution is added EtOAc and sat. aq. NaHCO$_3$ solution. The phases are separated and the aqueous layer is extracted with EtOAc. The organic layers are combined, washed with 1.0 N HCl aq. solution, brine, dried over Na$_2$SO$_4$ and concentrated. The residue is purified by silica gel chromatography (heptane/acetone, 1/1) to give product 1c 610 mg. Found MS ES+=577, ES−=575.

Example 2

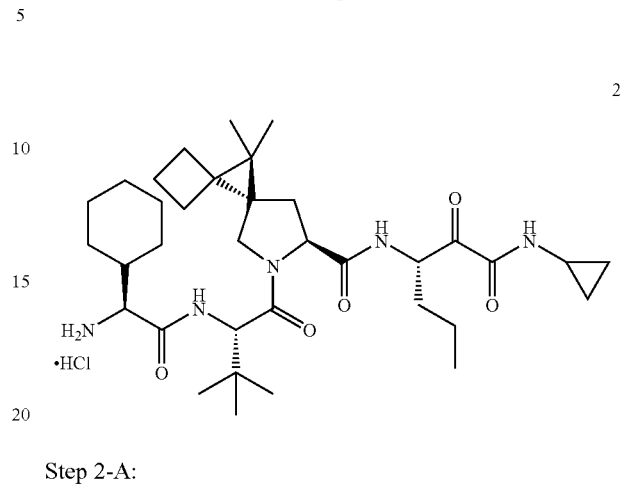

2

Step 2-A:

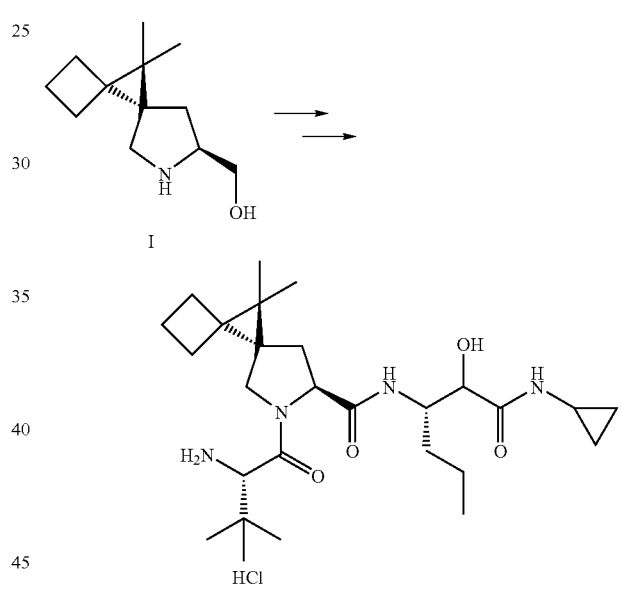

2a

Intermediate 2a is prepared according to the procedure described for the synthesis of 1f. Found MS ES+=491.

Step 2-B:

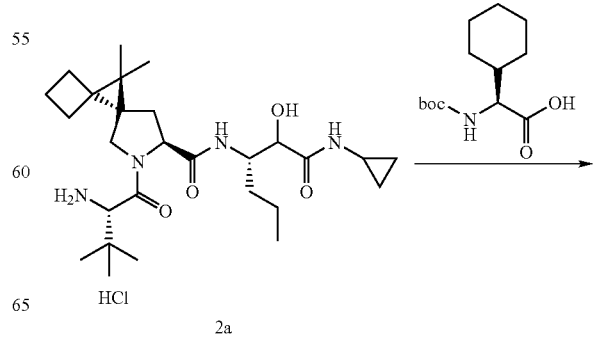

2a

115

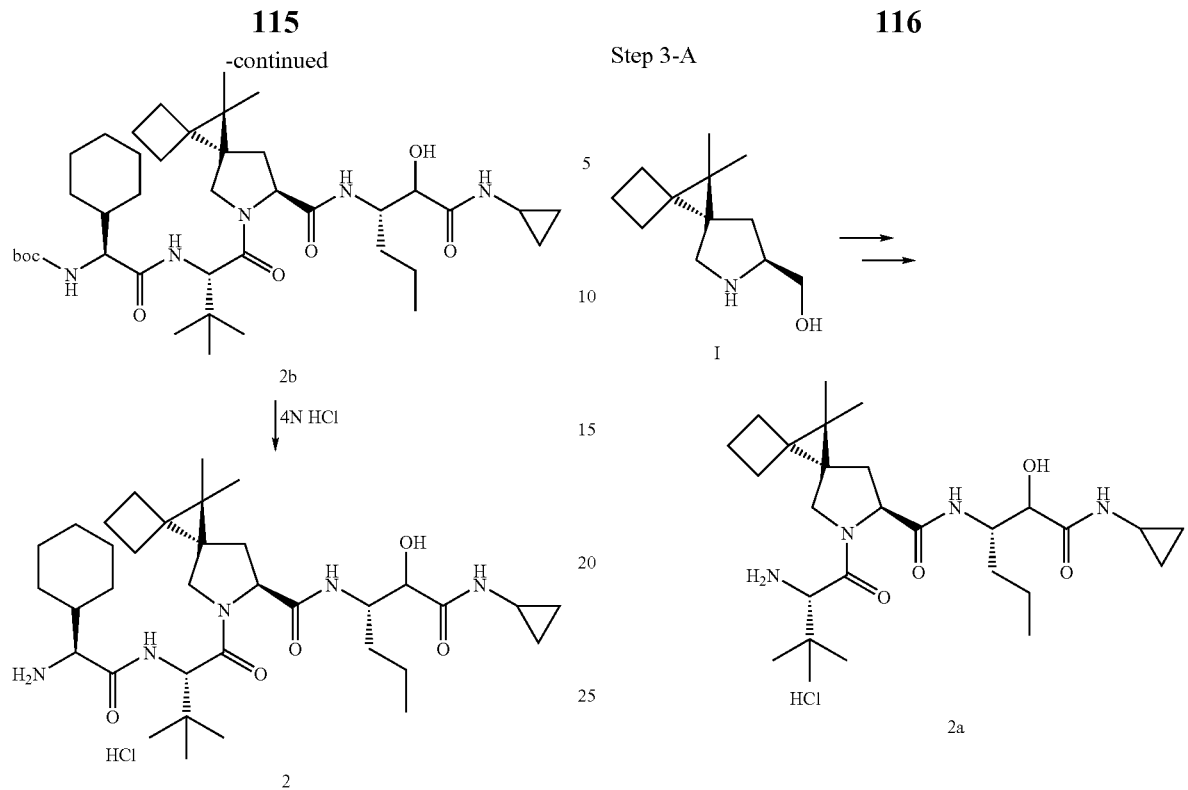

To a solution of Boc-L-cyclohexyl-gly-OH (0.391 g, 1.53 mmol) and 2a (800 mg, 1.53 mmol, 1.0 equiv) in CH$_2$Cl$_2$ (7.0 mL) and DMF (7.0 mL) at 0° C. added HATU (697 mg, 1.8 mmol, 1.2 equiv) and N-methyl morpholine (0.505 mL, 4.6 mmol, 3.0 equiv). The solution is stirred at room temperature for 4 hours. To the solution is added EtOAc and sat. aq. NaHCO$_3$. The phases are separated and the aqueous layer is extracted with EtOAc. The organic layers are combined, washed with 1.0 N HCl aq. solution, brine, dried over Na$_2$SO$_4$ and concentrated. The residue is purified by silica gel chromatography (heptane/acetone, 1/1) to give product 2b. Found MS ES+=730, ES−=728.

To a flask containing 2b (1.02 g) added 4.0 N HCl in dioxane (10.0 mL). The solvent is evaporated to give crude material 2, which is continued to the next step without purification. Found MZ ES+=630, ES−=628.

Example 3

116

Step 3-A

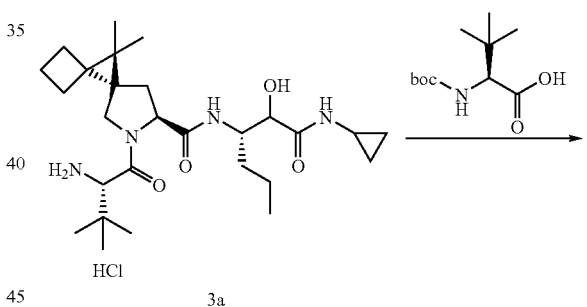

Intermediate 2a is prepared according to the procedure described for the synthesis of 1f. Found MS ES+=491.

Step 3-B

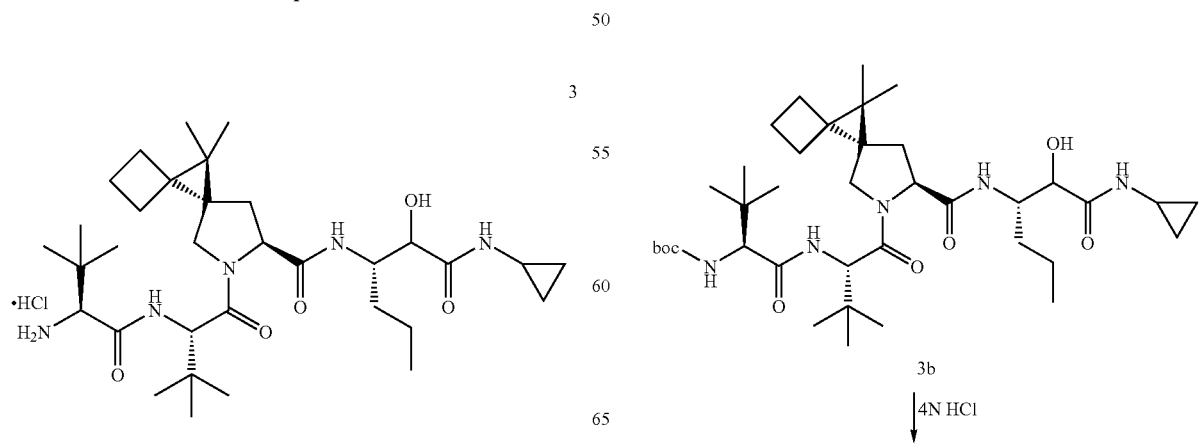

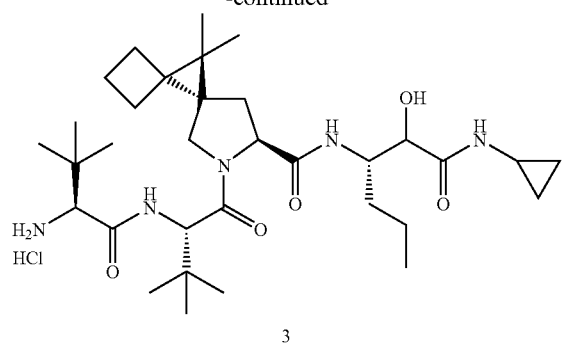

3

To a cooled solution (0° C.) of Boc-L-t-butyl-gly-OH (555 mg, 1.29 mmol, 1.0 equiv) in CH$_2$Cl$_2$ (20.0 mL) was added HATU (960 mg, 2.50 mmol, 1.05 equiv) and DIPEA (1.46 mL, 8.40 mmol, 3.5 equiv) and the solution stirred for 15 mins. A premixed solution of Amine 3a (1.28 g, 2.40 mmol, 1 equiv), DIPEA (0.43 mL, 2.40 mmol, 1.0 equiv) in CH$_2$Cl$_2$ (5.0 mL) was added to the activated acid. The solution is stirred at room temperature for 2 hours. To the solution is added EtOAc and sat. aq. NaHCO$_3$. The phases are separated and the aqueous layer is extracted with EtOAc. The organic layers are combined, washed with 1.0 N HCl aq. solution, brine, dried over Na$_2$SO$_4$ and concentrated. The residue is purified by silica gel chromatography (heptane/acetone, 1/1) to give product 3b. Found MS ES+=704, ES−=702.

To a flask containing 3b (1.02 g) added 4.0 N HCl in dioxane (10.0 mL). The solvent is evaporated to give crude material 3, which is continued to the next step without purification. Found MZ ES+=604, ES−=602.

Example 4

Compound A-6

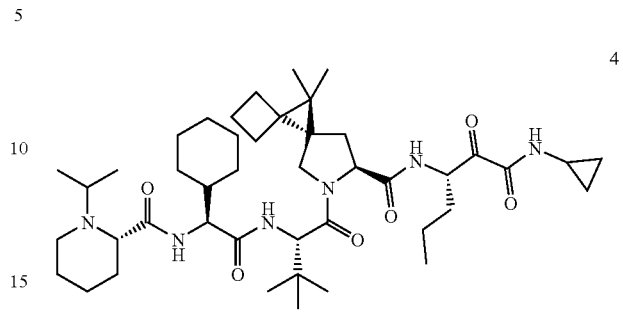

4

Step 4-A:

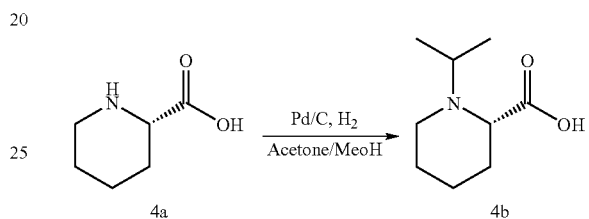

To mixtures of Pd/C (10% by wt., dry 30 mg) and methanol (5 mL) is added L-pipecolinic acid 4a (2.3 mmol, 300 mg) and acetone (1 mL). The reaction mixtures are stirred under 1 atm of H$_2$ for 16 hours. The reaction flask is then purged with N$_2$ and filtered through celite. Removal of the methanol under reduced pressure gave the desired product 4b (310 mg). Found m/z ES+=171.

Step 4-B

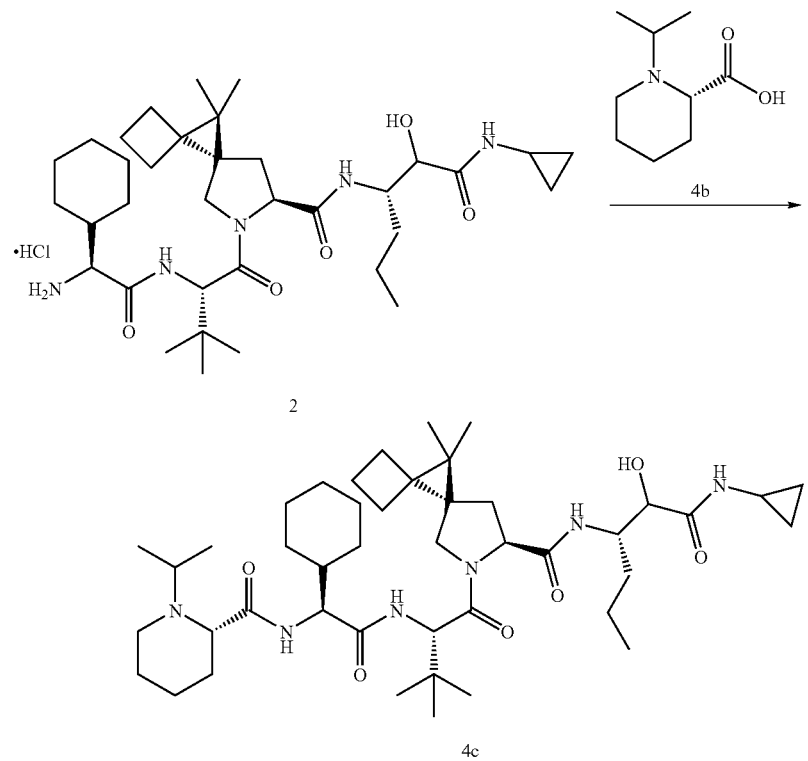

To a solution of the N-isopropyl-pipecolinic acid 4b (26 mg, 0.15 mmol) in DMF (0.8 mL) and $CH_2Cl_2$ (0.8 mL) at 0° C. is added HATU (63 mg, 0.17 mmol, 1.1 equiv), amine 2 (100 mg, 0.15 mmol, 1.0 equiv) and N-methyl-morpholine (0.07 mL, 0.60 mmol, 4.0 equiv). The solution is stirred at room temperature for 3 hours. To the reaction mixture is added saturated aqueous $NaHCO_3$ solution and EtOAc/diethyl ether 1/1. The two phases are separated and the aqueous layer is extracted with EtOAc. The organic layers are combined, washed with 1N HCl, brine, dried over $Na_2SO_4$ and concentrated. The crude material is purified by silica gel column chromatography (acetone/heptane, 6/4) to give product 4c. Found m/z ES+=783.

Step 4-C

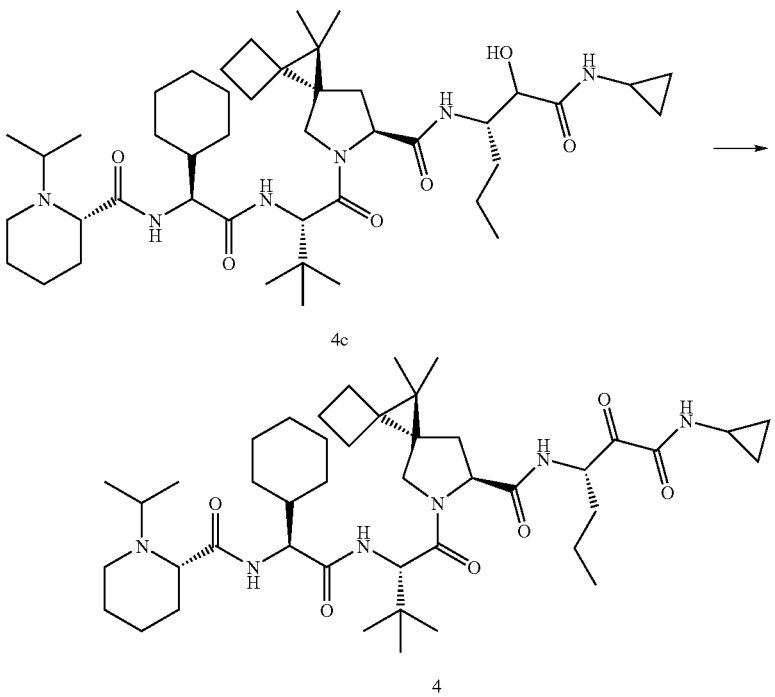

To a solution of alcohol 4c (122 mg, 0.16 mmol) in $CH_2Cl_2$ (1.0 mL) at 0° C. is added DIPEA (0.109 mL, 0.62 mmol) followed by a solution of sulfur trioxide pyridine complex (50 mg, 0.31 mmol) in DMSO (1.0 mL). The solution is stirred at 0° C. for 10 mins. The mixture is loaded directly onto a silica gel column and flushed with Acetone/Heptane 20-75% to give product 4 (50 mg). Found ES $(M+H^+)$=781.65.

Example 5

Compound A-44

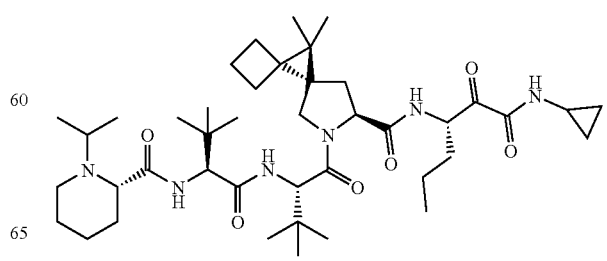

Step 5-A

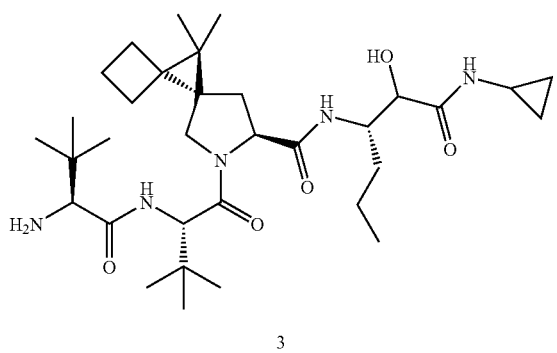

Step 6-A

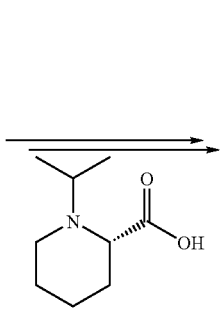

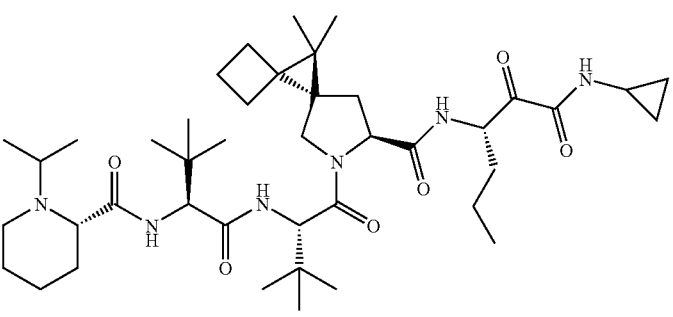

Amine 3 (synthesized as in Example 3) was coupled with 4b as in Step 4-B and oxidized as in Step 4-C to give 5 (ES (M+H$^+$)=755.61).

Example 6

Compound A-15

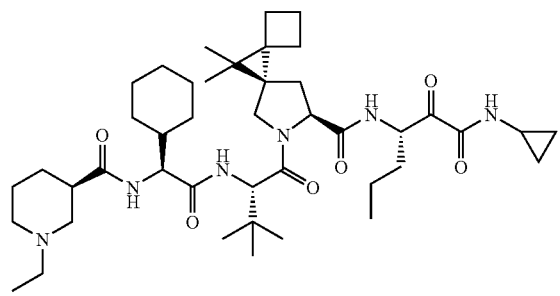

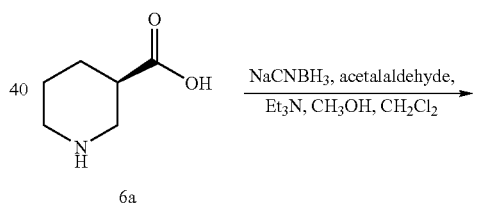

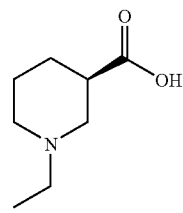

To a solution of (R)-3-piperidine-carboxylic acid 6a (1.0 eq, 5.0 g, 38.7 mmol), Et$_3$N (0.9 eq, 5.0 mL, 35.9 mmol) in DCM (80.0 mL) and methanol (80 mL) at 0° C., is added NaCNBH$_3$ (2.6 eq, 6.4 g, 102 mmol) in one portion. Acetaldehyde (3.0 eq, 6.5 mL, 116 mmol) is added dropwise, and the resulted mixtures are stirred at room temperature overnight. The mixtures are then concentrated on vacuo. Acetonitrile (80 mL) is added to the residue and the mixtures are filtered. The filtrate is concentrated in vacuo. 4N HCl in dioxane (80 mL) is added and ethyl ether (80 mL) is added. The solid is then collected by filtration to give product 6b (0.90 g).

Step 6-B

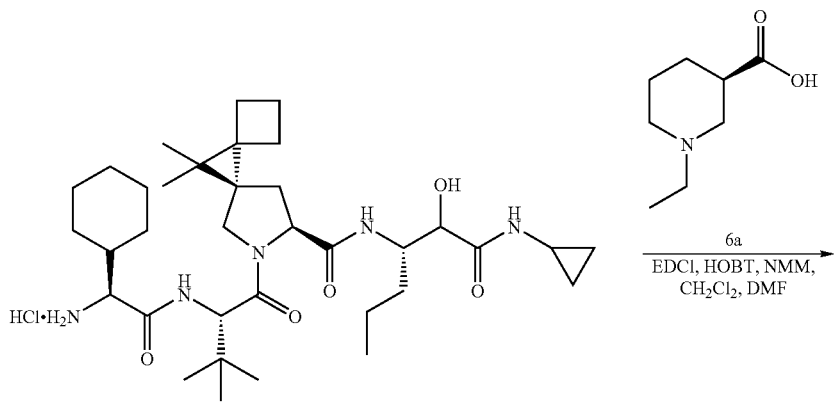

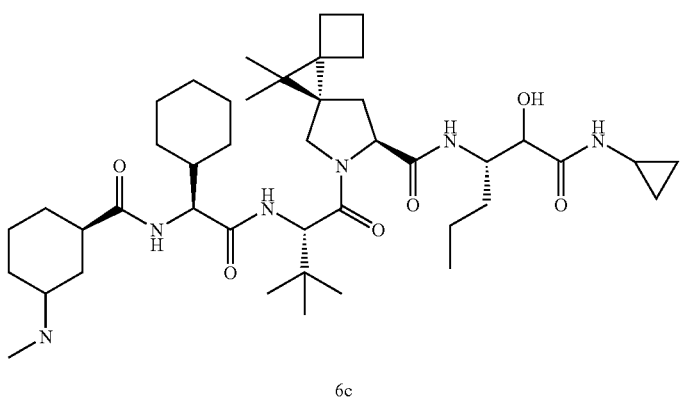

To a solution of the acid 6a (26 mg, 0.15 mmol) in DMF (1.0 mL) was added HOBt (31 mg, 0.23 mmol) and EDCI (43 mg, 0.23 mmol) and solution stirred at rt for 15 min. Then a solution of amine 2 (100 mg, 0.15 mmol) and N-methylmorpholine (0.07 mL, 0.60 mmol, 4.0 equiv). in CH$_2$Cl$_2$ (0.8 mL) was added and the mixture stirred overnight. To the reaction mixture is added saturated aqueous NaHCO$_3$ solution and EtOAc. The two phases are separated and the aqueous layer is extracted with EtOAc. The organic layers are combined, washed with brine, dried over Na$_2$SO$_4$ and concentrated. The crude material is purified by silica gel column chromatography (acetone/heptane, 6/4) to give product 6c. Found m/z ES+=769.

Step 6-C

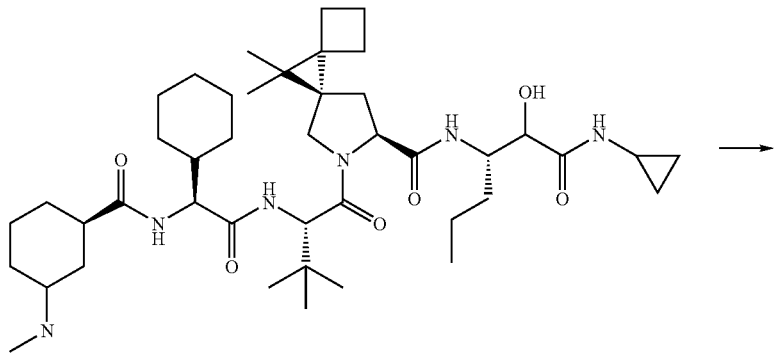

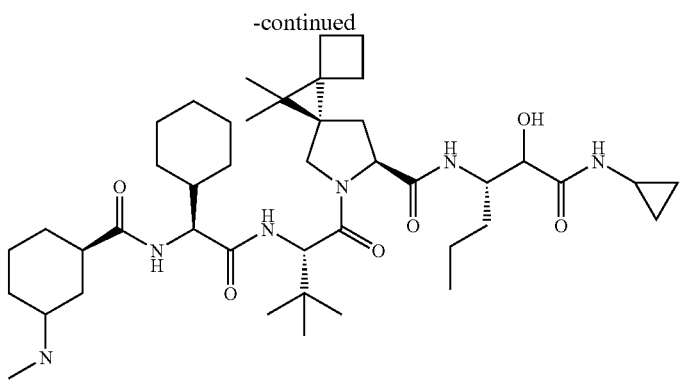

6

To a solution of alcohol 6c (44 mg, 0.06 mmol) in CH$_2$Cl$_2$ (1.0 mL) at 0° C. is added DIPEA (0.3 mL, 0.24 mmol) followed by a solution of sulfur trioxide pyridine complex (19 mg, 0.12 mmol) in DMSO (1.0 mL). The solution is stirred at 0° C. for 10 mins. The mixture is loaded directly onto a silica gel column and flushed with Acetone/Heptane 20-75% to give product 6 (22 mg). Found ES (M+H$^+$)=767.79

Step 7-A

Example 7

Compound A-4

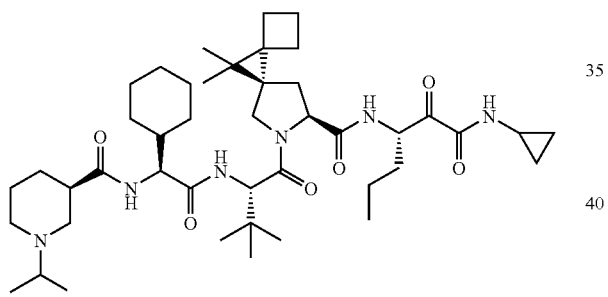

7

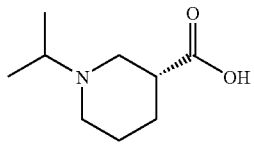

7a

Prepared in a similar manner as described in Step 4-A

Step 7-B

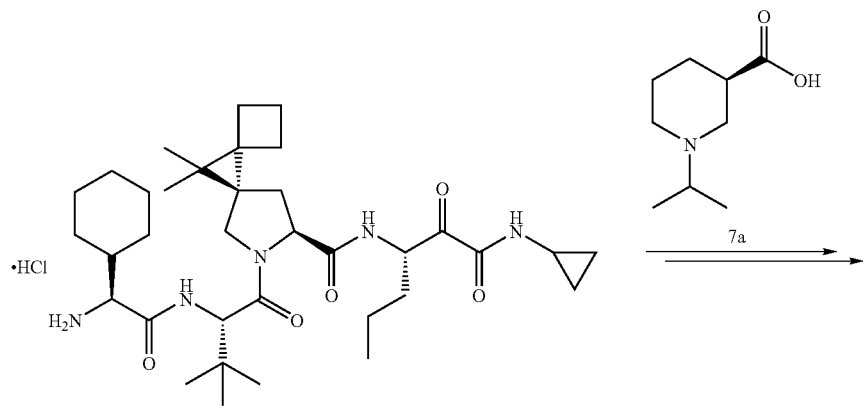

2

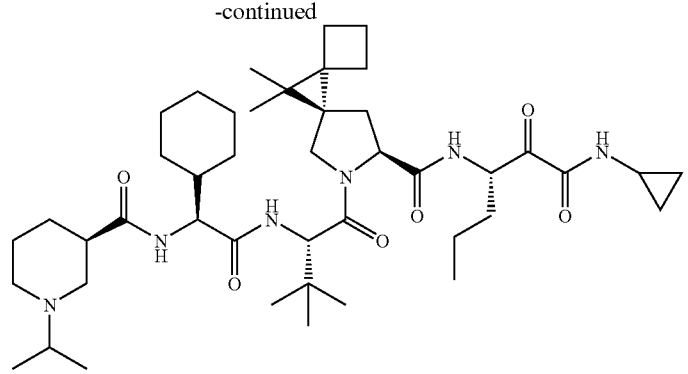

Coupled and oxidized as in Example 6. Obtained 7, Found ES (M+H⁺)=781.56.

Example 8

Compound A-50

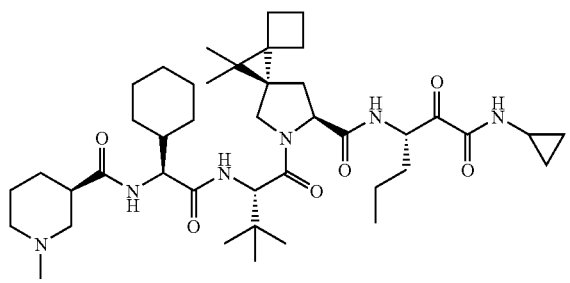

Step 8-A

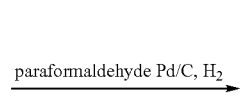

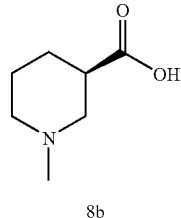

To a suspension of Pd/C (10% by wt., dry 50 mg) in methanol (8.0 mL) added R-nipecotic acid 8a (3.87 mmol, 500 mg) and paraformaldehyde (5.8 mmol, 174 mg). The flask is charged with $H_2$ and is kept stirring under a balloon of $H_2$ for 3 hours at 50° C. At this time the reaction is judged to be complete by $^{13}C$ NMR. The reaction mixture is then purged with $N_2$ and filtered through celite. Removal of the methanol under reduced pressure gave the desired product 8b (500 mg).

Step 8-B

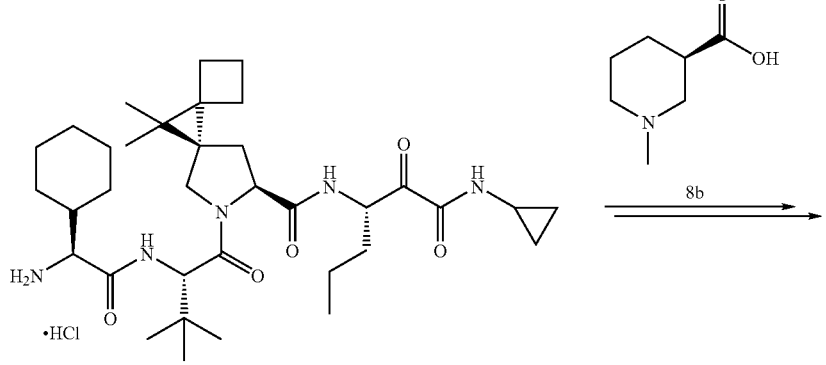

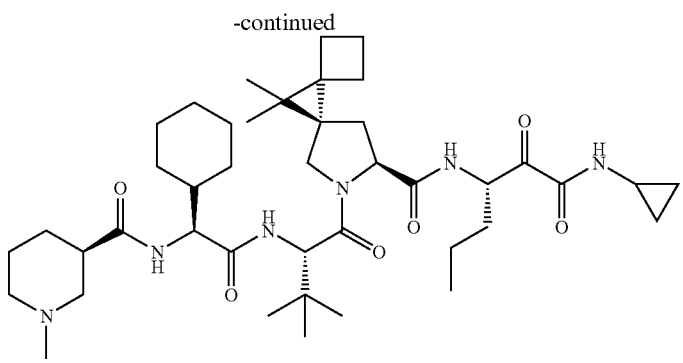
8
Coupled and oxidized as in Example 6. Obtained 8, Found ES (M+H$^+$)=753.42
Example 9
Compound A-73
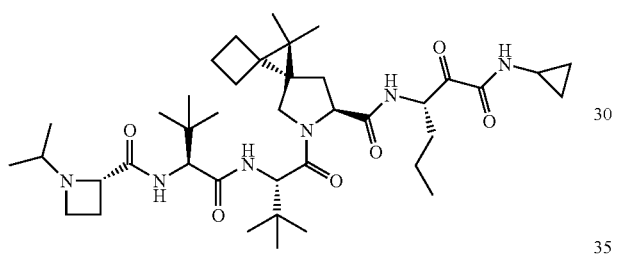
9
Step 9-A
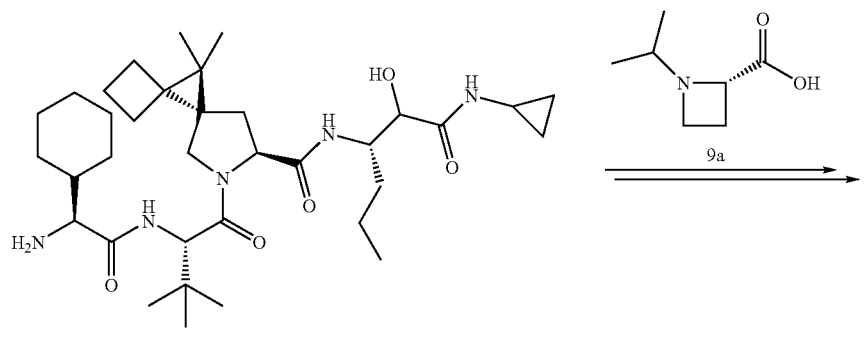
2
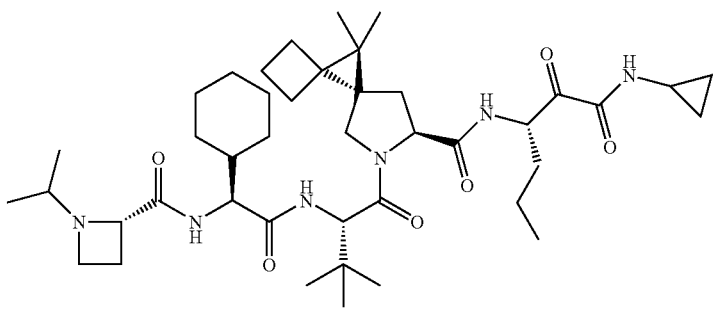
9

9a is synthesized as in step 4-A, Coupling and Oxidation as in Example 6. Found 9 m/z ES (M+H⁺)=727.37

Example 10

Synthetic Preparation of Amino-Alcohol D-9

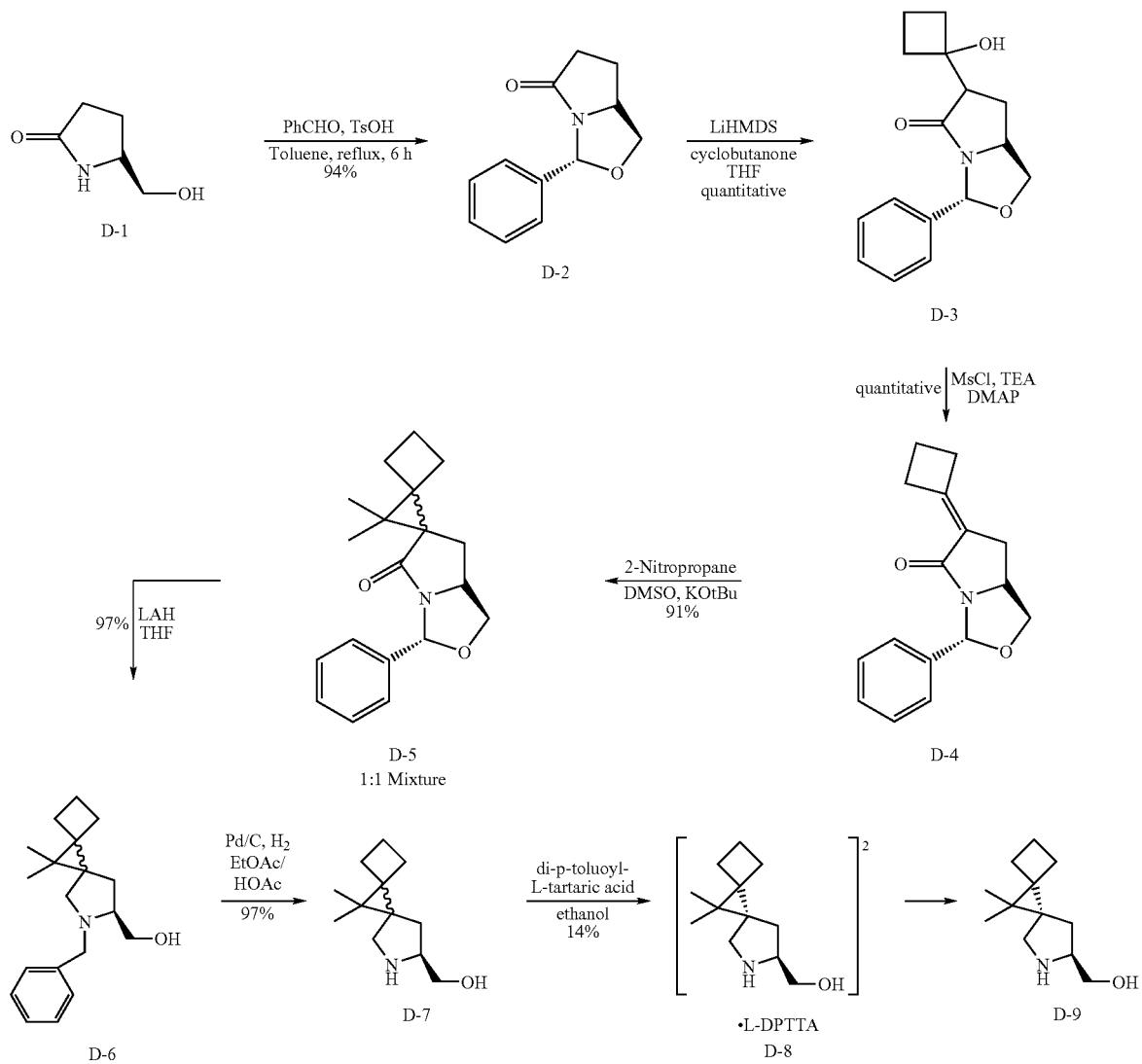

Step 1: Preparation of Intermediate D-2

A mixture of (S)-(+)-5-hydroxymethyl-2-pyrrolidinone D-1 (20.0 g, 0.17 mol), benzaldehyde (20.3 g, 0.19 mol), and p-toluenosulfonic acid (0.38 g, 0.002 mol) in toluene (235 mL) is refluxed for 17 h while collecting water using a Dean-Stark water separator. The cooled reaction mixture is washed with 5% NaHCO₃ (2×50 mL), saturated NaHSO₃ (4×50 mL), and brine (2×5 mL). The organic layer is dried over MgSO₄ and concentrated to give compound D-2 (31.2 g, 88.5%) as a light yellow oil which is used directly in the next step without further purification.

Step 2: Preparation of Intermediate D-3

The 2-L, 4-necked round-bottomed flask equipped with a mechanical stirrer, addition funnel, digital thermometer and condenser with nitrogen inlet-outlet is charged with 50.8 g (0.250 mol) of crude compound D-2 and 400 mL of THF. Cool the solution to an internal temperature of −75±2° C. and add 262.5 mL (0.263 mol) of lithium bis(trimethylsilyl)amide 1.0 M solution in THF over 1.5 h while maintaining an internal temperature at −75±2° C. Stir the reaction mixture at an internal temperature −75±2° C. for 1.5 h. Add the solution of 19.3 g (0.275 mol) of cyclobutanone in 200 mL of THF over 1 h while maintaining an internal temperature at −75±2° C. and stir at this temperature for 1.5 h. Add to the reaction mixture 700 mL of saturated aqueous solution of ammonium chloride over 0.5 h at an internal temperature of −75 to −35° C. Warm up the reaction mixture to an internal temperature 20±2° C. and add 700 mL of ethyl acetate. Separate the phases and extract the aqueous phase with 2×500 mL of ethyl acetate. Combine the organic layers and wash with 700 mL of 15% aqueous of sodium chloride. Separate the phases and concentrate the organic layer (~2.7 L) under reduced pressure (75-32 mbar) at an internal temperature 30-35° C. to afford 71.7 g of crude compound D-3 as an oil.

Step 3: Preparation of Intermediate D-4

The 1-L, 4-necked round-bottomed flask equipped with a mechanical stirrer, addition funnel, digital thermometer and condenser with nitrogen inlet-outlet is charged with 34.2 g (0.125 mol) of crude compound D-3 and 420 mL of $CH_2Cl_2$. Cool the solution to an internal temperature of 0±2° C. and add 63.2 g (0.63 mol) of triethylamine over 25 minutes while maintaining an internal temperature at 0±2° C. Then add 3.1 g (0.025 mol) of 4-(dimethylamino)pyridine. Stir the reaction mixture at an internal temperature 0±2° C. for 20 min. Add 21.5 g (0.19 mol) of methanesulfonyl chloride over 25 minutes while maintaining an internal temperature at 0±2° C. and stir at this temperature for 0.5 h. Warm up the reaction mixture to an internal temperature 43±2° C. and stir at this temperature for 20 h. Cool the reaction mixture to an internal temperature of 0±2° C. and add 280 mL of sat. aqueous solution of ammonium chloride and 280 mL of ethyl acetate. Separate the phases and extract the aqueous phase with 2×250 mL of ethyl acetate. Combine the organic layers and wash with 350 mL of 15% aqueous of sodium chloride. Separate the phases and concentrate the organic layer (~1.4 L) under reduced pressure (150-12 mbar) at an internal temperature 35-40° C. to afford 32.5 g of crude compound D-4 as an oil.

Step 4: Preparation of Intermediate D-5

The 2-L, 4-necked round-bottomed flask equipped with a mechanical stirrer, addition funnel, digital thermometer and condenser with nitrogen inlet-outlet is charged with 28.0 g (0.25 mol) of potassium tert-butoxide and 215 mL of DMSO. Stir the mixture at an internal temperature 22±2° C. for 15 minutes to get a solution and add 22.3 g (0.25 mol) g of 2-nitropropane over 45 minutes while maintaining an internal temperature at 22-32° C. Stir the reaction mixture at an internal temperature 22±2° C. for 0.5 h. Then add the solution of 31.9 g (0.125 mol) of crude compound D-4 in 90 mL of DMSO over 25 minutes while maintaining an internal temperature at 22±2° C. Stir the reaction mixture at an internal temperature 22±2° C. for 0.5 h. Warm up the reaction mixture to an internal temperature 100±2° C. and stir at this temperature for 85 h. Cool the reaction mixture to an internal temperature of 0±2° C. and add 610 mL of water and 600 mL of ethyl acetate. Separate the phases and extract the aqueous phase with 2×300 mL of ethyl acetate. Combine the organic layers and wash with 3×400 mL of 15% aqueous of sodium chloride. Separate the phases and concentrate the organic layer (~1.2 L) under reduced pressure (100-12 mbar) at an internal temperature 35-40° C. to afford 34.3 g of crude compound D-5 as dark orange oil.

Step 5: Preparation of Intermediate D-6

The 1-L, 4-necked round-bottomed flask equipped with a mechanical stirrer, addition funnel, digital thermometer and condenser with nitrogen inlet-outlet is charged with 32.7 g (0.11 mol) of crude compound D-5 and 0.7 L of THF. Cool the reaction mixture to an internal temperature of 0±2° C. and add 12.5 g (0.33 mol) of $LiAlH_4$ over 1 h while maintaining an internal temperature at 0±2° C. Stir the mixture at an internal temperature 0±2° C. for 1 h. Warm up the reaction mixture to an internal temperature 22±2° C. and stir at this temperature for 20 h. Cool the reaction mixture to an internal temperature of 0±2° C. and add 12.5 mL of water and 12.5 mL of 15% aqueous solution of sodium hydroxide and 37.5 mL of water over 25 minutes while maintaining an internal temperature at 0-5° C. Warm up the reaction mixture to an internal temperature 22±2° C. and add 180 mL of ethyl acetate and 35 mL of water. Collect the solid by filtration over a Büchner funnel, and wash the solid with 2×90 mL of ethyl acetate and 2×20 mL of water. Separate the phases of filtrate and extract the aqueous phase with 2×15 mL of ethyl acetate. Combine the organic layers (~1.1 L) and concentrate under reduced pressure (100-12 mbar) at an internal temperature 35-40° C. The residue dissolve in 220 mL of ethyl acetate and wash with 70 mL of 15% aqueous solution of sodium chloride. Separate the phases and concentrate the organic layer (~0.27 L) under reduced pressure (100-12 mbar) at an internal temperature 35-40° C. to afford 30.5 g of crude compound D-6 as dark orange oil.

Step 6: Preparation of Intermediate D-7

The Paar hydrogenation bottle is charged with 15.0 g (0.053 mol) of crude compound D-6, 75 mL of isopropyl acetate, 9 mL (0.158 mol) of acetic acid and 7.5 g of 10% Pd/C (50% wet). Flush and vent the Parr bottle first with nitrogen (40 psi) three times and next with hydrogen (50 psi) three times. Then pressurize the Parr bottle with hydrogen (60 psi) and shake at an internal temperature 22±2° C. for 16 h. Filter the reaction mixture over the pad of 4.0 g of celite. Wash the celite pad with 3×15 mL of isopropyl acetate. Concentrate the filtrate under reduced pressure (100-12 mbar) at an internal temperature 35-40° C. To the residue add 3×25 mL of isopropyl acetate and concentrate under reduced pressure (100-12 mbar) at an internal temperature 35-40° C. To the residue add 50 mL of water and 25 mL of 6 N aqueous solution of sodium hydroxide to pH~12. Then add 3×100 mL of isopropyl acetate and separated the phases. Combine the organic layers and wash with 80 mL of 15% aqueous solution of sodium chloride. Separate the phases and concentrate the organic layer (~0.35 L) under reduced pressure (100-12 mbar) at an internal temperature 35-40° C. to afford 10 g of crude compound D-7 (diastereoisomeric mixture) as dark orange oil.

Step 7: Preparation of Intermediate D-8

Separation of diastereoisomeric mixture D-7 by treatment first with di-p-toluoyl-D-tartaric acid and next with di-p-toluoyl-L-tartaric acid:

The 100-mL, 4-necked round-bottomed flask equipped with a mechanical stirrer, addition funnel, digital thermometer and condenser with nitrogen inlet-outlet is charged with 4.77 g (0.0244 mol) of crude compound D-7 (diastereomeric mixture 1:1) and 50 mL of ethanol 200 proof. Then add the solution of 9.44 g (0.0244 mol) of (+)-di-p-toluoyl-D-tartaric acid 30 mL of ethanol 200 proof over 7 minutes while maintaining an internal temperature at 20-25° C. and stir the mixture at an internal temperature 22±2° C. for 14 h. Warm up the mixture to internal temperature 50±2° C. and stir at this temperature for an additional 2 h. Collect the solid by hot filtration over a Büchner funnel, and wash the solid with 3×5 mL of ethanol 200 proof. Concentrate the filtrate under reduced pressure (100-12 mbar) at an internal temperature 35-40° C. To the residue add 20 mL of water and 8 mL of 6 N aqueous solution of sodium hydroxide to pH~12. Then add 3×35 mL of isopropyl acetate and separated the phases. Combine the organic layers and wash with 25 mL of 15% aqueous solution of sodium chloride. Separate the phases and concentrate the organic layer under reduced pressure (100-12 mbar) at an internal temperature 35-40° C. To the residue (~3.1 g; 0.0159 mol) add 20 mL of ethanol 200 proof and then add the solution of 4.29 g (0.0111 mol) of (−)-di-p-toluoyl-L-tartaric acid in 10 mL of ethanol 200 proof over 7 minutes while maintaining an internal temperature at 20-23° C. Stir the reaction mixture at an internal temperature 22±2° C. for 7 h. Warm up the mixture to an internal temperature 50±2° C. and stir at this temperature for an additional 2 h. Cool to an internal temperature 22±2° C. and collect the solid by filtration over a Büchner funnel, and wash the solid with 3×5 mL of ethanol 200 proof. Then suspend the solid (~2.03 g) in 25 mL of ethanol 200 proof at an internal temperature 22±2° C. and warm up the mixture to an internal temperature 77±2° C. Then add slowly 40 mL of methanol to get a solution at reflux. Cool the solution to an internal temperature 40±2° C. and concentrate the solution under reduced pressure (50-40 mbar) at an internal temperature 38±2° C. to a batch volume of ~25-30 mL (light suspension). Then cool to an internal temperature 22±2° C. and stir the suspension for 48 h. Collect the solid by filtration over a Büchner funnel, and wash the solid with 3×2 mL of ethanol 200 proof. Dry the solid under reduced pressure (20 mbar) at 35° C. for 12 h to give 1.27 g of D-8 salts in ratio of desired diastereomer/undesired=97.4/2.6. (The desired diastereomer is forming salt with (−)-di-p-toluoyl-L-tartaric acid in ratio 2/1).

Step 8: Preparation of Intermediate D-9

To D-8 (1.27 g) add 6 mL of water and 1 mL of 6 N aqueous solution of sodium hydroxide to pH~12. Then add 3×10 mL of isopropyl acetate and separated the phases. Combine the organic layers and wash with 10 mL of 15% aqueous solution of sodium chloride. Separate the phases and concentrate the organic layer under reduced pressure (100-12 mbar) at an internal temperature 35-40° C. to get 0.656 g of D-9 compound as very light yellow oil.

Example 11

Synthesis of E-5 Synthetic Intermediate to Spirocyclic Aminoalcohols

Step 1: Synthesis of E-2

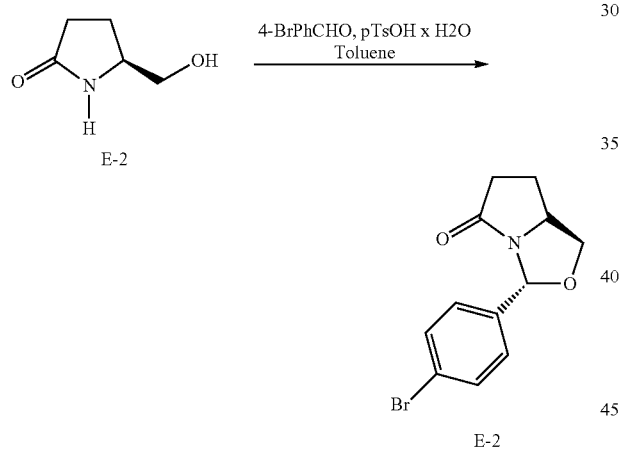

The 1-L, 4-necked round-bottomed flask equipped with a mechanical stirrer, Dean-Stark separator, digital thermometer and condenser with nitrogen inlet-outlet is charged with 46.1 g (0.4 mol) of (S)-(+)-5-hydroxymethyl-2-pyrrolidinone E-1, 81.4 g (0.44 mol) of 4-bromobenzaldehyde, 0.84 g (0.0044 mol) of p-toluenosulfonic acid and 300 mL of THF. Warm up the reaction mixture to an internal temperature 110±2° C. Stir the reaction mixture at this temperature for ~20 h while collecting water (~7 mL) using a Dean-Stark water separator. Then cool the reaction mixture to an internal temperature of 20±2° C. and wash with 2×25 mL of 5% aqueous solution of sodium bicarbonate and 3×50 mL of saturated aqueous solution of sodium bisulfite and 2×50 mL of water. Dry the organic layer over anhydrous magnesium sulfate, filter, wash with toluene and concentrate the organic layer under reduced pressure (75-32 mbar) at an internal temperature 30-35° C. to afford 94.8 g of crude compound E-2 as an oil, which crystallized at RT after couple days. Crude compound E-2 was used directly to the next step.

Step 2: Synthesis of E-3

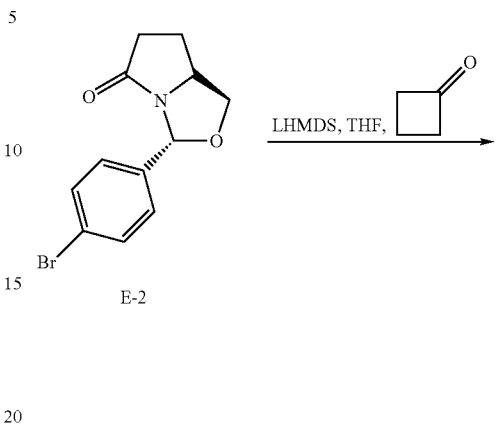

A 2-L, 4-necked round-bottomed flask equipped with a mechanical stirrer, addition funnel, digital thermometer and condenser with nitrogen inlet-outlet is charged with 52.8 g (0.187 mol) of crude compound E-2 and 300 mL of THF. Cool the solution to an internal temperature of −75±2° C. and add 196.6 mL (0.197 mol) of lithium bis(trimethylsilyl)amide 1.0 M solution in THF over 1 h while maintaining an internal temperature at −75±2° C. Stir the reaction mixture at an internal temperature −75±2° C. for 2 h. Add the solution of 14.5 g (0.207 mol) of cyclobutanone in 150 mL of THF over 45 min while maintaining an internal temperature at −75±2° C. and stir at this temperature for 1.5 h. Add to the reaction mixture 510 mL of saturated aqueous solution of ammonium chloride over 20 min at an internal temperature of −75 to −35° C. Warm up the reaction mixture to an internal temperature 20±2° C. and add 510 mL of ethyl acetate. Separate the phases and extract the aqueous phase with 2×360 mL of ethyl acetate. Combine the organic layers and wash with 480 mL of 15% aqueous of sodium chloride. Separate the phases and concentrate the organic layer (~2 L) under reduced pressure (75-32 mbar) at an internal temperature 30-35° C. to afford 64.8 g of crude compound E-3 as an oil, which crystallized at RT after couple days. Crude compound E-3 was used directly to the next step.

Step 3: Synthesis of E-4

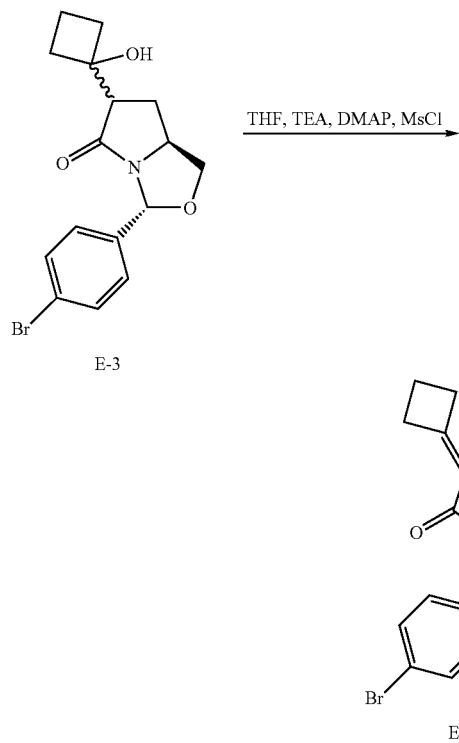

Step 4: Synthesis of E-5 and E-6

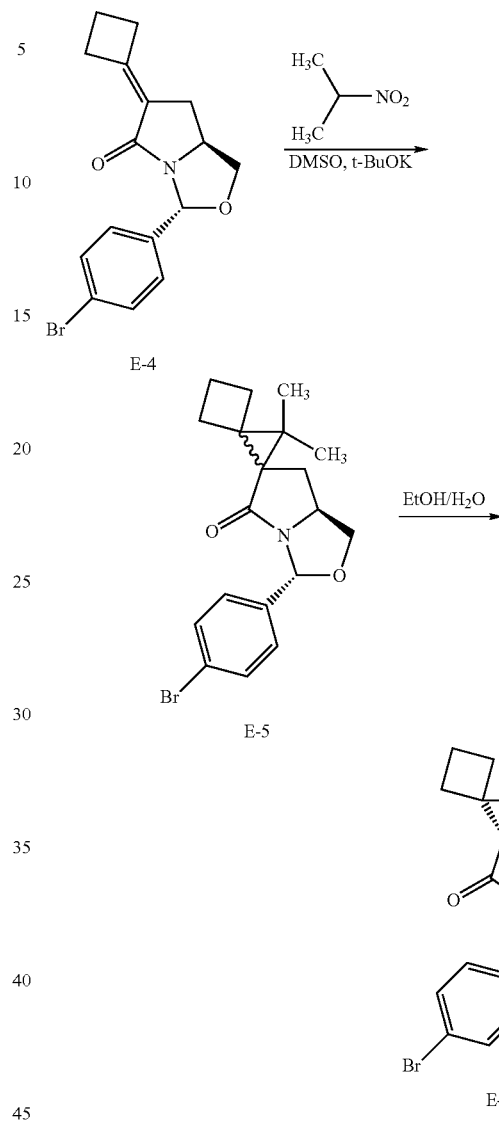

A 2-L, 4-necked round-bottomed flask equipped with a mechanical stirrer, addition funnel, digital thermometer and condenser with nitrogen inlet-outlet is charged with 51.0 g (0.145 mol) of crude compound E-3 and 450 mL of THF. Cool the solution to an internal temperature of 0±2° C. and add 73.3 g (0.73 mol) of triethylamine over 20 min while maintaining an internal temperature at 0±2° C. Then add 3.54 g (0.029 mol) of 4-(dimethylamino)pyridine. Stir the reaction mixture at an internal temperature 0±2° C. for 25 min. Add 26.1 g (0.23 mol) of methanesulfonyl chloride over 30 min while maintaining an internal temperature at 0±2° C. and stir at this temperature for 0.5 h. Warm up the reaction mixture to an internal temperature 65±2° C. and stir at this temperature for ~17 h. Cool the reaction mixture to an internal temperature of 22±2° C. and add 315 mL of sat. aqueous solution of ammonium chloride and 315 mL of ethyl acetate. Separate the phases and extract the aqueous phase with 2×315 mL of ethyl acetate. Combine the organic layers and wash with 300 mL of 12% aqueous of sodium chloride. Separate the phases and concentrate the organic layer (~1.4 L) under reduced pressure (150-12 mbar) at an internal temperature 35-40° C. to afford 52.6 g of crude compound E-4 as brown solid.

Compound E-4 is crystallized by charging a 0.5-L, 4-necked round-bottomed flask equipped with a mechanical stirrer, addition funnel, digital thermometer and condenser with nitrogen inlet-outlet with 52.6 g of crude compound E-4 and 120 mL of ethanol 200 proof. Warm up the reaction to an internal temperature 65±2° C. to get a dark solution. Cool the reaction mixture to an internal temperature of 22±2° C. over ~1 h and stir at this temperature for 17 h. Then filter the suspension and wash solid with 4×10 mL of cold ethanol 200 proof. Dry the solid under reduced pressure (20 mbar) at 35° C. for 24 h to get 25.8 g of pure compound E-4.

A 250-mL, 4-necked round-bottomed flask equipped with a mechanical stirrer, addition funnel, digital thermometer and condenser with nitrogen inlet-outlet is charged with 11.73 g (0.105 mol) of potassium tert-butoxide and 45 mL of DMSO. Stir the mixture at an internal temperature 22±2° C. for 15 min to get a solution and add 9.32 g (0.105 mol) g of 2-nitropropane over 15 min while maintaining an internal temperature at 23-43° C. Warm up to an internal temperature 65±2° C. and stir the reaction mixture at this temperature for 0.5 h. Then add as a solid 25.0 g (0.075 mol) of compound E-4 over 15 min while maintaining an internal temperature at 65-68° C. Wash with 2 mL of DMSO. Warm up the reaction mixture to an internal temperature 100±2° C. and stir at this temperature for 84 h. Cool the reaction mixture to an internal temperature of 22±2° C. and add 47 mL of 6% aqueous solution of sodium chloride and 26 mL of TBME. Separate the phases and extract the aqueous phase with 2×30 mL of TBME. Combine the organic layers and wash with 30 mL of 6% aqueous solution of sodium chloride. Separate the phases and concentrate the organic layer (~100 mL) under reduced pressure (150-12 mbar) at an internal temperature 35-40° C. to afford 26.0 g of crude compound E-5 as dense dark orange oil. Dissolve this oil in 20 mL of toluene and load it on the column containing 90.0 g of silica gel. Ellute the column with 1.6 L of toluene collecting the elluent in 0.2 L aliquots. Combine first seven aliquots and concentrate (~1.4 L) under reduced pressure (80-12 mbar) at an internal temperature 35-40° C. to afford 19.7 g of crude compound E-5 as dense orange oil.

A 250-mL, 4-necked round-bottomed flask equipped with a mechanical stirrer, addition funnel, digital thermometer and condenser with nitrogen inlet-outlet is charged with 19.4 g of crude compound E-5 and 55.8 mL of ethanol 200 proof. A homogeneous solution is obtained by warming the flask to an internal temperature 50±2° C. Add 12.2 mL of water over 5 min while maintaining an internal temperature at 47-50° C. Cool the reaction mixture to an internal temperature of 40±2° C. and seed it with about 15 mg of compound E-6 (desired diastereomer).

Then cool to an internal temperature 22±2° C. over about 30 minutes and stir at this temperature for 12 h. Then filter the suspension and wash solid with 3×15 mL of ethanol/water (80% v/v). Dry the solid under reduced pressure (20 mbar) at 35° C. for 5 h to get 11.26 g of compound 5 (ratio ~34/66—undesired/desired).

A 250-mL, 4-necked round-bottomed flask equipped with a mechanical stirrer, addition funnel, digital thermometer and condenser with nitrogen inlet-outlet is charged with 11.26 g of compound E-5 (ratio ~34/66—undesired/desired) and 55.8 mL of ethanol 200 proof. Warm up the reaction to an internal temperature 50±2° C. to get a solution. Add 12.2 mL of water over 5 min while maintaining an internal temperature at 47-50° C. Seed it with about 15 mg of compound E-6 (desired diastereomer) at an internal temperature 50±2° C. Then cool to an internal temperature 22±2° C. over 0.5 h and stir at this temperature for 12 h. Then filter the suspension and wash solid with 3×15 mL of ethanol/water (80% v/v). Dry the solid under reduced pressure (20 mbar) at 35° C. for 5 h to get 7.39 g of compound 5 (ratio ~17/83—undesired/desired).

Additional crystallizations may be carried out to obtain a desired level of diasteromeric excess.

Mass spectral analysis for the compounds of Table A, e.g., Compounds A-1 through A-87 has been measured using a Waters ZQ MS device.

TABLE C

| Compound No. | MS (M + H$^+$) Found |
| --- | --- |
| A-1 | 767.6 |
| A-2 | 767.6 |
| A-3 | 741.6 |
| A-4 | 781.6 |
| A-5 | 781.7 |
| A-6 | 781.7 |
| A-7 | 801.4 |
| A-8 | 781.6 |
| A-9 | 781.6 |
| A-10 | 753.7 |
| A-11 | 753.7 |
| A-12 | 767.1 |
| A-13 | 767.7 |
| A-14 | 767.8 |
| A-15 | 767.8 |
| A-16 | 803.7 |
| A-17 | 803.6 |
| A-18 | 793.7 |
| A-19 | 785.6 |
| A-20 | 771.6 |
| A-21 | 779.4 |
| A-22 | 779.8 |

TABLE C-continued

| Compound No. | MS (M + H$^+$) Found |
| --- | --- |
| A-23 | 794.0 |
| A-24 | 783.8 |
| A-25 | 771.5 |
| A-26 | 765.7 |
| A-27 | 779.7 |
| A-28 | 793.6 |
| A-29 | 793.8 |
| A-30 | 765.4 |
| A-31 | 779.6 |
| A-32 | 779.7 |
| A-33 | 739.4 |
| A-34 | 796.6 |
| A-35 | 796.7 |
| A-36 | 785.6 |
| A-37 | 767.6 |
| A-38 | 781.7 |
| A-39 | 795.9 |
| A-40 | 781.7 |
| A-41 | 795.6 |
| A-42 | 796.6 |
| A-43 | 796.7 |
| A-44 | 755.6 |
| A-45 | 781.5 |
| A-46 | 781.2 |
| A-47 | 753.7 |
| A-48 | 753.6 |
| A-49 | 753.4 |
| A-50 | 753.4 |
| A-51 | 795.5 |
| A-52 | 767.4 |
| A-53 | 795.8 |
| A-54 | 783.6 |
| A-55 | 739.7 |
| A-56 | 739.6 |
| A-57 | 727.5 |
| A-58 | 727.5 |
| A-59 | 741.5 |
| A-60 | 781.7 |
| A-61 | 753.8 |
| A-62 | 753.4 |
| A-63 | 783.4 |
| A-64 | 767.5 |
| A-65 | 767.7 |
| A-66 | 753.4 |
| A-67 | 753.5 |
| A-68 | 753.7 |
| A-69 | 741.7 |
| A-70 | 799.8 |
| A-71 | 755.8 |
| A-72 | 741.5 |
| A-73 | 727.4 |
| A-74 | 797.4 |
| A-75 | 753.4 |
| A-76 | 757.7 |
| A-77 | 743.6 |
| A-78 | 757.8 |
| A-79 | 743.8 |
| A-80 | 769.6 |
| A-81 | 755.6 |
| A-82 | 769.6 |
| A-83 | 755.6 |
| A-84 | 725.6 |
| A-85 | 741.9 |
| A-86 | 797.7 |
| A-87 | 797.7 |

Biological Activity

Example 12

HCV NS3-4A Protease Assay

The inhibitory activity of certain compounds of Table A against HCV NS3-4A serine protease is determined in a homogenous assay using the full-length NS3-4A protein (genotype 1a, strain HCV-1) and a commercially available internally-quenched fluorogenic peptide substrate as described by Taliani, M., et al. 1996 Anal. Biochem. 240:60-67, which is incorporated by reference in its entirety.

Example 13

Luciferase-Based HCV Replicon Assay

The antiviral activity and cytotoxicity of certain compounds of Table A is determined using a subgenomic genotype 1b HCV replicon cell line (Huh-Luc/neo-ET) containing a luciferase reporter gene, the expression of which is under the control of HCV RNA replication and translation. Briefly, 5,000 replicon cells are seeded in each well of 96-well tissue culture plates and are allowed to attach in complete culture media without G418 overnight. On the next day, the culture media are replaced with media containing a serially diluted compound of Table A in the presence of 10% FBS and 0.5% DMSO. After a 48-h treatment with the compound of Table A, the remaining luciferase activities in the cells are determined using BriteLite reagent (Perkin Elmer, Wellesley, Mass.) with a LMaxII plate reader (Molecular Probe, Invitrogen). Each data point represents the average of four replicates in cell culture. $IC_{50}$ is the concentration of the at which the luciferase activity in the replicon cells is reduced by 50%. The cytotoxicity of the compound of Table A is evaluated using an MTS-based cell viability assay.

Compounds in Table A supra have been tested in at least one of the protease assay of Example 12 or the replicon assay of Example 13 and exhibit an $IC_{50}$ of less than about 100 nM or less in at least one of the assays recited in Example 12 and 13.

Example 14

Measurement of Thermodynamic Solubility of Compounds of the Invention

Thermodynamic solubility for the compounds of the invention listed in Table C is measured by a published literature procedure, e.g., Liping Zhou, et al., *J. Pharm. Sci.* (2007) 96(11): 3052-3071.

The DMSO stocks of test compounds previously dissolved in 25 μL of DMSO (~10 mM) in mini-prep vial (MPV: Whatman, with PVDF filter and 0.45 μm pore size) chamber were evaporated via a GeneVac HT-4X evaporator for approximately 1 hour, at the guard temperature of 30° C. An aliquot of 250 μL buffer solution (pH 1.0 or 6.8) was added into each MPV chamber containing powders reconstituted from DMSO stock solutions. The MPV filter plungers were pushed down into the chamber until the membrane of the filter plunger slightly touched the surface of the buffer to promote equilibrium between the two compartments and to minimize the adsorption due to non-specific binding of samples during the subsequent 24-hr incubation (at 600 RPM at room temperature). Immediately after the 24-hr incubation, the plungers were further pushed down to the bottom of the chambers. More solution was pushed through the membrane and entered the plunger compartment. The filter/chamber assemblies were then put on a shaker for another 30 minutes at 600 RPM. Afterwards, filtrates were further diluted (1:10) with 50/50 acetonitrile/water solvent followed by a thorough mixing process. Both plates with diluted and undiluted filtrates were analyzed by HPLC and quantified against the four-point standard dilution curve of the same test compound (5 μM, 35 μM, 65 μM and 100 μM, respectively). In the current study, solubility reflects the average of triplicate samples tested at each pH.

Table D recites solubility data for certain compounds of Table A and comparative Examples 1 and 2 (which correspond, respectively, to Examples A-106 and A-125 of copending international application PCT/US2007/066204).

TABLE D

| Ex. # | Solubility (pH 1) mM | Solubility (pH 6.8) mM |
|---|---|---|
| A-4 | 0.63 | 0.2 |
| A-5 | 0.48 | 0.044 |
| A-6 | 0.93 | <0.005 |
| A-10 | 0.91 | 0.024 |
| A-11 | 0.87 | 0.092 |
| A-15 | 0.7 | 0.17 |
| A-33 | 0.79 | 0.11 |
| A-43 | 0.64 | 0.29 |
| A-44 | 0.69 | 0.064 |
| A-45 | 0.72 | <0.005 |
| A-50 | 0.83 | 0.24 |
| A-54 | 0.79 | 0.028 |
| A-58 | 0.96 | 0.93 |
| A-59 | 0.84 | 0.55 |
| A-62 | 0.93 | <0.005 |
| A-64 | 0.71 | <0.085 |
| A-66 | 0.84 | 0.6 |
| A-67 | 0.74 | 0.69 |
| A-72 | 0.84 | 0.34 |
| A-73 | 0.81 | <0.005 |
| A-82 | 0.83 | <0.005 |
| A-7 | 0.9 | 0.84 |
| Comparative Example 1 | <0.005 | <0.004 |
| Comparative Example 2 | 0.047 | <0.004 |

Example 15

Measurement of Pharmacokinetic Profile

Compounds listed in Table D are administered as a solution orally via gavage at 10 mg/kg to Sprague Dawley rats at a dosing volume of 10 ml/kg. Samples are collected via a surgically implanted cannula at selected timepoints deemed necessary to characterize pharmacokinetic parameters. Blood samples are placed on wet ice and spun down to plasma within 5 minutes of timepoint collection. Plasma samples are frozen until bioanalytical analysis.

Compounds listed in Table D are administered intravenously into a surgically implanted cannula as a solution at 1 mg/kg to Sprague Dawley rats at a dosing volume of 1 ml/kg. Samples are collected via another surgically implanted cannula at selected timepoints deemed necessary to characterize pharmacokinetic parameters. Blood samples are placed on wet ice and spun down to plasma within 5 minutes of timepoint collection. Plasma samples are frozen until bioanalytical analysis.

Table E recites pharmacodynamic data for certain compounds of Table A and comparative examples 1 and 2 (which correspond, respectively, to Examples A-106 and A-125 of copending international application PCT/US2007/066204).

TABLE E

| Example # | AUC (nM · h/mg/kg) | Cmax (nM) | Bioavailability (% F) |
|---|---|---|---|
| A-10 | 460 | 1473 | 46 |
| A-15 | 474 | 2032 | 42 |
| A-44 | 523 | 1108 | 43 |
| A-54 | 416 | 1428 | 28 |
| A-59 | 203 | 653 | n.d. |
| A-62 | 241 | 796 | 36 |
| A64 | 274 | 904 | n.d. |
| Comparative Example 1 | 65 | 228 | 12 |
| Comparative Example 2 | 87 | 388 | 9 | n.d.—not determined due to lack of corresponding intravenous administration data.

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A compound of the Formula I:

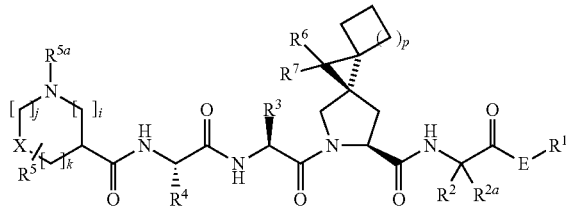

I and pharmaceutically acceptable salts and stereoisomers thereof;
wherein
X is absent or selected from NR$^{5a}$ or oxygen;
i and k are independently selected integers selected from the group consisting of 0, 1, 2, 3 and 4;
j is an integer selected from the group consisting of 1, 2, 3 and 4, wherein the sum of i+j+k is less than or equal to 5 and greater than or equal to 2 when X is absent and the sum of i+j+k is less than or equal to 4 and greater than or equal to 1 when X is oxygen;
p is 0, 1, 2 or 3;
E is OH, NH$_2$, N(H)C$_{1-4}$alkyl, N(H)C$_{3-6}$cycloalkyl, —C(O)NH— or —N(H)S(O)$_2$—;
R$^1$ is absent, hydrogen, C$_{1-4}$alkyl or C$_{3-6}$cycloalkyl;
R$^2$ is C$_{1-4}$alkyl, haloC$_{1-4}$alkyl, or C$_{3-6}$cycloalkylC$_{0-2}$alkyl;
R$^{2a}$ is hydrogen, C$_{1-4}$alkyl, haloC$_{1-4}$alkyl, or C$_{3-6}$cycloalkylC$_{0-2}$alkyl; or
R$^2$ and R$^{2a}$, taken in combination form a three membered saturated ring, which ring is substituted with zero, one or two substituents independently selected from C$_{1-4}$alkyl and C$_{2-4}$alkenyl;
R$^3$ and R$^4$ are independently selected from the group consisting of C$_{1-6}$alkyl, C$_{4-7}$cycloalkyl and C$_{4-7}$cycloalkyl substituted with a C$_{1-4}$alkyl residue;
R$^5$ represents zero to three residues on

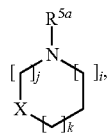

each independently selected at each occurrence from the group consisting of halogen, hydroxy, amino, C$_{1-4}$alkyl, C$_{3-6}$cycloalkyl, C$_{1-4}$alkoxy, mono- and di-C$_{1-4}$alkylamino, hydroxyC$_{1-4}$alkyl, and C$_{1-4}$alkoxyC$_{1-4}$alkyl;
R$^{5a}$ is independently selected at each occurrence from the group consisting of hydrogen, C$_{1-4}$alkyl, haloC$_{1-4}$alkyl, C$_{3-6}$cycloalkyl, hydroxyC$_{1-4}$alkyl, and C$_{1-4}$alkoxyC$_{1-4}$alkyl; and
R$^6$ and R$^7$ are independently selected from hydrogen and C$_{1-4}$alkyl.

2. A compound of the Formula Ia:

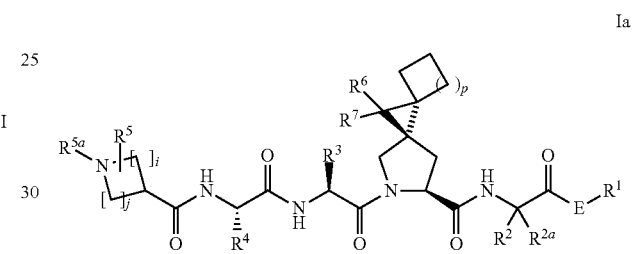

Ia and pharmaceutically acceptable salts and stereoisomers thereof;
wherein
i is an integer selected from the group consisting of 0, 1, 2, 3 and 4;
j is an integer selected from the group consisting of 1, 2, 3 and 4, wherein the sum of i+j is less than or equal to 5 and greater than or equal to 2;
p is 0, 1, 2 or 3;
E is OH, NH$_2$, N(H)C$_{1-4}$alkyl, N(H)C$_{3-6}$cycloalkyl, —C(O)NH— or —N(H)S(O)$_2$—;
R$^1$ is absent, hydrogen, C$_{1-4}$alkyl or C$_{3-6}$cycloalkyl;
R$^2$ is C$_{1-4}$alkyl, haloC$_{1-4}$alkyl, or C$_{3-6}$cycloalkylC$_{0-2}$alkyl;
R$^{2a}$ is hydrogen, C$_{1-4}$alkyl, haloC$_{1-4}$alkyl, or C$_{3-6}$cycloalkylC$_{0-2}$alkyl; or
R$^2$ and R$^{2a}$, taken in combination form a three membered saturated ring, which ring is substituted with zero, one or two substituents independently selected from C$_{1-4}$alkyl and C$_{2-4}$alkenyl;
R$^3$ and R$^4$ are independently selected from the group consisting of C$_{1-6}$alkyl, C$_{4-7}$cycloalkyl and C$_{4-7}$cycloalkyl substituted with a C$_{1-4}$alkyl residue;
R$^5$ represents zero to three residues on

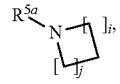

each independently selected at each occurrence from the group consisting of halogen, hydroxy, amino, C$_{1-4}$alkyl, C$_{3-6}$cycloalkyl, C$_{1-4}$alkoxy, mono- and di-C$_{1-4}$alkylamino, hydroxylC$_{1-4}$alkyl, and C$_{1-4}$alkoxyC$_{1-4}$alkyl;

$R^{5a}$ is independently selected at each occurrence from the group consisting of hydrogen, $C_{1-4}$alkyl, halo$C_{1-4}$alkyl, $C_{3-6}$cycloalkyl, hydroxy$C_{1-4}$alkyl, and $C_{1-4}$alkoxy$C_{1-4}$alkyl; and $R^6$ and $R^7$ are independently selected from hydrogen and $C_{1-4}$alkyl.

3. The compound of claim 1, wherein

X is carbon;
i is 0 or 1;
j+k is 2, 3, or 4;
p is 1;
E is C(O)NH or N(H)SO$_2$;
$R^1$ is cyclopropyl or $C_{2-4}$alkyl;
$R^2$ is propyl or cyclobutylmethyl;
$R^{2a}$ is hydrogen; or
$R^2$ and $R^{2a}$ form a cyclopropyl ring substituted by zero or one ethyl or vinyl residues;
$R^3$ and $R^4$ are independently selected from tert-butyl, cyclohexyl, and 1-methylcyclohexyl;
$R^5$ represents zero or one $C_{1-4}$alkyl residues;
$R^{5a}$ is $C_{1-4}$alkyl;
$R^6$ and $R^7$ are independently selected from hydrogen and methyl.

4. The compound of claim 1, wherein

X is carbon;
i is 0 or 1;
j+k is 2, 3, or 4;
p is 1;
E is C(O)NH;
$R^1$ is cyclopropyl, ethyl, iso-propyl, or tert-butyl;
$R^2$ is propyl;
$R^{2a}$ is hydrogen;
$R^3$ and $R^4$ are independently selected from tert-butyl and cyclohexyl;
$R^5$ is absent;
$R^{5a}$ is ethyl, iso-propyl, or tert-butyl; and
$R^6$ and $R^7$ are methyl.

5. The compound of claim 1, wherein the compound is selected from the group consisting of:

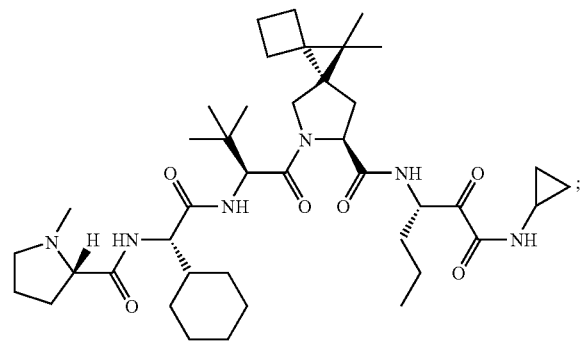

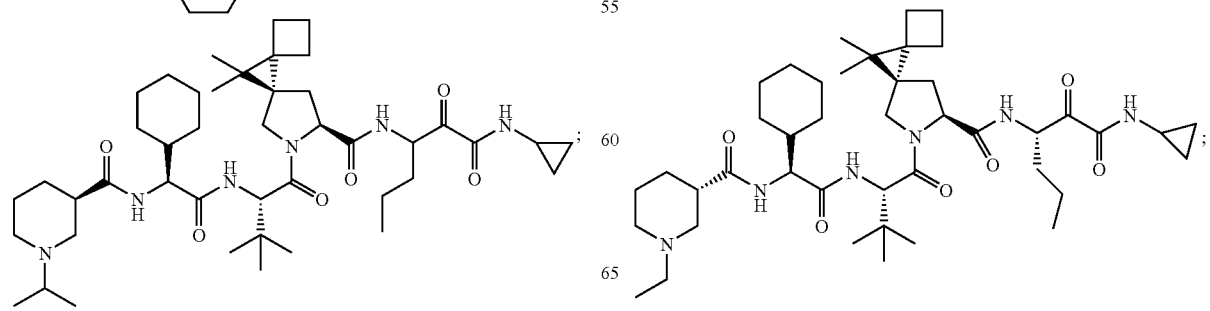

-continued

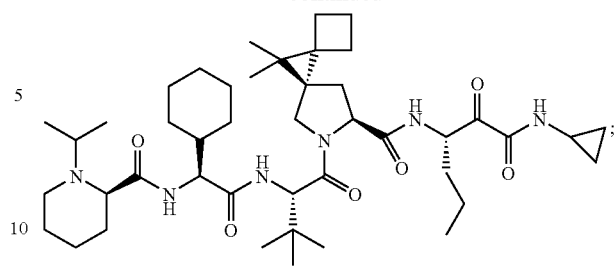

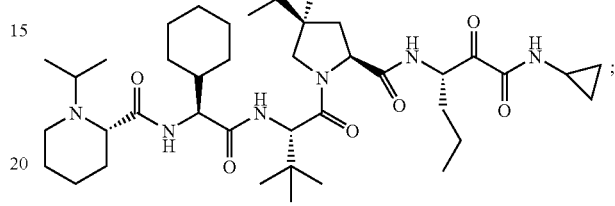

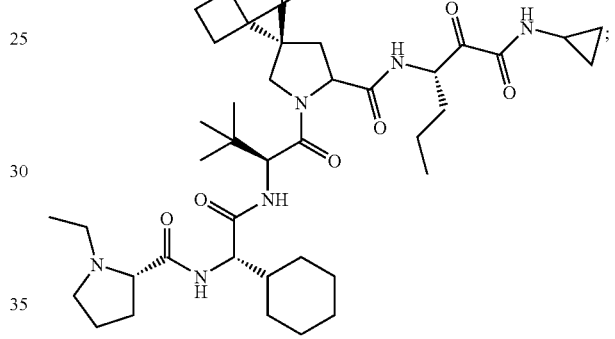

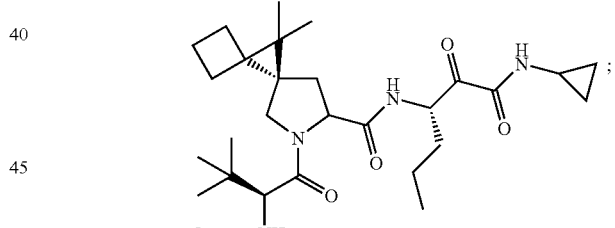

147
-continued
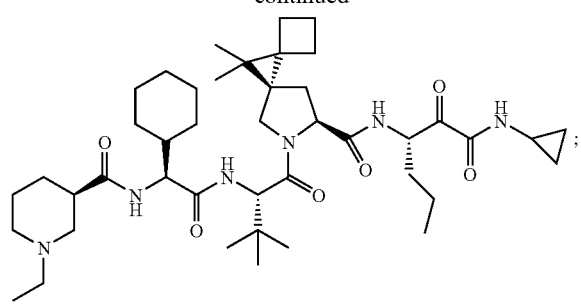
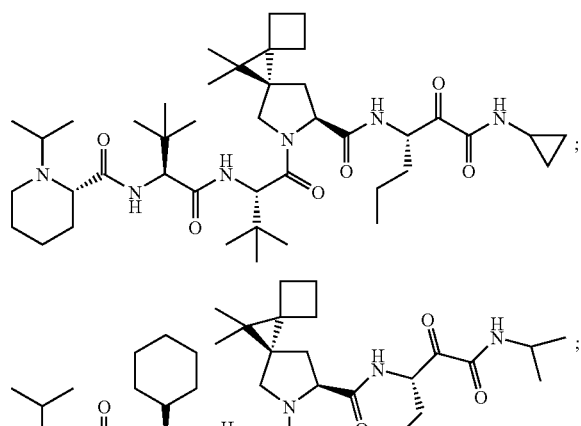
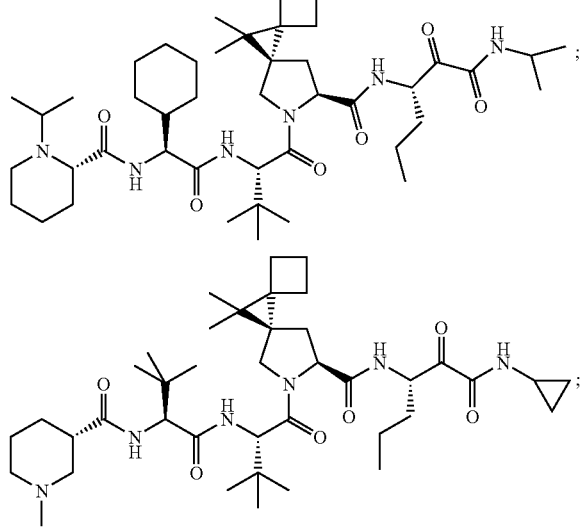
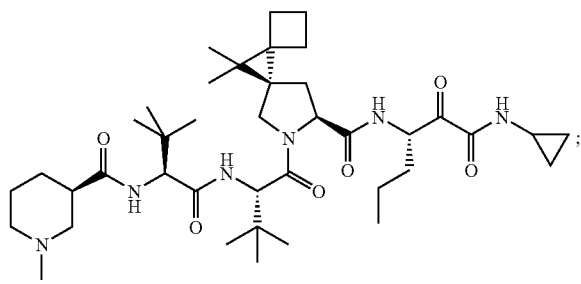
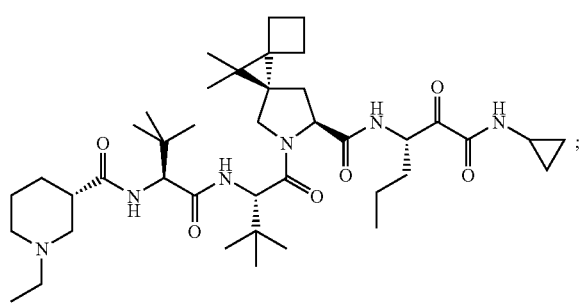
148
-continued
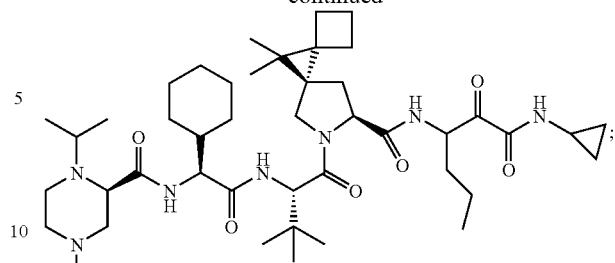
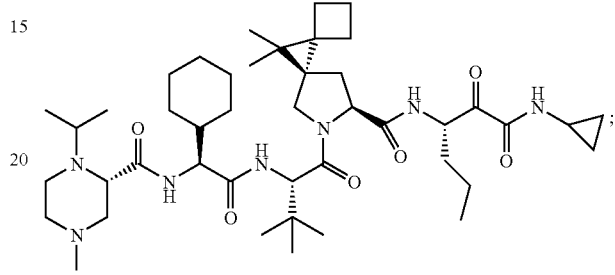
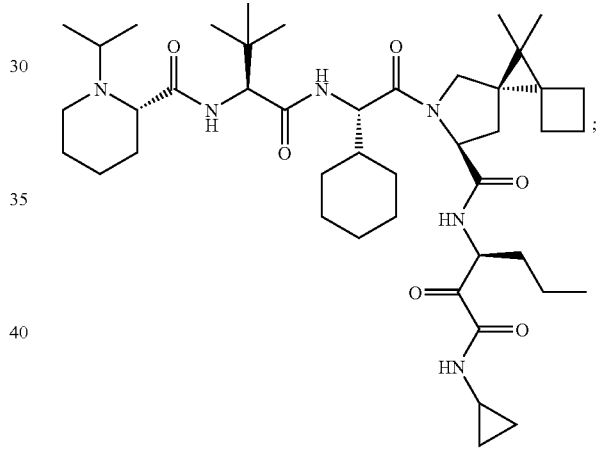
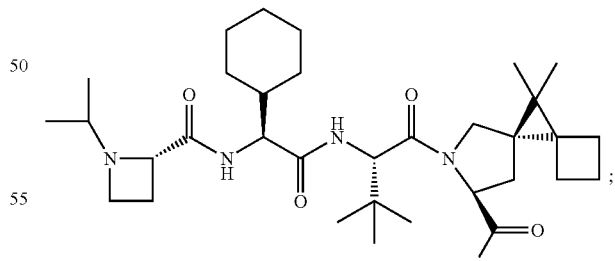

149
-continued
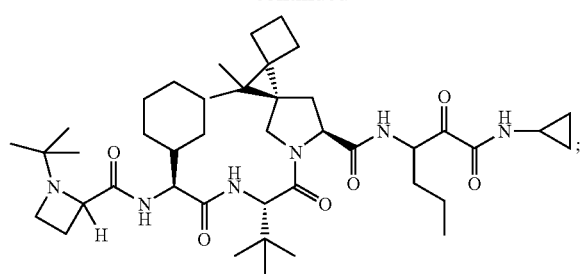
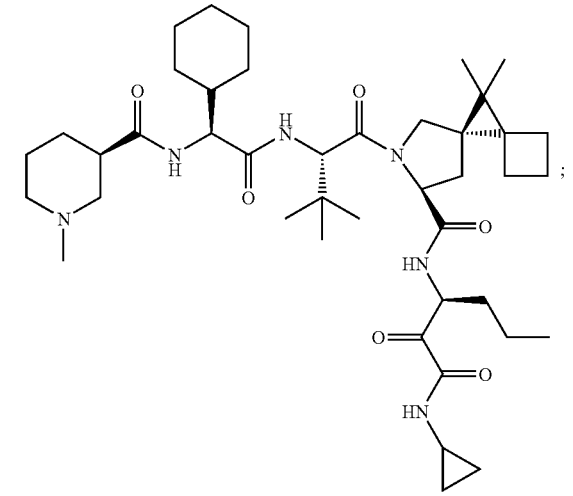
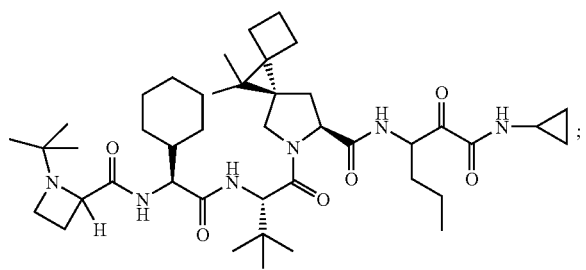
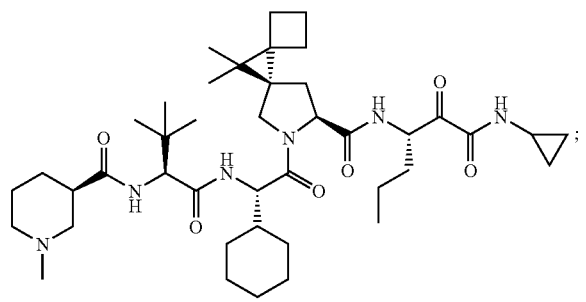
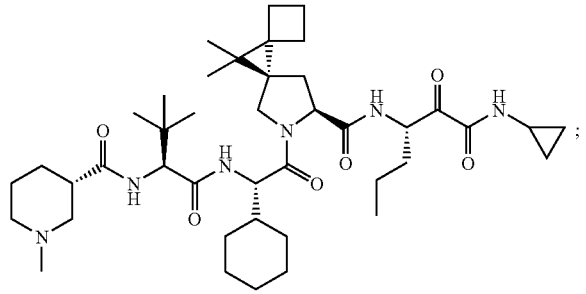
150
-continued
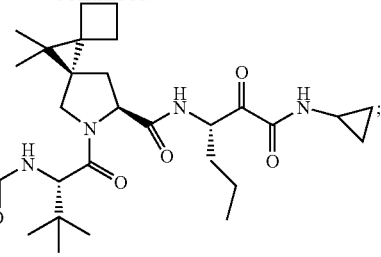
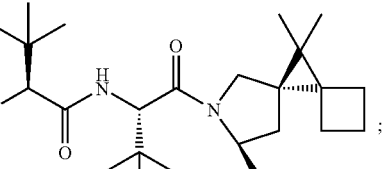
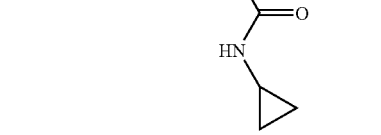 ; and
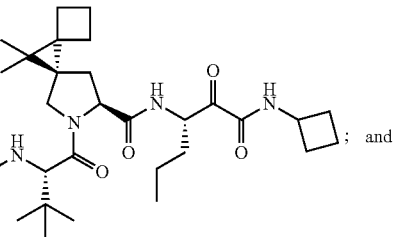
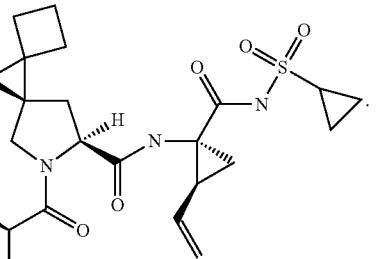

6. A compound selected from the group consisting of:
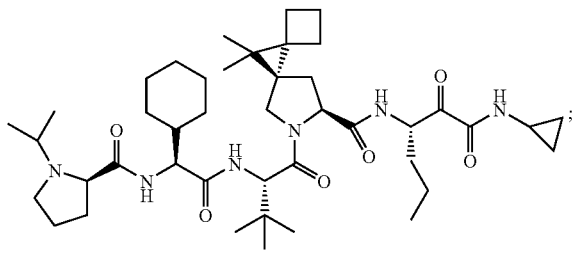
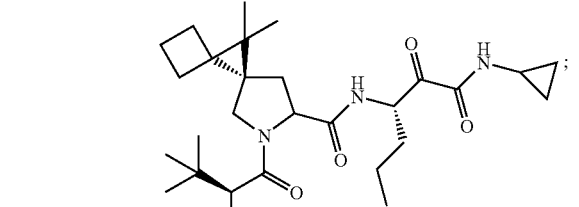
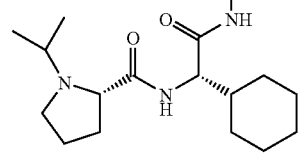
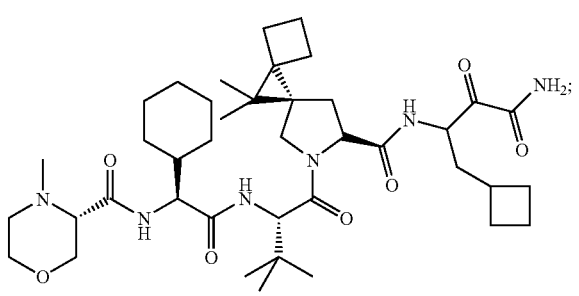
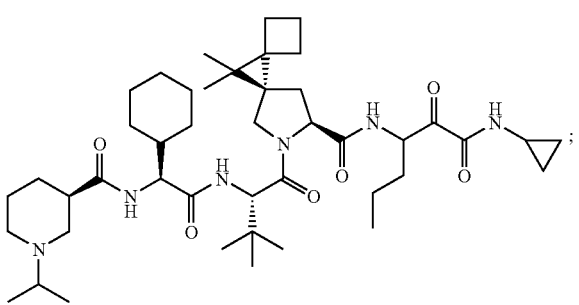
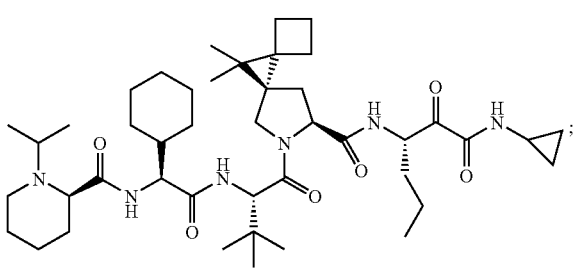
-continued
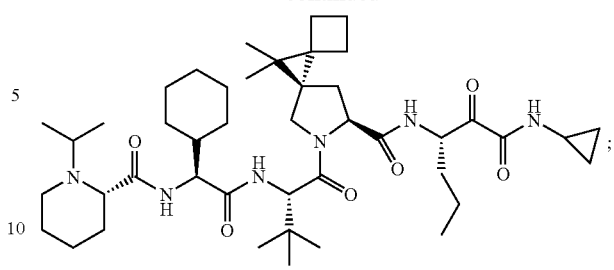
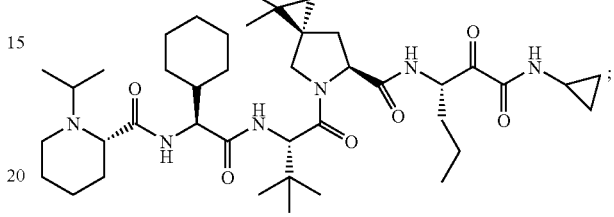
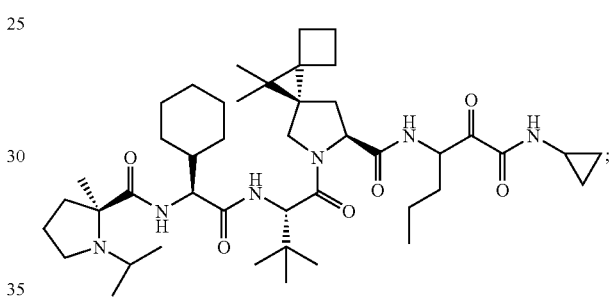
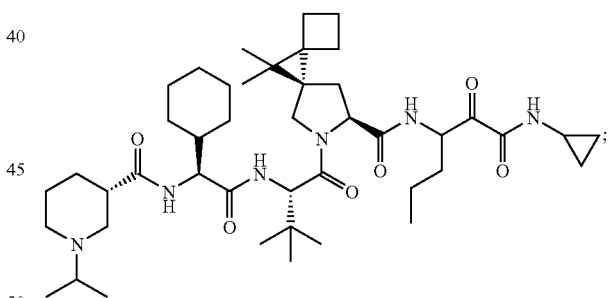
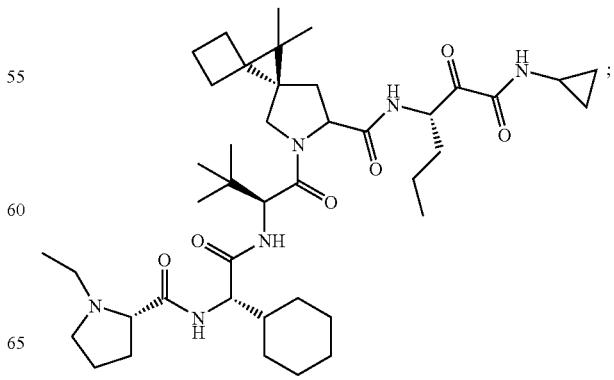

153 -continued
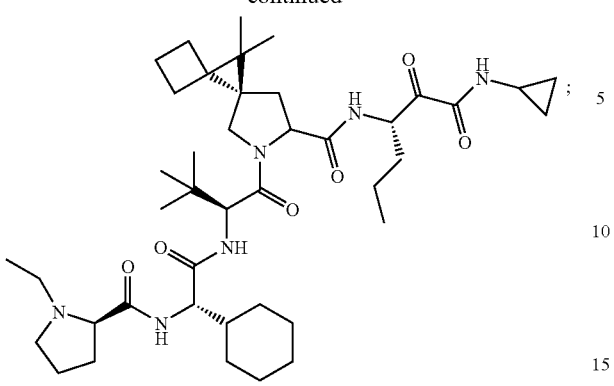
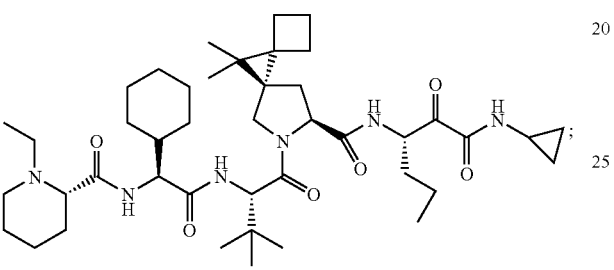
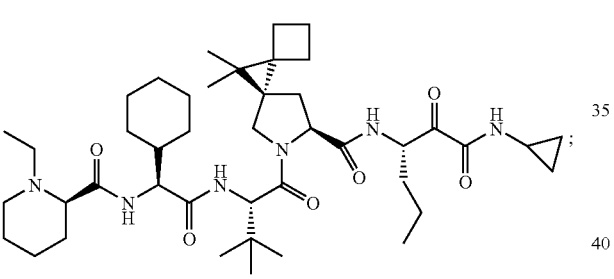
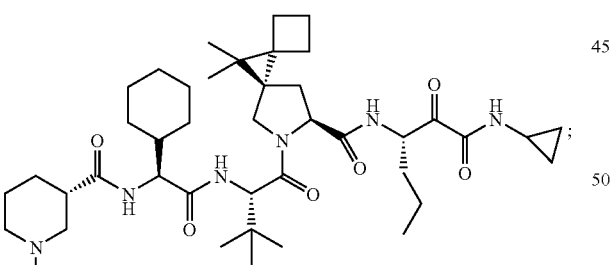
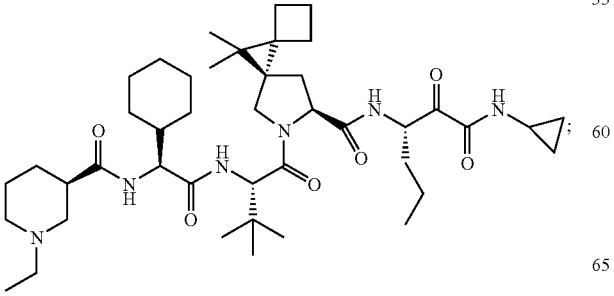
154 -continued
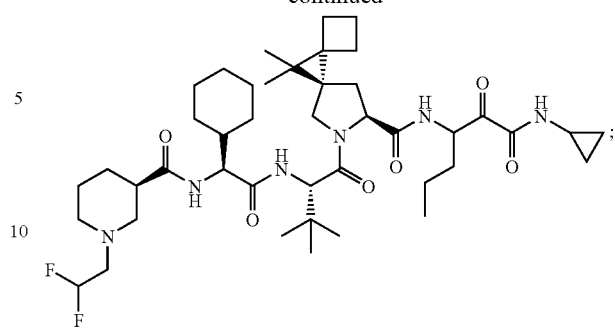
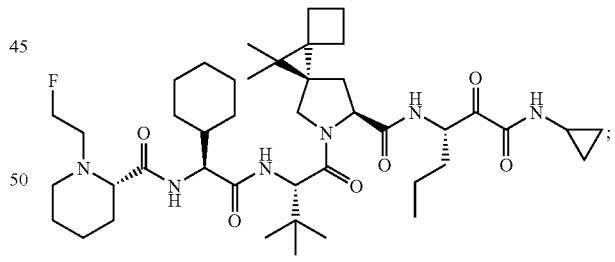
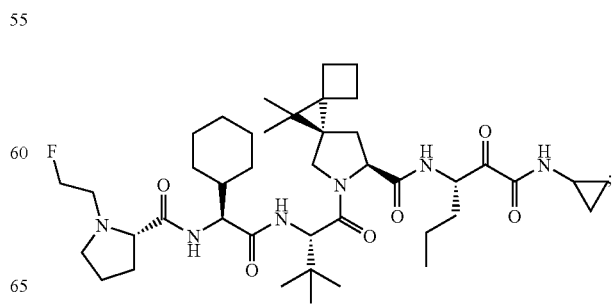

155
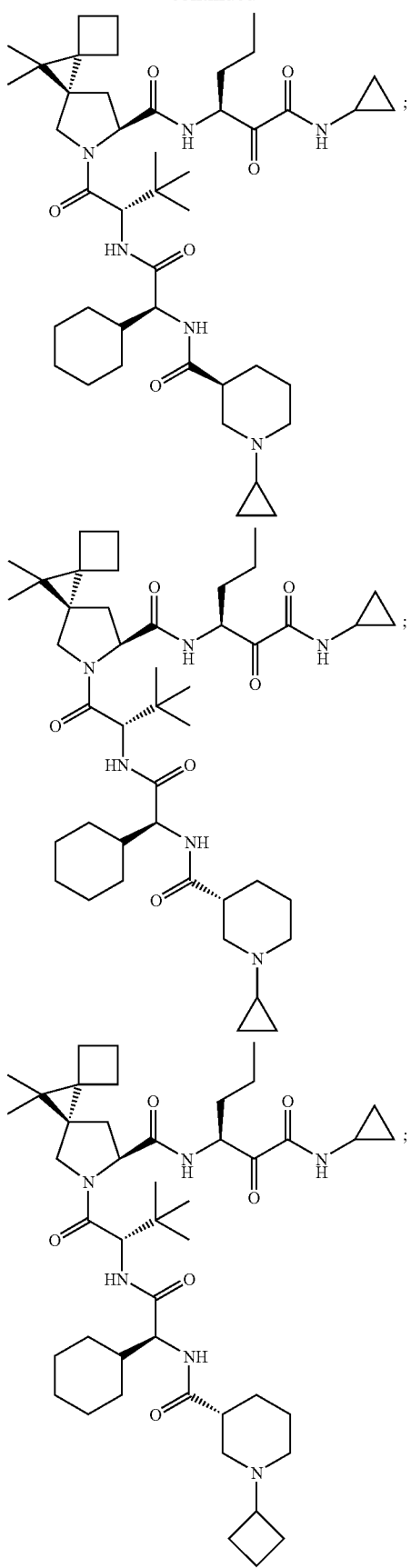
156
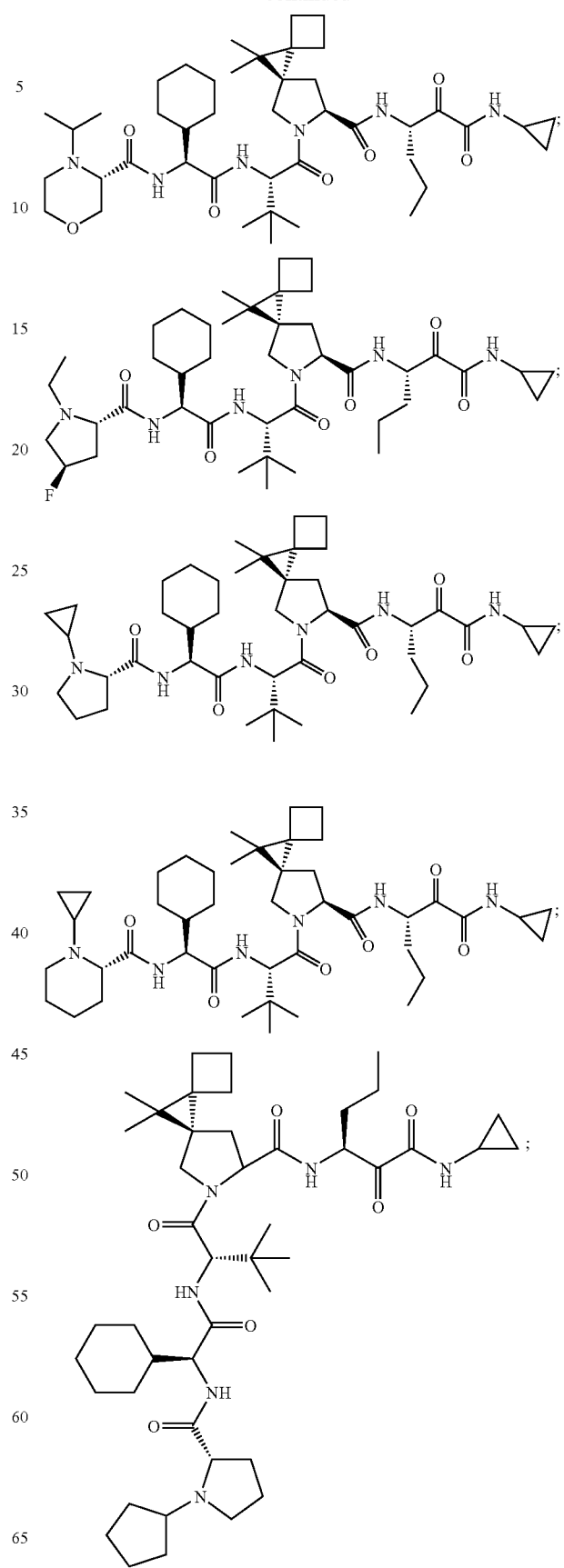

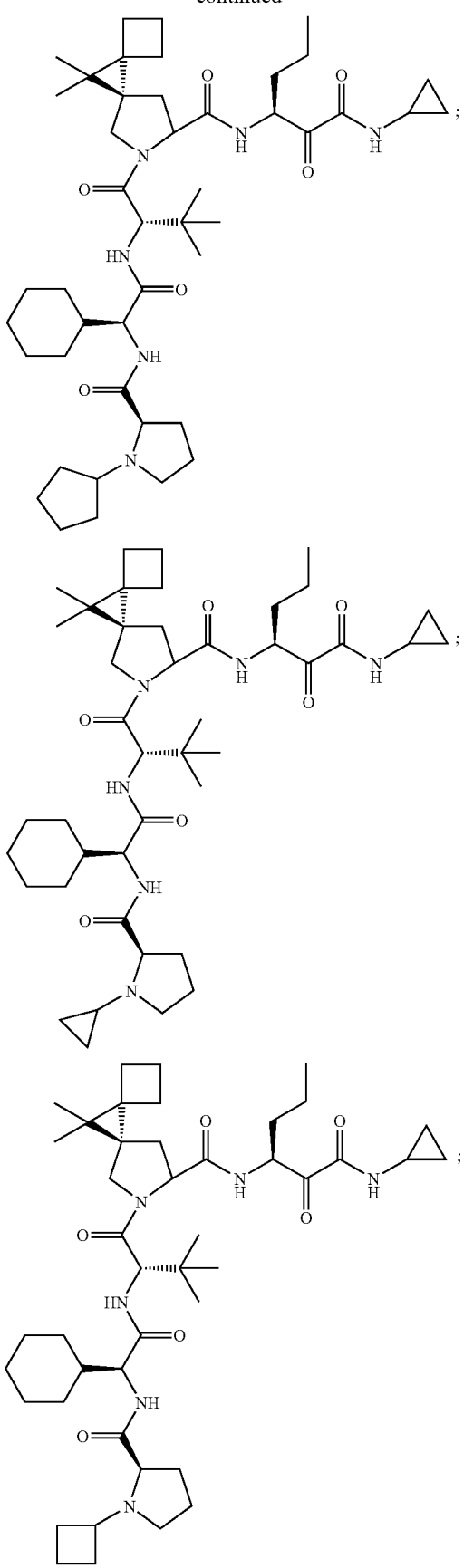
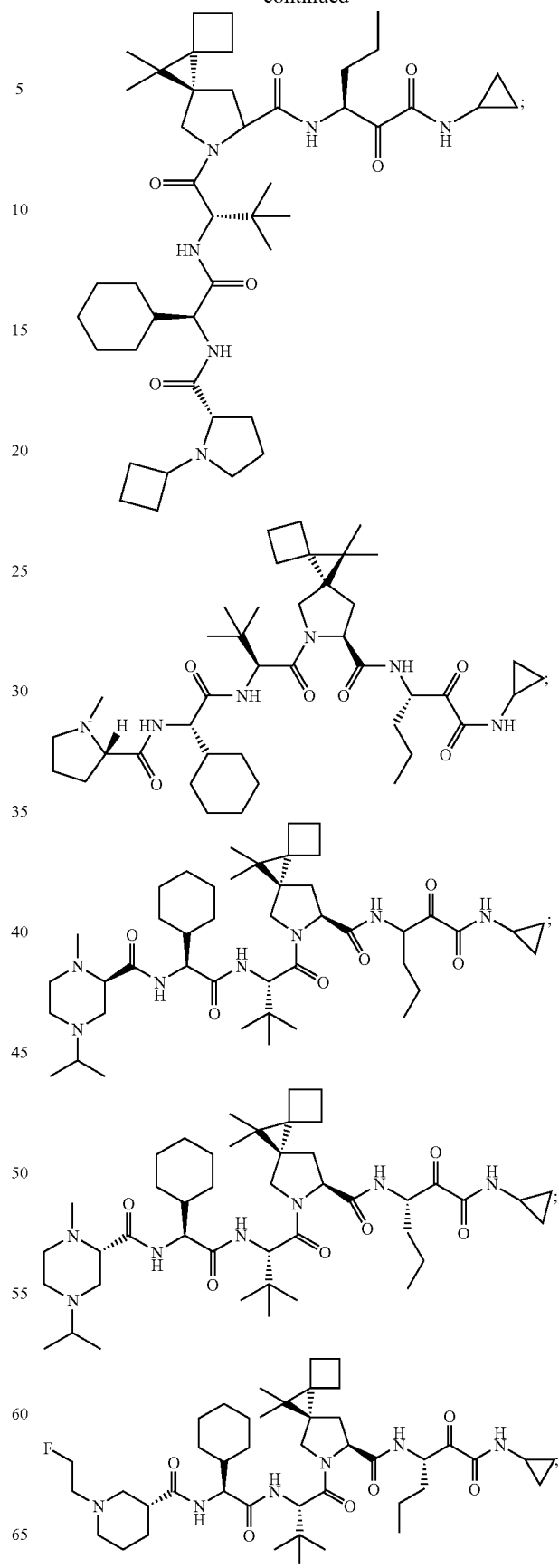

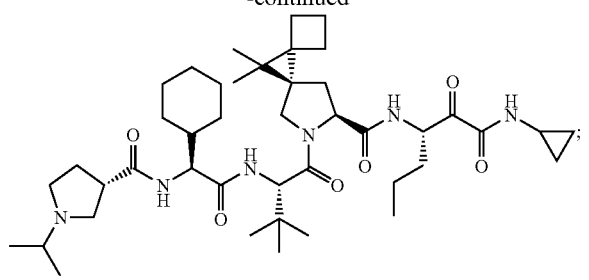
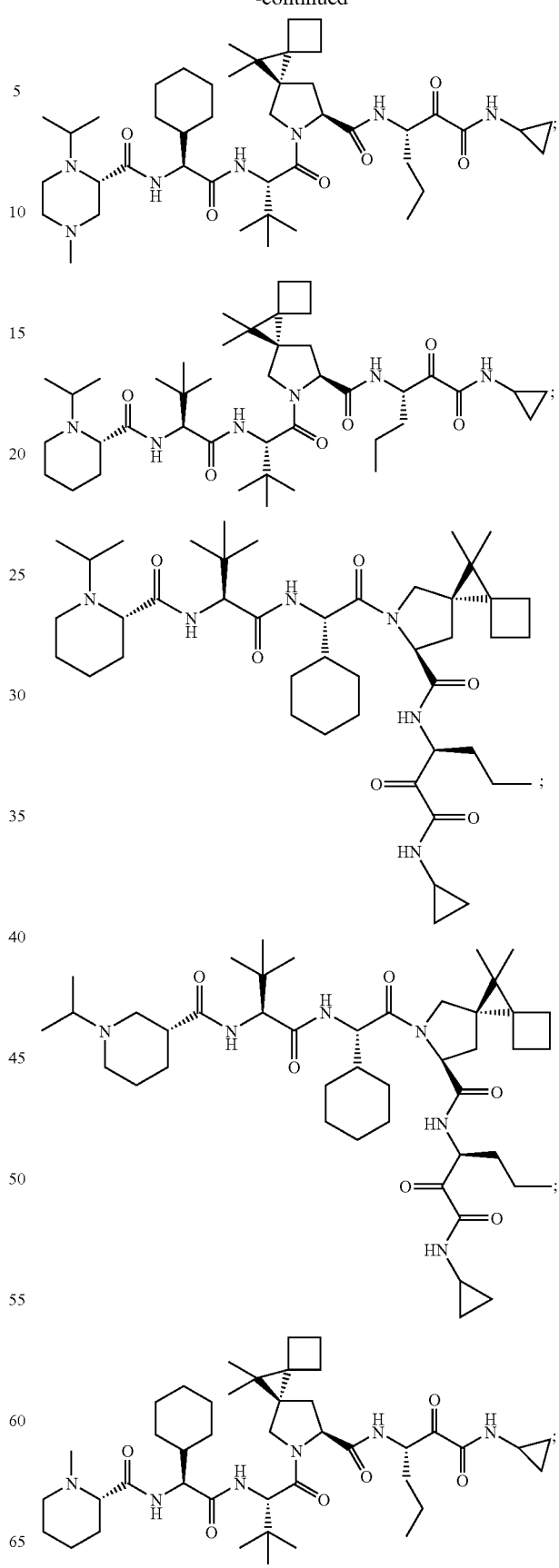

161
-continued
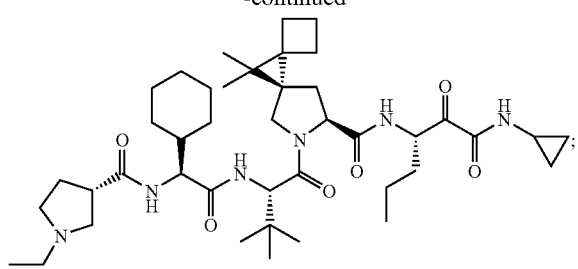
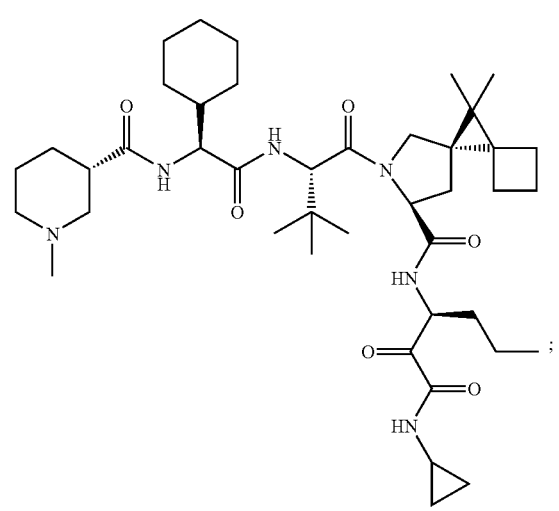
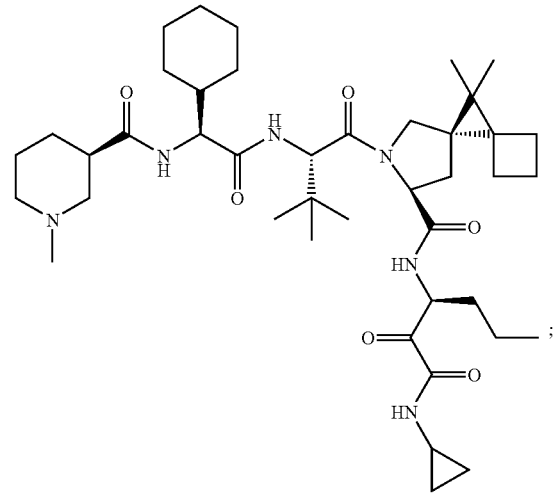
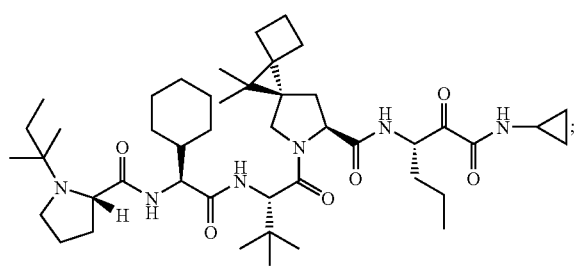
162
-continued
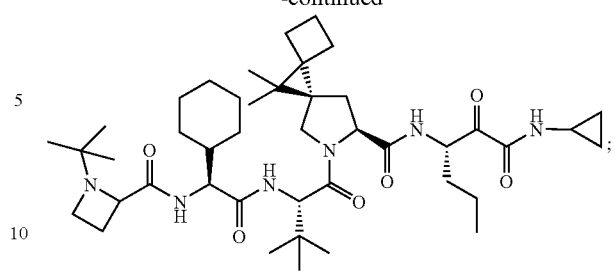
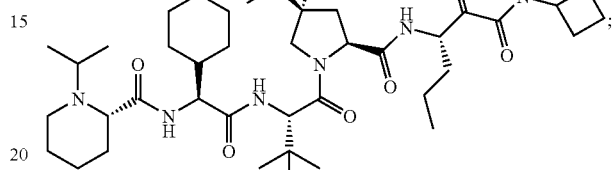
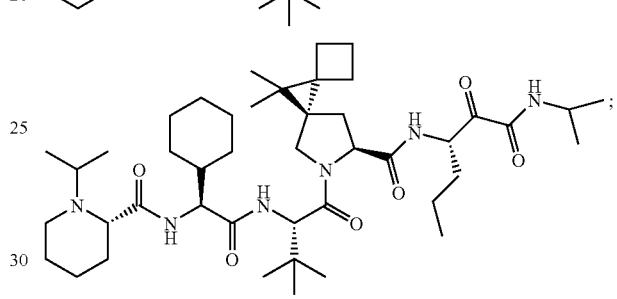
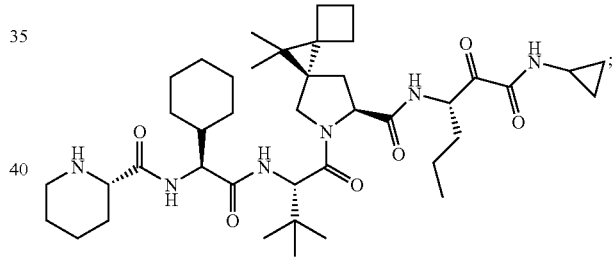
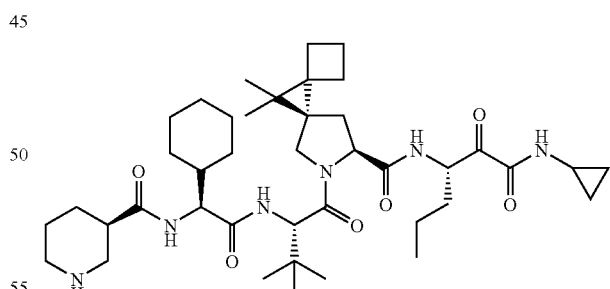
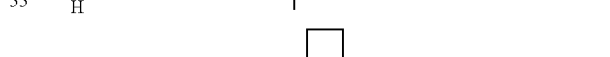
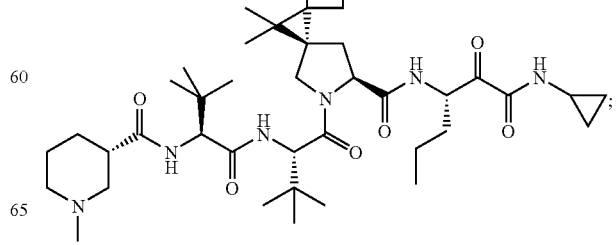

-continued
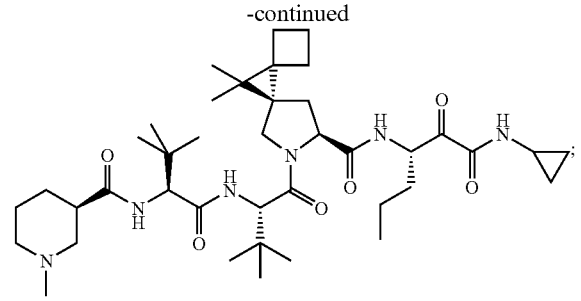
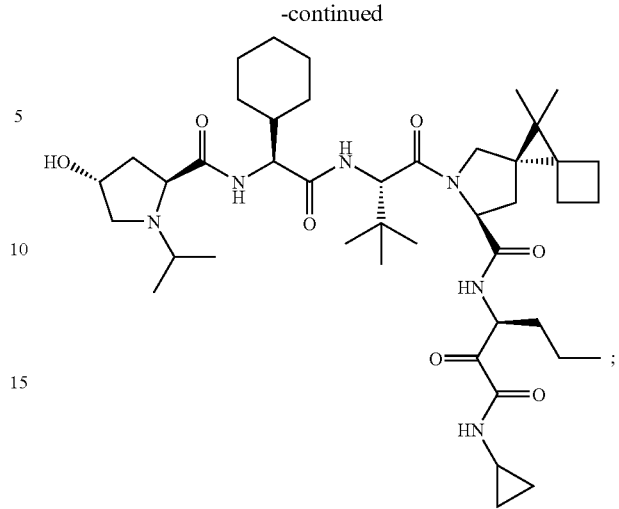
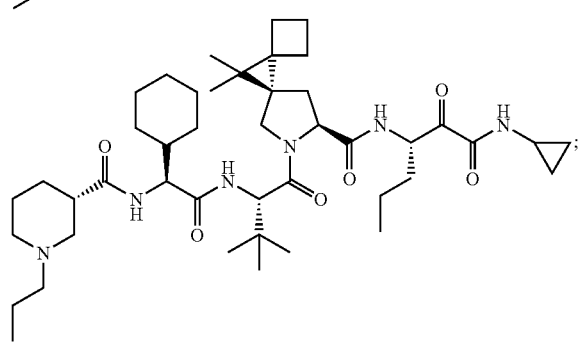
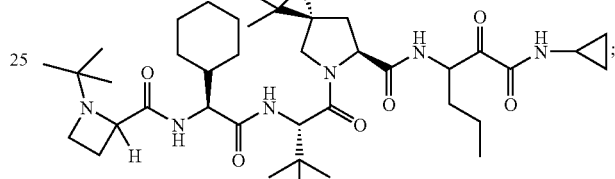
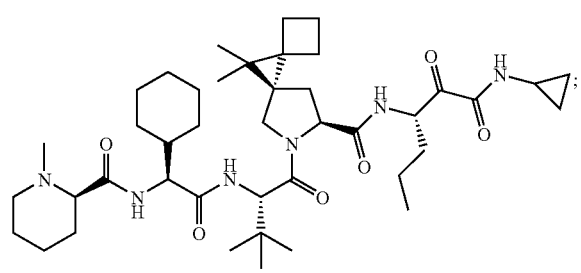
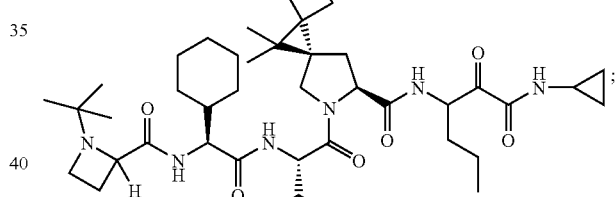
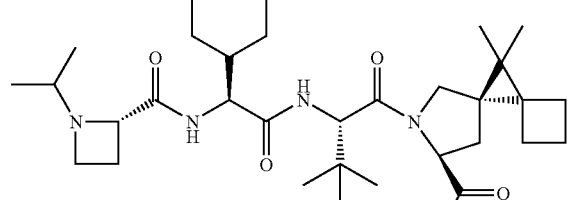
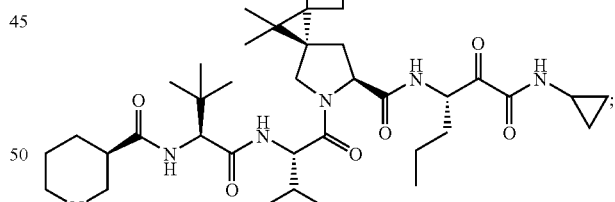
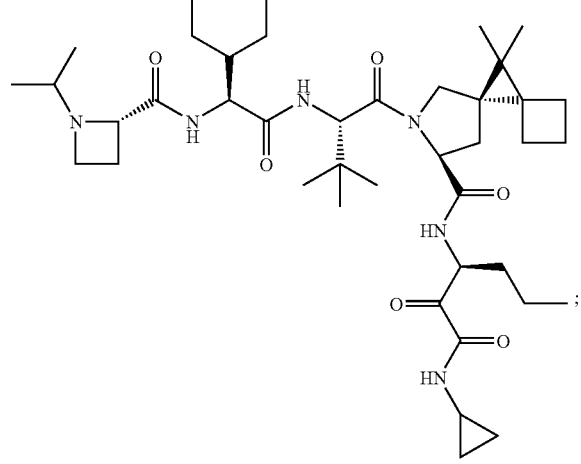
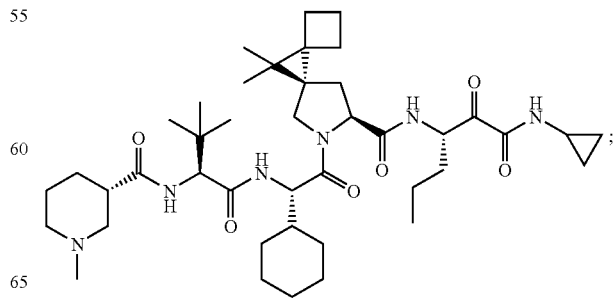

165
-continued
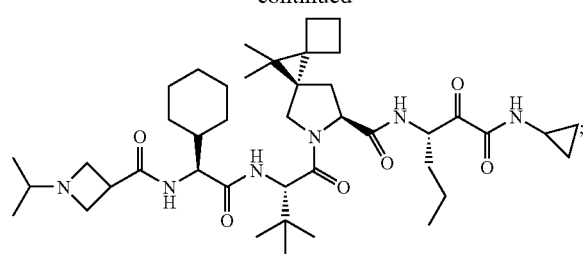
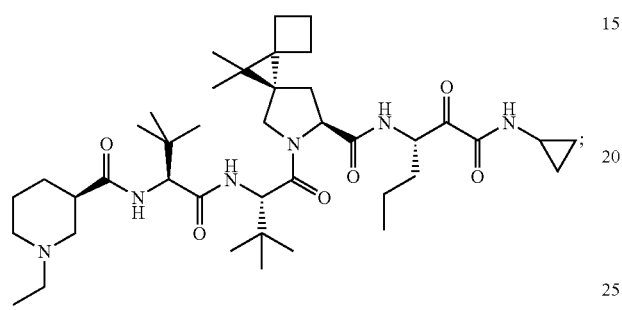
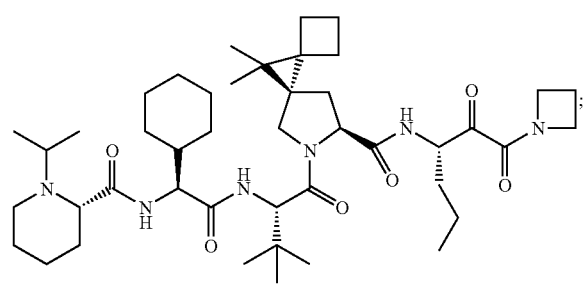
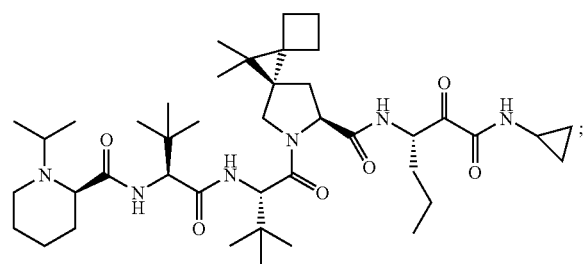
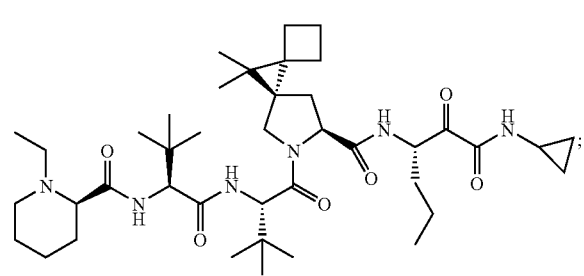
166
-continued
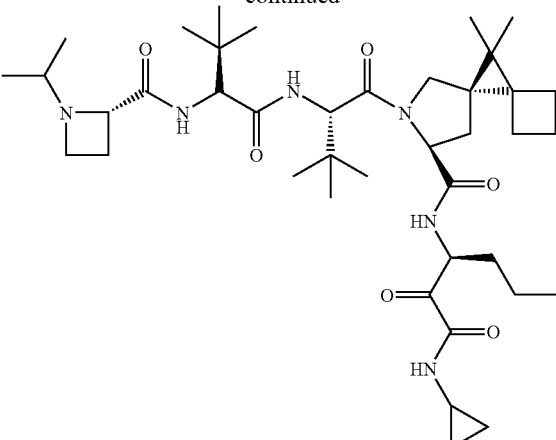
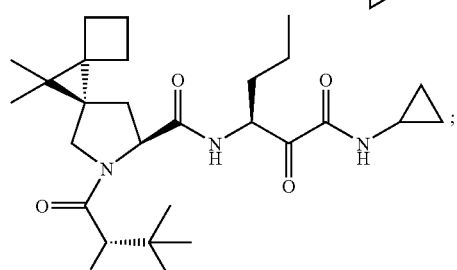
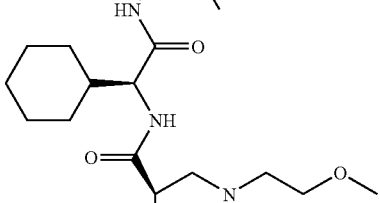
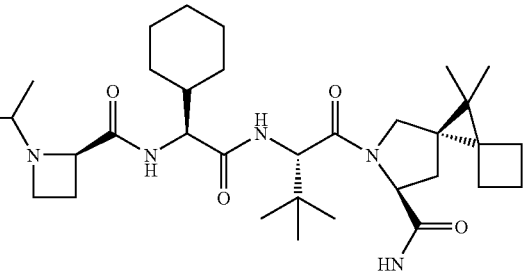
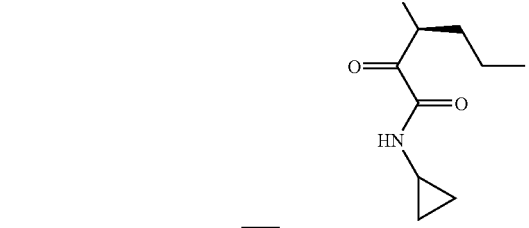
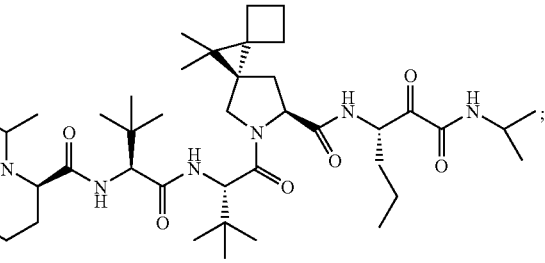
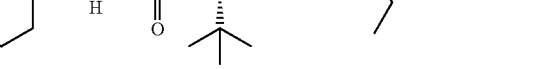

167
-continued
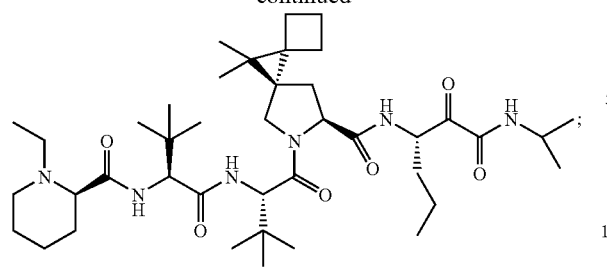
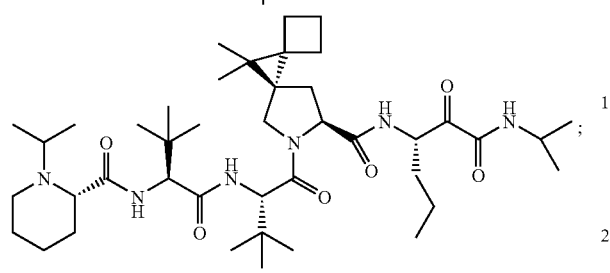
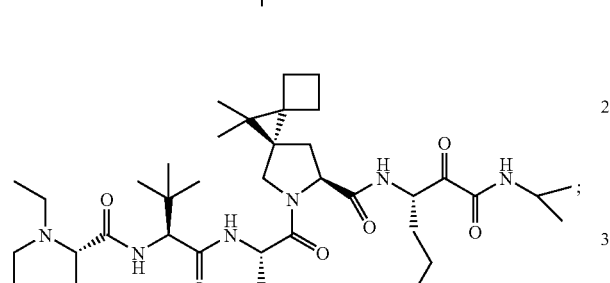
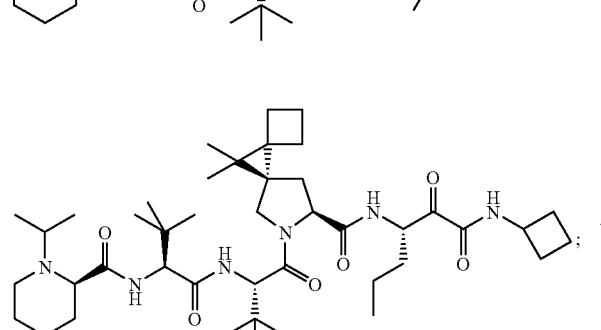
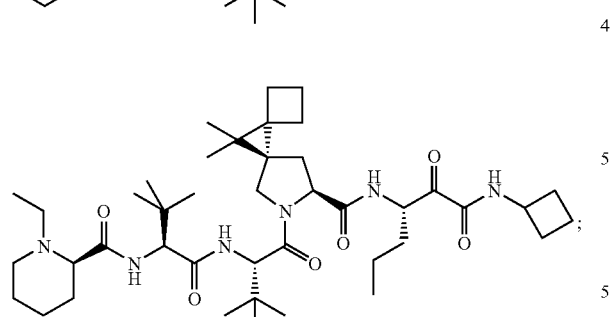
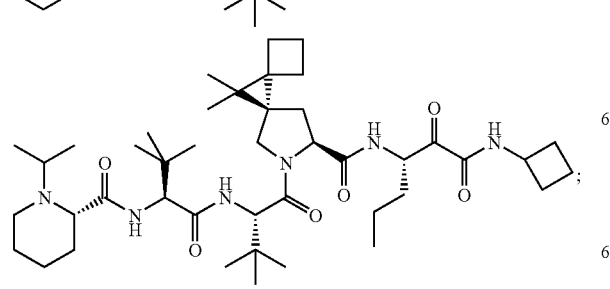
168
-continued
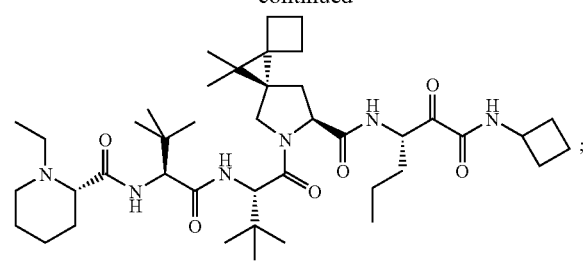
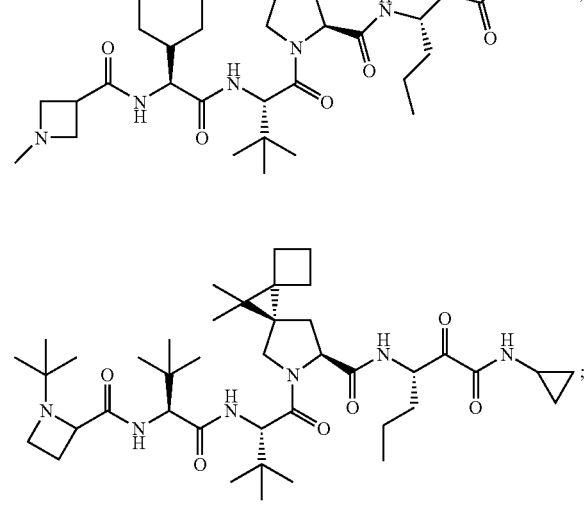
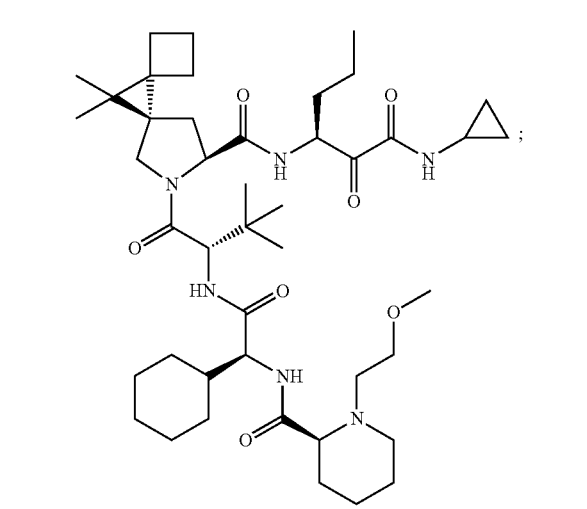
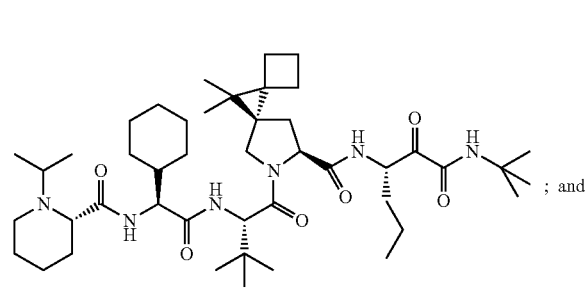

169
-continued
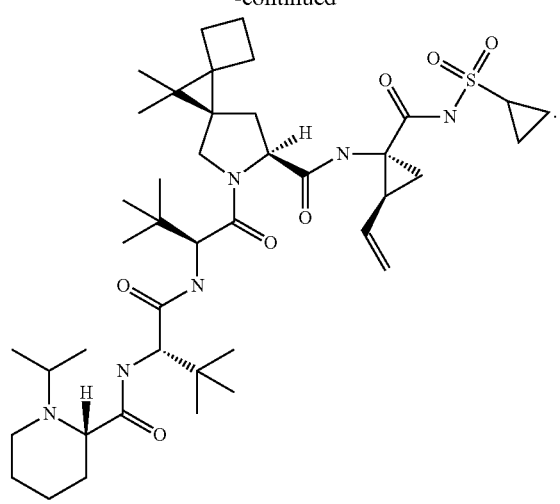
7. The compound of claim 6, wherein the compound is selected from the group consisting of:
170
-continued
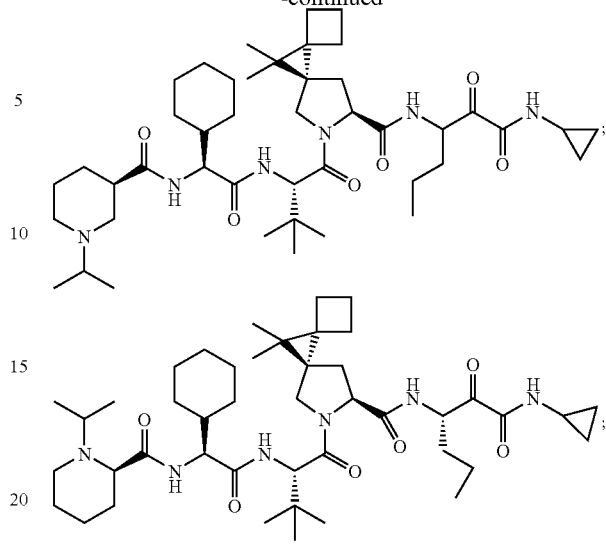
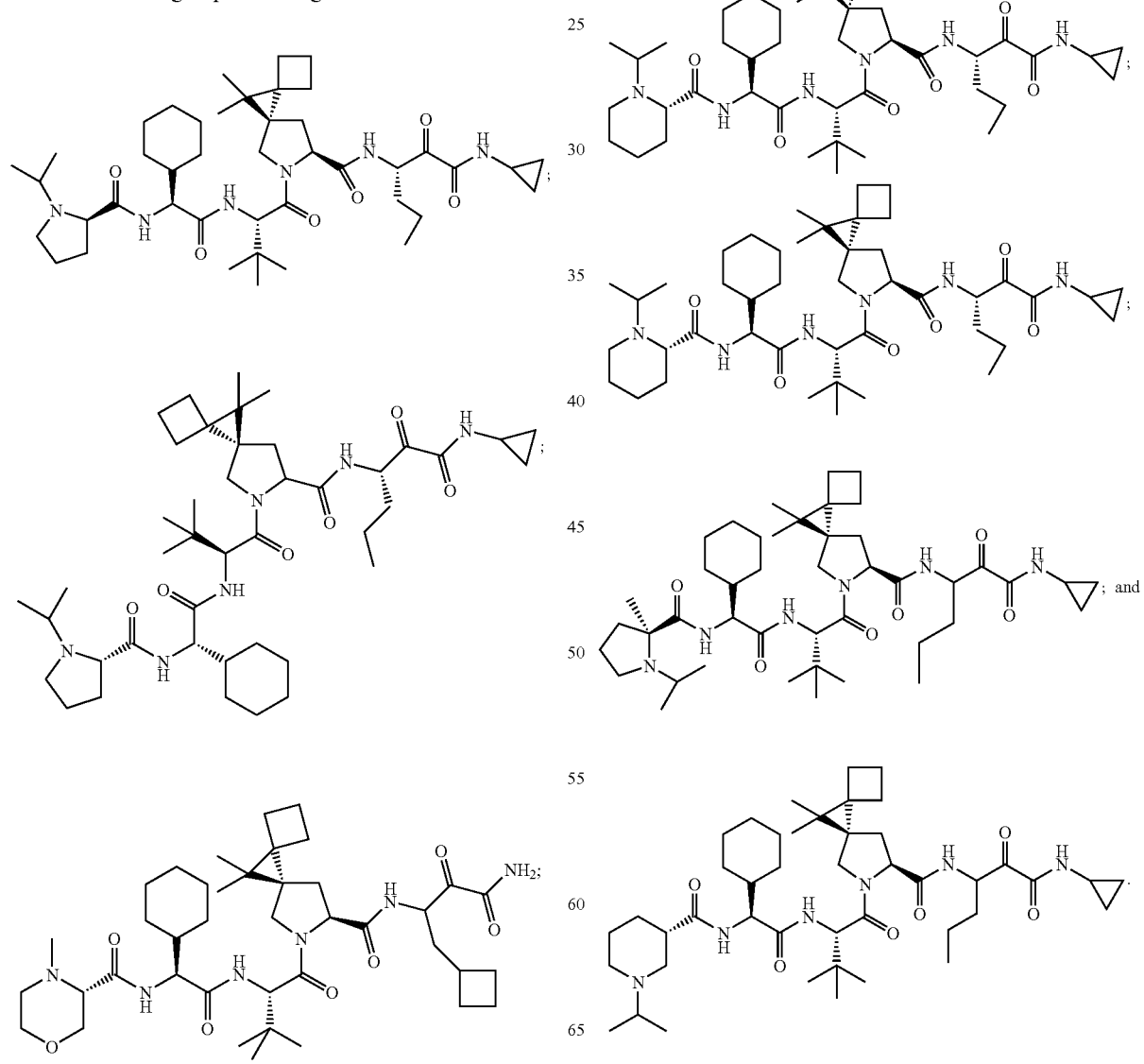

8. The compound of claim 6, wherein the compound is selected from the group consisting of:
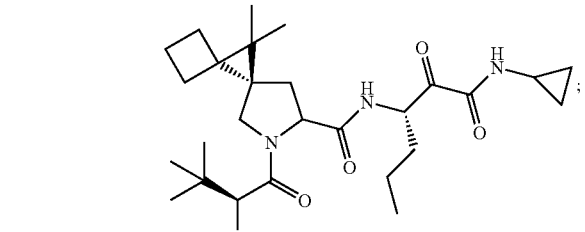
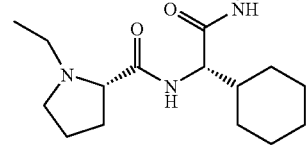
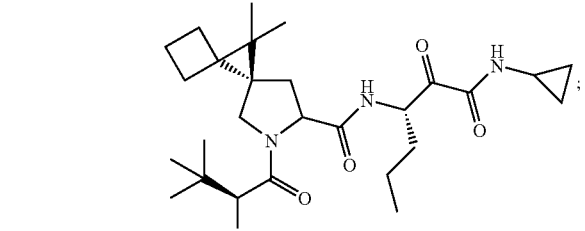
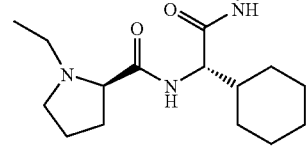
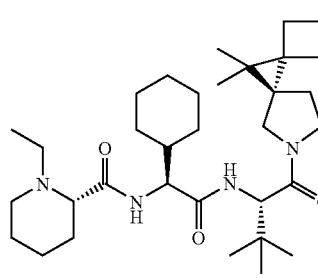
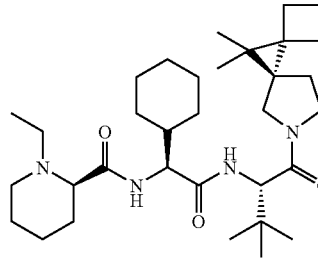
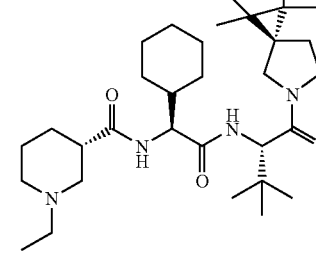
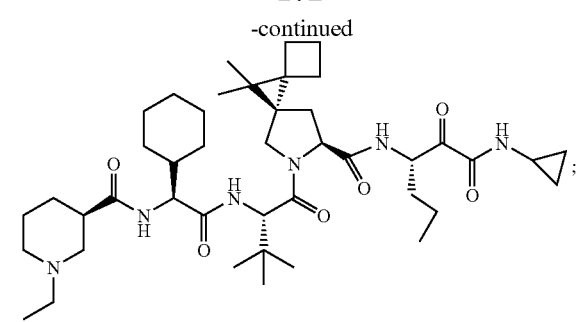
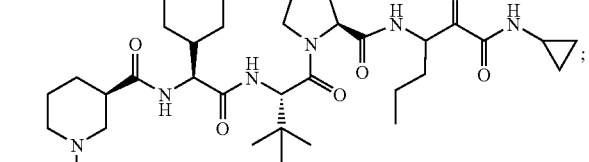
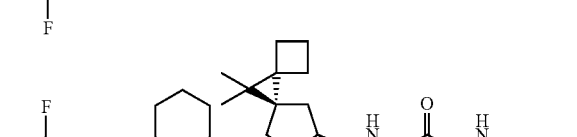
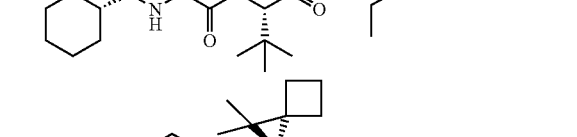
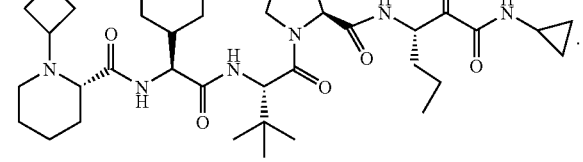
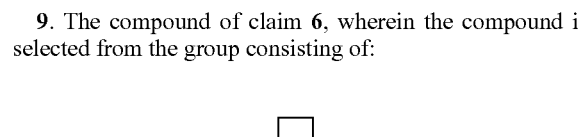
9. The compound of claim 6, wherein the compound is selected from the group consisting of:
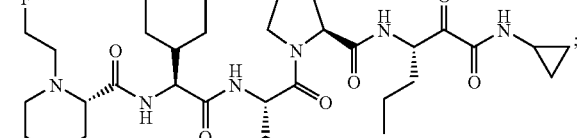
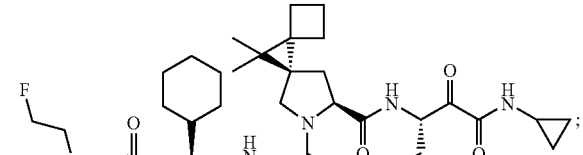

-continued
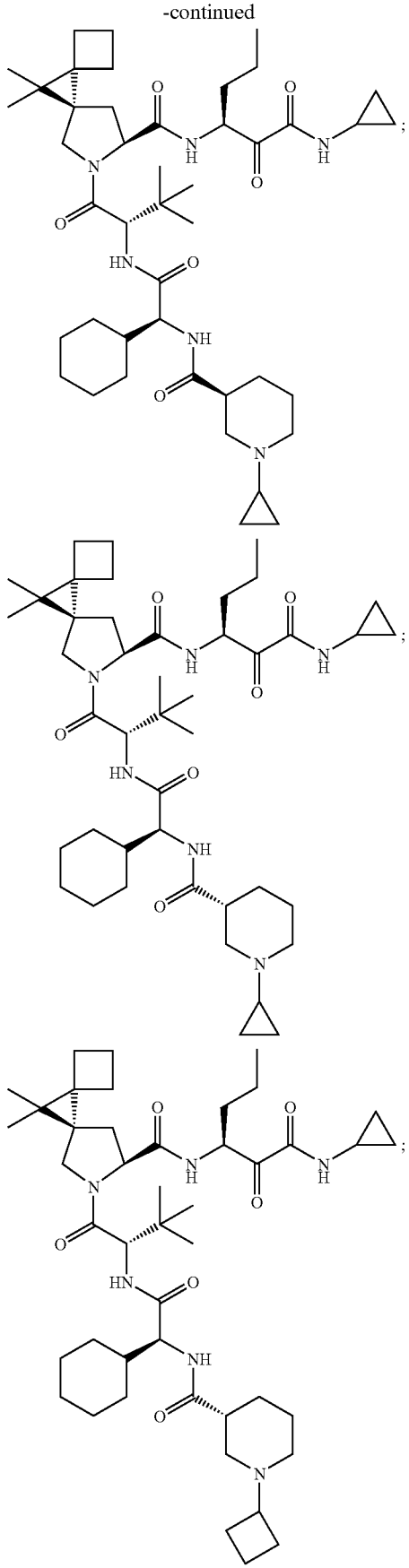
-continued
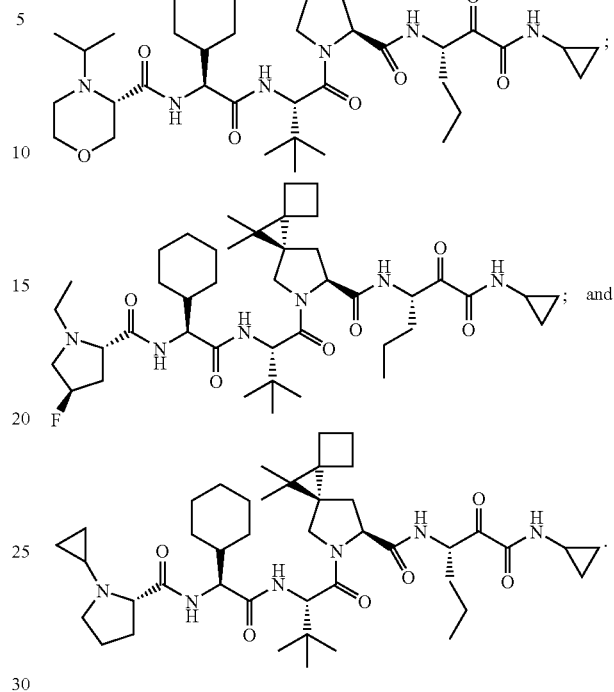
10. The compound of claim 6, wherein the compound is selected from the group consisting of:
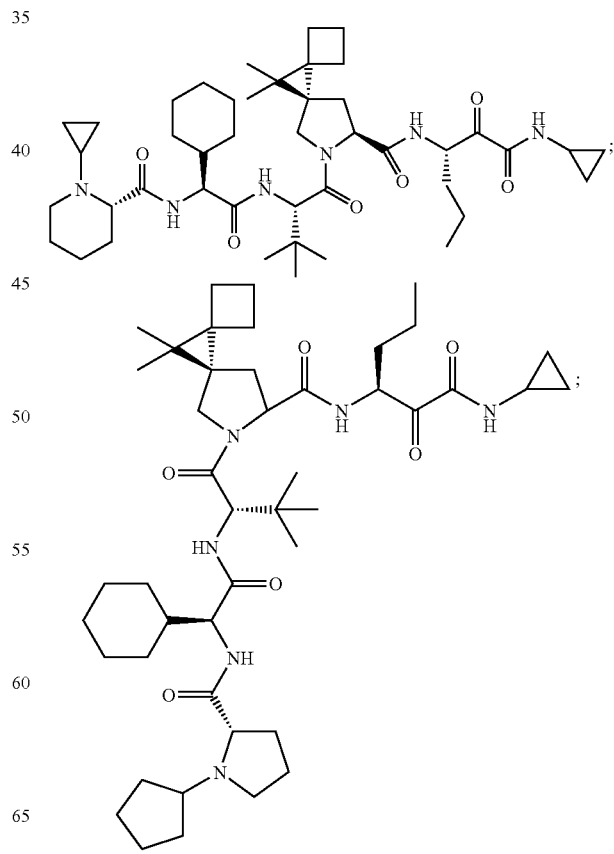

175
-continued
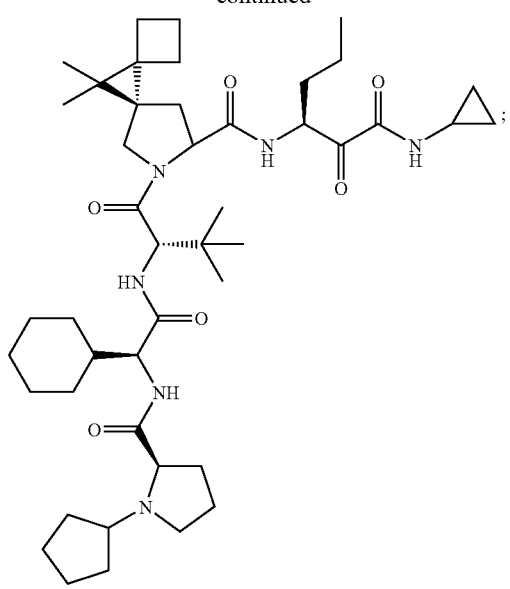
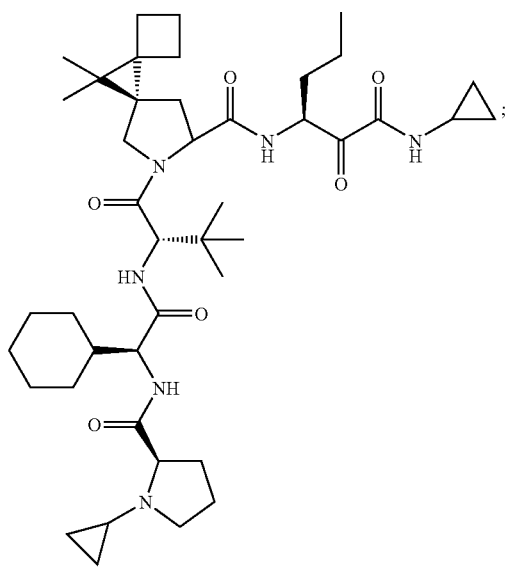
176
-continued
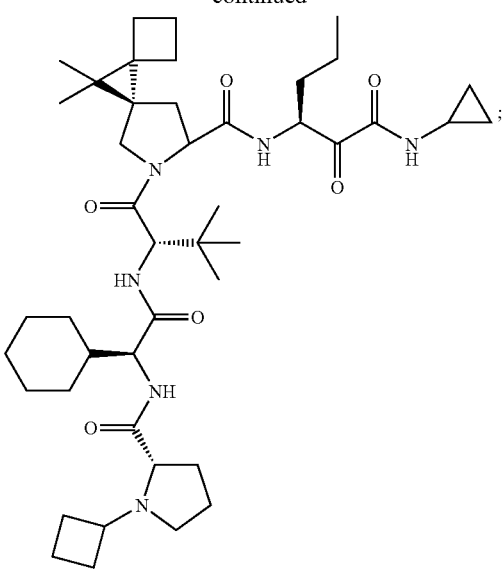
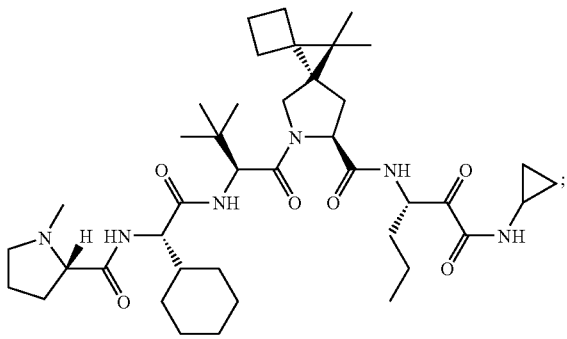
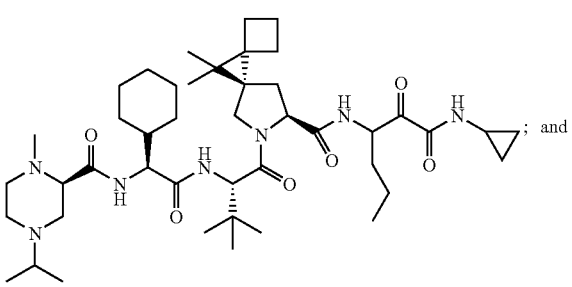
; and
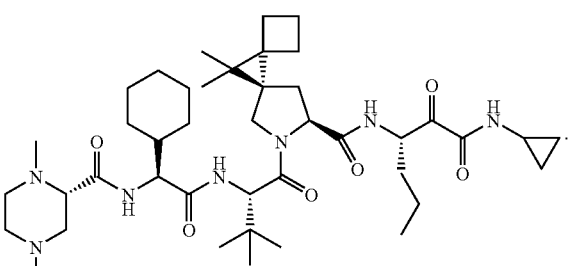

11. The compound of claim 6, wherein the compound is selected from the group consisting of:
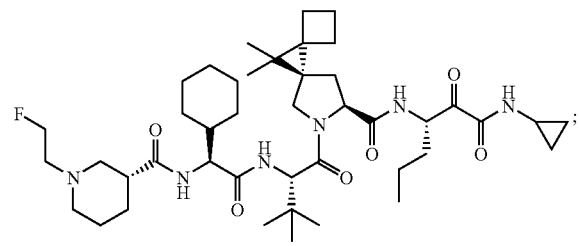
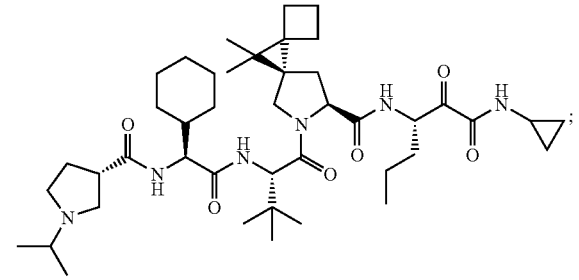
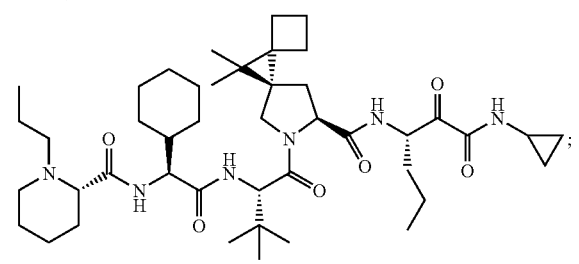
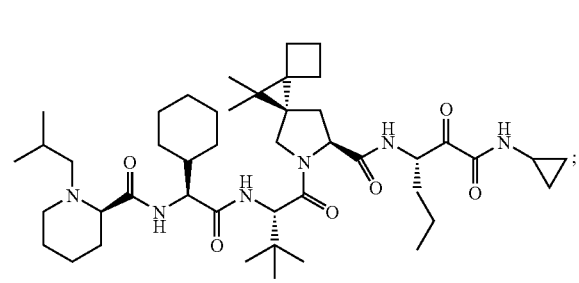
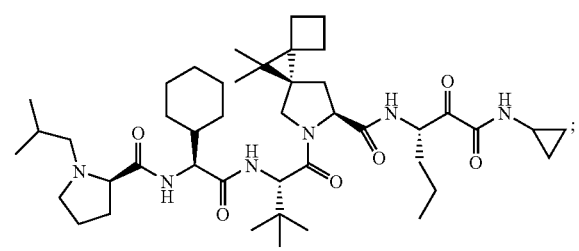
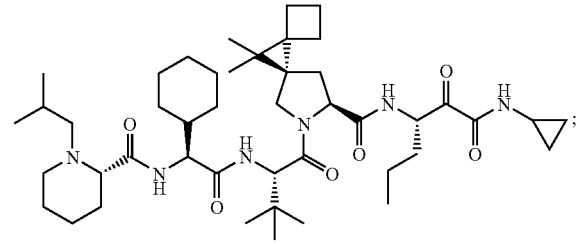
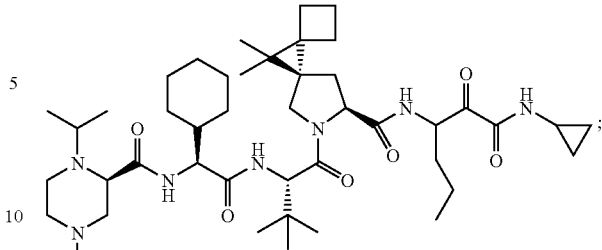
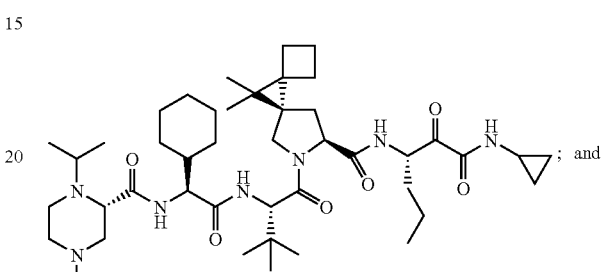
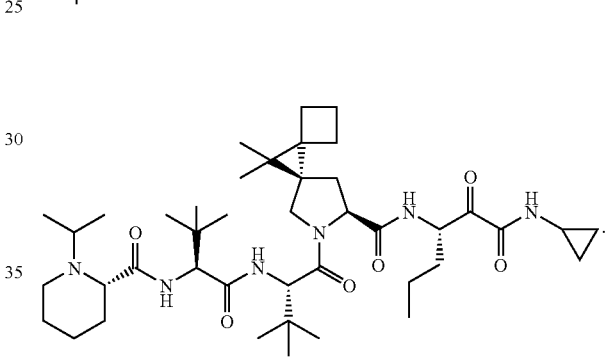
12. The compound of claim 6, wherein the compound is selected from the group consisting of:
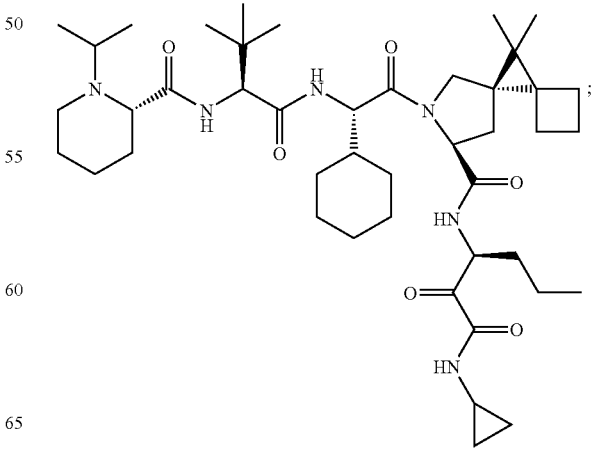

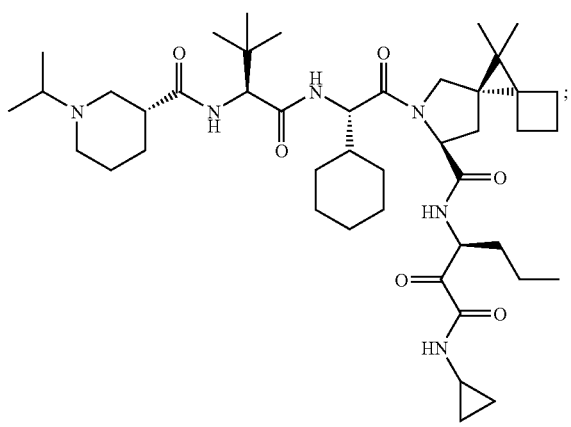
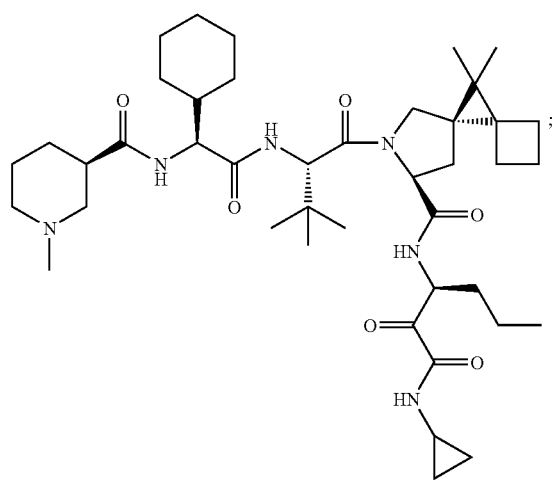
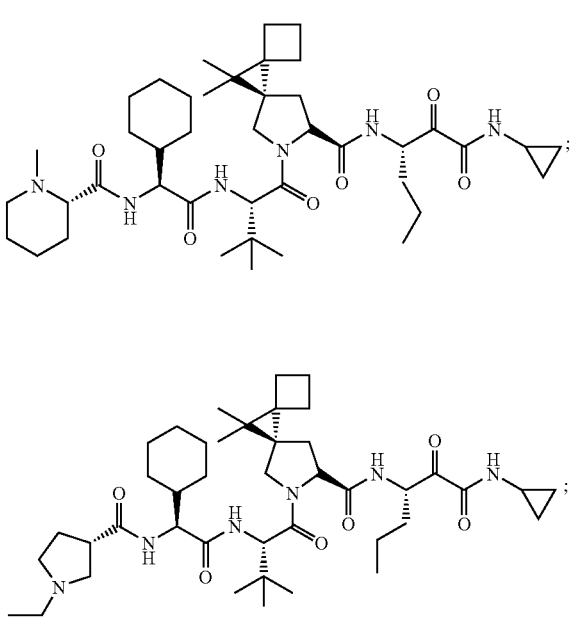
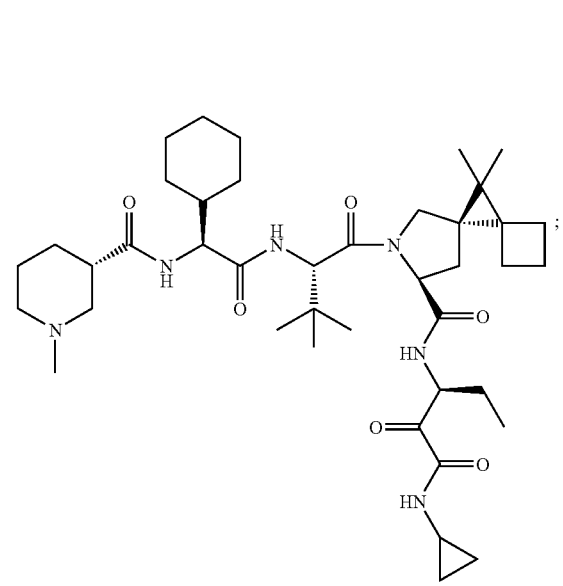
13. The compound of claim 6, wherein the compound is selected from the group consisting of:
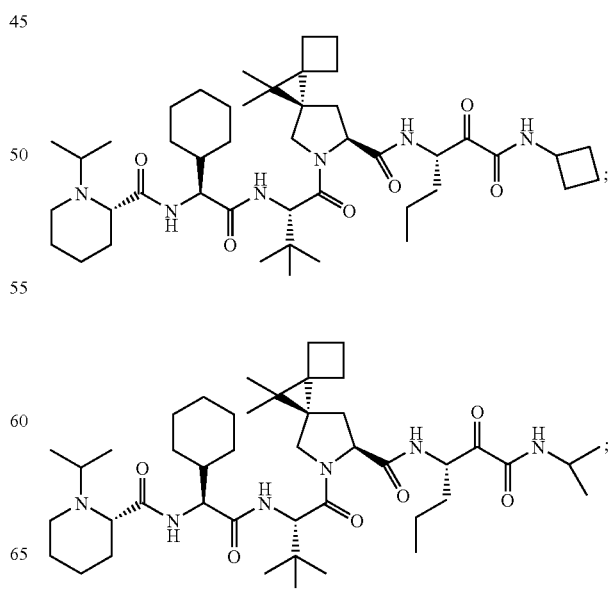

181
-continued
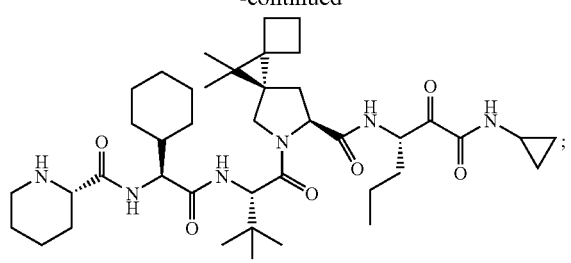
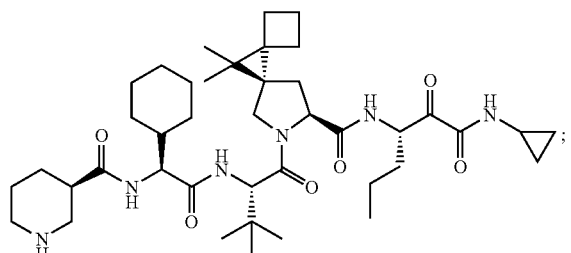
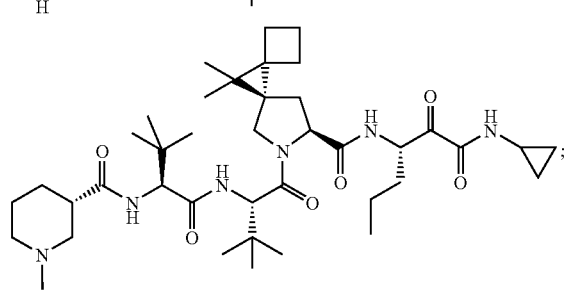
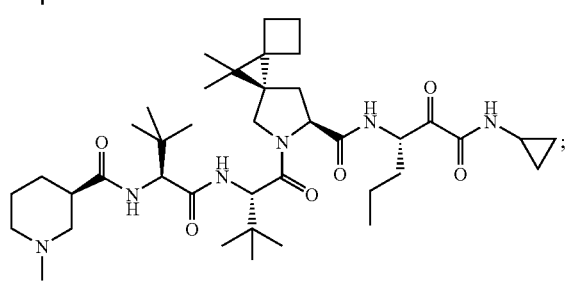
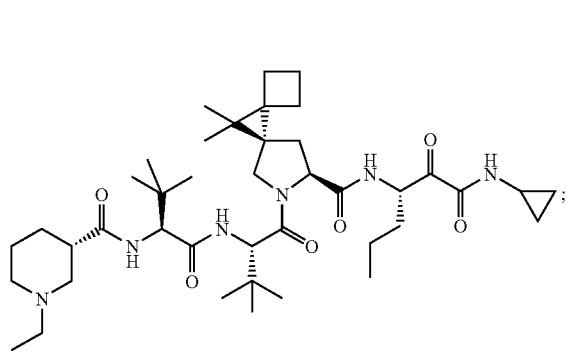
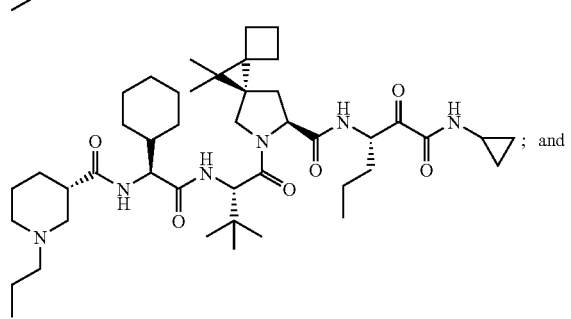; and
182
-continued
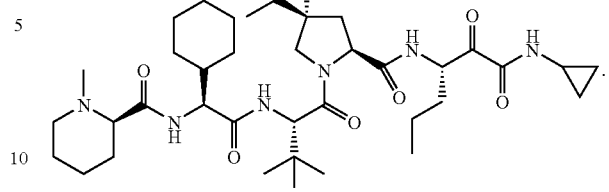.
14. The compound of claim 6, wherein the compound is selected from the group consisting of:
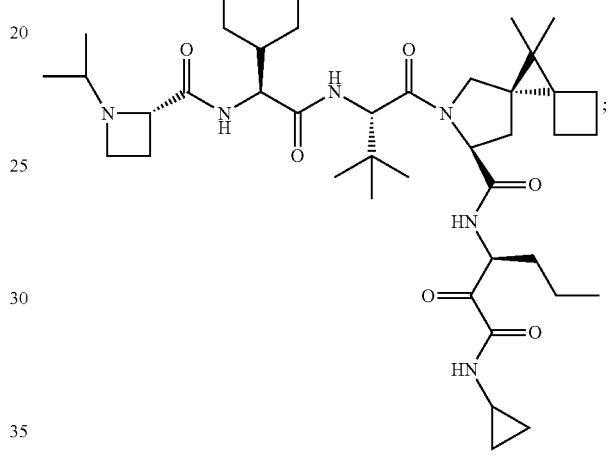;
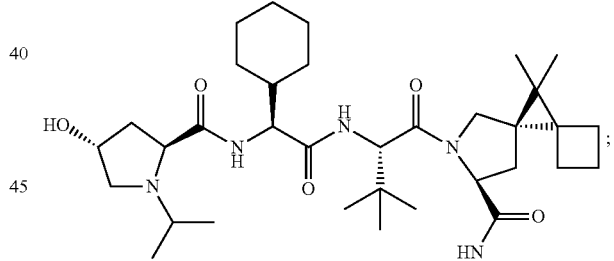;
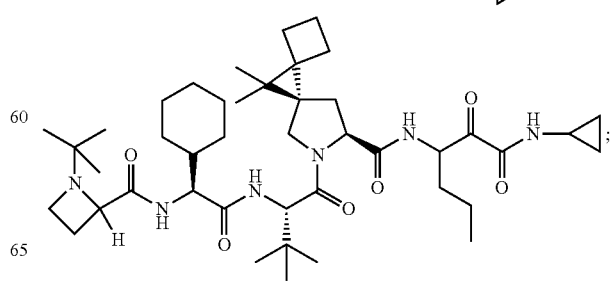;

-continued
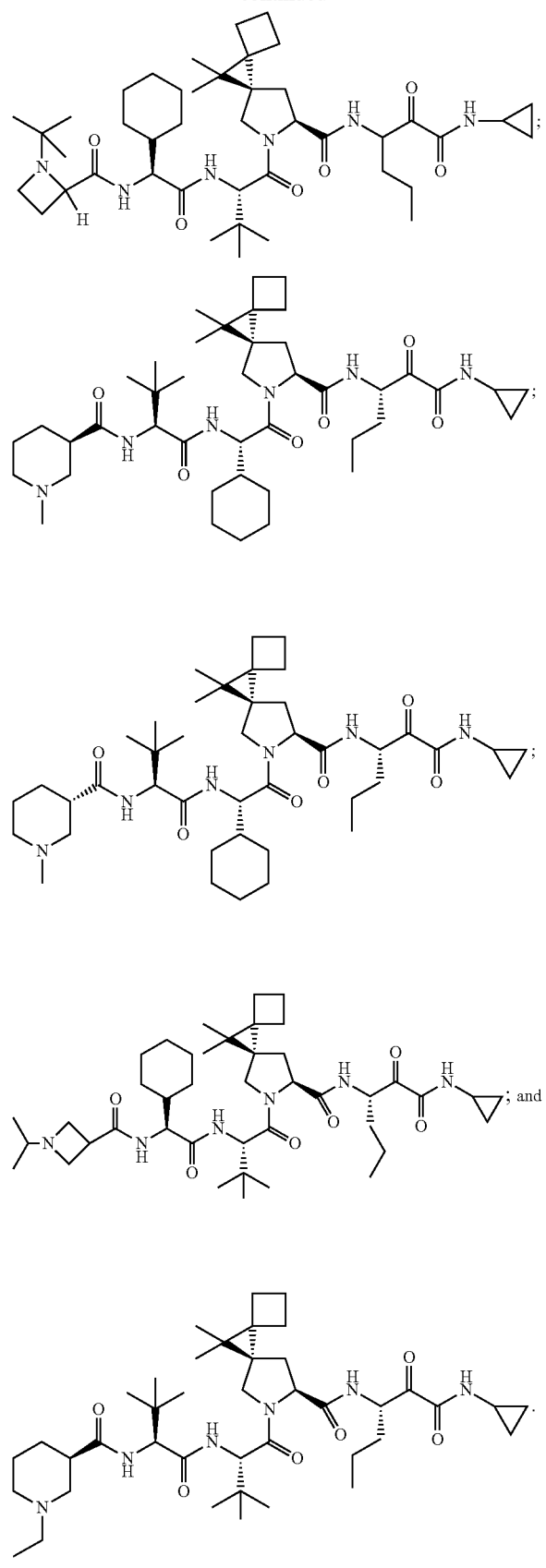
15. The compound of claim 6, wherein the compound is selected from the group consisting of:
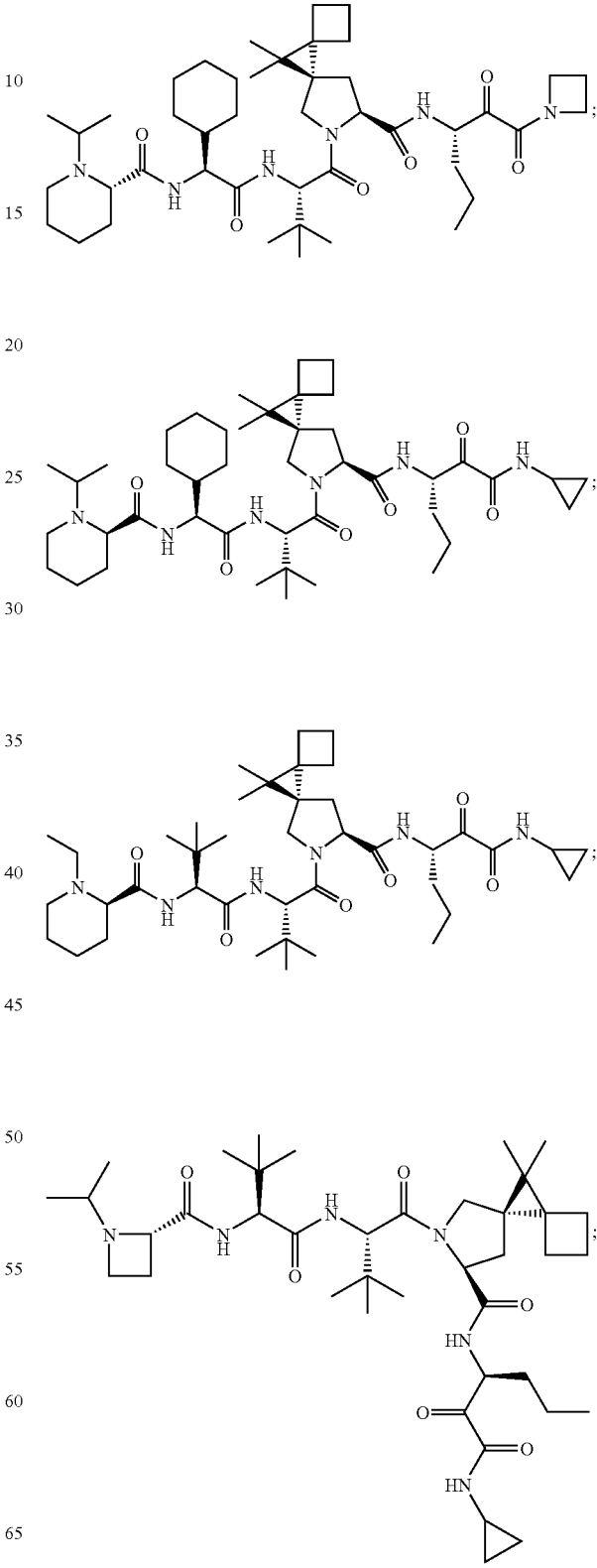

-continued
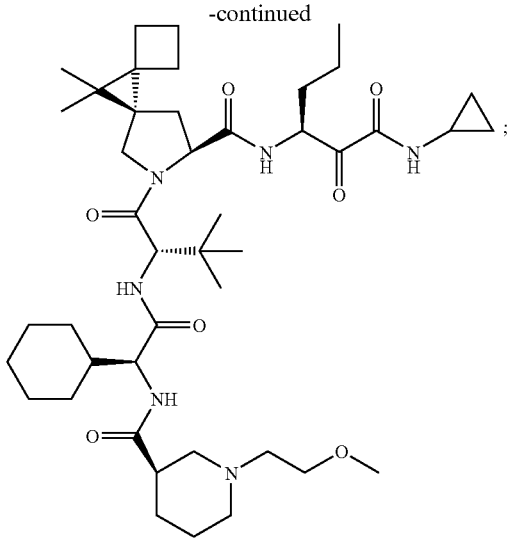
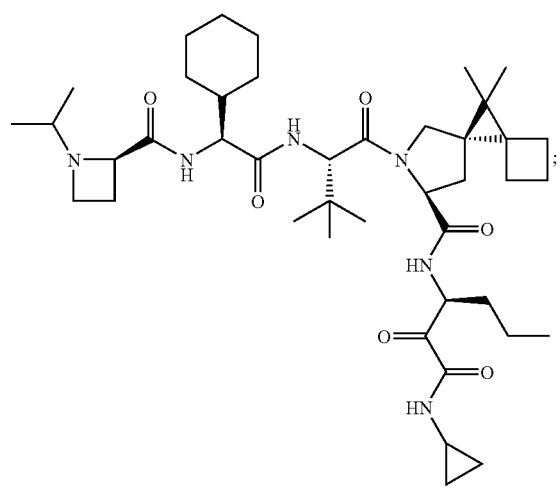
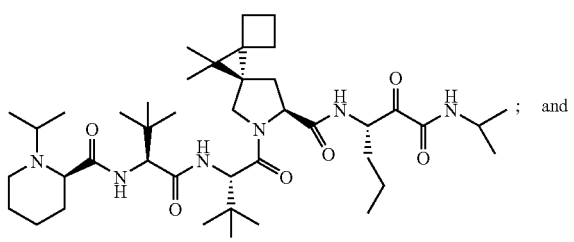
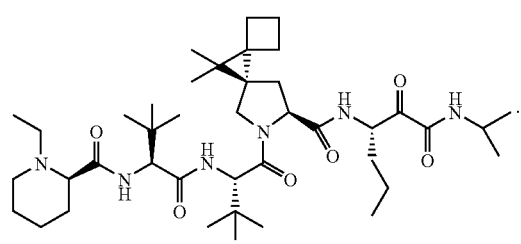
16. The compound of claim 6, wherein the compound is selected from the group consisting of:
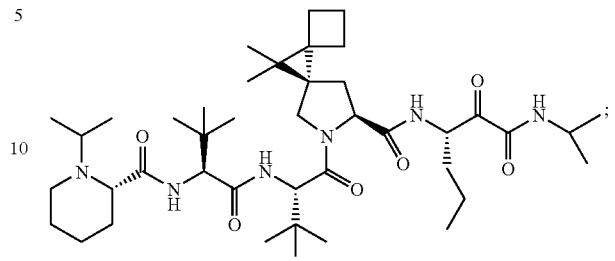
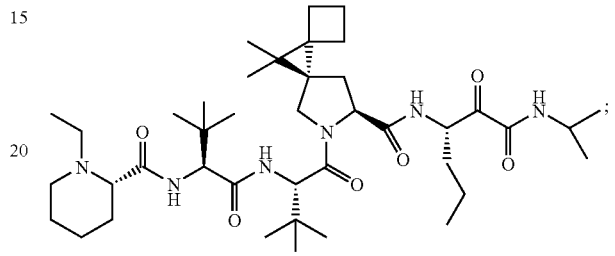
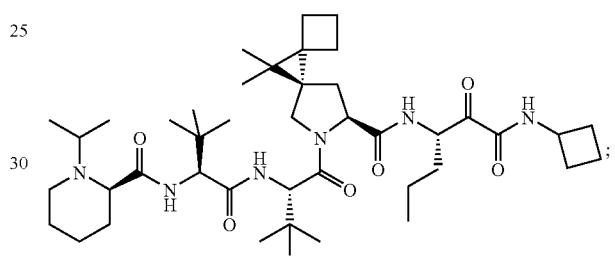
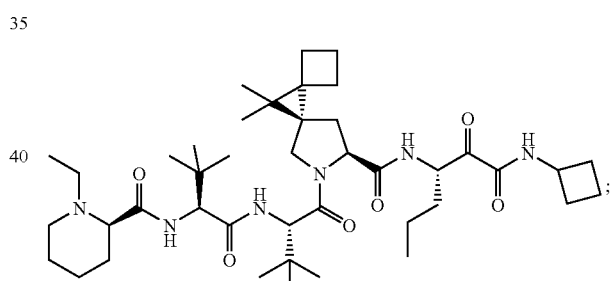
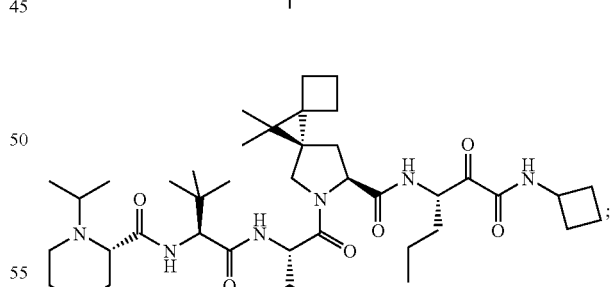
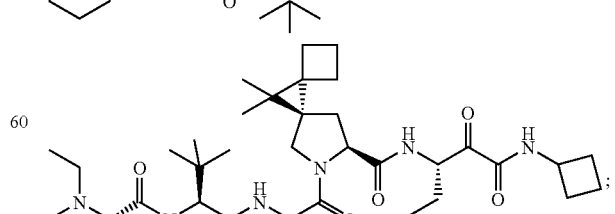
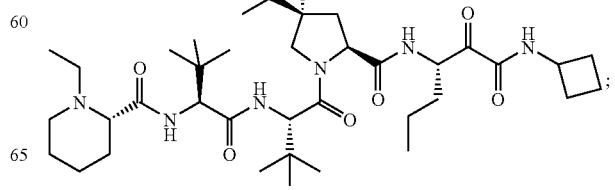

-continued
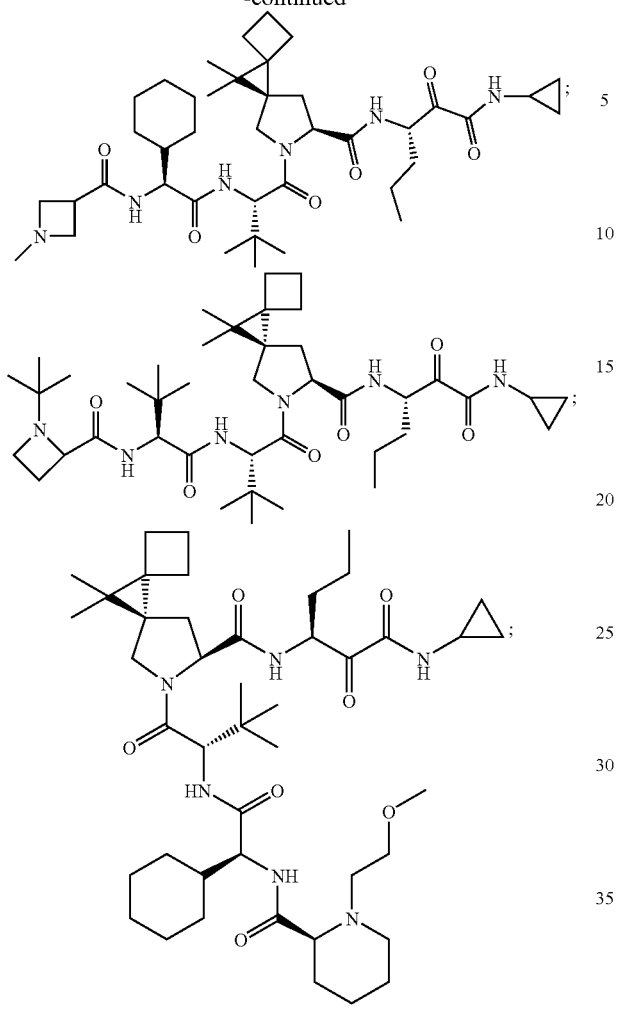
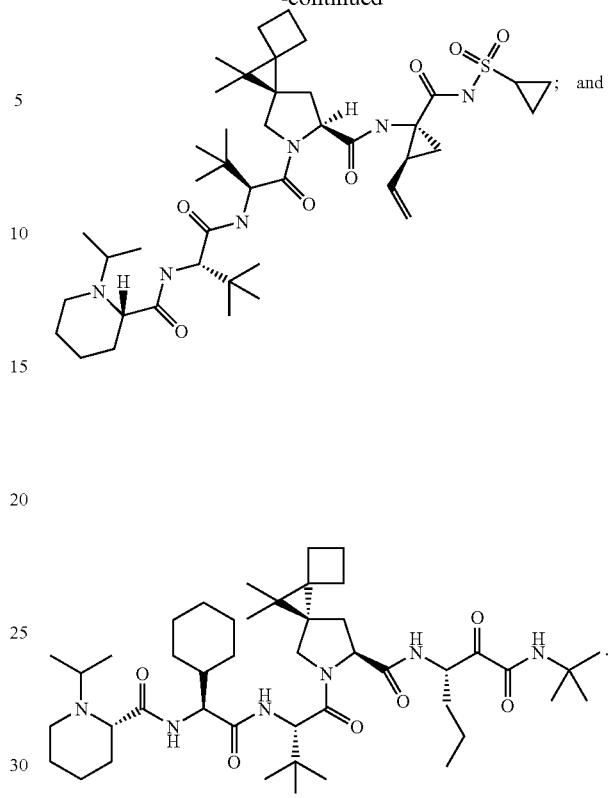
17. A pharmaceutically acceptable formulation for the treatment of an HCV-associated disorder, the formulation comprising a compound of claim 1 and a pharmaceutically acceptable excipient.
* * * * *